United States Patent [19]
Pasquale et al.

[11] Patent Number: 5,457,048
[45] Date of Patent: Oct. 10, 1995

[54] EPH-RELATED TYROSINE KINASES, NUCLEOTIDE SEQUENCES AND METHODS OF USE

[75] Inventors: Elena B. Pasquale; Fereydoun G. Sajjadi, both of San Diego, Calif.

[73] Assignee: La Jolla Cancer Research Foundation, La Jolla, Calif.

[21] Appl. No.: 162,809

[22] Filed: Dec. 3, 1993

[51] Int. Cl.$^6$ .............................. C12N 9/12; C12N 15/54
[52] U.S. Cl. .................................. 435/252.3; 435/320.1; 435/194; 536/23.2; 536/23.5
[58] Field of Search ................................. 536/23.2, 23.5; 435/240.2, 252.3, 320.1, 194

OTHER PUBLICATIONS

Wicks et al (1992) Proc. Natl Acad. Sci. 89, 1611–1615.
Pasquale (1991) Cell Regul. 2, 523–534.
Frohman et al (1988) Proc. Natl Acad. Sci 85, 8998–9002.
Roux et al (1980) BioTechniques 8(1) 48–57.
Sambrook et al. in "Molecular Cloning: A Laboratory Manual" 2nd Ed. CHS Press, (1989) pp. 11–2–11.57.
Lhotak, Vladmir, et al. "Characterization of Elk, a Brain–Specific Receptor Tyrosine Kinase." Mole. Cell. Biol. 11(5):2496–2502 (1991).
Gilardi–Hebenstreit, Pascale et al. "An Eph–Related Receptor Protein Tyrosine Kinase Gene Segmentally Expressed in the Developing Mouse Hindbrain." Oncogene 7:2499–2506 (1992).
Nieto, M. Angela et al. "A Receptor Protein Tyrosine Kinase Implicated in the Segmental Patterning of the Hindbrain and Mesoderm." Development 116:1137–1150 (1992).
Letwin, Kenneth et al. "Novel Protein–Tyrosine Kinase cDNAS Related to fps/fes and eph Cloned Using Anti–Phosphotyrosine Antibody." Oncogene 3:621–627 (1988).
Maisonpierre, Peter C. et al. "Ehk–1 and Ehk–2: Two Novel Members of the Eph Receptor–like Tyrosine Kinase Family with Distinctive Structures and Neuronal Expression." Oncogene 8:3277–3288 (1993).
Böhme, Beatrix, et al., "PCR Mediated Detection of a New Human Receptor–Tyrosine–Kinase, HEK 2." Oncogene 8:2857–2862 (1993).

*Primary Examiner*—Keith C. Furman
*Assistant Examiner*—Keith D. Hendricks
*Attorney, Agent, or Firm*—Campbell and Flores

[57] ABSTRACT

The invention is directed to substantially purified Eph-related protein tyrosine kinases, or functional fragments thereof, having about 23 to 66 percent amino acid sequence identity in their carboxyl terminal variable regions compared to known members of the Eph subclass of tyrosine kinases. Nucleic acids encoding such Eph-related protein tyrosine kinases, vectors and host cells are also provided. The invention is also directed to a method of diagnosing cancer and determining cancer prognosis. The method includes removing a tissue or cell sample from a subject suspected of having cancer and determining the level of Eph-related protein tyrosine kinase in the sample, wherein a change in the level or activity of a Eph-related protein tyrosine kinase compared to a normal sample indicates the presence of a cancer or indicates the level of malignancy of a cancer.

4 Claims, 7 Drawing Sheets

```
Cek5     1   MPGPERTMGPLWFCCIPLALIPLIAAVEETLMDSTTATAELGWMVHP-PSGWEEVSGYDENMNTIRTYQVCNVFE-SSQNNWLRTKYIRRR-GAHRIH
Cek10    1                GVSSRARRPPGSSRSSRRGV.S..A.TT..-ET.........A.QP.......Q.R.-AQ.QQ......F.N.Q-DVQ.VY
Cek6     1                                      .....TR........TAN.-.................L........-PN.....L.TF.N..-......Y
Cek4     1            DRRRLPLIL.CAALGSAGR.SARPGN.VN.L..K.IQG...ISY.-SH...I.V..HYTP....ES..MD-H.......NW.P.N-S..QK.Y
EcK      1   MELQAARACFAL..G.--A..AAAAQGK.VV.L.FAA.GG....LT..YGK..DLMQNIMND.-P.YM.S....MS-GD.D....NWVY.G-E.E.NN
Eph      1   MERRW.LGLGIV.LL.---AP.P.GAR.K.V....TSK.QG.....LLD.PKD...S.QQQILNGT-PLYM...D.PMQGRRDTDH...SNW.Y.GEE.S.V.

=
Cek5    96   VEMKFSVRDCSSIPNVPG---SCKETFNLYYESDFDSATKTFPNWMENPWMKVDTIAADESFSQVDLGGRVMKINTEVRSFGPVSKNGFYLAFQDYGGCM
Cek10   79   ..L..T....K..KI..-...........F.....T...SANS.F.....YI......P....KLES.-....K......L..............L.A..
Cek6    68   T..R.T......L.....-........T.SVI..KSAF.T.A.YL.........F..L.GF---..........................
Cek8     1                             GESQ---FA.I...........T...I.D.I.L.....DV..L..K........V.A.I
Cek4    96   ..L..TL...N...L.L.-T.............M...D.IL.L.....EV......K........V.A.V
Eck     96   F.LN.T....N.F.GGAS---............A...L.YG.N-.QKRL---FT.I....P.ITVSS.FEA.HV.L.V.E..V..LTRK........I.A.V
Eph     97   ..LQ.T....K.F.GGA.PLG......L.M...Q.VGIQ-LRRPL....FQ..T.V...Q..TIR..ASGSV.L.V.RC.L.RLTRR.L....HNP.A.V

=                            =
Cek5   194   SLIAVRVFYRKCPRVIQNGAVFQETLSGAESTSLVAARGTCISNA---EEVDVPIKLYCNGDGEWLVPIGRCMCRPGYESVENGTVCRGCPSGTFKASQG
Cek10  173   ..L..A..K..SNT.AGF.I.P...T...P....I.P....PQ.---V..s..L......M.V.A.T.AA..PAMKD.Q.QA.GP....SK..
Cek6   141   -----..FK...S.V..F.I.P..MT.........T......P.-...........M.......T.KA...PEN.-VA..A..A........
Cek8    56   A.VS.....K....LTVR.L.Q.PD.IT..DTS...EV..S.VN.S----..K.....M..GA........N.L.NA...ERNG--E.QA.KI.YY...LST
Cek4   190   A.VS...YFK...FTVK.L.M.PD.VPM-D.Q...EV..S.VNHS---..K.EEP...-M..STE........K.L.NA....ERGF--A.QA.RP.FY...A.
Eck    190   A.LS...Y.K...ELL.GL.H.P..IA.SDAP..ATVA...VDH.VVPPGGEE.-RMH.AV......Q.L.QA....K..D-A.QA.SP.F..FEAS
Eph    193   A.VS......QR..ETLNGL.Q.PD..P.--PAG..EVA....LPH.RASPRP.SGAPRMH.SP......V...H.E....EGGS.EA.VA.....SYRMDMD
```

FIG. IA

```
Cek5   291  DEGCVHCPINSRTTSEGATNCVCRNGYYRADADPVDMPCTTIPSAPQAVISSVNETSLMLEWTPPRDSGGREDLVYNIICKSCGS----GRGACTRCGDNV
Cek10  270  EGP.SP..P.....AGA.V.I..S.FF........A.SA..SV....RS....N......FV...SE.Q.A...D.L..V...K.SV----E.RL.S...D...
Cek6   230  AGL.AR..P...SSA.ASPL.A.....F....L..PTAA..SV..G.RN....I.....N....ET...D.VT...V..K.RA----D.R..S...D....
Cek9     1  ..............................................................................................V........
Cek8   150  .VA.AK...PH.YSIW..S.S.T.DR.FF..EN.AAS.....RP.......NL..N......VN....SA.QNK....D.IS..VV..R..A---EPSH.RS...SG.
Cek4   283  NVK.AK..PH.S.YEDASLN.R.EKN.F.SEK..PS.A..RP....RN...NI...VI.D.SW.L.T...K.VTF....K..G---SSKI.EP.S...
Cek7   287  ESP.LE..EHTLPSP....S.E.EE.FF..PQ..AS....RP.....HYLTAVGMGAKVE.R.....Q......I..SVT.EQ.WP---ES.E.GP.EAS.
Eck    291  TPH.LT..QQ.TAE......I.T.ES..H...PGEGPQVA..GP....RNLSF.ASG.Q.S.R.E..A.T....Q.VR.SVR.SQ.QGTAQDG.P..QP...VG.
Eph

Cek5   388  QFAPRQLGLTEPRIYISDLLAHTQYTFEIQAVNGVTDQSPFSPQFASVNITTNQAAPSAVSIMHQVSRTVDSITLSWSQPDQPNGVILDYELQYYEKNL-
Cek10  367  E.V..........R.....KVM..P........ISSK..YP..H........VL...PT..LH..S.GN.M....TP.ER....I......IK..S...QGQ
Cek6   327  E.V..........T.VF..S.W...P.........SNK...P..HV.............T.P.....A.MR.......P..E....I......R...LS+
Cek9     8  ..E....V....S.VQV.N...RV........L..EL.SEA..Y.TI.VS..S.SV...IPM......ATS.....P..............Q.R.FD..AE-
Cek8   248  H.S.Q.N..KTTKVS..T..........VW........SKHN..SQD.AV..TV........PIALIQAKEI.RH..VA.A..LE..R.....E..VK.....DQ-
Cek4   380  R.L...T...NTTVTVV.....N.......D.....S.L.TL.R...A.S........PITVIRKDRTSRN..VS....QE.EH....I......VK.....QE-
Cek7   384  RYSEPPH...RTSVTV...EP.MN...TVE.R...SGLVT-.RS.RTASVSI..TE.PK.RL---EGRSTT.LSV...I.PPQQSRVWKELVT.RKNGD-
Eck    391  H.S.GARA..T.AVHVNG..EPYAN....NVE.Q....SGLGSSGHAST...S.SMGH..ESLSGLSLRL..KKEPRQLE.T.AGSRPRSP..AN.T....HVLNQD-
Eph

Cek5   487  SELNSTAVKSPTNTVTVQNLKAGTIYVFQVRARTVAGYGRYSGKMYFQTMTEAEYQTSVQEKLPLIGSSAAGIVFLAVVIIVCN----
Cek10  467  GDGIANT.T.QK.S.RLDG...NAR.MV...........LPTE....TA.DGSTSKTFQE....V..AT..L.VV..I.A..F----(RKGMVT
Cek6   445  N.Y...SVAR.Q...ARLEG.RP.MV..V.........K......C....L.DDD.KSELR.Q....A..A..V..IVSL.A..S----
Cek9   107  D.D..FTLT.E..MA.IL..SP.K.........AV...P.........LMGG.HSEMA.DR.....V..ALG..A..VIAAIA.IAII----
Cek8   347  N.RTYRI..TASRNTDIKG.NPL.S....H......A.....DF..PFE.T.N.VPSP-IIGDGTN.TYIHV.V..S.V.VVILIAAF.IS----
Cek7     1  ...........................I.....A....A.R..TS.R.FE..E.SPDSFSIS..ENSQVVM.AI.A.VAIIL.TV..YVL.G----
Cek4   479  Q.TSY..ILRAKSTN...ISG..PD.T...I......A.R...TS.R.FE..E.SPDSFSIS..ENSQVVM.AI.A.VAIIL.TV..YVL.G----
Eck    479  -SNSYNVRRTEGFS..LDD.APD.T.LV...Q.L.QE-Q.AG.KVHE...LS-----PEGSGNLAV..GV.V.V.L.IVLAGVGEFIH----
Eph    491  ----ERYQMVLEPR..LLTE.QPD.T.IVR...ML.PL.P..PF..PDHE.R.SPPVSR-GLTGGEIVAV.FGLIL.AAL.IGIL.ERSRRA----
```

```
         STYRGPPPGLGVRLFV
.PA
Cek5+                     MTPGMKIYIDPFTYEDPNEAVREFAKEIDISCVKIEQVIGAGEFGEVCSGHLK
Cek5   575  ------RRRGFERADSEYTDKLQHYTSGH---------------------------------------------------
Cek10  555  EQLLSSPLG).KQRNST.P...E...Q.VT--------V............................E........R.R..
Cek6   533  ---------.KRAYSKEVV.S......ST.R------GS.................V.F....E...........YK.R..
Cek9   195  ---------FKSK.RETP...R..Q.I.TR-------GL.V.Y...S.........V.FI...E...S.......F.R..
Cek8   434  -------R..SKYSK.KQ.ADEEKHLN----------------Q.VRT.V.........Q........A...I...K...V........R..
Cek7    75  RAVAYPSLIW.C.YSK.KQDPEEEKM.FHN..-----------IKL..VRT...H......Q..H......EA..IT..R...........R..
Cek4   565  --------FC.YKKSKHGTDE.RL.FGN..-------------LKL.LRT.V..H......Q..H......L.A.NIS.DK.V..........R..
Eck    560  ---------.RKNQRARQSPEDVYFSK.EQ-------------LKPL.T.V..H......Q..LK.TT..HP...TRQK..........YK.M..
Eph    574  ---------.QRQQ.HVTAPPMWIERTSCAE------------ALCG.SRHTRTLHREPWTL.GGWSNFPSR.L.PAWLMVDT...E.......YR.T.R

L-PGKREIFVAIKTLKSGYTEKQRRDFLSEASIMGQFDHPNVIHLEGVVTKSSPVMIITEFMENGSLDSFLRQNDGQFTVIQLVGMLRGIAAGMKYLADM
Cek5   651  .-..R....................R..............I......R..............CA........L................SE..
Cek10  626  .-.......Y.......A..S.....................I.R......R....A.......................E..
Cek6   608  .-.......YT........DE..E..................I.R.........R................KE....S.L.......R..S..
Cek9   268  H-.......C........A..D....................I.......CK........Y.....A..K...R.............GS....S..
Cek8   505  V-....Q..FP........V........G.............I.......K...V.Y......T..KK...................S..
Cek7   161  .-Q...S.K..S......A.........G.............I.......K...V.Y......KH.A...................S..
Cek4   642  .-.S.K..S.........A.........G.............S.H.I.R....IS.YK.M....Y.....A..K...EK..E.S.L..........N.
Eck    634  TSS..K.VP........A......V..G.G.............S.HIL.....RK.I............AA...A.....ERED.LVPG...A..Q...S..N..SNH
Eph    653  .-.SQDCKT......DTSPGG.WWN..R..T......
```

FIG. IC

EPH-RELATED TYROSINE KINASES, NUCLEOTIDE SEQUENCES AND METHODS OF USE

This invention was funded in part by NIH Grants HD 26351 and CA 56721. Accordingly, the United States government has certain rights in the invention.

BACKGROUND OF THE INVENTION

This invention relates generally to protein tyrosine kinases and, more particularly, to Eph-related receptor tyrosine kinases and their manipulation for the control of cellular processes.

Receptor tyrosine kinases comprise a large family of proteins that share a number of structural features such as a glycosylated extracellular ligand-binding domain, a hydrophobic transmembrane domain and a conserved cytoplasmic catalytic domain. Integral membrane tyrosine kinases have been shown to mediate cellular signals important for growth and differentiation. The transduction of many extracellular signals to the cytoplasm occurs as a result of the binding of ligands such as growth factors, for example, to receptor tyrosine kinases at the cell surface. In most cases, ligand binding activates the cytoplasmic tyrosine kinase catalytic domain and culminates in tyrosine phosphorylation of multiple substrates in the cytoplasm.

Increased expression of membrane-spanning receptor tyrosine kinases frequently has been associated with alterations in normal cellular processes. The affected cellular processes include cell proliferation, differentiation and cancer, including, for example, human cancers. Specific examples of such cancers can include glioblastomas, squamous carcinomas and mammary carcinomas, which are associated with the amplification of the EGF receptor gene. Adenocarcinomas, breast cancers and gastric cancers similarly are associated with aberrant expression of the HER2/neu receptor and certain breast carcinomas overexpress the erbB-3 gene, for example.

The correlation between aberrant expression and transforming ability also extends to members of the Eph subclass of receptor tyrosine kinases. For example, carcinomas of the liver, lung, breast and colon show elevated expression of Eph. Unlike many other tyrosine kinases, this elevated expression can occur in the absence of gene amplification or rearrangement. Such involvement of Eph in carcinogenesis also has been shown by the formation of foci of NIH 3T3 cells in soft agar and of tumors in nude mice following overexpression of Eph. Moreover, an antigen present on the surface of a pre-B cell leukemia cell line also has been identified as a member of the Eph subclass. Wicks et al., *Proc. Natl. Acad. Sci., USA* 89:1611–1615 (1992). This leukemia- specific marker, termed Hek, appears to be similar to the chicken Cek4 and mouse Mek4 of the Eph subclass of receptor tyrosine kinases (see Sajjadi et al., *The New Biologist* 3:769–778 (1991), which is incorporated herein by reference). As with Eph, Hek also was overexpressed in the absence of gene amplification or rearrangements in, for example, hemopoietic tumors and lymphoid tumor cell lines.

In addition to their roles in carcinogenesis, a number of transmembrane tyrosine kinases have been reported to play key roles during development. Examples include the mouse c-kit proto-oncogene and the Drosophila genes "sevenless" and "torso," which are involved in pattern formation. Consistent with this developmental role, many receptor tyrosine kinases other than those described above also have been shown to be developmentally regulated and predominantly expressed in embryonic tissues. Examples of these other tyrosine kinases include Cek1, which belongs to the FGF subclass, and the Cek4 and Cek5 tyrosine kinases (Pasquale et al., *Proc. Natl. Acad. Sci., USA* 86:5449–5453 (1989); Sajjadi et al. (1991); and Pasquale, E. B., *Cell Regulation* 2:523–534 (1991), all of which are incorporated herein by reference).

Eph was the first member of the Eph subclass of tyrosine kinases to be identified and characterized by molecular cloning (Hirai et al., *Science* 238:1717–1720 (1987)). The name Eph is derived from the name of the cell line from which the Eph cDNA was first isolated, the erythropoietin-producing human hepatocellular carcinoma cell line, ETL-1. The general structure of Eph is similar to that of other receptor tyrosine kinases and consists of an extracellular domain, a single membrane spanning region and a conserved tyrosine kinase catalytic domain. However, the structure of the extracellular domain of Eph, which comprises an immunoglobulin (Ig) domain at the amino terminus, followed by a cysteine-rich region and two fibronectin type III repeats in close proximity to the transmembrane domain, is completely distinct from that of previously described receptor tyrosine kinases. The juxtamembrane domain and carboxy-terminus regions of Eph also are unrelated to the corresponding regions of other tyrosine kinase receptors. Thus, the discovery of Eph defined a new subclass of receptor-type tyrosine kinases.

In addition to the isolation and characterization of Eph, other related tyrosine kinases now have been identified. Cek4 and Cek5 were identified by screening a chicken embryo cDNA expression library with anti-phosphotyrosine antibodies (Sajjadi et al. (1991) and Pasquale, E. B. (1991)). This method of identification was successful because Cek4 and Cek5 are expressed in embryonic tissues and have tyrosine kinase activity even when expressed as partial fragments in bacteria. Other Eph-related kinases that have been identified include Hek (Wicks et al. (1992)), Sek (Gilardi-Hebenstreit et al, *Oncogene* 7:2499–2506 (1992)), Eck (Lindberg and Hunter, *Mol. Cell. Biol* 10:6316–6324 (1990)), Elk (Lhotak et al., *Mol. Cell. Biol.* 11:2496–2502 (1991)) and Eek (Chan and Watt, *Oncogene* 6:1057–1061 (1991)). These tyrosine kinases were cloned using a variety of methods.

The number of existing Eph-related kinases is not known and cannot be predicted. However, the Eph subclass already represents the largest known subclass of receptor tyrosine kinases, comprising at least 10 distinct members. The kinases belonging to the Eph subclass are so classified because each includes features such as the amino terminal Ig domain, the cysteine-rich stretch and two fibronectin type III repeats in the extracellular domain, which are conserved within the Eph subclass. However, despite these common structural features, the overall amino acid sequences outside the catalytic domain are quite different, indicating that different members of the Eph subclass interact with distinct ligands and substrates and, thus, exert distinct functions. This notion is supported by the differential distribution of different Eph-related kinases in adult tissues.

There is no indication whether other Eph-related kinases exist and, if so, what their relationship is to the known Eph-related kinases. Nevertheless, despite similarities among the Eph-related receptor tyrosine kinases, each is different and, as such, functions in related but distinct cellular processes. For example, many members of the Eph subclass are expressed in the nervous system during development and thus are likely to be involved in nerve regeneration processes. The aberrant expression or uncontrolled regulation of any one of these receptor tyrosine kinases can result in different malignancies and pathological disorders. Therefore, the identification and characterization of novel transmembrane tyrosine kinases should provide important insights into the mechanisms underlying oncogenesis and cellular growth control pathways.

There thus exists a need to identify additional receptor tyrosine kinases and to manipulate them in order to diagnose pathological conditions and control cellular processes. The present invention satisfies this need and provides related advantages as well.

SUMMARY

The invention is directed to substantially purified Eph-related protein tyrosine kinases, or functional fragments thereof, having about 23 to 66 percent amino acid sequence identity in their carboxyl terminal variable region compared to the other known members of the Eph subclass of tyrosine kinases. Nucleic acids encoding such Eph-related protein tyrosine kinases, vectors and host cells also are provided. The invention also is directed to a method of diagnosing cancer. The method includes removing a tissue or cell sample from a subject suspected of having cancer and determining the level of Eph-related protein tyrosine kinase in the sample, wherein a change in the level or activity of a Eph-related protein tyrosine kinase compared to a normal sample indicates the presence of a cancer or correlates with a specific prognosis.

DETAILED DESCRIPTION OF THE INVENTION

Figure 1D:
FIG. 1 shows a comparison of the amino acid sequences from members of the Eph family. Dots replace residues in Cek4, Cek6, Cek7, Cek8, Cek9 Cek10, Eck and Eph that are identical to the corresponding residue in Cek5. Dashes represent gaps introduced in the sequences to aid in the alignment. The insertion sequence of Cek5 also is presented (Cek5$^+$) and the insertion sequences of Cek7$^+$ and Cek10$^+$ are in parentheses. The conserved cysteines are indicated by the symbol " and the kinase domain is delimited by arrows. Open circles indicate the hydrophobic and aromatic residues that are conserved in the first fibronectin type III repeat and asterisks indicate the conserved residues of the second fibronectin type III repeat. The filled circle indicates the site of putative tyrosine autophosphorylation in the catalytic domain. The putative signal peptide sequences and transmembrane domains are underlined. Amino acids are numbered at the left of the sequences. The symbol + indicates the location of the extracellular domain amino acid insertion RICTPDVSGTVGSRPAADH (SEQ. ID. NO. 23), corresponding to Cek6 amino acids 426–444. Alignments were made by eye in the regions corresponding to Cek5 residues 1–615 and using the program DFALIGN (Feng and Doolittle, *J. Mol. Evol.*, 25:351–360 (1987), which is incorporated herein by reference) in the regions corresponding to Cek5 residues 616–995.

The invention relates to the identification and characterization of seven novel members of the Eph subclass of membrane-spanning tyrosine kinases. The identification of these members doubles the number of kinases within this subclass, bringing the total to at least ten different Eph-related kinases. These Eph-related kinases therefore comprise the largest known subclass of integral membrane tyrosine kinases. The large number of different Eph-related kinases indicates that these receptors regulate a number of distinct cellular processes during development as well as in the adult organism. Therefore, identification of novel proteins within this subclass and isolation of their encoding nucleic acids allows the control of different cellular processes through the-production of specific agonists and antagonists and through genetic therapy.

In one embodiment seven novel kinases of the Eph subclass of receptor protein tyrosine kinases have been identified. The cDNAs encoding these Eph-related kinases were identified by hybridization at differential stringencies to identify distinct, but related receptor tyrosine kinases. All of the kinases exhibit gross structural features of known receptor tyrosine kinases in that they contain an extracellular ligand binding domain, a transmembrane domain and a cytoplasmic catalytic domain. These novel kinases are related to the Eph subclass of receptor tyrosine kinases and are designated Cek6 through Cek10$^+$ (SEQ. ID. NOS. 1–14, and 19–22.) The overall sequence identity between these Eph-related kinases varies significantly with each of the novel Eph-related receptors being identified by its carboxyl terminal variable region.

In another embodiment, the novel Eph-related kinases exhibit distinct tissue distribution patterns and developmental expression. Six of the kinases can be found to be expressed in both the embryonic brain and body tissues. The seventh Eph-related kinase, Cek5$^+$ is expressed only in the embryonic brain. Indicative of their roles in cellular processes, such as embryonic signal transduction pathways, these Eph-related kinases display distinct patterns of expression in adult tissues, including the neuronal specific expression of Cek5$^+$. These distinct patterns can be used to diagnose aberrations in normal cellular processes, such as those leading to uncontrolled malignant cell growth.

In addition to diagnosing such aberrations, it is also possible to treat defects caused by the unregulated expression of Eph-related kinases through the use of gene therapy. Reagents affecting the expression or activity of Eph-related kinases can also be useful for inducing nerve regeneration following injury.

As used herein, the term "Eph-related protein tyrosine kinase" or "Eph-related kinase" refers to a receptor tyrosine kinase having an extracellular ligand binding domain, a transmembrane domain and a cytoplasmic catalytic domain, and belonging to the Eph subclass of receptor tyrosine kinases. Eph-related kinases include, for example, the receptor tyrosine kinases Cek6, Cek7, Cek7$^+$, Cek7', Cek8, Cek9, Cek10, Cek5$^+$ and Cek10$^+$ (SEQ. ID. NOS. 1–14 and 19–22.) Such kinases exhibit an overall amino acid sequence identity to Eph of greater than about 40 percent. The extreme carboxyl terminal cytoplasmic regions of the kinases are not well conserved and can be used to differentiate among them. This extreme carboxyl terminal cytoplasmic region begins just after the catalytic domain at about residue number 900 and extends to the C-terminal most residue. Therefore, the term "carboxyl terminal variable region" as used herein, refers to this extreme C-terminal region of the sequence which is divergent between the different members of the Eph subclass of tyrosine kinases. The actual sequence identities between different kinases within the Eph subclass are as follows: Cek5-Cek10: 66%; Cek5-Cek6: 54%; Cek5-Cek9: 50%; Cek5-Cek8: 38%; Cek5-Cek7: 34%; Cek5-Cek4: 24%; Cek5-Eek: 39%; Cek5-Eck: 36%; Cek5-Eph: 33%; Cek10-Cek6: 64%; Cek10-Cek 9: 56%; Cek10-Cek8: 47%; Cek10-Cek7: 45%; Cek10-Cek 4:32%; Cek10-Eek: 41%; Cek10-Eck: 39%; Cek10-Eph: 37%; Cek6-Cek9: 46%; Cek6-Cek8: 50%; Cek6-Cek7: 40%; Cek6-Cek4: 31%; Cek6-Eek: 39%; Cek6-Eck: 36%; Cek6-Eph: 32%; Cek9-Cek8: 46%; Cek9-Cek7: 47%; Cek9-Cek4: 29%; Cek9-Eek: 36%; Cek9-Eck: 33%; Cek9-Eph: 35%; Cek8-Cek7: 37%; Cek8-Cek4: 26%; Cek8-Eek: 39%; Cek8-Eck: 36%; Cek8-Eph: 30%; Cek7-Cek 4: 36%; Cek7-Eek: 35%; Cek7-Eck: 43%; Cek7-Eph: 37%; Cek4-Eek: 29%; Cek4-Eck: 27%; Cek4-Eph: 23%; Eek-Eck: 26%; Eek-Eph: 32%; Eck-Eph: 52%. Therefore, the carboxyl terminal variable region exhibits an amino acid sequence identity of about 23 to 66 percent between the different Eph-related kinases. The novel Eph-related kinases described herein fall within this level of sequence divergence and can therefore be distinguished by comparison to the known members of the Eph subclass. Known members of this subclass include, for example, Eph, Cek4, Cek5, Mek4, Hek, Sek (or mouse Cek8), Eck, Elk (or rat Cek6) and Eek.

It is understood that limited modifications may be made without destroying biological functions of Eph-related kinases and that only a portion of the entire primary structure may be required in order to effect a particular activity. Such biological functions and activities can include, for example, signal transduction, ligand binding and/or tyrosine kinase activity. For example, the Eph-related kinases of the invention have amino acid sequences substantially similar to those shown for Cek7, Cek7$^+$, Cek7', Cek9, Cek10, Cek5$^+$, Cek10$^+$ and chicken Cek6 and Cek8 in FIG. 1 (hereinafter referred to as Cek6 through Cek10$^+$; SEQ. ID. NOS. 2, 4, 6, 8, 10, 12, 14, 20 and 22,) but minor modifications of these sequences which do not destroy their activity also fall within the definition of Eph-related kinases and within the definition of the protein claimed as such. Moreover, fragments of the sequences of Cek6 through Cek10$^+$ in FIG. 1 (SEQ. ID. NOS. 2, 4, 6, 8, 10, 12, 14, 20 and 22) which retain the function of the entire protein as well as functional domains that contain at least one function of the intact protein are included within the definition. Functional domains can include, for example, active ligand binding and catalytic domains. The boundaries of such domains are not important so long as activity is maintained. It is also understood that minor modifications of the primary amino acid sequence can result in proteins which have substantially equivalent or enhanced function as compared to the sequences set forth in FIG. 1 (SEQ. ID. NOS. 2, 4, 6, 8, 10, 12, 14, 20 and 22.) These modifications may be deliberate, as through site-directed mutagenesis, or may be accidental such as through mutation in hosts which produce Eph-related kinases. All of these modifications are included as long as biological function is retained. Further, various molecules can be attached to Eph-related kinases, for example, other proteins, carbohydrates, or lipids. Such modifications are included within the definition of Eph-related tyrosine kinase.

The term "substantially purified," when used to describe the state of Eph-related tyrosine kinases denotes the protein free of a portion of the other proteins and molecules normally associated with or occurring with Eph-related kinases in their native environment. Such substantially purified Eph-related kinases can be derived from natural sources, recombinantly expressed or synthesized by in vitro methods so long as some portion of normally associated molecules is absent.

"Isolated" when used to describe the state of the nucleic acids encoding Eph-related tyrosine kinases denotes the nucleic acids free of at least a portion of the molecules associated with or occurring with Eph-related nucleic acids in the native environment.

As used herein, the term "vector" includes nucleic acids that are capable of harboring a natural or recombinant DNA sequence of interest. Vectors are usually derived from, or contain some sequences from, a natural source. For example, bacteriophage vectors containing specially engineered features that are largely derived from the phage's genome and are capable of carrying out some part of its infectious cycle. On the other hand, the sequences contained within plasmids are usually derived from different sources and compiled into a single molecule to carry out specific tasks. Thus, there are many different types of vectors and each is used according to the need to perform a desired function. Functions can include, for example, propagation in a desired host, cloning recombinant or natural fragments of DNA, mutagenesis, expression and the like. In sum, "vector" is given a operative definition, and any DNA sequence which is capable of effecting a function of a specified DNA sequence disposed therein is included in this term as it is applied to the specified sequence.

The invention provides a substantially purified Eph-related protein tyrosine kinase, or functional fragment thereof. Also provided is a substantially purified chicken Eph-related protein tyrosine kinase. The substantially purified Eph-related protein tyrosine kinase exhibits about 23 to 66 percent amino acid sequence identity in its carboxyl terminal variable region compared to known members of the Eph subclass of tyrosine kinases. The amino acid sequences are substantially the same as that shown for Cek6 through Cek10$^+$ in FIG. 1 (SEQ. ID. NOS. 2, 4, 6, 8, 10, 12, 14, 20 and 22.)

The invention also provides an isolated nucleic acid encoding a Eph-related protein tyrosine kinase, or functional fragment thereof. The isolated nucleic acid encoding a Eph-related protein tyrosine kinase exhibits about 23 to 66 percent amino acid sequence identity in its carboxyl terminal variable region compared to known members of the Eph subclass of tyrosine kinases. The encoding nucleotide sequences are substantially the same as that shown for Cek6 through Cek10+ in the sequence listing (SEQ. ID. NOS. 1, 3, 5, 7, 9, 11, 13, 19 and 21.)

The isolation of seven cDNAs that encode novel Eph-related receptor tyrosine kinases is disclosed herein. The predicted amino acid sequences of these Eph-related kinases are shown in FIG. 1 along with other known Cek kinase sequences and those of Eph and Eck. A number of conserved features serve to define the newly discovered kinases as members of the Eph subclass. These include an amino terminal immunoglobulin domain followed by a cysteine-rich stretch in the extracellular domain, with the position of most cysteines conserved, and sequences corresponding to two fibronectin type III repeats in close proximity to the transmembrane domain (O'Bryan et al., *Mol. Cell. Biol.* 11:5016–5031 (1991) and Pasquale, E. B. (1991), the former of which is incorporated herein by reference). Potential sites of N-glycosylation are primarily localized in the C-terminal half of the extracellular regions. The homologies in the extracellular domains indicates that the different members of the Eph family can bind a similar class of ligands. FIG. 1 also shows that the Eph family, with the inclusion of the new members that have been identified, can now be considered the largest known family of membrane-spanning tyrosine kinases. Such a large number of tyrosine kinases in this one class is surprising in view of the fact that the other families of receptor tyrosine kinases have fewer members.

The catalytic domains of the Eph-related kinases are highly conserved and exhibit amino acid identities ranging between 61% and 90%. The C-terminal tails are less conserved (FIG. 1) and therefore constitute a variable region which can be used to specify the distinct Eph-related kinases. Only one of the tyrosines in the C-terminal variable region, corresponding to tyrosine 939 of Cek5, is conserved in all the members of the Eph family, with the exception of Cek4. This conserved tyrosine residue represents a likely site of autophosphorylation and regulation, Ullrich and Schlessinger, *Cell* 61:203–212 (1990). The large size of the Eph subclass of receptor tyrosine kinases, the variability within their sequences and their different tissue distributions indicate that each receptor can, for example, serve distinct functions during cellular processes.

The variability in both the lengths and sequences of the juxtamembrane domains observed in the Eph-related kinases is unusual among tyrosine kinases belonging to the same subclass, Ullrich et al., supra. Because clones encoding variants with amino acid insertions in the juxtamembrane domain were isolated for Cek5, Cek7 and Cek10, the variability in the lengths of the juxtamembrane domains is likely to originate by alternative splicing (FIG. 1). Juxtamembrane domains are important for the modulation of receptor functions by heterologous stimuli, for example, through phosphorylation by other kinases. The juxtamembrane domains of the members of the Eph family contain numerous serines, threonines and tyrosines that can serve as sites of regulation by phosphorylation, Kemp et al., *Trends Biol. Sciences* 15:342–346 (1990), which is incorporated herein by reference. For example, Cek9 and Cek10, as well as Cek5, Cek6, and Eck contain the consensus sequence (S/T)P, which is recognized by proline-dependent protein kinases such as cdc2, Kemp et al. (1990). Juxtamembrane domains have also been indicated to be important in the regulation of the subcellular distribution of the kinase and in the binding of some substrates (Ullrich et al., supra).

The mRNA corresponding to Cek5+, the variant form of Cek5, was shown to be specifically expressed in the central nervous system, indicating that Cek5+ functions primarily in neuronal cellular functions. Indicative of this is another tyrosine kinase, src, which has been shown to encode neuronal specific variants containing 6 to 17 amino acid insertions in the regulatory (non-catalytic) region (Brugge et al., *Nature* 316:554–557 (1985); Martinez et al., *Science* 237:411–415 (1987); Pyper et al., *Mol. Cell. Biol.* 10:2035–2040 (1990), all of which are incorporated herein by reference). These neuronal forms of c-src have higher specific catalytic activity than non-neuronal c-src.

Although the predicted molecular masses of the different members of the Eph family are similar, the sizes of their transcripts appear quite varied (4 to 10 Kb). In addition, several mRNA species for each of the Eph-related kinases, particularly in the central nervous system, were detected using a panel of probes. As described below, the patterns of expression of these novel Eph-related kinases are also distinct.

DNA sequences encoding the polypeptides of Eph-related kinases can be obtained by methods known to one skilled in the art. The sequences described herein are sufficient for one skilled in the art to practice the invention. Such methods include, for example, cDNA synthesis and polymerase chain reaction (PCR). The need will determine which method or combination of methods is to be used to obtain the desired sequence. Expression can be performed in any compatible vector/host system. Such systems include, for example, plasmids or phagemids in procaryotes such as *E. coli*, yeast systems and other eucaryotic systems such as mammalian cells. Additionally, the Eph-related kinases can also be expressed in soluble or secreted form depending on the need and the vector/host system employed.

Such vectors and vector/host systems are known, or can be constructed by those skilled in the art and should contain all expression elements necessary for the transcription, translation, regulation, and sorting of the polypeptide which makes up the Eph-related kinase. Other beneficial characteristics may also be contained within the vectors such as mechanisms for recovery of the nucleic acids in a different form. Phagemids are a specific example of this because they can be used either as plasmids or as bacteriophage vectors. The vectors can also be for use in either procaryotic or eucaryotic host systems so long as the expression elements are of a compatible origin. One of ordinary skill in the art will know which host systems are compatible with a particular vector. Thus, the invention provides vectors, host cells transformed with the vectors and Eph-related kinases produced from the host cells containing a nucleic acid encoding a Eph-related kinase.

The invention also provides methods of diagnosing cancer and determining cancer prognosis. The method includes removing a tissue or cell sample from a subject suspected of having cancer and determining the level of Eph-related protein tyrosine kinase in said sample, wherein a change in the level or activity of a Eph-related protein tyrosine kinase compared to a normal sample indicates the presence of a cancer or indicates the level of malignancy of a cancer and, therefore, the most appropriate course of treatment.

As stated previously, receptor tyrosine kinases are involved in many signal transduction events that regulate important cellular processes. Such processes include, for example, cellular differentiation and proliferation. Abnormal regulation or expression of the signal transduction machinery can lead to aberrant and malignant growth of the abnormally regulated cells. Abnormal expression of Eph is known to be associated with carcinomas of the liver, lung, breast and colon, for example. Likewise, since some Eph-related tyrosine kinases are, at least, found within the same tissues as Eph, their abnormal expression may also lead to the development of the carcinomas described above as well as other types of cancers. Additionally, cancers of the neuronal linage are likely to be caused by the abnormal expression or regulation of Cek5+ since this Eph-related kinase is found exclusively in neuronal tissues. Cek5+, Cek5 and the other Eph-related kinases expressed in the nervous system also are likely to be involved in nerve regeneration.

The important role that these receptor tyrosine kinases play in cellular processes can be advantageously used to diagnose early stages of cancer within a cell sample or tissue. A change in the amount or activity of an Eph-related kinase in a suspected sample, compared to a normal sample, will be indicative of cancerous stages and of their level of malignancy. Depending on whether the normal state is caused by the presence or absence of an Eph-related kinase, the change can involve either an increase or decrease in the amount or activity of the Eph-related kinase. One skilled in the art can measure these parameters and compare them to those obtained from a normal sample. Methods for determining the levels or activity of Eph-related kinases are known to one skilled in the art and include, for example, RNA and protein blot analysis, ELISA using specific antibodies to each of the Eph-related kinases and direct measurement of catalytic activity such as tyrosine kinase activity. Such methods can be found in Harlow et al., *Antibodies: A Laboratory Manual* Cold Spring Harbor Laboratory (1989), which is incorporated herein by reference.

The following examples are intended to illustrate, but not limit the invention.

EXAMPLE I

Isolation and Characterization of Eph-Related Tyrosine Kinases

This example shows the cloning and sequencing of the Eph-related kinases Cek4 through Cek10+. Structural characteristics and patterns of expression are also described.

To find novel members of the Eph family, various cDNA probes were used at different stringencies to screen a 10 day embryonic library as well as a 13 day embryonic brain cDNA library. The probes were derived from cek4 or Cek5 which had been previously isolated based on phosphotyrosine content. Following subcloning and sequence analysis, it was found that the newly isolated cDNA clones encoded seven different Eph-related tyrosine kinases. Their isolation and structure are described below.

Briefly, a 10-day chicken embryo λgt11 cDNA library (Clontech) and a 13-day embryonic brain λgt11 cDNA library were used to isolate the cDNA clones. Screening was performed at different stringencies using the following procedure. Plaques were transferred to nylon membranes (Micron Separations Inc.) on duplicate filters and hybridized to the appropriate probes at one of two stringencies (50% formamide, 42° C.; or 50% formamide, 37° C.). Conditions used were those recommended by the manufacturer and probes were detected using a nonradioactive DNA labeling and detection method (Boehringer Mannheim). Plaques identified as positive were subjected to three rounds of purification prior to DNA extraction using Lambda-TRAP (Clontech). Inserts from recombinant lambda DNA were subcloned in pBluescript vectors (Stratagene, San Diego, Calif.) using standard procedures and the sequences were analyzed on both strands, using the dideoxynucleotide chain-termination technique with Sequenase (United States Biochemical, Cleveland, Ohio).

Several clones distinguishable over known Eph tyrosine kinases were isolated. The clones include: one Cek5+ cDNA clone (from the chick embryo library); three Cek6 clones (two from the embryonic brain and one from the chick embryo library); one Cek7 clone (from the chick embryo library); one Cek7+ clone (from the chick embryo library); one Cek7'+ clone (from the embryonic brain library); one Cek9 clone (from the chick embryo library); one Cek10+ clone (from the chick embryo library) and two Cek10 or Cek10+ clones, which are indistinguishable because they do not encode the juxtamembrane domain, (one from the chick embryo and one from the embryonic brain library). A Cek4 probe (corresponding to nucleotides 748–1756; see Sajjadi et al. 1991), on the other hand, was used to isolate one Cek8 clone (from the chick embryo library). Also, following its initial isolation, a Cek10 probe, corresponding to residues 400–596 in FIG. 2, was used to isolate clones extending further into the 5' end from the chick embryo library. Of the two clones isolated, one represented Cek10 and one Cek10+.

The above-identified Eph-related kinases were characterized in terms of tissue distribution and expression by RNA blot analysis. Poly-A RNA was prepared from chicken tissues using the procedure of Badley et al., *Biotechniques* 6:114–116 (1988), which is incorporated herein by reference. Poly-A RNA (4–5 μg) was size-fractionated alongside RNA molecular weight markers on 0.9% agarose gels containing formaldehyde (Sambrook et al., *Molecular Cloning: A Laboratory Manual* (Cold Spring Harbor Laboratory Press, Cold Spring Harbor, N.Y., 1989), which is incorporated herein be reference) and transferred to nitrocellulose filters (Schleicher & Schuell) according to methods known to one skilled in the art. The membranes were prehybridized for 2 hours and then hybridized under stringent conditions (50% formamide, 5× SSPE, 5× Denhardt's reagent, 0.5% SDS, 100 μg/ml salmon testes DNA, 42° C.). Probes were labeled with $^{32}$P dATP by the random-primed method of Feinberg & Vogelstein *Anal. Biochem.* 132:6–13 (1983), which is incorporated herein by reference. T4 polynucleotide kinase was used to label the 5' end of the Cek5+ specific oligonucleotide (Sambrook et al. 1989). Filters were washed to a final stringency of 0.1× SSPE, 0.1% SDS at 58° C. prior to exposure to Kodak XAR-5 X-ray film. For autoradiography of β-actin controls, intensifying screens were typically omitted and exposure time was reduced to 2 hours.

The following cDNA probes were used for RNA blot analysis: Cek4, 1.2 Kb, same probe used for the library screening described previously, hybridizes to the region encoding amino acid residues 240–575; Cek5 probe, 1.2 Kb, hybridizes to the 3' untranslated region; Cek6 5' probe, 1.3 Kb, hybridizes to amino acid residues 1–438; Cek6 3' probe, 0.6 Kb, hybridizes to the region following amino acid 844; Cek7 5' probe, 0.4 Kb, hybridizes to amino acid residues 1–136; Cek7 3' probe, 2.0 Kb, hybridizes to the region following amino acid 137, including the 3' untranslated region; Cek8 probe, 1.2 Kb, hybridizes to the region encoding amino acid residues 1–406; Cek9 probe, 0.6 Kb, hybridizes to the region encoding amino acid residues 1–208; Cek10 probe, 0.6 Kb, hybridizes to the region encoding the 10 C-terminal amino acids and to about 600 nucleotides of 3' untranslated region. For Cek6 and Cek7, the 3' Cek6 probe and the 5' Cek7 probe were used for the embryonic tissues mRNAs and a mixture of 5' and 3' probes for the adult tissues mRNAs.

Polyadenylated RNA was isolated from a number of adult chick tissues, as well as from brain and body tissues of 10-day embryos. These RNAs were then used for RNA blot analysis using the above specific probes. Probes were designed to minimize the possibility of cross-hybridization among the related kinases. Chicken β-actin DNA was used as a control probe (Cleveland et al., *Cell* 20:95–105 (1980), which is incorporated herein by reference).

The amino acid sequence of Cek4 (SEQ ID NO: 16) is 67% identical to that of Cek5 (SEQ. ID. NO. 18) in the catalytic and C-terminal regions and is most closely related to that of Cek7 (SEQ ID NO: 4) (75% amino acid identity in the same regions) (FIG. 1). Preliminary data had indicated that Cek4 was highly expressed in the chicken developing brain and embryonic tissues, but no information was obtained on the adult pattern of expression in the chick. These data were therefore included in FIG. 2. The 7.5 Kb Cek4 transcript previously described was confirmed to be abundant in 10 day embryonic tissues. Expression was pronounced in the adult brain and retina, and lower but detectable in all other adult tissues examined, except the liver. In addition to the major 7.5 kb transcript, a smaller Cek4 transcript (of about 5 Kb) was found to be expressed at lower levels in the adult brain.

Figure 2:
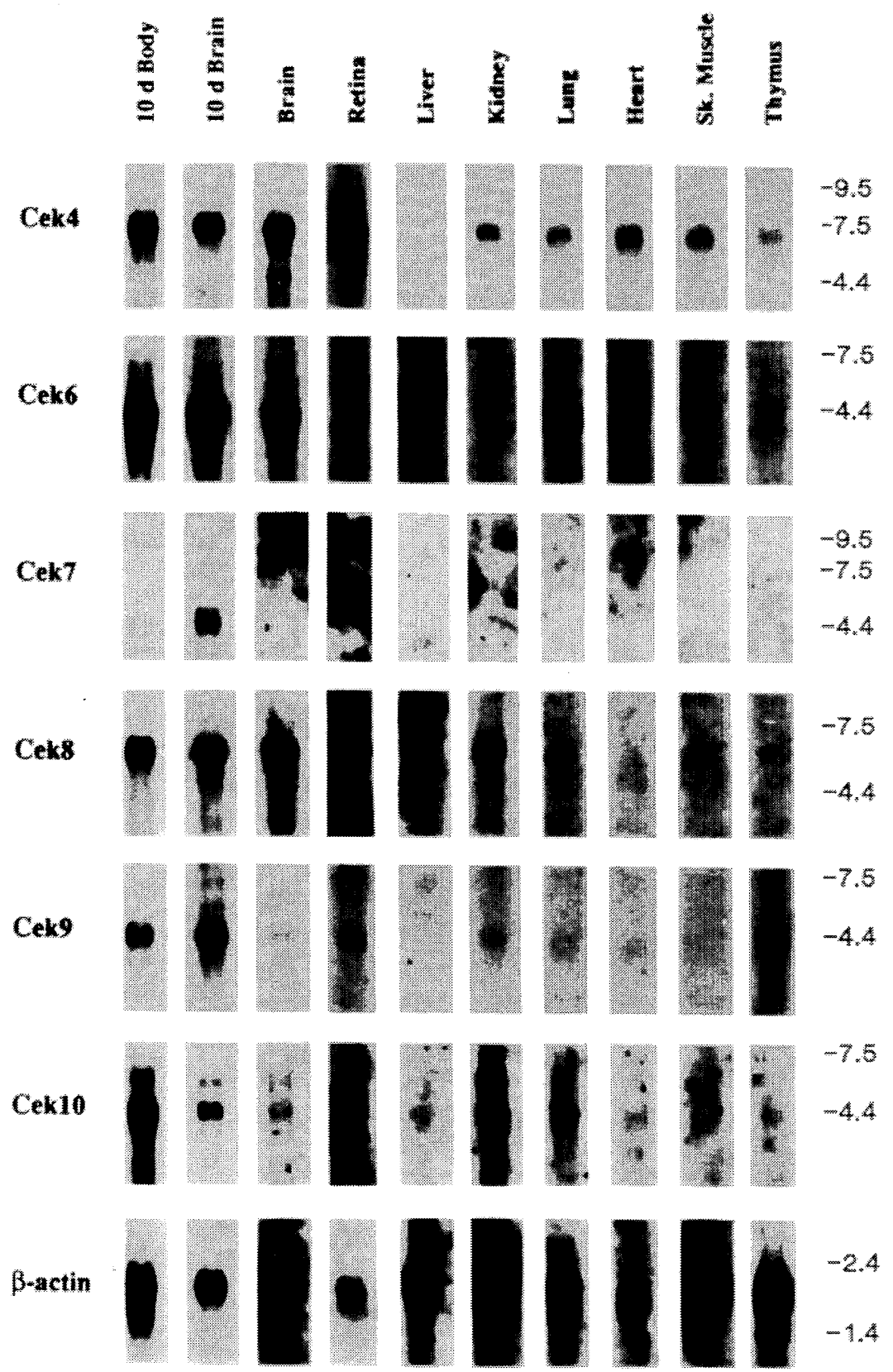
FIG. 2 shows a RNA blot analysis of Cek mRNAs. Polyadenylated chicken RNA from 10-day embryonic and adult tissues was hybridized with Cek-specific cDNA probes and with a chicken β-actin probe. Hybridization conditions were as described in Example I. The positions of RNA molecular weight standards (in kilobases, kb) are indicated on the right. β-actin transcripts are present in the ~2.0 kb size range.

The Cek6 amino acid sequence (SEQ ID NO: 2) is most closely related to that of rat Elk (96% identity in the catalytic and C-terminal regions). Of the Cek members of the Eph subclass, Cek6 is most closely related to Cek5 (SEQ ID NO: 18) and Cek10 (SEQ ID NO: 10) (82% amino acid identity with both, in the catalytic and C-terminal regions) (FIG. 1). The two Cek6 cDNAs that were isolated from a 13-day chick embryo brain library were identical and both encoded a protein with a deletion of 32 amino acids and an insertion of 19 amino acids in the extracellular region (FIG. 1). However, these may be cloning artifacts, particularly the deletion, since it causes a shift in the reading frame and the premature termination of the encoded protein. A 4.4 Kb Cek6 transcript was found to be expressed at high levels in the 10-days embryo and in adult brain, lung, heart and skeletal muscle (FIG. 2). Low levels of Cek6 expression were detected in all other adult tissues tested. A second larger Cek6 transcript (of about 6.5 Kb) was detected at low levels in the adult brain.

The amino acid sequence of Cek7 (SEQ ID NO: 4) is 71% identical to that of Cek5 (SEQ ID NO: 18) in the catalytic and C-terminal regions and is most closely related to those of Cek4 (SEQ ID NO: 16) and Cek9 (SEQ ID NO: 8) (75% amino acid identity with both, in the same regions) (FIG. 1). A variant form of Cek7, containing a 22 amino acid insertion in the juxtamembrane domain (FIG. 1) also was isolated and designated Cek7$^+$. Cek7 and Cek7$^+$ (SEQ ID NO: 22) may originate from the same gene by alternative splicing. A second variant form of Cek7, designated Cek7' (SEQ ID NO: 20), which also presumably originates via alternative splicing, differs from Cek7 in the C-terminal 33 amino acids. Cek7 appears to have the lowest levels of expression among all the Eph related kinases examined. Three different transcripts of about 4.4 Kb, 7 Kb and 8.5 Kb were detected in the 10-day embryonic brain. Expression was weaker in the rest of the 10-day embryo, where only the 4.4 Kb transcript could be detected (FIG. 2). Cek7 transcripts were not detected in the adult tissues, except for a barely detectable 8.5 Kb transcript in the brain (FIG. 2).

Cek8 (SEQ ID NO: 6) is equally related to Cek5 (SEQ ID NO: 18), Cek6 (SEQ ID NO: 2), Cek7 (SEQ ID NO: 4) and Cek10 (SEQ ID NO: 10) (74% amino acid identity in the catalytic and C-terminal regions) (FIG. 1). A single 6 Kb Cek8 transcript was found to be present in both the 10-day embryonic brain and body tissues (FIG. 2). Cek8 expression appears to be the highest in adult brain and retina and is also detectable in kidney, lung, skeletal muscle and thymus (FIG. 2). Cek8 expression was not detected in heart and liver.

Cek9 (SEQ ID NO: 8) is most closely related to Cek5 (SEQ ID NO: 18) (77% identity at the amino acid level in the catalytic and C-terminal regions (FIG. 1). A 4.4 Kb Cek9 transcript is present in embryonic brain and body tissues. Two additional and very minor transcripts of about 5.5 Kb and 6.5 Kb were detected exclusively in the 10-day embryonic brain (FIG. 2). Among the adult tissues examined, Cek9 expression is prominent in the thymus and detectable in brain, retina, kidney, lung and heart. None of the other kinases examined displays such an elevated level of expression in the thymus. Cek9 expression was not detected in skeletal muscle and liver.

Cek10 (SEQ ID NO: 10) is most closely related to Cek5 (SEQ ID NO: 18) and Cek6 (SEQ ID NO: 2) (84% amino acid identity with both in the catalytic and C-terminal regions) (FIG. 1). A variant form of Cek10, containing a 15 amino acid insertion in the juxtamembrane domain (FIG. 1), was also isolated and designated Cek10$^+$ (SEQ ID NO: 14). Cek10 and Cek10$^+$ may originate from the same gene by alternative splicing. Northern blot analysis identified two Cek10 transcripts of about 4.4 Kb and 6 Kb, present at different relative levels in 10-day embryonic brain and body tissues as well as in a number of adult tissues (FIG. 2). Among the adult tissues examined, Cek10 expression was particularly prominent in the kidney. Lower Cek10 expression was detected in the lung and barely detectable transcripts were also present in brain, liver, heart, skeletal muscle and thymus.

Figure 3:
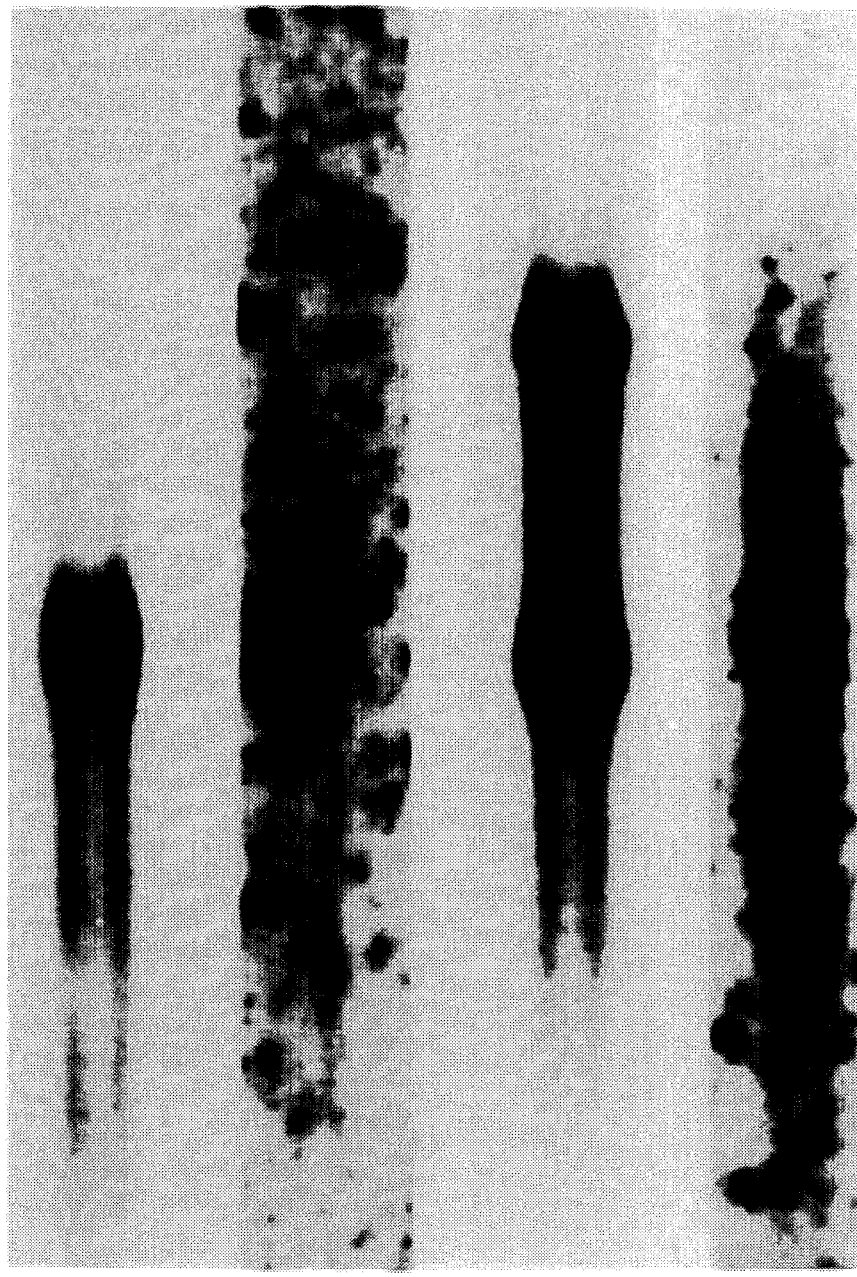
FIG. 3 shows a RNA blot analysis of Cek5mRNAs. Polyadenylated RNA from body tissues (lanes 1 and 2) and brain (lanes 3 and 4) of 10-day chicken embryos was hybridized with a Cek5-specific cDNA (lanes 1 and 3). The same blots were then stripped and rehybridized with a 48 bp oligonucleotide antisense probe corresponding to the juxtamembrane insertion sequence of Cek5 (lanes 2 and 4). Hybridization conditions were as described in Example I. The positions of RNA molecular weight standards (in kb) are indicated on the right.

A variant form of Cek5, containing a 16 amino acid insertion in the juxtamembrane domain, was also identified and termed Cek5$^+$ (SEQ ID NO: 12) (FIG. 1). This Cek5 variant may originate as a result of alternative splicing. With a Cek5 DNA probe recognizing both Cek5 and Cek5$^+$(see Material and Methods), a 4.4 Kb transcript was detected in both 10-day embryonic brain and body tissues (FIG. 3, lanes 1 and 3). In addition, a much larger transcript (of about 10 Kb) was detected in the 10-day embryonic brain (FIG. 3, lane 3). Consistently with the previously reported expression of the Cek5 protein, Cek5 transcripts are more abundant in the brain than in other 10-day embryonic tissues. Using a probe corresponding to the 16 amino insertion in the juxtamembrane domain (FIG. 3, lanes 2 and 4), Cek5$^+$ was found to be exclusively expressed in the central nervous system and only as the 4.4 Kb transcript. Because Cek5 immunoreactivity in the central nervous system has been previously found to be confined to neurons, Cek5$^+$ appears to be a neuronal specific variant of Cek5.

Figure 4:
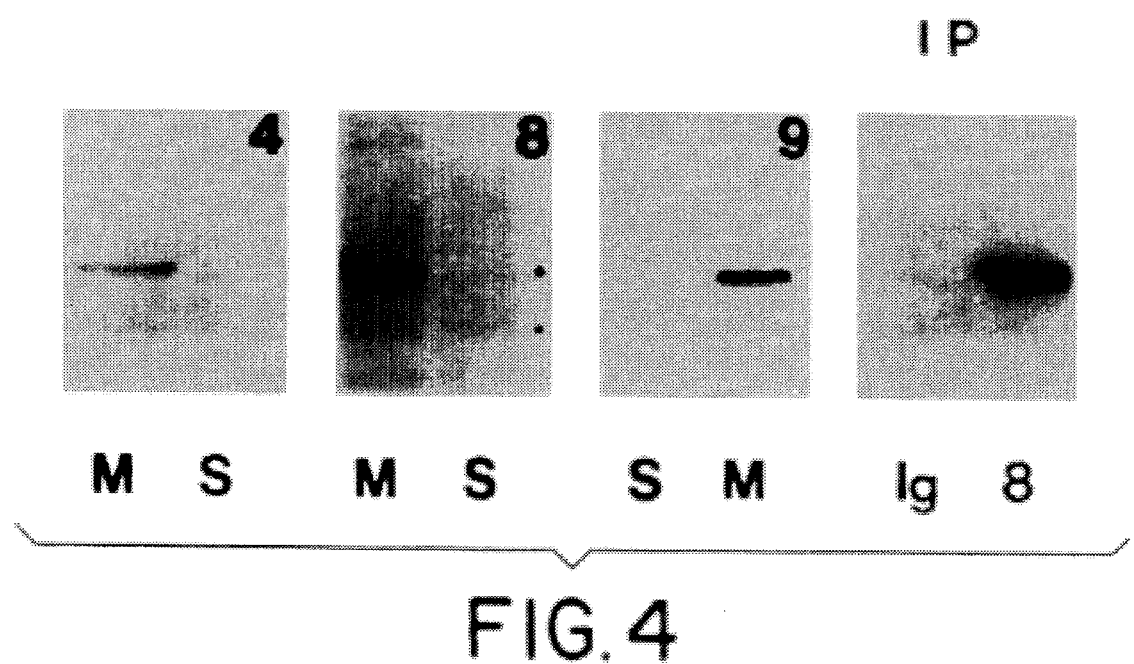
FIG. 4 shows immunoblotting with antibodies to different Eph-related kinases. Fractions from 10-day embryonic brain containing either membrane-associated proteins (M) or soluble proteins (S) were probed with anti-Cek4 (4), anti-Cek8 (8,) or anti-Cek9 (9) antibodies. Equal amounts of protein were loaded in all the lanes. IP, immunoprecipitates from 11-day embryonic retina with anti-Cek8 antibodies (8) or with normal rabbit IgGs (Ig). The immunoprecipitates were then probed with anti-Cek8 antibodies.

Polyclonal antibodies recognizing specifically Cek4, Cek8 and Cek9 have been obtained and will be used for the characterization of these kinases. Peptides corresponding to the carboxy-terminal ends of Cek4, Cek8 and Cek9 were coupled to bovine serum albumin with m-Maleimido benzoyl-N-hydroxysuccinimide ester (Cek4) or with glutaraldehyde (Cek8 and Cek9) and used as immunogens. The peptides used were the following: Cek4, CLETHTKNSPVPV (SEQ ID NO 24); Cek8, KMQQMHGRMVPV (SEQ ID NO 25) and Cek9, KVHLNQLEPVEV (SEQ ID NO 26). The carboxy-terminal regions were chosen because they are poorly conserved within the Eph subclass, increasing the likelihood of obtaining antibodies specific for each kinase. The antibodies were purified from the antiserum by affinity-chromatography on the appropriate peptides coupled to N-hydroxy-succinimide-activated agarose (BioRad). As shown in FIG. 4, after affinity purification the antibodies to Cek4, Cek8 and Cek9 recognize a single band of the expected molecular weight (about 120 kd) in membranes-containing fractions isolated from 10-day embryonic brain, but not in fractions containing soluble proteins. These antibodies do not cross-react significantly with related members of the Eph subclass (not shown) and can be used for different applications, such as immunoblotting (FIG. 4), immunofluorescence microscopy and immunoprecipitation (FIG. 4). All of the antibodies are capable of immunoprecipitating the kinases from tissue extracts and, as expected, the immunoprecipitated kinases undergo in vitro autophosphorylation in the presence of ATP. These techniques will allow the characterization of the kinases of the Eph subclass at the protein level. Coupled to a solid support, the antibodies can also be used to purify the kinases from tissues and cell lines. In the cases tested, antibodies generated to the chicken Eph-related kinases recognize the corresponding mammalian homologues. Thus, these antibodies could be used, for example, to screen tumor samples for the presence of the appropriate Eph-related kinases.

Although the invention has been described with reference to the disclosed embodiments, it should be understood that various modifications can be made without departing from the spirit of the invention. Accordingly, the invention is limited only by the claims.

What is claimed is:

1. An isolated nucleic acid molecule encoding an Eph-related protein tyrosine kinase, having a nucleotide sequence selected from the group consisting of Cek7 (SEQ ID NO: 3), Cek 9 (SEQ ID NO: 7), Cek10 (SEQ ID NO: 9), Cek5+ (SEQ ID NO: 11), Cek10+ (SEQ ID NO: 13), Cek7+ (SEQ ID NO: 19) and Cek7' (SEQ ID NO: 21) as shown in FIG. 1.

2. A composition of matter, comprising a vector containing the nucleic acid of claim 1.

3. The composition of claim 2, wherein said vector is for the expression of a recombinant EPH-related protein tyrosine kinase in a eucaryotic host.

4. A composition of matter, comprising a host cell containing the vector of claim 2.

* * * * *

UNITED STATES PATENT AND TRADEMARK OFFICE
CERTIFICATE OF CORRECTION

PATENT NO. : 5,457,048
DATED : October 10, 1995
INVENTOR(S) : Pasquale et al.

It is certified that error appears in the above-identified patent and that said Letters Patent is hereby corrected as shown below:

In the Drawings:

Please delete Figure 1 and replace it therefor with the corrected Figure 1, as shown on attached pages.

In column 2, line 13, please delete "erythropoietin" and replace therefor with --$\underline{e}$rythropoietin--.

In column 2, line 14, please delete "hepatocellular" and replace therefor with --$\underline{h}$epatocellular--.

In column 3, line 36, please delete "Cek9Cek10," and replace therefor with --Cek9, Cek10,--.

In column 3, line 67, please delete "Cek5mRNAs." and replace therefor with --Cek5 mRNAs--.

In column 4, line 58, please delete "Cek5$^+$" and replace therefor with --Cek5$^+$,--.

In column 5, line 29, please delete "Cek10-Cek 4:32%;" and replace therefor with --Cek10-Cek4: 32%;--.

In column 9, line 45, please delete "cek4" and replace with --Cek4--.

In column 10, line 32, please delete "be" and replace with --by--.

UNITED STATES PATENT AND TRADEMARK OFFICE
CERTIFICATE OF CORRECTION

PATENT NO. : 5,457,048
DATED : October 10, 1995
INVENTOR(S) : Pasquale, et al

It is certified that error appears in the above-identified patent and that said Letters Patent is hereby corrected as shown below:

In column 12, line 45, please delete 'amino insertion" and replace therefor with --amino acid insertion--.

Signed and Sealed this

Second Day of February, 1999

Attest:

Attesting Officer

Acting Commissioner of Patents and Trademarks

FIG. 1B

```
        MPGPERTMGPLWFCCLPLALLPLLAAVEETLMDSTTATAELGMVHP-PSGWEEVSGYDENMNTIRTYQVCNVFE-SSQNWLRTKYIRRR-GAHRIH
        GVSSRARRPPGSSRSSRRGV.S..A.TT..-ET.............A.QP..........Q.R.-AQ.QQ......F.N.Q-DVQ.VY
        ................TR............TAN.-.......................L....-PN.........L.TF.N..-....Y
        MT.I.L.T.GE.S.I..TS...-.D........VR.DKERQ...F...-.MD.-PG.......HF.E..-....VH
.DRRRLPLLL.CAALGSAGR.SARPGN.VN.L..K.IQG......ISY.-SH....I.V..HYTP......ES..MD-H.......NW.P.N-S..QK.Y
MELQAARACFAL...G....-A..AAAAQGK.VV.L.FAA.GG....LT..YGK.DLMQNIMND.-P.YM.S.....MS-GD.D.....NWVY.G-E.E.NN
MERRW.LGLGLV.LL.----AP.P.GAR.K.V.....TSK.QG.....LLD.PKD..S.QQOILNGT-PLYM..D.PMQGRDTDH...SNW.Y.GEE.S.V.

1   VEMKFSVRDCSSIPNVPG--SCKETNLYYESDEDSATKFFNMENPWMKVDTIAADESFSQVDLGGRVMKINTEVRSFGPVSKNGFYLAFQDYGGCM
96  .L..T......K..KI.--..........F......YI....P..........KLES......-.....K......L........L.A..
79  T..R..T......L.....-.......T.SVI..KSAF.T.A.YL................F..L..GF.................
68  .RLH......A.MRT.AS--T.......HQ..V.I.SQEL.E.H.G..T................RT.KV.RM..VK.....LT.H........S.A..
70  ..................................GESQ---FA.I...........T..I.D.I..L.....DV..L..K.......V.A.I
1   L..TL.....N.L.GGL.--T............M..F...DEDGRN-IRENQ---YI.I......TEL..D...L.....DV..LT.K........V.A.I
1   .L.TL.....N..L.L.--T..................M...D.HLA..-.REHQ---FT.I......T.M..D.IL.L.....EV..K.........V.A.V
1   F.LN.T.....N.F.GGAS---.............A..L.YG.N-.QKRL---FT.I....P.ITVSS.FEA.HV.L.V.E..V..LTRK........I.A.V
1   .LQ..T.....K.F.GGA.PLG.........L.M...Q.VGIQ-LRRPL--FQ..T.V...Q..TIR..ASGSV.L.V.RC.L.RLTRR.L....HNP.A.V

194 SLIAVRVFEYRKCPRVIQNGAVFQETLSGAESTSLVAARGTCISNA---EEVDVPIKLYCNGDGEWLVPIGRCMCRPGYESVENGTVCRGCPSGTFKASQG
173 ...L..A..K..SNT.AGF.I.P..T...P....I.P....PQ.---V..S..L.......M..V.A.T.AA...PAMKD.Q.QA.GP....SK..
141 -----....EK...S.V..F.I.P..MT........T......P....-.........M.......T.KA...PEN.-VA..A..A......
168 ..V..Q..FY...A.VKGFAS.P..EA.G.R...ESL..VA..EEASTTGS+VR.H...E....M.AT...S.KA..Q.D.EQA.QA..I.S....V.
56  A.VS........K...LTVR.L.Q.PD.IT..DTS...EV..S.VN.S---..K....-.M..GA.......N.L.NA.....ERNG--E..QA.KI.YY..LST
93  A.VS.....Y.K...S..R.L.R.PD.IT...D.SQ.LEVS.V.VNHS---VTDEA.-KMH.SSE.......K.L.KR......EKN..-T.QA----------
190 A.VS....YFK....FTVK.L.M.PD.VPM-D.Q...EV..S.VNHS---K.EEP.-M..STE......K.L.NA...ERGF--A.QA.RP.FY..A..
190 A.LS....Y.K..ELL.GL.H.P..IA.SDAP..ATVA...VDH.VVPPGGEE.-RMH.AV........Q.L.QA...K..D--A.QA.SP..F..FEAS
193 A.VS......QR..ETLNGL.Q.PD..P.--PAG..EVA...LPH.RASPRPSGAPRMH..SP.........V..H.E....EGGS.EA.VA....SYRMDMD
```

FIG. 1A

FIG. 1C

```
751 MNYVHRDLAARNILVNSNLVCKVSDFGLSRFLEDDTSDPTYTSALGGKIPIRWTAPEAIQYRKFTSASDVWSYGIVMWEVMSYGERPYWDMTNQDVINAI
726 ...........................................PA....S.........A..............................V
708 ...........................................Y.Q..............S.............F................S....
725 ...........................................A.N...G..C.......V..........A...................S....
605 .S.......................................M..V...............A..........................S...K...
479 .G......................................I...-PEAA.TR---.....V............F.................E...
742 .G......................................I...-PEAA.TR---.....V.............AF..............K.V
735 ........................................-PEAA.TR---.....S..A............A...L..............E.SF...K.V
753 .H.........................................Q..C.......T.L.D.--F.G..ETQ-........S..........F.....ELS.HE.MK..
                                                                                       T.....L.F.DK..GE.S..E.MKS

851 EQDYRLPPEMDCPNALHQLMLDCWQKDRNHRPKFGQIVNTLDKMIRNPNSLKAMAPLSSGVNLPLLDRTIPDYTSFNTVDEWLDAIKMSQYKESFASAGF
826 ...........T..........A......VR...L..A.........L..AA..VI.SVQ...SQ......V..T.T..GD....GR...N.VN...
808 ...........A..TV.L...........T..RLAE...........A..TV.TITAVPSQ......S..F.A.TS.ED..S.V....RDN.L....
825 .D......P..TV.L..............VQ......E..SA.....K.SA...TGTG..RPSQ....SNSP..FP.LSNAH........GR...N.DQ..L
703 .EG........I.................E.SD......M..L..........RTGSE..RPSTA...PSS.EFSAVVS.SD..Q......ER...DN.TA..Y
577 .EG........S..A.Y...............S....DE..SM...L...S..TLVNA..R.SNL.VEHSPVGSGAYRS.G...E.....GR.T.I.MEN.Y
840 DEG........A.Y................N...E..SI..L...S..IITNAAARPSNL..QSNI.ISA.R.AGD..NGERTG.C.GI..TGVEY
833 NDGF....T.....S.IY....MQ..QE.AR......AD..SI..L.A.D..TL.DEDPR..SIR..PSTSGSEGVP..R...S....ES..Q..T.H.MA..Y
850 .DG........V...AP.YE..KN..AY..AR...H.QKLQAH..EQLLA..H..RTI.NEDPR.T.R.PSLSGS..GIPYR..S....ES.R.KR..ILH.H...L

951 TTFDIVSQMTVEDILRVGVTLAGHQKKILNSIQVMRAQMNQIQSVEV
925 AS..L.A...L..A..L..I................S...D..L...TLP.Q.
908 .SLQL.A...S..L..I...................S..V..S.SPTSMA
925 I...VI.R..L..LQ.I.I..V..............L.KVHL..LEP...
803 ..LEA.VH.NQD.LA.I.I.AIT..N...S.V.A..S..Q.MHGRM..PV
677 SSM.S.A.V.L..LR.L...V.....M..L.E.KV.LVNGMVPL
677 SSM.S.A.V.L..------ESPCE..WSLTLHPLFPTGY..T
940 SSC.TIAKISTD.MKK....VV.P....VS..KTLETHTKNSPVPV
933 .AIEK.V...ND..K.I..R.P....R.AY.LLGLKD..V.TVGIPI
950 D.MEC.LEL.A..LTQM.I..P....R..C...GFKD
```

FIG. 1D

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
        ( A ) LENGTH: 3133 base pairs
        ( B ) TYPE: nucleic acid
        ( C ) STRANDEDNESS: both
        ( D ) TOPOLOGY: linear ( i x ) FEATURE:
        ( A ) NAME/KEY: CDS
        ( B ) LOCATION: join(3..419, 421..2858)

( x i ) SEQUENCE DESCRIPTION: SEQ ID NO:1:

```
CA  GAA  ACC  CTG  ATG  GAC  ACA  CGG  ACA  GCG  ACG  GCT  GAG  CTG  GGC  TGG         47
    Glu  Thr  Leu  Met  Asp  Thr  Arg  Thr  Ala  Thr  Ala  Glu  Leu  Gly  Trp
    1              5                        10                       15

ACT  GCC  AAC  CCT  CCG  TCA  GGG  TGG  GAA  GAA  GTG  AGT  GGC  TAC  GAC  GAG         95
Thr  Ala  Asn  Pro  Pro  Ser  Gly  Trp  Glu  Glu  Val  Ser  Gly  Tyr  Asp  Glu
               20                       25                       30

AAC  CTG  AAC  ACC  ATC  CGT  ACC  TAC  CAG  GTG  TGC  AAC  GTC  TTC  GAG  CCA        143
Asn  Leu  Asn  Thr  Ile  Arg  Thr  Tyr  Gln  Val  Cys  Asn  Val  Phe  Glu  Pro
              35                        40                       45

AAC  CAG  AAC  AAC  TGG  CTC  CTC  ACC  ACC  TTC  ATC  AAC  CGG  CGC  GGA  GCC        191
Asn  Gln  Asn  Asn  Trp  Leu  Leu  Thr  Thr  Phe  Ile  Asn  Arg  Arg  Gly  Ala
              50                        55                       60

CAC  CGC  ATC  TAC  ACT  GAG  ATG  CGC  TTC  ACT  GTG  CGG  GAC  TGC  AGC  AGC        239
His  Arg  Ile  Tyr  Thr  Glu  Met  Arg  Phe  Thr  Val  Arg  Asp  Cys  Ser  Ser
     65                        70                       75

CTC  CCC  AAC  GTC  CCC  GGC  TCC  TGC  AAG  GAG  ACC  TTC  AAC  CTC  TAC  TAC        287
Leu  Pro  Asn  Val  Pro  Gly  Ser  Cys  Lys  Glu  Thr  Phe  Asn  Leu  Tyr  Tyr
80                       85                        90                       95

TAT  GAG  ACA  GAC  TCT  GTC  ATT  GCC  ACT  AAG  AAG  TCG  GCC  TTC  TGG  ACG        335
Tyr  Glu  Thr  Asp  Ser  Val  Ile  Ala  Thr  Lys  Lys  Ser  Ala  Phe  Trp  Thr
                    100                       105                      110

GAG  GCA  CCC  TAC  CTC  AAA  GTG  GAC  ACC  ATT  GCT  GCT  GAC  GAG  AGC  TTT        383
Glu  Ala  Pro  Tyr  Leu  Lys  Val  Asp  Thr  Ile  Ala  Ala  Asp  Glu  Ser  Phe
               115                       120                      125

TCC  CAG  GTG  GAC  TTT  GGT  GGC  AGG  TTG  ATG  AAG  GGT  T    TTC  TTC  AAG        429
Ser  Gln  Val  Asp  Phe  Gly  Gly  Arg  Leu  Met  Lys  Gly      Phe  Phe  Lys
               130                       135                      140

AAG  TGC  CCA  AGC  GTG  GTG  CAG  AAC  TTC  GCT  ATC  TTC  CCT  GAG  ACG  ATG        477
Lys  Cys  Pro  Ser  Val  Val  Gln  Asn  Phe  Ala  Ile  Phe  Pro  Glu  Thr  Met
              145                       150                      155
```

-continued

| | | | | | | | | | | | | | | | | |
|---|---|---|---|---|---|---|---|---|---|---|---|---|---|---|---|---|
| ACG | GGG | GCA | GAG | AGC | ACC | TCT | CTG | GTG | ACA | GCA | CGG | GGC | ACC | TGC | ATC | 525 |
| Thr | Gly | Ala | Glu | Ser | Thr | Ser | Leu | Val | Thr | Ala | Arg | Gly | Thr | Cys | Ile | |
| | 160 | | | | | 165 | | | | | 170 | | | | | |
| CCC | AAC | GCT | GAG | GAG | GTG | GAC | GTG | CCC | ATC | AAG | CTG | TAC | TGC | AAC | GGG | 573 |
| Pro | Asn | Ala | Glu | Glu | Val | Asp | Val | Pro | Ile | Lys | Leu | Tyr | Cys | Asn | Gly | |
| 175 | | | | | 180 | | | | | 185 | | | | | 190 | |
| GAT | GGG | GAG | TGG | ATG | GTA | CCC | ATA | GGT | CGC | TGC | ACC | TGC | AAG | GCT | GGT | 621 |
| Asp | Gly | Glu | Trp | Met | Val | Pro | Ile | Gly | Arg | Cys | Thr | Cys | Lys | Ala | Gly | |
| | | | | 195 | | | | | 200 | | | | | 205 | | |
| TAT | GAG | CCG | GAA | AAC | AAC | GTG | GCT | TGC | AGA | GCC | TGC | CCG | GCT | GGG | ACA | 669 |
| Tyr | Glu | Pro | Glu | Asn | Asn | Val | Ala | Cys | Arg | Ala | Cys | Pro | Ala | Gly | Thr | |
| | | | 210 | | | | | 215 | | | | | 220 | | | |
| TTC | AAA | GCC | AGT | CAG | GGT | GCG | GGG | CTG | TGT | GCC | CGC | TGT | CCC | CCC | AAC | 717 |
| Phe | Lys | Ala | Ser | Gln | Gly | Ala | Gly | Leu | Cys | Ala | Arg | Cys | Pro | Pro | Asn | |
| | | 225 | | | | | 230 | | | | | 235 | | | | |
| AGC | CGC | TCC | AGC | GCC | GAG | GCC | TCA | CCG | CTC | TGC | GCC | TGC | CGC | AAC | GGC | 765 |
| Ser | Arg | Ser | Ser | Ala | Glu | Ala | Ser | Pro | Leu | Cys | Ala | Cys | Arg | Asn | Gly | |
| | 240 | | | | | 245 | | | | | 250 | | | | | |
| TAC | TTT | CGG | GCT | GAC | CTG | GAC | CCA | CCG | ACA | GCT | GCC | TGC | ACC | AGC | GTC | 813 |
| Tyr | Phe | Arg | Ala | Asp | Leu | Asp | Pro | Pro | Thr | Ala | Ala | Cys | Thr | Ser | Val | |
| 255 | | | | | 260 | | | | | 265 | | | | | 270 | |
| CCC | TCT | GGT | CCA | CGC | AAC | GTC | ATC | TCC | ATT | GTC | AAT | GAG | ACC | TCC | ATC | 861 |
| Pro | Ser | Gly | Pro | Arg | Asn | Val | Ile | Ser | Ile | Val | Asn | Glu | Thr | Ser | Ile | |
| | | | | 275 | | | | | 280 | | | | | 285 | | |
| ATC | CTG | GAG | TGG | AAC | CCG | CCA | CGG | GAG | ACA | GGA | GGC | CGG | GAT | GAT | GTC | 909 |
| Ile | Leu | Glu | Trp | Asn | Pro | Pro | Arg | Glu | Thr | Gly | Gly | Arg | Asp | Asp | Val | |
| | | | 290 | | | | | 295 | | | | | 300 | | | |
| ACT | TAC | AAC | ATT | GTC | TGC | AAG | AAG | TGC | CGG | GCA | GAC | CGG | CGT | GCC | TGC | 957 |
| Thr | Tyr | Asn | Ile | Val | Cys | Lys | Lys | Cys | Arg | Ala | Asp | Arg | Arg | Ala | Cys | |
| | | 305 | | | | | 310 | | | | | 315 | | | | |
| TCC | CGC | TGC | GAC | GAC | AAC | GTG | GAG | TTT | GTG | CCC | CGA | CAG | CTG | GGG | CTG | 1005 |
| Ser | Arg | Cys | Asp | Asp | Asn | Val | Glu | Phe | Val | Pro | Arg | Gln | Leu | Gly | Leu | |
| | 320 | | | | | 325 | | | | | 330 | | | | | |
| ACA | GAG | ACC | CGC | GTC | TTC | ATC | AGC | AGC | CTC | TGG | GCA | CAC | ACA | CCC | TAC | 1053 |
| Thr | Glu | Thr | Arg | Val | Phe | Ile | Ser | Ser | Leu | Trp | Ala | His | Thr | Pro | Tyr | |
| 335 | | | | | 340 | | | | | 345 | | | | | 350 | |
| ACC | TTT | GAG | ATC | CAG | GCG | GTC | AAC | GGG | GTT | TCC | AAC | AAG | AGC | CCC | TTC | 1101 |
| Thr | Phe | Glu | Ile | Gln | Ala | Val | Asn | Gly | Val | Ser | Asn | Lys | Ser | Pro | Phe | |
| | | | | 355 | | | | | 360 | | | | | 365 | | |
| CCA | CCC | CAG | CAC | GTC | TCC | GTG | AAC | ATC | ACC | ACC | AAC | CAA | GCT | GCA | CCC | 1149 |
| Pro | Pro | Gln | His | Val | Ser | Val | Asn | Ile | Thr | Thr | Asn | Gln | Ala | Ala | Pro | |
| | | | 370 | | | | | 375 | | | | | 380 | | | |
| TCC | ACT | GTC | CCC | ATC | ATG | CAC | CAG | GTG | AGT | GCC | ACC | ATG | AGG | AGC | ATC | 1197 |
| Ser | Thr | Val | Pro | Ile | Met | His | Gln | Val | Ser | Ala | Thr | Met | Arg | Ser | Ile | |
| | | 385 | | | | | 390 | | | | | 395 | | | | |
| ACG | CTA | TCC | TGG | CCG | CAG | CCG | GAG | CAG | CCC | AAC | GGC | ATC | ATC | CTG | GAC | 1245 |
| Thr | Leu | Ser | Trp | Pro | Gln | Pro | Glu | Gln | Pro | Asn | Gly | Ile | Ile | Leu | Asp | |
| | 400 | | | | | 405 | | | | | 410 | | | | | |
| TAC | GAG | CTG | CGC | TAC | TAC | GAG | AAG | CTG | AGC | CGC | ATC | TGC | ACG | CCC | GAT | 1293 |
| Tyr | Glu | Leu | Arg | Tyr | Tyr | Glu | Lys | Leu | Ser | Arg | Ile | Cys | Thr | Pro | Asp | |
| 415 | | | | | 420 | | | | | 425 | | | | | 430 | |
| GTC | AGC | GGC | ACT | GTG | GGC | TCG | AGA | CCG | GCG | GCG | GAC | CAC | AAC | GAG | TAC | 1341 |
| Val | Ser | Gly | Thr | Val | Gly | Ser | Arg | Pro | Ala | Ala | Asp | His | Asn | Glu | Tyr | |
| | | | | 435 | | | | | 440 | | | | | 445 | | |
| AAC | TCC | TCT | GTG | GCC | CGC | AGT | CAG | ACC | AAC | ACG | GCC | CGG | CTG | GAG | GGG | 1389 |
| Asn | Ser | Ser | Val | Ala | Arg | Ser | Gln | Thr | Asn | Thr | Ala | Arg | Leu | Glu | Gly | |
| | | | 450 | | | | | 455 | | | | | 460 | | | |
| CTG | CGC | CCT | GGC | ATG | GTG | TAC | GTG | GTG | CAG | GTG | CGA | GCA | AGG | ACG | GTG | 1437 |
| Leu | Arg | Pro | Gly | Met | Val | Tyr | Val | Val | Gln | Val | Arg | Ala | Arg | Thr | Val | |
| | | 465 | | | | | 470 | | | | | 475 | | | | |

```
GCC GGC TAT GGG AAG TAC AGT GGG AAG ATG TGC TTC CAG ACA CTG ACC      1485
Ala Gly Tyr Gly Lys Tyr Ser Gly Lys Met Cys Phe Gln Thr Leu Thr
    480                 485                 490

GAT GAT GAC TAC AAG TCT GAG CTG AGG GAG CAG CTG CCA TTG ATT GCG      1533
Asp Asp Asp Tyr Lys Ser Glu Leu Arg Glu Gln Leu Pro Leu Ile Ala
495                 500                 505                 510

GGG TCT GCA GCG GCC GGC GTG GTC TTC ATT GTT TCG CTG GTG GCC ATT      1581
Gly Ser Ala Ala Ala Gly Val Val Phe Ile Val Ser Leu Val Ala Ile
                    515                 520                 525

TCC ATA GTG TGC AGC AGG AAG CGA GCG TAC AGC AAG GAG GTC GTT TAC      1629
Ser Ile Val Cys Ser Arg Lys Arg Ala Tyr Ser Lys Glu Val Val Tyr
                530                 535                 540

AGC GAT AAG CTG CAG CAC TAC AGC ACC GGG AGA GGG TCT CCG GGA ATG      1677
Ser Asp Lys Leu Gln His Tyr Ser Thr Gly Arg Gly Ser Pro Gly Met
            545                 550                 555

AAG ATT TAC ATC GAC CCC TTC ACT TAT GAG GAC CCC AAC GAG GCA GTG      1725
Lys Ile Tyr Ile Asp Pro Phe Thr Tyr Glu Asp Pro Asn Glu Ala Val
        560                 565                 570

CGT GAG TTC GCC AAG GAG ATT GAC GTC TCC TTT GTG AAG ATT GAA GAG      1773
Arg Glu Phe Ala Lys Glu Ile Asp Val Ser Phe Val Lys Ile Glu Glu
575                 580                 585                 590

GTC ATT GGA GCA GGG GAG TTT GGA GAG GTG TAC AAA GGC CGC CTG AAG      1821
Val Ile Gly Ala Gly Glu Phe Gly Glu Val Tyr Lys Gly Arg Leu Lys
                    595                 600                 605

TTG CCT GGC AAG CGG GAG ATC TAT GTG GCC ATC AAA ACA CTG AAG GCT      1869
Leu Pro Gly Lys Arg Glu Ile Tyr Val Ala Ile Lys Thr Leu Lys Ala
                610                 615                 620

GGC TAC TCA GAG AAG CAG CGC CGG GAT TTC CTG AGC GAA GCC AGC ATC      1917
Gly Tyr Ser Glu Lys Gln Arg Arg Asp Phe Leu Ser Glu Ala Ser Ile
            625                 630                 635

ATG GGG CAG TTT GAC CAC CCC AAC ATC ATC CGG CTG GAA GGG GTG GTG      1965
Met Gly Gln Phe Asp His Pro Asn Ile Ile Arg Leu Glu Gly Val Val
        640                 645                 650

ACC AAG AGC CGA CCA GTC ATG ATT ATC ACA GAG TTC ATG GAG AAT GGG      2013
Thr Lys Ser Arg Pro Val Met Ile Ile Thr Glu Phe Met Glu Asn Gly
655                 660                 665                 670

GCC CTG GAC TCG TTC CTG CGG CAA AAT GAT GGG CAG TTC ACA GTG ATC      2061
Ala Leu Asp Ser Phe Leu Arg Gln Asn Asp Gly Gln Phe Thr Val Ile
                    675                 680                 685

CAG CTG GTG GGG ATG CTC AGA GGG ATT GCT GCT GGG ATG AAG TAC CTG      2109
Gln Leu Val Gly Met Leu Arg Gly Ile Ala Ala Gly Met Lys Tyr Leu
                690                 695                 700

GCA GAG ATG AAC TAT GTC CAC AGG GAT CTG GCG GCC AGG AAC ATT CTG      2157
Ala Glu Met Asn Tyr Val His Arg Asp Leu Ala Ala Arg Asn Ile Leu
            705                 710                 715

GTC AAC AGC AAC CTG GTG TGC AAA GTG TCA GAC TTT GGC CTC TCG CGC      2205
Val Asn Ser Asn Leu Val Cys Lys Val Ser Asp Phe Gly Leu Ser Arg
        720                 725                 730

TAC CTG CAG GAC GAC ACC TCT GAT CCC ACC TAC ACC AGC TCC TTG GGT      2253
Tyr Leu Gln Asp Asp Thr Ser Asp Pro Thr Tyr Thr Ser Ser Leu Gly
735                 740                 745                 750

GGG AAG ATC CCT GTG CGA TGG ACA GCA CCA GAG GCC ATT GCG TAC CGC      2301
Gly Lys Ile Pro Val Arg Trp Thr Ala Pro Glu Ala Ile Ala Tyr Arg
                    755                 760                 765

AAG TTC ACG TCA GCC AGT GAC GTC TGG AGC TAT GGC ATC GTC ATG TGG      2349
Lys Phe Thr Ser Ala Ser Asp Val Trp Ser Tyr Gly Ile Val Met Trp
                770                 775                 780

GAG GTG ATG TCG TTC GGA GAG AGG CCC TAC TGG GAC ATG TCC AAC CAG      2397
Glu Val Met Ser Phe Gly Glu Arg Pro Tyr Trp Asp Met Ser Asn Gln
```

-continued

|  |  |  |  |  |  |  |  |  |  |  |  |  |  |  |  |  |
|---|---|---|---|---|---|---|---|---|---|---|---|---|---|---|---|---|
|  | 785 |  |  |  |  | 790 |  |  |  |  | 795 |  |  |  |  |  |
| GAC | GTC | ATC | AAT | GCC | ATC | GAG | CAG | GAC | TAC | CGG | CTC | CCG | CCG | CCC | ATG | 2445 |
| Asp | Val | Ile | Asn | Ala | Ile | Glu | Gln | Asp | Tyr | Arg | Leu | Pro | Pro | Pro | Met |  |
|  | 800 |  |  |  | 805 |  |  |  |  |  | 810 |  |  |  |  |  |
| GAC | TGC | CCA | GCT | GCC | CTG | CAC | CAA | CTG | ATG | CTG | GAC | TGC | TGG | CAG | AAG | 2493 |
| Asp | Cys | Pro | Ala | Ala | Leu | His | Gln | Leu | Met | Leu | Asp | Cys | Trp | Gln | Lys |  |
| 815 |  |  |  |  | 820 |  |  |  |  | 825 |  |  |  |  | 830 |  |
| GAC | CGC | AAC | ACC | CGG | CCT | CGC | TTG | GCC | GAG | ATT | GTC | AAC | ACC | CTG | GAC | 2541 |
| Asp | Arg | Asn | Thr | Arg | Pro | Arg | Leu | Ala | Glu | Ile | Val | Asn | Thr | Leu | Asp |  |
|  |  |  |  | 835 |  |  |  |  | 840 |  |  |  |  | 845 |  |  |
| AAA | ATG | ATC | CGC | AAC | CCG | GCA | AGC | CTC | AAA | ACT | GTG | GCT | ACC | ATC | ACC | 2589 |
| Lys | Met | Ile | Arg | Asn | Pro | Ala | Ser | Leu | Lys | Thr | Val | Ala | Thr | Ile | Thr |  |
|  |  |  | 850 |  |  |  |  | 855 |  |  |  |  | 860 |  |  |  |
| GCT | GTG | CCT | TCT | CAG | CCC | CTC | CTC | GAC | CGC | TCT | ATC | CCT | GAT | TTC | ACT | 2637 |
| Ala | Val | Pro | Ser | Gln | Pro | Leu | Leu | Asp | Arg | Ser | Ile | Pro | Asp | Phe | Thr |  |
|  |  | 865 |  |  |  |  | 870 |  |  |  |  | 875 |  |  |  |  |
| GCC | TTT | ACC | TCA | GTA | GAA | GAC | TGG | CTG | AGT | GCC | GTC | AAG | ATG | AGC | CAG | 2685 |
| Ala | Phe | Thr | Ser | Val | Glu | Asp | Trp | Leu | Ser | Ala | Val | Lys | Met | Ser | Gln |  |
|  |  | 880 |  |  |  | 885 |  |  |  |  | 890 |  |  |  |  |  |
| TAT | AGA | GAC | AAC | TTC | CTG | AGC | GCT | GGA | TTC | ACC | TCC | CTC | CAG | CTG | GTC | 2733 |
| Tyr | Arg | Asp | Asn | Phe | Leu | Ser | Ala | Gly | Phe | Thr | Ser | Leu | Gln | Leu | Val |  |
| 895 |  |  |  |  | 900 |  |  |  |  | 905 |  |  |  |  | 910 |  |
| GCC | CAG | ATG | ACA | TCT | GAA | GAC | CTC | CTG | AGA | ATA | GGA | GTA | ACG | CTG | GCT | 2781 |
| Ala | Gln | Met | Thr | Ser | Glu | Asp | Leu | Leu | Arg | Ile | Gly | Val | Thr | Leu | Ala |  |
|  |  |  |  | 915 |  |  |  |  | 920 |  |  |  |  | 925 |  |  |
| GGG | CAC | CAG | AAG | AAG | ATC | CTG | AAC | AGC | ATC | CAG | TCC | ATG | CGC | GTG | CAG | 2829 |
| Gly | His | Gln | Lys | Lys | Ile | Leu | Asn | Ser | Ile | Gln | Ser | Met | Arg | Val | Gln |  |
|  |  |  | 930 |  |  |  |  | 935 |  |  |  |  | 940 |  |  |  |
| ATG | AGT | CAG | TCT | CCG | ACC | TCG | ATG | GCGTGACGTC | CCTCGCTCGA | CGAGGAGGGG |  |  |  |  |  | 2883 |
| Met | Ser | Gln | Ser | Pro | Thr | Ser | Met | Ala |  |  |  |  |  |  |  |  |
|  |  | 945 |  |  |  |  | 950 |  |  |  |  |  |  |  |  |  |

| GACGGGGAGG | GCAGGTGGCA | GAGGTGGGAG | GGGAGGAACT | GATCTGATGG | GAGCCGTGGG | 2943 |
| GCCGCAGCTG | GAGAGGGGCA | GCCACGGCCG | GGGCTGTGCC | TGACCGCGGA | GGACGTTCCT | 3003 |
| GGGACTCGCC | TCGGCCTGGT | GACTTCCATC | CCTCACCAAC | AGAAGCACAC | TTACCGATGT | 3063 |
| CACGGGGGAC | AGCGTATAAA | TAAGTATAAA | TATGTACAAA | TCATATATTT | AAAAAAAAAA | 3123 |
| AAAAAAAAAG |  |  |  |  |  | 3133 |

( 2 ) INFORMATION FOR SEQ ID NO:2:

( i ) SEQUENCE CHARACTERISTICS:
    ( A ) LENGTH: 951 amino acids
    ( B ) TYPE: amino acid
    ( D ) TOPOLOGY: linear ( i i ) MOLECULE TYPE: protein ( x i ) SEQUENCE DESCRIPTION: SEQ ID NO:2:

| Glu | Thr | Leu | Met | Asp | Thr | Arg | Thr | Ala | Thr | Ala | Glu | Leu | Gly | Trp | Thr |
|---|---|---|---|---|---|---|---|---|---|---|---|---|---|---|---|
| 1 |  |  |  | 5 |  |  |  |  | 10 |  |  |  |  | 15 |  |
| Ala | Asn | Pro | Pro | Ser | Gly | Trp | Glu | Glu | Val | Ser | Gly | Tyr | Asp | Glu | Asn |
|  |  |  | 20 |  |  |  |  | 25 |  |  |  |  | 30 |  |  |
| Leu | Asn | Thr | Ile | Arg | Thr | Tyr | Gln | Val | Cys | Asn | Val | Phe | Glu | Pro | Asn |
|  |  | 35 |  |  |  |  | 40 |  |  |  |  | 45 |  |  |  |
| Gln | Asn | Asn | Trp | Leu | Leu | Thr | Thr | Phe | Ile | Asn | Arg | Arg | Gly | Ala | His |
|  |  | 50 |  |  |  |  | 55 |  |  |  |  | 60 |  |  |  |
| Arg | Ile | Tyr | Thr | Glu | Met | Arg | Phe | Thr | Val | Arg | Asp | Cys | Ser | Ser | Leu |
| 65 |  |  |  |  | 70 |  |  |  |  | 75 |  |  |  |  | 80 |

-continued

| | | | | | | | | | | | | | | |
|---|---|---|---|---|---|---|---|---|---|---|---|---|---|---|
| Pro | Asn | Val | Pro | Gly | Ser | Cys | Lys | Glu | Thr | Phe | Asn | Leu | Tyr | Tyr | Tyr |
| | | | | 85 | | | | | 90 | | | | | 95 | |
| Glu | Thr | Asp | Ser | Val | Ile | Ala | Thr | Lys | Lys | Ser | Ala | Phe | Trp | Thr | Glu |
| | | | | 100 | | | | | 105 | | | | | 110 | |
| Ala | Pro | Tyr | Leu | Lys | Val | Asp | Thr | Ile | Ala | Ala | Asp | Glu | Ser | Phe | Ser |
| | | | 115 | | | | | 120 | | | | | 125 | | |
| Gln | Val | Asp | Phe | Gly | Gly | Arg | Leu | Met | Lys | Gly | Phe | Phe | Lys | Lys | Cys |
| | 130 | | | | | 135 | | | | | 140 | | | | |
| Pro | Ser | Val | Val | Gln | Asn | Phe | Ala | Ile | Phe | Pro | Glu | Thr | Met | Thr | Gly |
| 145 | | | | | 150 | | | | | 155 | | | | | 160 |
| Ala | Glu | Ser | Thr | Ser | Leu | Val | Thr | Ala | Arg | Gly | Thr | Cys | Ile | Pro | Asn |
| | | | | 165 | | | | | 170 | | | | | 175 | |
| Ala | Glu | Glu | Val | Asp | Val | Pro | Ile | Lys | Leu | Tyr | Cys | Asn | Gly | Asp | Gly |
| | | | | 180 | | | | | 185 | | | | | 190 | |
| Glu | Trp | Met | Val | Pro | Ile | Gly | Arg | Cys | Thr | Cys | Lys | Ala | Gly | Tyr | Glu |
| | | | 195 | | | | | 200 | | | | | 205 | | |
| Pro | Glu | Asn | Asn | Val | Ala | Cys | Arg | Ala | Cys | Pro | Ala | Gly | Thr | Phe | Lys |
| | 210 | | | | | 215 | | | | | 220 | | | | |
| Ala | Ser | Gln | Gly | Ala | Gly | Leu | Cys | Ala | Arg | Cys | Pro | Pro | Asn | Ser | Arg |
| 225 | | | | | 230 | | | | | 235 | | | | | 240 |
| Ser | Ser | Ala | Glu | Ala | Ser | Pro | Leu | Cys | Ala | Cys | Arg | Asn | Gly | Tyr | Phe |
| | | | | 245 | | | | | 250 | | | | | 255 | |
| Arg | Ala | Asp | Leu | Asp | Pro | Pro | Thr | Ala | Ala | Cys | Thr | Ser | Val | Pro | Ser |
| | | | 260 | | | | | 265 | | | | | 270 | | |
| Gly | Pro | Arg | Asn | Val | Ile | Ser | Ile | Val | Asn | Glu | Thr | Ser | Ile | Ile | Leu |
| | | 275 | | | | | 280 | | | | | 285 | | | |
| Glu | Trp | Asn | Pro | Pro | Arg | Glu | Thr | Gly | Gly | Arg | Asp | Asp | Val | Thr | Tyr |
| | 290 | | | | | 295 | | | | | 300 | | | | |
| Asn | Ile | Val | Cys | Lys | Lys | Cys | Arg | Ala | Asp | Arg | Arg | Ala | Cys | Ser | Arg |
| 305 | | | | | 310 | | | | | 315 | | | | | 320 |
| Cys | Asp | Asp | Asn | Val | Glu | Phe | Val | Pro | Arg | Gln | Leu | Gly | Leu | Thr | Glu |
| | | | | 325 | | | | | 330 | | | | | 335 | |
| Thr | Arg | Val | Phe | Ile | Ser | Ser | Leu | Trp | Ala | His | Thr | Pro | Tyr | Thr | Phe |
| | | | 340 | | | | | 345 | | | | | 350 | | |
| Glu | Ile | Gln | Ala | Val | Asn | Gly | Val | Ser | Asn | Lys | Ser | Pro | Phe | Pro | Pro |
| | | 355 | | | | | 360 | | | | | 365 | | | |
| Gln | His | Val | Ser | Val | Asn | Ile | Thr | Thr | Asn | Gln | Ala | Ala | Pro | Ser | Thr |
| | 370 | | | | | 375 | | | | | 380 | | | | |
| Val | Pro | Ile | Met | His | Gln | Val | Ser | Ala | Thr | Met | Arg | Ser | Ile | Thr | Leu |
| 385 | | | | | 390 | | | | | 395 | | | | | 400 |
| Ser | Trp | Pro | Gln | Pro | Glu | Gln | Pro | Asn | Gly | Ile | Ile | Leu | Asp | Tyr | Glu |
| | | | | 405 | | | | | 410 | | | | | 415 | |
| Leu | Arg | Tyr | Tyr | Glu | Lys | Leu | Ser | Arg | Ile | Cys | Thr | Pro | Asp | Val | Ser |
| | | | 420 | | | | | 425 | | | | | 430 | | |
| Gly | Thr | Val | Gly | Ser | Arg | Pro | Ala | Ala | Asp | His | Asn | Glu | Tyr | Asn | Ser |
| | | 435 | | | | | 440 | | | | | 445 | | | |
| Ser | Val | Ala | Arg | Ser | Gln | Thr | Asn | Thr | Ala | Arg | Leu | Glu | Gly | Leu | Arg |
| | 450 | | | | | 455 | | | | | 460 | | | | |
| Pro | Gly | Met | Val | Tyr | Val | Val | Gln | Val | Arg | Ala | Arg | Thr | Val | Ala | Gly |
| 465 | | | | | 470 | | | | | 475 | | | | | 480 |
| Tyr | Gly | Lys | Tyr | Ser | Gly | Lys | Met | Cys | Phe | Gln | Thr | Leu | Thr | Asp | Asp |
| | | | | 485 | | | | | 490 | | | | | 495 | |
| Asp | Tyr | Lys | Ser | Glu | Leu | Arg | Glu | Gln | Leu | Pro | Leu | Ile | Ala | Gly | Ser |

|  | 500 |  |  |  | 505 |  |  |  | 510 |  |  |  |
|---|---|---|---|---|---|---|---|---|---|---|---|---|

Ala Ala Ala Gly Val Val Phe Ile Val Ser Leu Val Ala Ile Ser Ile
            515                 520                 525

Val Cys Ser Arg Lys Arg Ala Tyr Ser Lys Glu Val Tyr Ser Asp
    530                 535                 540

Lys Leu Gln His Tyr Ser Thr Gly Arg Gly Ser Pro Gly Met Lys Ile
545             550                 555                     560

Tyr Ile Asp Pro Phe Thr Tyr Glu Asp Pro Asn Glu Ala Val Arg Glu
            565                 570                     575

Phe Ala Lys Glu Ile Asp Val Ser Phe Val Lys Ile Glu Glu Val Ile
            580                 585                 590

Gly Ala Gly Glu Phe Gly Glu Val Tyr Lys Gly Arg Leu Lys Leu Pro
        595                 600                 605

Gly Lys Arg Glu Ile Tyr Val Ala Ile Lys Thr Leu Lys Ala Gly Tyr
    610                 615                 620

Ser Glu Lys Gln Arg Arg Asp Phe Leu Ser Glu Ala Ser Ile Met Gly
625                 630                 635                 640

Gln Phe Asp His Pro Asn Ile Ile Arg Leu Glu Gly Val Val Thr Lys
            645                 650                 655

Ser Arg Pro Val Met Ile Ile Thr Glu Phe Met Glu Asn Gly Ala Leu
            660                 665                 670

Asp Ser Phe Leu Arg Gln Asn Asp Gly Gln Phe Thr Val Ile Gln Leu
        675                 680                 685

Val Gly Met Leu Arg Gly Ile Ala Ala Gly Met Lys Tyr Leu Ala Glu
    690                 695                 700

Met Asn Tyr Val His Arg Asp Leu Ala Ala Arg Asn Ile Leu Val Asn
705             710                 715                     720

Ser Asn Leu Val Cys Lys Val Ser Asp Phe Gly Leu Ser Arg Tyr Leu
            725                 730                 735

Gln Asp Asp Thr Ser Asp Pro Thr Tyr Thr Ser Ser Leu Gly Gly Lys
            740                 745                 750

Ile Pro Val Arg Trp Thr Ala Pro Glu Ala Ile Ala Tyr Arg Lys Phe
        755                 760                 765

Thr Ser Ala Ser Asp Val Trp Ser Tyr Gly Ile Val Met Trp Glu Val
    770                 775                 780

Met Ser Phe Gly Glu Arg Pro Tyr Trp Asp Met Ser Asn Gln Asp Val
785             790                 795                     800

Ile Asn Ala Ile Glu Gln Asp Tyr Arg Leu Pro Pro Met Asp Cys
            805                 810                 815

Pro Ala Ala Leu His Gln Leu Met Leu Asp Cys Trp Gln Lys Asp Arg
            820                 825                 830

Asn Thr Arg Pro Arg Leu Ala Glu Ile Val Asn Thr Leu Asp Lys Met
        835                 840                 845

Ile Arg Asn Pro Ala Ser Leu Lys Thr Val Ala Thr Ile Thr Ala Val
    850                 855                 860

Pro Ser Gln Pro Leu Leu Asp Arg Ser Ile Pro Asp Phe Thr Ala Phe
865             870                 875                     880

Thr Ser Val Glu Asp Trp Leu Ser Ala Val Lys Met Ser Gln Tyr Arg
            885                 890                 895

Asp Asn Phe Leu Ser Ala Gly Phe Thr Ser Leu Gln Leu Val Ala Gln
            900                 905                 910

Met Thr Ser Glu Asp Leu Leu Arg Ile Gly Val Thr Leu Ala Gly His
            915                 920                 925

```
Gln  Lys  Lys  Ile  Leu  Asn  Ser  Ile  Gln  Ser  Met  Arg  Val  Gln  Met  Ser
     930                 935                      940

Gln  Ser  Pro  Thr  Ser  Met  Ala
945                      950
```

( 2 ) INFORMATION FOR SEQ ID NO:3:

( i ) SEQUENCE CHARACTERISTICS:
        ( A ) LENGTH: 3059 base pairs
        ( B ) TYPE: nucleic acid
        ( C ) STRANDEDNESS: both
        ( D ) TOPOLOGY: linear ( i x ) FEATURE:
        ( A ) NAME/KEY: CDS
        ( B ) LOCATION: 2..2167

( x i ) SEQUENCE DESCRIPTION: SEQ ID NO:3:

```
C  CTC  AAA  TTC  ACC  CTG  AGG  GAC  TGT  AAC  AGC  CTT  CCA  GGA  GGA  CTT      46
   Leu  Lys  Phe  Thr  Leu  Arg  Asp  Cys  Asn  Ser  Leu  Pro  Gly  Gly  Leu
   1              5                        10                       15

GGG  ACT  TGC  AAG  GAG  ACT  TTT  AAC  ATG  TAC  TAC  TTT  GAG  TCA  GAT  GAT      94
Gly  Thr  Cys  Lys  Glu  Thr  Phe  Asn  Met  Tyr  Tyr  Phe  Glu  Ser  Asp  Asp
               20                       25                            30

GAA  GAT  GGG  AGG  AAC  ATC  AGA  GAG  AAT  CAG  TAC  ATC  AAG  ATA  GAT  ACC     142
Glu  Asp  Gly  Arg  Asn  Ile  Arg  Glu  Asn  Gln  Tyr  Ile  Lys  Ile  Asp  Thr
               35                       40                       45

ATT  GCT  GCT  GAT  GAG  AGC  TTC  ACG  GAG  TTG  GAC  CTC  GGC  GAC  AGA  GTT     190
Ile  Ala  Ala  Asp  Glu  Ser  Phe  Thr  Glu  Leu  Asp  Leu  Gly  Asp  Arg  Val
          50                       55                       60

ATG  AAG  TTA  AAC  ACA  GAA  GTG  AGA  GAT  GTT  GGG  CCT  CTA  ACA  AAA  AAA     238
Met  Lys  Leu  Asn  Thr  Glu  Val  Arg  Asp  Val  Gly  Pro  Leu  Thr  Lys  Lys
     65                       70                       75

GGA  TTT  TAC  CTT  GCT  TTC  CAG  GAT  GTG  GGC  GCC  TGC  ATT  GCC  CTG  GTC     286
Gly  Phe  Tyr  Leu  Ala  Phe  Gln  Asp  Val  Gly  Ala  Cys  Ile  Ala  Leu  Val
80                       85                       90                       95

TCT  GTG  CGT  GTG  TAC  TAC  AAG  AAA  TGC  CCA  TCA  GTG  ATC  CGC  AAC  CTG     334
Ser  Val  Arg  Val  Tyr  Tyr  Lys  Lys  Cys  Pro  Ser  Val  Ile  Arg  Asn  Leu
                    100                      105                      110

GCA  CGC  TTT  CCA  GAT  ACC  ATC  ACA  GGA  GCA  GAT  TCC  TCG  CAG  CTG  CTA     382
Ala  Arg  Phe  Pro  Asp  Thr  Ile  Thr  Gly  Ala  Asp  Ser  Ser  Gln  Leu  Leu
               115                      120                      125

GAA  GTG  TCA  GGC  GTC  TGT  GTC  AAC  CAC  TCA  GTG  ACT  GAT  GAG  GCA  CCA     430
Glu  Val  Ser  Gly  Val  Cys  Val  Asn  His  Ser  Val  Thr  Asp  Glu  Ala  Pro
          130                      135                      140

AAG  ATG  CAC  TGC  AGT  TCA  GAG  GGA  GAA  TGG  CTG  GTG  CCC  ATT  GGG  AAG     478
Lys  Met  His  Cys  Ser  Ser  Glu  Gly  Glu  Trp  Leu  Val  Pro  Ile  Gly  Lys
     145                      150                      155

TGT  TTG  TGC  AAG  GCA  GGG  TAC  GAG  GAG  AAG  AAC  AAC  ACC  TGC  CAA  GCA     526
Cys  Leu  Cys  Lys  Ala  Gly  Tyr  Glu  Glu  Lys  Asn  Asn  Thr  Cys  Gln  Ala
160                      165                      170                      175

CCT  TCT  CCA  GTC  AGT  AGT  GTG  AAA  AAA  GGG  AAG  ATA  ACT  AAA  AAT  AGC     574
Pro  Ser  Pro  Val  Ser  Ser  Val  Lys  Lys  Gly  Lys  Ile  Thr  Lys  Asn  Ser
               180                      185                      190

ATC  TCC  CTT  TCC  TGG  CAG  GAG  CCA  GAT  CGA  CCC  AAC  GGC  ATC  ATC  CTG     622
Ile  Ser  Leu  Ser  Trp  Gln  Glu  Pro  Asp  Arg  Pro  Asn  Gly  Ile  Ile  Leu
               195                      200                      205

GAA  TAC  GAA  ATC  AAA  TAT  TTT  GAA  AAG  GAC  CAG  GAG  ACA  AGC  TAC  ACC     670
Glu  Tyr  Glu  Ile  Lys  Tyr  Phe  Glu  Lys  Asp  Gln  Glu  Thr  Ser  Tyr  Thr
               210                      215                      220

ATC  ATC  AAA  TCC  AAA  GAG  ACC  GCA  ATT  ACG  GCA  GAT  GGC  TTG  AAA  CCA     718
```

```
Ile Ile Lys Ser Lys Glu Thr Ala Ile Thr Ala Asp Gly Leu Lys Pro
    225             230             235

GGC TCA GCG TAC GTC TTC CAG ATC CGA GCC CGG ACA GCT GCT GGC TAC        766
Gly Ser Ala Tyr Val Phe Gln Ile Arg Ala Arg Thr Ala Ala Gly Tyr
240             245             250             255

GGT GGC TTC AGT CGA AGA TTT GAG TTT GAA ACC AGC CCA GTG TTA GCT        814
Gly Gly Phe Ser Arg Arg Phe Glu Phe Glu Thr Ser Pro Val Leu Ala
                260             265             270

GCA TCC AGT GAC CAG AGC CAG ATT CCT ATA ATT GTT GTG TCT GTA ACA        862
Ala Ser Ser Asp Gln Ser Gln Ile Pro Ile Ile Val Val Ser Val Thr
            275             280             285

GTG GGA GTT ATT CTG CTG GCT GTT GTT ATC GGT TTC CTT CTC AGT GGA        910
Val Gly Val Ile Leu Leu Ala Val Val Ile Gly Phe Leu Leu Ser Gly
        290             295             300

AGG CGC TGT GGC TAC AGC AAG GCT AAA CAA GAC CCA GAA GAA GAA AAG        958
Arg Arg Cys Gly Tyr Ser Lys Ala Lys Gln Asp Pro Glu Glu Glu Lys
    305             310             315

ATG CAT TTT CAT AAT GGC CAC ATT AAA CTG CCT GGT GTA AGA ACC TAC       1006
Met His Phe His Asn Gly His Ile Lys Leu Pro Gly Val Arg Thr Tyr
320             325             330             335

ATT GAT CCC CAC ACC TAT GAG GAC CCT AAT CAA GCT GTC CAC GAG TTT       1054
Ile Asp Pro His Thr Tyr Glu Asp Pro Asn Gln Ala Val His Glu Phe
                340             345             350

GCC AAG GAA ATA GAA GCT TCG TGC ATA ACC ATC GAG AGA GTT ATC GGA       1102
Ala Lys Glu Ile Glu Ala Ser Cys Ile Thr Ile Glu Arg Val Ile Gly
            355             360             365

GCT GGT GAA TTT GGA GAA GTC TGC AGT GGA CGG CTG AAA CTG CAG GGA       1150
Ala Gly Glu Phe Gly Glu Val Cys Ser Gly Arg Leu Lys Leu Gln Gly
        370             375             380

AAA CGC GAG TTT CCA GTG GCT ATC AAA ACC CTG AAG GTG GGC TAC ACA       1198
Lys Arg Glu Phe Pro Val Ala Ile Lys Thr Leu Lys Val Gly Tyr Thr
    385             390             395

GAG AAG CAA AGG CGA GAT TTC CTG GGA GAA GCG AGC ATC ATG GGG CAG       1246
Glu Lys Gln Arg Arg Asp Phe Leu Gly Glu Ala Ser Ile Met Gly Gln
400             405             410             415

TTC GAC CAC CCC AAC ATC ATC CAC CTG GAA GGT GTC GTC ACA AAA AGC       1294
Phe Asp His Pro Asn Ile Ile His Leu Glu Gly Val Val Thr Lys Ser
                420             425             430

AAA CCT GTA ATG ATA GTA ACG GAA TAC ATG GAA AAT GGT TCT CTG GAT       1342
Lys Pro Val Met Ile Val Thr Glu Tyr Met Glu Asn Gly Ser Leu Asp
            435             440             445

ACA TTT TTA AAG AAG AAC GAT GGG CAG TTC ACG GTC ATT CAG CTG GTC       1390
Thr Phe Leu Lys Lys Asn Asp Gly Gln Phe Thr Val Ile Gln Leu Val
        450             455             460

GGG ATG CTG CGA GGC ATC GCA TCA GGG ATG AAG TAC CTG TCT GAC ATG       1438
Gly Met Leu Arg Gly Ile Ala Ser Gly Met Lys Tyr Leu Ser Asp Met
    465             470             475

GGT TAC GTA CAC AGA GAC CTC GCT GCC AGG AAT ATC CTC ATC AAC AGC       1486
Gly Tyr Val His Arg Asp Leu Ala Ala Arg Asn Ile Leu Ile Asn Ser
480             485             490             495

AAC TTA GTC TGC AAG GTG TCT GAC TTT GGC CTC TCC AGA GTC CTA GAA       1534
Asn Leu Val Cys Lys Val Ser Asp Phe Gly Leu Ser Arg Val Leu Glu
                500             505             510

GAT GAT CCT GAA GCA GCG TAC ACA ACC AGG GGA GGG AAG ATC CCC ATC       1582
Asp Asp Pro Glu Ala Ala Tyr Thr Thr Arg Gly Gly Lys Ile Pro Ile
            515             520             525

CGA TGG ACG GCA CCT GAA GCA ATC GCC TTC CGC AAA TTC ACG TCG GCC       1630
Arg Trp Thr Ala Pro Glu Ala Ile Ala Phe Arg Lys Phe Thr Ser Ala
        530             535             540
```

| | | | | | | | | | | | | | | | | |
|---|---|---|---|---|---|---|---|---|---|---|---|---|---|---|---|---|
| AGC | GAT | GTG | TGG | AGC | TAC | GGC | ATT | GTG | ATG | TGG | GAA | GTG | ATG | TCC | TAT | 1678 |
| Ser | Asp | Val | Trp | Ser | Tyr | Gly | Ile | Val | Met | Trp | Glu | Val | Met | Ser | Tyr | |
| 545 | | | | | 550 | | | | | 555 | | | | | | |
| GGC | GAG | AGA | CCT | TAC | TGG | GAA | ATG | ACA | AAC | CAA | GAT | GTG | ATT | AAA | GCC | 1726 |
| Gly | Glu | Arg | Pro | Tyr | Trp | Glu | Met | Thr | Asn | Gln | Asp | Val | Ile | Lys | Ala | |
| 560 | | | | | 565 | | | | 570 | | | | | | 575 | |
| GTG | GAG | GAA | GGC | TAT | CGC | CTG | CCA | AGT | CCC | ATG | GAC | TGC | CCT | GCT | GCT | 1774 |
| Val | Glu | Glu | Gly | Tyr | Arg | Leu | Pro | Ser | Pro | Met | Asp | Cys | Pro | Ala | Ala | |
| | | | | 580 | | | | | 585 | | | | | 590 | | |
| CTC | TAC | CAG | TTG | ATG | CTT | GAC | TGC | TGG | CAG | AAA | GAC | CGC | AAC | AGC | AGG | 1822 |
| Leu | Tyr | Gln | Leu | Met | Leu | Asp | Cys | Trp | Gln | Lys | Asp | Arg | Asn | Ser | Arg | |
| | | 595 | | | | | 600 | | | | | 605 | | | | |
| CCC | AAG | TTT | GAT | GAA | ATT | GTC | AGC | ATG | TTG | GAC | AAG | CTC | ATC | CGT | AAC | 1870 |
| Pro | Lys | Phe | Asp | Glu | Ile | Val | Ser | Met | Leu | Asp | Lys | Leu | Ile | Arg | Asn | |
| | | 610 | | | | | 615 | | | | | 620 | | | | |
| CCA | AGC | AGC | TTG | AAG | ACG | TTG | GTT | AAT | GCA | TCG | AGC | AGA | GTA | TCA | AAT | 1918 |
| Pro | Ser | Ser | Leu | Lys | Thr | Leu | Val | Asn | Ala | Ser | Ser | Arg | Val | Ser | Asn | |
| | 625 | | | | | 630 | | | | | 635 | | | | | |
| TTG | TTG | GTA | GAA | CAC | AGT | CCA | GTG | GGG | AGC | GGT | GCC | TAC | AGG | TCA | GTG | 1966 |
| Leu | Leu | Val | Glu | His | Ser | Pro | Val | Gly | Ser | Gly | Ala | Tyr | Arg | Ser | Val | |
| 640 | | | | 645 | | | | | 650 | | | | | | 655 | |
| GGT | GAG | TGG | CTG | GAA | GCC | ATC | AAA | ATG | GGT | CGA | TAC | ACC | GAG | ATT | TTC | 2014 |
| Gly | Glu | Trp | Leu | Glu | Ala | Ile | Lys | Met | Gly | Arg | Tyr | Thr | Glu | Ile | Phe | |
| | | | | 660 | | | | | 665 | | | | | 670 | | |
| ATG | GAG | AAT | GGA | TAC | AGT | TCG | ATG | GAT | TCT | GTG | GCT | CAG | GTG | ACC | CTA | 2062 |
| Met | Glu | Asn | Gly | Tyr | Ser | Ser | Met | Asp | Ser | Val | Ala | Gln | Val | Thr | Leu | |
| | | | 675 | | | | | 680 | | | | | 685 | | | |
| GAG | GAT | TTG | AGG | CGG | CTG | GGA | GTG | ACA | CTT | GTT | GGT | CAC | CAG | AAG | AAG | 2110 |
| Glu | Asp | Leu | Arg | Arg | Leu | Gly | Val | Thr | Leu | Val | Gly | His | Gln | Lys | Lys | |
| | | | 690 | | | | | 695 | | | | | 700 | | | |
| ATA | ATG | AAC | AGC | CTT | CAA | GAG | ATG | AAG | GTC | CAG | TTG | GTG | AAT | GGG | ATG | 2158 |
| Ile | Met | Asn | Ser | Leu | Gln | Glu | Met | Lys | Val | Gln | Leu | Val | Asn | Gly | Met | |
| | | 705 | | | | | 710 | | | | | 715 | | | | |
| GTG | CCA | TTG | TAACTCGGTT | | TTTAAGTCAC | | TTCCTCGAGT | | GGTCGGTCCT | | | | | | | 2207 |
| Val | Pro | Leu | | | | | | | | | | | | | | |
| 720 | | | | | | | | | | | | | | | | |

| | | | | | |
|---|---|---|---|---|---|
| GCACTTTGTA | TACTAGCTCT | GAGATTTATT | TTGACTAAAG | AAGAAAAAAG | GGAAATTCAG | 2267 |
| TGGTTTCTGT | AACTGAAGGA | CGCTGGCTTC | TGCCACAGCA | TTTATAAAGC | AGTGTTTGAC | 2327 |
| TGAAGTTTTC | ATTTTCTTCC | TATTTGTGTC | CTCATTCTCA | TGAAGTAAAT | GTAACATGCA | 2387 |
| TGGAACATGG | AAATGGATCT | ACTGTACATG | AGGTTACCCA | ATTTCTTGCG | CTTCAGCATG | 2447 |
| ACAACAGCAA | GCCTTCCCAC | CACATGTTGT | CTATACATGG | GAGATATATA | TATATGCATA | 2507 |
| TATATATATA | GCACCTTTAT | ATACTGAATT | ACAGCAGCAG | CACATGTTAA | TACTTCCAAG | 2567 |
| GACTTACTTG | ACTAGAGAAG | TTTTGCAGCC | ATTGTGGGCT | CACACAAGCT | GCGGTTTACT | 2627 |
| GAAGTTTACT | TCAAGTCTTA | CTTGTCTACA | GAAGTGTATT | GAAGAGCAAT | ATGATTAGAT | 2687 |
| TATTTCTGGA | TAGATATTTT | GTTTTGTAAA | TTTAAAAAAT | CGTGTTACAC | AGCGTTAAGT | 2747 |
| TATAGAGACT | AGTGTATAAA | CATGTTGCTT | GCTCAATGGC | AAATACAATA | CAGGGTGTAT | 2807 |
| ATTTTTTTCT | CTCTGTGTTG | CAAAGTTCTT | TTAGTTTGCT | CTTCTGTGAG | GATAATACGT | 2867 |
| TATGATGTAT | ATACTGTACA | GTTTGCTACA | CATCAGGTAC | AAGATTGGGG | CTTTCTCAAT | 2927 |
| GTTTTGTTCT | TTTTCCCTCT | TTTGTTTCAT | TTTGTCTTCC | TTTTGTGTTA | ACCACTATGC | 2987 |
| TTTGTATTTT | TGCTGCTGTT | TGGTTTGAGG | CAACATATAA | AGCTTTCAGG | TGTTTTGATT | 3047 |
| ATAAAAAAAA | AG | | | | | 3059 |

( 2 ) INFORMATION FOR SEQ ID NO:4:

( i ) SEQUENCE CHARACTERISTICS:
        ( A ) LENGTH: 722 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Leu Lys Phe Thr Leu Arg Asp Cys Asn Ser Leu Pro Gly Gly Leu Gly
 1               5                  10                  15
Thr Cys Lys Glu Thr Phe Asn Met Tyr Tyr Phe Glu Ser Asp Asp Glu
                20                  25                  30
Asp Gly Arg Asn Ile Arg Glu Asn Gln Tyr Ile Lys Ile Asp Thr Ile
            35                  40                  45
Ala Ala Asp Glu Ser Phe Thr Glu Leu Asp Leu Gly Asp Arg Val Met
         50                  55                  60
Lys Leu Asn Thr Glu Val Arg Asp Val Gly Pro Leu Thr Lys Lys Gly
 65                  70                  75                  80
Phe Tyr Leu Ala Phe Gln Asp Val Gly Ala Cys Ile Ala Leu Val Ser
                85                  90                  95
Val Arg Val Tyr Tyr Lys Lys Cys Pro Ser Val Ile Arg Asn Leu Ala
                100                 105                 110
Arg Phe Pro Asp Thr Ile Thr Gly Ala Asp Ser Ser Gln Leu Leu Glu
            115                 120                 125
Val Ser Gly Val Cys Val Asn His Ser Val Thr Asp Glu Ala Pro Lys
         130                 135                 140
Met His Cys Ser Ser Glu Gly Glu Trp Leu Val Pro Ile Gly Lys Cys
145                 150                 155                 160
Leu Cys Lys Ala Gly Tyr Glu Glu Lys Asn Asn Thr Cys Gln Ala Pro
                165                 170                 175
Ser Pro Val Ser Ser Val Lys Lys Gly Lys Ile Thr Lys Asn Ser Ile
                180                 185                 190
Ser Leu Ser Trp Gln Glu Pro Asp Arg Pro Asn Gly Ile Ile Leu Glu
            195                 200                 205
Tyr Glu Ile Lys Tyr Phe Glu Lys Asp Gln Glu Thr Ser Tyr Thr Ile
         210                 215                 220
Ile Lys Ser Lys Glu Thr Ala Ile Thr Ala Asp Gly Leu Lys Pro Gly
225                 230                 235                 240
Ser Ala Tyr Val Phe Gln Ile Arg Ala Arg Thr Ala Ala Gly Tyr Gly
                245                 250                 255
Gly Phe Ser Arg Arg Phe Glu Phe Glu Thr Ser Pro Val Leu Ala Ala
            260                 265                 270
Ser Ser Asp Gln Ser Gln Ile Pro Ile Ile Val Val Ser Val Thr Val
         275                 280                 285
Gly Val Ile Leu Leu Ala Val Val Ile Gly Phe Leu Leu Ser Gly Arg
         290                 295                 300
Arg Cys Gly Tyr Ser Lys Ala Lys Gln Asp Pro Glu Glu Glu Lys Met
305                 310                 315                 320
His Phe His Asn Gly His Ile Lys Leu Pro Gly Val Arg Thr Tyr Ile
                325                 330                 335
Asp Pro His Thr Tyr Glu Asp Pro Asn Gln Ala Val His Glu Phe Ala
            340                 345                 350
Lys Glu Ile Glu Ala Ser Cys Ile Thr Ile Glu Arg Val Ile Gly Ala
         355                 360                 365
```

-continued

| | | | | | | | | | | | | |
|---|---|---|---|---|---|---|---|---|---|---|---|---|
| Gly | Glu 370 | Phe | Gly | Glu | Val 375 | Cys | Ser | Gly | Arg | Leu 380 | Lys | Leu | Gln | Gly | Lys |
| Arg 385 | Glu | Phe | Pro | Val 390 | Ala | Ile | Lys | Thr | Leu 395 | Lys | Val | Gly | Tyr | Thr | Glu 400 |
| Lys | Gln | Arg | Arg 405 | Asp | Phe | Leu | Gly | Glu 410 | Ala | Ser | Ile | Met | Gly 415 | Gln | Phe |
| Asp | His | Pro | Asn 420 | Ile | Ile | His | Leu | Glu 425 | Gly | Val | Val | Thr | Lys 430 | Ser | Lys |
| Pro | Val | Met 435 | Ile | Val | Thr | Glu | Tyr 440 | Met | Glu | Asn | Gly | Ser 445 | Leu | Asp | Thr |
| Phe | Leu 450 | Lys | Lys | Asn | Asp | Gly 455 | Gln | Phe | Thr | Val | Ile 460 | Gln | Leu | Val | Gly |
| Met 465 | Leu | Arg | Gly | Ile | Ala 470 | Ser | Gly | Met | Lys | Tyr 475 | Leu | Ser | Asp | Met | Gly 480 |
| Tyr | Val | His | Arg | Asp 485 | Leu | Ala | Ala | Arg | Asn 490 | Ile | Leu | Ile | Asn | Ser 495 | Asn |
| Leu | Val | Cys | Lys 500 | Val | Ser | Asp | Phe | Gly 505 | Leu | Ser | Arg | Val | Leu 510 | Glu | Asp |
| Asp | Pro | Glu 515 | Ala | Ala | Tyr | Thr | Thr 520 | Arg | Gly | Gly | Lys | Ile 525 | Pro | Ile | Arg |
| Trp | Thr 530 | Ala | Pro | Glu | Ala | Ile 535 | Ala | Phe | Arg | Lys | Phe 540 | Thr | Ser | Ala | Ser |
| Asp 545 | Val | Trp | Ser | Tyr | Gly 550 | Ile | Val | Met | Trp | Glu 555 | Val | Met | Ser | Tyr | Gly 560 |
| Glu | Arg | Pro | Tyr | Trp 565 | Glu | Met | Thr | Asn | Gln 570 | Asp | Val | Ile | Lys 575 | Ala | Val |
| Glu | Glu | Gly | Tyr 580 | Arg | Leu | Pro | Ser | Pro 585 | Met | Asp | Cys | Pro | Ala 590 | Ala | Leu |
| Tyr | Gln | Leu 595 | Met | Leu | Asp | Cys | Trp 600 | Gln | Lys | Asp | Arg | Asn 605 | Ser | Arg | Pro |
| Lys | Phe 610 | Asp | Glu | Ile | Val | Ser 615 | Met | Leu | Asp | Lys | Leu 620 | Ile | Arg | Asn | Pro |
| Ser 625 | Ser | Leu | Lys | Thr | Leu 630 | Val | Asn | Ala | Ser | Ser 635 | Arg | Val | Ser | Asn | Leu 640 |
| Leu | Val | Glu | His | Ser 645 | Pro | Val | Gly | Ser | Gly 650 | Ala | Tyr | Arg | Ser | Val 655 | Gly |
| Glu | Trp | Leu | Glu 660 | Ala | Ile | Lys | Met | Gly 665 | Arg | Tyr | Thr | Glu | Ile 670 | Phe | Met |
| Glu | Asn | Gly 675 | Tyr | Ser | Ser | Met | Asp 680 | Ser | Val | Ala | Gln | Val 685 | Thr | Leu | Glu |
| Asp | Leu 690 | Arg | Arg | Leu | Gly | Val 695 | Thr | Leu | Val | Gly | His 700 | Gln | Lys | Lys | Ile |
| Met 705 | Asn | Ser | Leu | Gln | Glu 710 | Met | Lys | Val | Gln | Leu 715 | Val | Asn | Gly | Met | Val 720 |
| Pro | Leu | | | | | | | | | | | | | | |

( 2 ) INFORMATION FOR SEQ ID NO:5:

( i ) SEQUENCE CHARACTERISTICS:
        ( A ) LENGTH: 2820 base pairs
        ( B ) TYPE: nucleic acid
        ( C ) STRANDEDNESS: both
        ( D ) TOPOLOGY: linear ( i x ) FEATURE:

-continued ( A ) NAME/KEY: CDS
( B ) LOCATION: 2..2548

( x i ) SEQUENCE DESCRIPTION: SEQ ID NO:5:

```
C  GGA GAG AGC CAG TTT GCC AAG ATT GAC ACC ATT GCT GCT GAT GAG        46
   Gly Glu Ser Gln Phe Ala Lys Ile Asp Thr Ile Ala Ala Asp Glu
   1               5                   10                  15

AGC TTC ACC CAG GTG GAC ATT GGT GAC AGG ATC ATG AAG CTG AAT ACA       94
Ser Phe Thr Gln Val Asp Ile Gly Asp Arg Ile Met Lys Leu Asn Thr
                    20                  25                  30

GAG GTG CGG GAC GTG GGG CCT CTC AGC AAG AAA GGG TTT TAC TTG GCT       142
Glu Val Arg Asp Val Gly Pro Leu Ser Lys Lys Gly Phe Tyr Leu Ala
                35                  40                  45

TTC CAG GAC GTC GGT GCC TGC ATT GCT TTG GTG TCT GTT CGT GTC TTC       190
Phe Gln Asp Val Gly Ala Cys Ile Ala Leu Val Ser Val Arg Val Phe
            50                  55                  60

TAT AAG AAG TGC CCA CTG ACA GTT CGA AAC CTG GCA CAG TTT CCA GAC       238
Tyr Lys Lys Cys Pro Leu Thr Val Arg Asn Leu Ala Gln Phe Pro Asp
        65                  70                  75

ACC ATT ACT GGG GCT GAT ACA TCC TCT CTG GTG GAG GTT CGT GGC TCC       286
Thr Ile Thr Gly Ala Asp Thr Ser Ser Leu Val Glu Val Arg Gly Ser
80                  85                  90                  95

TGT GTC AAC AAC TCG GAA GAG AAG GAC GTG CCA AAA ATG TAC TGC GGG       334
Cys Val Asn Asn Ser Glu Glu Lys Asp Val Pro Lys Met Tyr Cys Gly
                100                 105                 110

GCA GAT GGT GAA TGG CTG GTA CCC ATT GGC AAC TGT CTG TGC AAT GCT       382
Ala Asp Gly Glu Trp Leu Val Pro Ile Gly Asn Cys Leu Cys Asn Ala
                115                 120                 125

GGC TAT GAA GAA CGC AAT GGT GAA TGC CAA GCT TGC AAA ATC GGA TAC       430
Gly Tyr Glu Glu Arg Asn Gly Glu Cys Gln Ala Cys Lys Ile Gly Tyr
            130                 135                 140

TAC AAG GCG CTC TCA ACA GAT GTT GCA TGT GCC AAA TGC CCG CCT CAC       478
Tyr Lys Ala Leu Ser Thr Asp Val Ala Cys Ala Lys Cys Pro Pro His
        145                 150                 155

AGC TAC TCC ATC TGG GAA GGC TCT ACC TCC TGC ACC TGT GAT CGG GGC       526
Ser Tyr Ser Ile Trp Glu Gly Ser Thr Ser Cys Thr Cys Asp Arg Gly
160                 165                 170                 175

TTC TTC CGA GCA GAA AAT GAT GCT GCA TCC ATG CCC TGC ACT CGC CCT       574
Phe Phe Arg Ala Glu Asn Asp Ala Ala Ser Met Pro Cys Thr Arg Pro
                180                 185                 190

CCA TCC GCA CCC CAG AAC CTG ATT TCC AAC GTC AAC GAG ACG TCA GTG       622
Pro Ser Ala Pro Gln Asn Leu Ile Ser Asn Val Asn Glu Thr Ser Val
                195                 200                 205

AAC TTG GAG TGG AGC GCC CCA CAG AAC AAG GGA GGA CGG GAC GAC ATC       670
Asn Leu Glu Trp Ser Ala Pro Gln Asn Lys Gly Gly Arg Asp Asp Ile
            210                 215                 220

TCC TAC AAC GTG GTG TGC AAG CGC TGC GGG GCA GGG GAG CCC AGC CAC       718
Ser Tyr Asn Val Val Cys Lys Arg Cys Gly Ala Gly Glu Pro Ser His
        225                 230                 235

TGC CGG TCC TGT GGC AGT GGT GTA CAT TTC AGC CCC CAG CAG AAC GGG       766
Cys Arg Ser Cys Gly Ser Gly Val His Phe Ser Pro Gln Gln Asn Gly
240                 245                 250                 255

CTG AAA ACC ACG AAG GTT TCC ATC ACT GAC CTC CTG GCA CAC ACC AAC       814
Leu Lys Thr Thr Lys Val Ser Ile Thr Asp Leu Leu Ala His Thr Asn
                260                 265                 270

TAC ACC TTT GAG GTC TGG GCA GTG AAT GGA GTG TCC AAG CAC AAC CCC       862
Tyr Thr Phe Glu Val Trp Ala Val Asn Gly Val Ser Lys His Asn Pro
                275                 280                 285

AGC CAG GAC CAA GCT GTG TCG GTC ACT GTG ACA ACT AAC CAA GCA GCT       910
Ser Gln Asp Gln Ala Val Ser Val Thr Val Thr Thr Asn Gln Ala Ala
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 290 |     |     |     |     | 295 |     |     |     |     |     | 300 |     |     |      |
| CCA | TCC | CCA | ATT | GCA | TTG | ATC | CAG | GCT | AAA | GAG | ATA | ACG | AGG | CAC | AGC | 958  |
| Pro | Ser | Pro | Ile | Ala | Leu | Ile | Gln | Ala | Lys | Glu | Ile | Thr | Arg | His | Ser |      |
|     | 305 |     |     |     |     | 310 |     |     |     |     | 315 |     |     |     |     |      |
| GTT | GCC | TTG | GCC | TGG | CTG | GAA | CCT | GAC | AGG | CCC | AAT | GGA | GTC | ATC | CTG | 1006 |
| Val | Ala | Leu | Ala | Trp | Leu | Glu | Pro | Asp | Arg | Pro | Asn | Gly | Val | Ile | Leu |      |
| 320 |     |     |     |     | 325 |     |     |     |     | 330 |     |     |     |     | 335 |      |
| GAG | TAC | GAA | GTC | AAG | TAC | TAC | GAA | AAG | GAC | CAA | AAC | GAG | CGC | ACG | TAT | 1054 |
| Glu | Tyr | Glu | Val | Lys | Tyr | Tyr | Glu | Lys | Asp | Gln | Asn | Glu | Arg | Thr | Tyr |      |
|     |     |     |     | 340 |     |     |     |     | 345 |     |     |     |     | 350 |     |      |
| CGC | ATT | GTG | AAG | ACA | GCC | TCC | AGG | AAT | ACT | GAC | ATC | AAA | GGT | TTG | AAC | 1102 |
| Arg | Ile | Val | Lys | Thr | Ala | Ser | Arg | Asn | Thr | Asp | Ile | Lys | Gly | Leu | Asn |      |
|     |     |     | 355 |     |     |     |     | 360 |     |     |     |     | 365 |     |     |      |
| CCC | CTG | ACT | TCA | TAT | GTA | TTT | CAT | GTG | CGG | GCC | AGG | ACA | GCA | GCA | GGA | 1150 |
| Pro | Leu | Thr | Ser | Tyr | Val | Phe | His | Val | Arg | Ala | Arg | Thr | Ala | Ala | Gly |      |
|     |     | 370 |     |     |     |     | 375 |     |     |     |     | 380 |     |     |     |      |
| TAC | GGA | GAC | TTC | AGT | GGG | CCG | TTT | GAG | TTC | ACA | ACT | AAC | ACA | GTT | CCT | 1198 |
| Tyr | Gly | Asp | Phe | Ser | Gly | Pro | Phe | Glu | Phe | Thr | Thr | Asn | Thr | Val | Pro |      |
| 385 |     |     |     |     | 390 |     |     |     |     | 395 |     |     |     |     |     |      |
| TCC | CCC | ATC | ATT | GGC | GAT | GGT | ACC | AAT | CCC | ACA | GTG | CTG | CTT | GTT | TCA | 1246 |
| Ser | Pro | Ile | Ile | Gly | Asp | Gly | Thr | Asn | Pro | Thr | Val | Leu | Leu | Val | Ser |      |
| 400 |     |     |     |     | 405 |     |     |     |     | 410 |     |     |     |     | 415 |      |
| GTG | GCT | GGC | AGT | GTT | GTT | CTT | GTG | GTC | ATT | CTC | ATT | GCA | GCC | TTT | GTC | 1294 |
| Val | Ala | Gly | Ser | Val | Val | Leu | Val | Val | Ile | Leu | Ile | Ala | Ala | Phe | Val |      |
|     |     |     |     | 420 |     |     |     |     | 425 |     |     |     |     | 430 |     |      |
| ATC | AGC | AGG | AGG | CGC | AGC | AAA | TAC | AGT | AAA | GCT | AAG | CAA | GAG | GCA | GAT | 1342 |
| Ile | Ser | Arg | Arg | Arg | Ser | Lys | Tyr | Ser | Lys | Ala | Lys | Gln | Glu | Ala | Asp |      |
|     |     |     | 435 |     |     |     |     | 440 |     |     |     |     | 445 |     |     |      |
| GAG | GAG | AAA | CAT | TTG | AAC | CAA | GGT | GTC | AGA | ACA | TAT | GTG | GAT | CCT | TTT | 1390 |
| Glu | Glu | Lys | His | Leu | Asn | Gln | Gly | Val | Arg | Thr | Tyr | Val | Asp | Pro | Phe |      |
|     |     | 450 |     |     |     |     | 455 |     |     |     |     | 460 |     |     |     |      |
| ACA | TAT | GAG | GAT | CCA | AAT | CAA | GCT | GTG | AGG | GAA | TTT | GCC | AAA | GAA | ATT | 1438 |
| Thr | Tyr | Glu | Asp | Pro | Asn | Gln | Ala | Val | Arg | Glu | Phe | Ala | Lys | Glu | Ile |      |
| 465 |     |     |     |     | 470 |     |     |     |     | 475 |     |     |     |     |     |      |
| GAT | GCC | TCC | TGC | ATA | AAG | ATT | GAG | AAA | GTT | ATT | GGT | GTG | GGG | GAA | TTT | 1486 |
| Asp | Ala | Ser | Cys | Ile | Lys | Ile | Glu | Lys | Val | Ile | Gly | Val | Gly | Glu | Phe |      |
| 480 |     |     |     |     | 485 |     |     |     |     | 490 |     |     |     |     | 495 |      |
| GGT | GAA | GTA | TGC | AGT | GGA | CGT | CTC | AAA | GTT | CCA | GGA | AAA | AGA | GAA | ATC | 1534 |
| Gly | Glu | Val | Cys | Ser | Gly | Arg | Leu | Lys | Val | Pro | Gly | Lys | Arg | Glu | Ile |      |
|     |     |     |     | 500 |     |     |     |     | 505 |     |     |     |     | 510 |     |      |
| TGT | GTG | GCT | ATC | AAG | ACT | CTG | AAA | GCT | GGT | TAC | ACT | GAC | AAA | CAA | CGG | 1582 |
| Cys | Val | Ala | Ile | Lys | Thr | Leu | Lys | Ala | Gly | Tyr | Thr | Asp | Lys | Gln | Arg |      |
|     |     |     | 515 |     |     |     |     | 520 |     |     |     |     | 525 |     |     |      |
| AGA | GAC | TTC | CTG | AGT | GAG | GCC | AGC | ATC | ATG | GGA | CAA | TTT | GAC | CAC | CCC | 1630 |
| Arg | Asp | Phe | Leu | Ser | Glu | Ala | Ser | Ile | Met | Gly | Gln | Phe | Asp | His | Pro |      |
|     |     | 530 |     |     |     |     | 535 |     |     |     |     | 540 |     |     |     |      |
| AAT | ATC | ATC | CAC | TTG | GAA | GGC | GTT | GTT | ACT | AAA | TGT | AAA | CCA | GTA | ATG | 1678 |
| Asn | Ile | Ile | His | Leu | Glu | Gly | Val | Val | Thr | Lys | Cys | Lys | Pro | Val | Met |      |
|     | 545 |     |     |     |     | 550 |     |     |     |     | 555 |     |     |     |     |      |
| ATC | ATA | ACT | GAG | TAC | ATG | GAG | AAT | GGC | TCC | TTG | GAT | GCC | TTC | CTC | CGG | 1726 |
| Ile | Ile | Thr | Glu | Tyr | Met | Glu | Asn | Gly | Ser | Leu | Asp | Ala | Phe | Leu | Arg |      |
| 560 |     |     |     |     | 565 |     |     |     |     | 570 |     |     |     |     | 575 |      |
| AAG | AAT | GAT | GGC | AGA | TTT | ACA | GTA | ATC | CAG | TTG | GTG | GGG | ATG | CTT | CGT | 1774 |
| Lys | Asn | Asp | Gly | Arg | Phe | Thr | Val | Ile | Gln | Leu | Val | Gly | Met | Leu | Arg |      |
|     |     |     |     | 580 |     |     |     |     | 585 |     |     |     |     | 590 |     |      |
| GGC | ATC | GGC | TCA | GGA | ATG | AAG | TAT | CTG | TCT | GAC | ATG | AGC | TAT | GTG | CAT | 1822 |
| Gly | Ile | Gly | Ser | Gly | Met | Lys | Tyr | Leu | Ser | Asp | Met | Ser | Tyr | Val | His |      |
|     |     |     | 595 |     |     |     |     | 600 |     |     |     |     | 605 |     |     |      |
| CGG | GAT | CTA | GCT | GCT | CGA | AAC | ATA | CTG | GTC | AAC | AGC | AAC | TTG | GTC | TGC | 1870 |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Arg | Asp | Leu | Ala | Ala | Arg | Asn | Ile | Leu | Val | Asn | Ser | Asn | Leu | Val | Cys |      |
|     |     | 610 |     |     |     |     | 615 |     |     |     |     | 620 |     |     |     |      |
| AAA | GTG | TCT | GAC | TTT | GGC | ATG | TCC | CGT | GTC | CTG | GAA | GAT | GAC | CCT | GAG | 1918 |
| Lys | Val | Ser | Asp | Phe | Gly | Met | Ser | Arg | Val | Leu | Glu | Asp | Asp | Pro | Glu |      |
|     | 625 |     |     |     | 630 |     |     |     |     | 635 |     |     |     |     |     |      |
| GCA | GCT | TAT | ACC | ACA | CGG | GGT | GGC | AAG | ATC | CCT | ATC | CGA | TGG | ACT | GCA | 1966 |
| Ala | Ala | Tyr | Thr | Thr | Arg | Gly | Gly | Lys | Ile | Pro | Ile | Arg | Trp | Thr | Ala |      |
| 640 |     |     |     |     | 645 |     |     |     |     | 650 |     |     |     |     | 655 |      |
| CCA | GAG | GCA | ATT | GCC | TAC | CGT | AAA | TTT | ACA | TCG | GCT | AGT | GAC | GTG | TGG | 2014 |
| Pro | Glu | Ala | Ile | Ala | Tyr | Arg | Lys | Phe | Thr | Ser | Ala | Ser | Asp | Val | Trp |      |
|     |     |     |     | 660 |     |     |     |     | 665 |     |     |     |     | 670 |     |      |
| AGC | TAT | GGC | ATC | GTC | ATG | TGG | GAA | GTG | ATG | TCC | TAT | GGA | GAG | AGA | CCT | 2062 |
| Ser | Tyr | Gly | Ile | Val | Met | Trp | Glu | Val | Met | Ser | Tyr | Gly | Glu | Arg | Pro |      |
|     |     |     | 675 |     |     |     |     | 680 |     |     |     |     | 685 |     |     |      |
| TAC | TGG | GAT | ATG | TCC | AAT | CAA | GAC | GTT | ATT | AAA | GCC | ATT | GAG | GAA | GGG | 2110 |
| Tyr | Trp | Asp | Met | Ser | Asn | Gln | Asp | Val | Ile | Lys | Ala | Ile | Glu | Glu | Gly |      |
|     |     |     | 690 |     |     |     | 695 |     |     |     |     | 700 |     |     |     |      |
| TAT | CGG | TTG | CCA | CCC | CCA | ATG | GAC | TGC | CCC | ATT | GCT | CTC | CAT | CAG | CTG | 2158 |
| Tyr | Arg | Leu | Pro | Pro | Pro | Met | Asp | Cys | Pro | Ile | Ala | Leu | His | Gln | Leu |      |
|     | 705 |     |     |     |     | 710 |     |     |     |     | 715 |     |     |     |     |      |
| ATG | TTA | GAC | TGC | TGG | CAG | AAG | GAA | CGC | AGC | GAC | AGA | CCT | AAA | TTT | GGA | 2206 |
| Met | Leu | Asp | Cys | Trp | Gln | Lys | Glu | Arg | Ser | Asp | Arg | Pro | Lys | Phe | Gly |      |
| 720 |     |     |     |     | 725 |     |     |     |     | 730 |     |     |     |     | 735 |      |
| CAG | ATT | GTC | AAC | ATG | CTG | GAC | AAA | CTC | ATC | CGC | AAC | CCT | AAC | AGC | CTG | 2254 |
| Gln | Ile | Val | Asn | Met | Leu | Asp | Lys | Leu | Ile | Arg | Asn | Pro | Asn | Ser | Leu |      |
|     |     |     |     | 740 |     |     |     |     | 745 |     |     |     |     | 750 |     |      |
| AAG | AGG | ACA | GGC | AGC | GAG | AGC | TCC | AGA | CCC | AGC | ACA | GCC | CTG | CTG | GAT | 2302 |
| Lys | Arg | Thr | Gly | Ser | Glu | Ser | Ser | Arg | Pro | Ser | Thr | Ala | Leu | Leu | Asp |      |
|     |     |     | 755 |     |     |     |     | 760 |     |     |     |     | 765 |     |     |      |
| CCC | AGC | TCC | CCG | GAG | TTC | TCG | GCG | GTT | GTT | TCT | GTC | AGT | GAC | TGG | CTC | 2350 |
| Pro | Ser | Ser | Pro | Glu | Phe | Ser | Ala | Val | Val | Ser | Val | Ser | Asp | Trp | Leu |      |
|     |     | 770 |     |     |     |     | 775 |     |     |     |     | 780 |     |     |     |      |
| CAA | GCC | ATT | AAA | ATG | GAG | CGA | TAC | AAG | GAT | AAC | TTC | ACA | GCT | GCT | GGC | 2398 |
| Gln | Ala | Ile | Lys | Met | Glu | Arg | Tyr | Lys | Asp | Asn | Phe | Thr | Ala | Ala | Gly |      |
|     | 785 |     |     |     |     | 790 |     |     |     |     | 795 |     |     |     |     |      |
| TAT | ACC | ACC | CTA | GAG | GCT | GTG | GTG | CAT | ATG | AAC | CAG | GAC | GAC | CTG | GCC | 2446 |
| Tyr | Thr | Thr | Leu | Glu | Ala | Val | Val | His | Met | Asn | Gln | Asp | Asp | Leu | Ala |      |
| 800 |     |     |     |     | 805 |     |     |     |     | 810 |     |     |     |     | 815 |      |
| AGG | ATC | GGG | ATC | ACT | GCC | ATC | ACA | CAC | CAG | AAC | AAG | ATC | TTG | AGC | AGC | 2494 |
| Arg | Ile | Gly | Ile | Thr | Ala | Ile | Thr | His | Gln | Asn | Lys | Ile | Leu | Ser | Ser |      |
|     |     |     |     | 820 |     |     |     |     | 825 |     |     |     |     | 830 |     |      |
| GTT | CAA | GCC | ATG | CGC | AGC | CAA | ATG | CAA | CAG | ATG | CAC | GGC | AGG | ATG | GTG | 2542 |
| Val | Gln | Ala | Met | Arg | Ser | Gln | Met | Gln | Gln | Met | His | Gly | Arg | Met | Val |      |
|     |     |     | 835 |     |     |     |     | 840 |     |     |     |     | 845 |     |     |      |

| | | | |
|---|---|---|---|
| CCC GTC TGAGCCAGTA CTGAATAAAC TCAAAACTCT TGAAATTAGT TTACCTCATC | | | 2598 |
| Pro Val | | | |
| CATGCACTTT AATTGAAGAA CTGCACTTTT TTTACTTCGT CTCCTCGCCC GTTGAAATAA | | | 2658 |
| AGATCTGCAG CATTGCTTGA TGTACAGATT GTGGAAACCG AGCGTGTGTT GGGAGGGGGG | | | 2718 |
| CCTCCAGAAA TGACAAGCCG TCATTTTAAA CCAGACCTGG AACAAATTGT TCTTGGAAC | | | 2778 |
| ATACTTCTCT GTTGATCAAC GATATGTAAA ATACATGTAT CC | | | 2820 |

( 2 ) INFORMATION FOR SEQ ID NO:6:

( i ) SEQUENCE CHARACTERISTICS:
        ( A ) LENGTH: 849 amino acids
        ( B ) TYPE: amino acid
        ( D ) TOPOLOGY: linear ( i i ) MOLECULE TYPE: protein (xi) SEQUENCE DESCRIPTION: SEQ ID NO:6:

```
Gly Glu Ser Gln Phe Ala Lys Ile Asp Thr Ile Ala Ala Asp Glu Ser
 1               5                  10                  15

Phe Thr Gln Val Asp Ile Gly Asp Arg Ile Met Lys Leu Asn Thr Glu
                20                  25                  30

Val Arg Asp Val Gly Pro Leu Ser Lys Lys Gly Phe Tyr Leu Ala Phe
            35                  40                  45

Gln Asp Val Gly Ala Cys Ile Ala Leu Val Ser Val Arg Val Phe Tyr
        50                  55                  60

Lys Lys Cys Pro Leu Thr Val Arg Asn Leu Ala Gln Phe Pro Asp Thr
65                  70                  75                  80

Ile Thr Gly Ala Asp Thr Ser Ser Leu Val Glu Val Arg Gly Ser Cys
                85                  90                  95

Val Asn Asn Ser Glu Glu Lys Asp Val Pro Lys Met Tyr Cys Gly Ala
               100                 105                 110

Asp Gly Glu Trp Leu Val Pro Ile Gly Asn Cys Leu Cys Asn Ala Gly
           115                 120                 125

Tyr Glu Glu Arg Asn Gly Glu Cys Gln Ala Cys Lys Ile Gly Tyr Tyr
           130                 135                 140

Lys Ala Leu Ser Thr Asp Val Ala Cys Ala Lys Cys Pro Pro His Ser
145                 150                 155                 160

Tyr Ser Ile Trp Glu Gly Ser Thr Ser Cys Thr Cys Asp Arg Gly Phe
                165                 170                 175

Phe Arg Ala Glu Asn Asp Ala Ala Ser Met Pro Cys Thr Arg Pro Pro
           180                 185                 190

Ser Ala Pro Gln Asn Leu Ile Ser Asn Val Asn Glu Thr Ser Val Asn
       195                 200                 205

Leu Glu Trp Ser Ala Pro Gln Asn Lys Gly Gly Arg Asp Asp Ile Ser
210                 215                 220

Tyr Asn Val Val Cys Lys Arg Cys Gly Ala Gly Glu Pro Ser His Cys
225                 230                 235                 240

Arg Ser Cys Gly Ser Gly Val His Phe Ser Pro Gln Gln Asn Gly Leu
           245                 250                 255

Lys Thr Thr Lys Val Ser Ile Thr Asp Leu Leu Ala His Thr Asn Tyr
           260                 265                 270

Thr Phe Glu Val Trp Ala Val Asn Gly Val Ser Lys His Asn Pro Ser
       275                 280                 285

Gln Asp Gln Ala Val Ser Val Thr Val Thr Thr Asn Gln Ala Ala Pro
   290                 295                 300

Ser Pro Ile Ala Leu Ile Gln Ala Lys Glu Ile Thr Arg His Ser Val
305                 310                 315                 320

Ala Leu Ala Trp Leu Glu Pro Asp Arg Pro Asn Gly Val Ile Leu Glu
                325                 330                 335

Tyr Glu Val Lys Tyr Tyr Glu Lys Asp Gln Asn Glu Arg Thr Tyr Arg
           340                 345                 350

Ile Val Lys Thr Ala Ser Arg Asn Thr Asp Ile Lys Gly Leu Asn Pro
       355                 360                 365

Leu Thr Ser Tyr Val Phe His Val Arg Ala Arg Thr Ala Ala Gly Tyr
   370                 375                 380

Gly Asp Phe Ser Gly Pro Phe Glu Phe Thr Thr Asn Thr Val Pro Ser
385                 390                 395                 400

Pro Ile Ile Gly Asp Gly Thr Asn Pro Thr Val Leu Leu Val Ser Val
```

-continued

|     |     |     |     | 405 |     |     |     | 410 |     |     |     | 415 |     |     |
|-----|-----|-----|-----|-----|-----|-----|-----|-----|-----|-----|-----|-----|-----|-----|
| Ala | Gly | Ser | Val | Val | Leu | Val | Val | Ile | Leu | Ile | Ala | Ala | Phe | Val | Ile |
|     |     |     | 420 |     |     |     |     | 425 |     |     |     |     | 430 |     |     |
| Ser | Arg | Arg | Arg | Ser | Lys | Tyr | Ser | Lys | Ala | Lys | Gln | Glu | Ala | Asp | Glu |
|     |     | 435 |     |     |     |     | 440 |     |     |     |     | 445 |     |     |     |
| Glu | Lys | His | Leu | Asn | Gln | Gly | Val | Arg | Thr | Tyr | Val | Asp | Pro | Phe | Thr |
|     | 450 |     |     |     |     | 455 |     |     |     |     | 460 |     |     |     |     |
| Tyr | Glu | Asp | Pro | Asn | Gln | Ala | Val | Arg | Glu | Phe | Ala | Lys | Glu | Ile | Asp |
| 465 |     |     |     |     | 470 |     |     |     |     | 475 |     |     |     |     | 480 |
| Ala | Ser | Cys | Ile | Lys | Ile | Glu | Lys | Val | Ile | Gly | Val | Gly | Glu | Phe | Gly |
|     |     |     |     | 485 |     |     |     |     | 490 |     |     |     |     | 495 |     |
| Glu | Val | Cys | Ser | Gly | Arg | Leu | Lys | Val | Pro | Gly | Lys | Arg | Glu | Ile | Cys |
|     |     |     | 500 |     |     |     |     | 505 |     |     |     |     | 510 |     |     |
| Val | Ala | Ile | Lys | Thr | Leu | Lys | Ala | Gly | Tyr | Thr | Asp | Lys | Gln | Arg | Arg |
|     |     | 515 |     |     |     |     | 520 |     |     |     |     | 525 |     |     |     |
| Asp | Phe | Leu | Ser | Glu | Ala | Ser | Ile | Met | Gly | Gln | Phe | Asp | His | Pro | Asn |
|     | 530 |     |     |     |     | 535 |     |     |     |     | 540 |     |     |     |     |
| Ile | Ile | His | Leu | Glu | Gly | Val | Val | Thr | Lys | Cys | Lys | Pro | Val | Met | Ile |
| 545 |     |     |     |     | 550 |     |     |     |     | 555 |     |     |     |     | 560 |
| Ile | Thr | Glu | Tyr | Met | Glu | Asn | Gly | Ser | Leu | Asp | Ala | Phe | Leu | Arg | Lys |
|     |     |     |     | 565 |     |     |     |     | 570 |     |     |     |     | 575 |     |
| Asn | Asp | Gly | Arg | Phe | Thr | Val | Ile | Gln | Leu | Val | Gly | Met | Leu | Arg | Gly |
|     |     |     | 580 |     |     |     |     | 585 |     |     |     |     | 590 |     |     |
| Ile | Gly | Ser | Gly | Met | Lys | Tyr | Leu | Ser | Asp | Met | Ser | Tyr | Val | His | Arg |
|     |     | 595 |     |     |     |     | 600 |     |     |     |     | 605 |     |     |     |
| Asp | Leu | Ala | Ala | Arg | Asn | Ile | Leu | Val | Asn | Ser | Asn | Leu | Val | Cys | Lys |
|     | 610 |     |     |     |     | 615 |     |     |     |     | 620 |     |     |     |     |
| Val | Ser | Asp | Phe | Gly | Met | Ser | Arg | Val | Leu | Glu | Asp | Asp | Pro | Glu | Ala |
| 625 |     |     |     |     | 630 |     |     |     |     | 635 |     |     |     |     | 640 |
| Ala | Tyr | Thr | Thr | Arg | Gly | Gly | Lys | Ile | Pro | Ile | Arg | Trp | Thr | Ala | Pro |
|     |     |     |     | 645 |     |     |     |     | 650 |     |     |     |     | 655 |     |
| Glu | Ala | Ile | Ala | Tyr | Arg | Lys | Phe | Thr | Ser | Ala | Ser | Asp | Val | Trp | Ser |
|     |     |     | 660 |     |     |     |     | 665 |     |     |     |     | 670 |     |     |
| Tyr | Gly | Ile | Val | Met | Trp | Glu | Val | Met | Ser | Tyr | Gly | Glu | Arg | Pro | Tyr |
|     |     | 675 |     |     |     |     | 680 |     |     |     |     | 685 |     |     |     |
| Trp | Asp | Met | Ser | Asn | Gln | Asp | Val | Ile | Lys | Ala | Ile | Glu | Glu | Gly | Tyr |
|     | 690 |     |     |     |     | 695 |     |     |     |     | 700 |     |     |     |     |
| Arg | Leu | Pro | Pro | Pro | Met | Asp | Cys | Pro | Ile | Ala | Leu | His | Gln | Leu | Met |
| 705 |     |     |     |     | 710 |     |     |     |     | 715 |     |     |     |     | 720 |
| Leu | Asp | Cys | Trp | Gln | Lys | Glu | Arg | Ser | Asp | Arg | Pro | Lys | Phe | Gly | Gln |
|     |     |     |     | 725 |     |     |     |     | 730 |     |     |     |     | 735 |     |
| Ile | Val | Asn | Met | Leu | Asp | Lys | Leu | Ile | Arg | Asn | Pro | Asn | Ser | Leu | Lys |
|     |     |     | 740 |     |     |     |     | 745 |     |     |     |     | 750 |     |     |
| Arg | Thr | Gly | Ser | Glu | Ser | Ser | Arg | Pro | Ser | Thr | Ala | Leu | Leu | Asp | Pro |
|     |     | 755 |     |     |     |     | 760 |     |     |     |     | 765 |     |     |     |
| Ser | Ser | Pro | Glu | Phe | Ser | Ala | Val | Val | Ser | Val | Ser | Asp | Trp | Leu | Gln |
|     | 770 |     |     |     |     | 775 |     |     |     |     | 780 |     |     |     |     |
| Ala | Ile | Lys | Met | Glu | Arg | Tyr | Lys | Asp | Asn | Phe | Thr | Ala | Ala | Gly | Tyr |
| 785 |     |     |     |     | 790 |     |     |     |     | 795 |     |     |     |     | 800 |
| Thr | Thr | Leu | Glu | Ala | Val | Val | His | Met | Asn | Gln | Asp | Asp | Leu | Ala | Arg |
|     |     |     |     | 805 |     |     |     |     | 810 |     |     |     |     | 815 |     |
| Ile | Gly | Ile | Thr | Ala | Ile | Thr | His | Gln | Asn | Lys | Ile | Leu | Ser | Ser | Val |
|     |     |     | 820 |     |     |     |     | 825 |     |     |     |     | 830 |     |     |

| | | | | | | | | | | | | | | |
|---|---|---|---|---|---|---|---|---|---|---|---|---|---|---|
| Gln | Ala | Met | Arg | Ser | Gln | Met | Gln | Gln | Met | His | Gly | Arg | Met | Val | Pro |
| | | 835 | | | | 840 | | | | | 845 | | | | |

Val (2) INFORMATION FOR SEQ ID NO:7:

(i) SEQUENCE CHARACTERISTICS:
        (A) LENGTH: 3776 base pairs
        (B) TYPE: nucleic acid
        (C) STRANDEDNESS: both
        (D) TOPOLOGY: linear (ix) FEATURE:
        (A) NAME/KEY: CDS
        (B) LOCATION: 290..3208

(xi) SEQUENCE DESCRIPTION: SEQ ID NO:7:

```
CGGCTCTGAC  TTTGTGTTAA  CGGTTTATGG  ACTGGTTCCA  AAGAGCTCAA  AGGTACCAAA      60

ACACTCCAAG  CAACCTCTGA  ACCATTCAAG  CAAGTAGTGT  GTGTTTATTG  GATATGGTGG     120

AGTCTACAGA  GAATCTTCAT  GGATTCTAAT  GCTGACATCA  GTGCAAGAAG  AGTGTCAGGA     180

ATGGATTGGC  TCTGGCTGGT  TTGCTTCTTT  CATCTAGTCA  CTTCACTAGA  AGACCTGCAT     240

CCTGACCAAC  CGGAAAGGTG  AGCAGGATGA  GGCCATTGGT  GGTGCTGTC  ATG ACT        295
                                                          Met Thr
                                                          1
```

| | | | | | | | | | | | | | | | |
|---|---|---|---|---|---|---|---|---|---|---|---|---|---|---|---|
| GAA | ATA | CTT | CTG | GAT | ACA | ACT | GGA | GAA | ACC | TCA | GAG | ATT | GGC | TGG | ACC | 343 |
| Glu | Ile | Leu | Leu | Asp | Thr | Thr | Gly | Glu | Thr | Ser | Glu | Ile | Gly | Trp | Thr |
| | | | 5 | | | | | 10 | | | | | 15 | | |

| | | | | | | | | | | | | | | | |
|---|---|---|---|---|---|---|---|---|---|---|---|---|---|---|---|
| TCT | CAC | CCT | CCT | GAT | GGG | TGG | GAA | GAA | GTA | AGT | GTC | CGG | GAT | GAT | AAG | 391 |
| Ser | His | Pro | Pro | Asp | Gly | Trp | Glu | Glu | Val | Ser | Val | Arg | Asp | Asp | Lys |
| | | 20 | | | | | 25 | | | | | 30 | | | |

| | | | | | | | | | | | | | | | |
|---|---|---|---|---|---|---|---|---|---|---|---|---|---|---|---|
| GAG | CGC | CAG | ATC | CGA | ACC | TTT | CAA | GTT | TGT | AAC | ATG | GAT | GAA | CCA | GGT | 439 |
| Glu | Arg | Gln | Ile | Arg | Thr | Phe | Gln | Val | Cys | Asn | Met | Asp | Glu | Pro | Gly |
| 35 | | | | | 40 | | | | | 45 | | | | | 50 |

| | | | | | | | | | | | | | | | |
|---|---|---|---|---|---|---|---|---|---|---|---|---|---|---|---|
| CAG | AAT | AAC | TGG | TTG | CGT | ACT | CAC | TTC | ATA | GAG | CGA | CGT | GGA | GCC | CAC | 487 |
| Gln | Asn | Asn | Trp | Leu | Arg | Thr | His | Phe | Ile | Glu | Arg | Arg | Gly | Ala | His |
| | | | | 55 | | | | | 60 | | | | | 65 | |

| | | | | | | | | | | | | | | | |
|---|---|---|---|---|---|---|---|---|---|---|---|---|---|---|---|
| CGA | GTC | CAT | GTC | CGC | CTT | CAT | TTC | TCA | GTG | AGG | GAC | TGT | GCC | AGC | ATG | 535 |
| Arg | Val | His | Val | Arg | Leu | His | Phe | Ser | Val | Arg | Asp | Cys | Ala | Ser | Met |
| | | | 70 | | | | | 75 | | | | | 80 | | |

| | | | | | | | | | | | | | | | |
|---|---|---|---|---|---|---|---|---|---|---|---|---|---|---|---|
| CGT | ACT | GTG | GCC | TCT | ACT | TGC | AAA | GAG | ACT | TTC | ACA | CTC | TAC | TAC | CAC | 583 |
| Arg | Thr | Val | Ala | Ser | Thr | Cys | Lys | Glu | Thr | Phe | Thr | Leu | Tyr | Tyr | His |
| | | 85 | | | | | 90 | | | | | 95 | | | |

| | | | | | | | | | | | | | | | |
|---|---|---|---|---|---|---|---|---|---|---|---|---|---|---|---|
| CAG | TCA | GAT | GTC | GAC | ATA | GCC | TCT | CAG | GAA | CTG | CCA | GAG | TGG | CAT | GAA | 631 |
| Gln | Ser | Asp | Val | Asp | Ile | Ala | Ser | Gln | Glu | Leu | Pro | Glu | Trp | His | Glu |
| | 100 | | | | | 105 | | | | | 110 | | | | |

| | | | | | | | | | | | | | | | |
|---|---|---|---|---|---|---|---|---|---|---|---|---|---|---|---|
| GGC | CCC | TGG | ACC | AAG | GTG | GAT | ACT | ATT | GCA | GCT | GAT | GAA | AGC | TTT | TCC | 679 |
| Gly | Pro | Trp | Thr | Lys | Val | Asp | Thr | Ile | Ala | Ala | Asp | Glu | Ser | Phe | Ser |
| 115 | | | | | 120 | | | | | 125 | | | | | 130 |

| | | | | | | | | | | | | | | | |
|---|---|---|---|---|---|---|---|---|---|---|---|---|---|---|---|
| CAG | GTG | GAC | AGA | ACT | GGG | AAG | GTG | GTA | AGG | ATG | AAT | GTT | AAA | GTA | CGC | 727 |
| Gln | Val | Asp | Arg | Thr | Gly | Lys | Val | Val | Arg | Met | Asn | Val | Lys | Val | Arg |
| | | | | 135 | | | | | 140 | | | | | 145 | |

| | | | | | | | | | | | | | | | |
|---|---|---|---|---|---|---|---|---|---|---|---|---|---|---|---|
| AGC | TTT | GGG | CCA | CTC | ACA | AAG | CAT | GGC | TTC | TAC | CTG | GCC | TTC | CAG | GAC | 775 |
| Ser | Phe | Gly | Pro | Leu | Thr | Lys | His | Gly | Phe | Tyr | Leu | Ala | Phe | Gln | Asp |
| | | | 150 | | | | | 155 | | | | | 160 | | |

| | | | | | | | | | | | | | | | |
|---|---|---|---|---|---|---|---|---|---|---|---|---|---|---|---|
| TCA | GGA | GCC | TGT | ATG | TCC | CTG | GTG | GCA | GTC | CAA | GTC | TTT | TTC | TAC | AAG | 823 |
| Ser | Gly | Ala | Cys | Met | Ser | Leu | Val | Ala | Val | Gln | Val | Phe | Phe | Tyr | Lys |
| | | 165 | | | | | 170 | | | | | 175 | | | |

| | | | | | | | | | | | | | | | |
|---|---|---|---|---|---|---|---|---|---|---|---|---|---|---|---|
| TGT | CCA | GCT | GTG | GTG | AAA | GGA | TTT | GCC | TCC | TTC | CCT | GAA | ACT | TTT | GCT | 871 |
| Cys | Pro | Ala | Val | Val | Lys | Gly | Phe | Ala | Ser | Phe | Pro | Glu | Thr | Phe | Ala |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     | 180 |     |     |     |     | 185 |     |     |     |     | 190 |     |     |     |     |      |
| GGA | GGA | GAG | AGG | ACC | TCA | CTG | GTG | GAG | TCA | CTA | GGG | ACG | TGT | GTA | GCA | 919  |
| Gly | Gly | Glu | Arg | Thr | Ser | Leu | Val | Glu | Ser | Leu | Gly | Thr | Cys | Val | Ala |      |
| 195 |     |     |     |     | 200 |     |     |     |     | 205 |     |     |     |     | 210 |      |
| AAT | GCT | GAA | GAG | GCA | AGC | ACA | ACT | GGG | TCA | TCA | GGT | GTT | CGG | TTG | CAC | 967  |
| Asn | Ala | Glu | Glu | Ala | Ser | Thr | Thr | Gly | Ser | Ser | Gly | Val | Arg | Leu | His |      |
|     |     |     |     | 215 |     |     |     |     | 220 |     |     |     |     | 225 |     |      |
| TGC | AAT | GGA | GAA | GGA | GAG | TGG | ATG | GTG | GCC | ACT | GGA | CGA | TGC | TCT | TGC | 1015 |
| Cys | Asn | Gly | Glu | Gly | Glu | Trp | Met | Val | Ala | Thr | Gly | Arg | Cys | Ser | Cys |      |
|     |     |     |     | 230 |     |     |     |     | 235 |     |     |     |     | 240 |     |      |
| AAG | GCT | GGT | TAC | CAA | TCT | GTT | GAC | AAT | GAG | CAA | GCT | TGT | CAA | GCT | TGT | 1063 |
| Lys | Ala | Gly | Tyr | Gln | Ser | Val | Asp | Asn | Glu | Gln | Ala | Cys | Gln | Ala | Cys |      |
|     |     |     | 245 |     |     |     |     | 250 |     |     |     |     | 255 |     |     |      |
| CCC | ATT | GGT | TCC | TTT | AAA | GCA | TCT | GTG | GGA | GAT | GAC | CCT | TGC | CTT | CTC | 1111 |
| Pro | Ile | Gly | Ser | Phe | Lys | Ala | Ser | Val | Gly | Asp | Asp | Pro | Cys | Leu | Leu |      |
|     | 260 |     |     |     |     | 265 |     |     |     |     | 270 |     |     |     |     |      |
| TGC | CCT | GCC | CAC | AGC | CAT | GCT | CCA | CTG | CCA | CTG | CCA | GGT | TCC | ATT | GAA | 1159 |
| Cys | Pro | Ala | His | Ser | His | Ala | Pro | Leu | Pro | Leu | Pro | Gly | Ser | Ile | Glu |      |
| 275 |     |     |     |     | 280 |     |     |     |     | 285 |     |     |     |     | 290 |      |
| TGT | GTG | TGT | CAG | AGT | CAC | TAC | TAC | CGA | TCT | GCT | TCT | GAC | AAT | TCT | GAT | 1207 |
| Cys | Val | Cys | Gln | Ser | His | Tyr | Tyr | Arg | Ser | Ala | Ser | Asp | Asn | Ser | Asp |      |
|     |     |     |     | 295 |     |     |     |     | 300 |     |     |     |     | 305 |     |      |
| GCT | CCC | TGC | ACT | GGC | ATC | CCC | TCT | GCT | CCC | CGT | GAC | CTC | AGT | TAT | GAA | 1255 |
| Ala | Pro | Cys | Thr | Gly | Ile | Pro | Ser | Ala | Pro | Arg | Asp | Leu | Ser | Tyr | Glu |      |
|     |     |     | 310 |     |     |     |     | 315 |     |     |     |     | 320 |     |     |      |
| ATT | GTT | GGC | TCC | AAC | GTG | CTC | CTG | ACC | TGG | CGC | CTC | CCC | AAG | GAC | TTG | 1303 |
| Ile | Val | Gly | Ser | Asn | Val | Leu | Leu | Thr | Trp | Arg | Leu | Pro | Lys | Asp | Leu |      |
|     |     | 325 |     |     |     |     | 330 |     |     |     |     | 335 |     |     |     |      |
| GGT | GGC | CGC | AAG | GAT | GTC | TTC | TTC | AAT | GTC | ATC | TGC | AAG | GAA | TGC | CCA | 1351 |
| Gly | Gly | Arg | Lys | Asp | Val | Phe | Phe | Asn | Val | Ile | Cys | Lys | Glu | Cys | Pro |      |
|     | 340 |     |     |     |     | 345 |     |     |     |     | 350 |     |     |     |     |      |
| ACA | AGG | TCA | GCA | GGG | ACA | TGT | GTG | CGC | TGT | GGG | GAC | AAT | GTA | CAG | TTT | 1399 |
| Thr | Arg | Ser | Ala | Gly | Thr | Cys | Val | Arg | Cys | Gly | Asp | Asn | Val | Gln | Phe |      |
| 355 |     |     |     |     | 360 |     |     |     |     | 365 |     |     |     |     | 370 |      |
| GAA | CCA | CGC | CAA | GTG | GGC | CTG | ACA | GAA | AGT | CGT | GTT | CAA | GTC | TCC | AAC | 1447 |
| Glu | Pro | Arg | Gln | Val | Gly | Leu | Thr | Glu | Ser | Arg | Val | Gln | Val | Ser | Asn |      |
|     |     |     |     | 375 |     |     |     |     | 380 |     |     |     |     | 385 |     |      |
| CTA | TTG | GCC | CGT | GTG | CAG | TAC | ACT | TTT | GAG | ATC | CAG | GCT | GTC | AAT | TTG | 1495 |
| Leu | Leu | Ala | Arg | Val | Gln | Tyr | Thr | Phe | Glu | Ile | Gln | Ala | Val | Asn | Leu |      |
|     |     |     | 390 |     |     |     |     | 395 |     |     |     |     | 400 |     |     |      |
| GTG | ACT | GAG | TTG | AGT | TCA | GAA | GCA | CCC | CAG | TAT | GCT | ACC | ATC | AAC | GTT | 1543 |
| Val | Thr | Glu | Leu | Ser | Ser | Glu | Ala | Pro | Gln | Tyr | Ala | Thr | Ile | Asn | Val |      |
|     |     |     | 405 |     |     |     |     | 410 |     |     |     |     | 415 |     |     |      |
| AGC | ACC | AGC | CAG | TCA | GTG | CCC | TCC | GCA | ATC | CCT | ATG | ATG | CAT | CAG | GTG | 1591 |
| Ser | Thr | Ser | Gln | Ser | Val | Pro | Ser | Ala | Ile | Pro | Met | Met | His | Gln | Val |      |
|     |     | 420 |     |     |     |     | 425 |     |     |     |     | 430 |     |     |     |      |
| AGT | CGT | GCT | ACC | AGT | AGC | ATC | ACA | CTG | TCT | TGG | CCT | CAG | CCA | GAC | CAG | 1639 |
| Ser | Arg | Ala | Thr | Ser | Ser | Ile | Thr | Leu | Ser | Trp | Pro | Gln | Pro | Asp | Gln |      |
| 435 |     |     |     |     | 440 |     |     |     |     | 445 |     |     |     |     | 450 |      |
| CCC | AAT | GGG | GTT | ATC | CTG | GAT | TAC | CAG | CTA | CGG | TAC | TTT | GAC | AAG | GCA | 1687 |
| Pro | Asn | Gly | Val | Ile | Leu | Asp | Tyr | Gln | Leu | Arg | Tyr | Phe | Asp | Lys | Ala |      |
|     |     |     |     | 455 |     |     |     |     | 460 |     |     |     |     | 465 |     |      |
| GAA | GAT | GAG | GAT | AAT | TCA | TTT | ACT | TTG | ACT | AGT | GAA | ACT | AAC | ATG | GCC | 1735 |
| Glu | Asp | Glu | Asp | Asn | Ser | Phe | Thr | Leu | Thr | Ser | Glu | Thr | Asn | Met | Ala |      |
|     |     |     | 470 |     |     |     |     | 475 |     |     |     |     | 480 |     |     |      |
| ACT | ATA | TTA | AAT | CTG | AGT | CCA | GGC | AAG | ATC | TAT | GTC | TTC | CAA | GTA | CGA | 1783 |
| Thr | Ile | Leu | Asn | Leu | Ser | Pro | Gly | Lys | Ile | Tyr | Val | Phe | Gln | Val | Arg |      |
|     |     | 485 |     |     |     |     | 490 |     |     |     |     | 495 |     |     |     |      |
| GCT | AGA | ACA | GCA | GTG | GGT | TAT | GGC | CCA | TAC | AGT | GGA | AAG | ATG | TAT | TTC | 1831 |

```
Ala  Arg  Thr  Ala  Val  Gly  Tyr  Gly  Pro  Tyr  Ser  Gly  Lys  Met  Tyr  Phe
     500            505                     510

CAG  ACT  TTA  ATG  GCA  GGA  GAG  CAC  TCG  GAG  ATG  GCA  CAG  GAC  CGA  CTG   1879
Gln  Thr  Leu  Met  Ala  Gly  Glu  His  Ser  Glu  Met  Ala  Gln  Asp  Arg  Leu
515            520                     525                          530

CCA  CTT  ATT  GTG  GGC  TCA  GCA  CTT  GGT  GGT  CTG  GCA  TTC  TTG  GTA  ATT   1927
Pro  Leu  Ile  Val  Gly  Ser  Ala  Leu  Gly  Gly  Leu  Ala  Phe  Leu  Val  Ile
               535                     540                          545

GCT  GCC  ATT  GCC  ATT  CTT  GCC  ATC  ATC  TTC  AAG  AGT  AAA  AGG  CGA  GAG   1975
Ala  Ala  Ile  Ala  Ile  Leu  Ala  Ile  Ile  Phe  Lys  Ser  Lys  Arg  Arg  Glu
               550                     555                     560

ACT  CCA  TAC  ACA  GAC  CGC  CTG  CAG  CAG  TAT  ATC  AGT  ACA  CGA  GGA  CTT   2023
Thr  Pro  Tyr  Thr  Asp  Arg  Leu  Gln  Gln  Tyr  Ile  Ser  Thr  Arg  Gly  Leu
          565                     570                     575

GGA  GTG  AAG  TAT  TAC  ATT  GAT  CCT  TCC  ACG  TAT  GAA  GAT  CCC  AAT  GAA   2071
Gly  Val  Lys  Tyr  Tyr  Ile  Asp  Pro  Ser  Thr  Tyr  Glu  Asp  Pro  Asn  Glu
     580                     585                     590

GCT  ATT  CGA  GAG  TTT  GCC  AAA  GAG  ATA  GAT  GTG  TCC  TTC  ATC  AAA  ATT   2119
Ala  Ile  Arg  Glu  Phe  Ala  Lys  Glu  Ile  Asp  Val  Ser  Phe  Ile  Lys  Ile
595                     600                     605                     610

GAG  GAG  GTC  ATT  GGA  TCA  GGA  GAA  TTT  GGA  GAG  GTG  TGC  TTT  GGG  CGC   2167
Glu  Glu  Val  Ile  Gly  Ser  Gly  Glu  Phe  Gly  Glu  Val  Cys  Phe  Gly  Arg
               615                     620                     625

CTA  AAA  CAC  CCA  GGG  AAA  CGT  GAA  TAC  ACA  GTA  GCT  ATT  AAA  ACC  CTG   2215
Leu  Lys  His  Pro  Gly  Lys  Arg  Glu  Tyr  Thr  Val  Ala  Ile  Lys  Thr  Leu
          630                     635                     640

AAG  TCA  GGT  TAT  ACT  GAT  GAA  CAG  CGT  CGA  GAG  TTC  CTG  AGC  GAG  GCC   2263
Lys  Ser  Gly  Tyr  Thr  Asp  Glu  Gln  Arg  Arg  Glu  Phe  Leu  Ser  Glu  Ala
     645                     650                     655

AGC  ATC  ATG  GGG  CAA  TTT  GAG  CAT  CCC  AAT  GTC  ATC  CAC  CTG  GAG  GGC   2311
Ser  Ile  Met  Gly  Gln  Phe  Glu  His  Pro  Asn  Val  Ile  His  Leu  Glu  Gly
     660                     665                     670

GTG  GTC  ACC  AAA  AGC  CGA  CCA  GTC  ATG  ATT  GTC  ACA  GAA  TTC  ATG  GAG   2359
Val  Val  Thr  Lys  Ser  Arg  Pro  Val  Met  Ile  Val  Thr  Glu  Phe  Met  Glu
675                     680                     685                     690

AAT  GGA  TCA  CTG  GAT  TCC  TTC  CTC  AGG  GAG  AAG  GAG  GGA  CAG  TTC  AGT   2407
Asn  Gly  Ser  Leu  Asp  Ser  Phe  Leu  Arg  Glu  Lys  Glu  Gly  Gln  Phe  Ser
               695                     700                     705

GTG  TTA  CAG  CTG  GTG  GGA  ATG  CTA  CGA  GGG  ATT  GCA  GCA  GGC  ATG  CGC   2455
Val  Leu  Gln  Leu  Val  Gly  Met  Leu  Arg  Gly  Ile  Ala  Ala  Gly  Met  Arg
          710                     715                     720

TAC  CTT  TCA  GAC  ATG  AAC  TAT  GTG  CAT  CGT  GAT  CTC  GCA  GCA  CGT  AAC   2503
Tyr  Leu  Ser  Asp  Met  Asn  Tyr  Val  His  Arg  Asp  Leu  Ala  Ala  Arg  Asn
          725                     730                     735

ATC  TTA  GTC  AAC  AGT  AAC  CTT  GTA  TGC  AAG  GTG  TCA  GAC  TTT  GGT  TTG   2551
Ile  Leu  Val  Asn  Ser  Asn  Leu  Val  Cys  Lys  Val  Ser  Asp  Phe  Gly  Leu
     740                     745                     750

TCT  CGC  TTT  CTG  GAA  GAT  GAT  GCT  TCA  AAT  CCC  ACT  TAT  ACT  GGA  GCT   2599
Ser  Arg  Phe  Leu  Glu  Asp  Asp  Ala  Ser  Asn  Pro  Thr  Tyr  Thr  Gly  Ala
755                     760                     765                     770

CTG  GGT  TGC  AAA  ATC  CCC  ATC  CGT  TGG  ACT  GCC  CCT  GAA  GCT  GTC  CAG   2647
Leu  Gly  Cys  Lys  Ile  Pro  Ile  Arg  Trp  Thr  Ala  Pro  Glu  Ala  Val  Gln
               775                     780                     785

TAT  CGC  AAG  TTC  ACC  TCC  TCC  AGT  GAT  GTC  TGG  AGC  TAT  GGC  ATT  GTC   2695
Tyr  Arg  Lys  Phe  Thr  Ser  Ser  Ser  Asp  Val  Trp  Ser  Tyr  Gly  Ile  Val
          790                     795                     800

ATG  TGG  GAG  GTG  ATG  TCC  TAT  GGT  GAG  AGA  CCT  TAC  TGG  GAC  ATG  TCC   2743
Met  Trp  Glu  Val  Met  Ser  Tyr  Gly  Glu  Arg  Pro  Tyr  Trp  Asp  Met  Ser
          805                     810                     815
```

|  |  |  |  |  |  |  |  |  |  |  |  |  |  |  |  |
|--|--|--|--|--|--|--|--|--|--|--|--|--|--|--|--|
| AAC | CAG | GAT | GTA | ATT | AAT | GCC | ATT | GAC | CAG | GAC | TAT | CGC | CTG | CCA | CCA | 2791 |
| Asn | Gln | Asp | Val | Ile | Asn | Ala | Ile | Asp | Gln | Asp | Tyr | Arg | Leu | Pro | Pro |
|  | 820 |  |  |  | 825 |  |  |  | 830 |  |  |  |  |  |  |
| CCC | CCA | GAC | TGC | CCA | ACT | GTT | TTG | CAT | CTG | CTG | ATG | CTT | GAC | TGC | TGG | 2839 |
| Pro | Pro | Asp | Cys | Pro | Thr | Val | Leu | His | Leu | Leu | Met | Leu | Asp | Cys | Trp |
| 835 |  |  |  | 840 |  |  |  |  | 845 |  |  |  |  |  | 850 |
| CAG | AAG | GAT | CGA | GTC | CAG | AGA | CCA | AAA | TTT | GAA | CAA | ATA | GTC | AGT | GCC | 2887 |
| Gln | Lys | Asp | Arg | Val | Gln | Arg | Pro | Lys | Phe | Glu | Gln | Ile | Val | Ser | Ala |
|  |  |  |  | 855 |  |  |  |  | 860 |  |  |  |  | 865 |  |
| CTA | GAT | AAA | ATG | ATC | CGC | AAG | CCA | TCT | GCT | CTC | AAA | GCC | ACT | GGC | ACT | 2935 |
| Leu | Asp | Lys | Met | Ile | Arg | Lys | Pro | Ser | Ala | Leu | Lys | Ala | Thr | Gly | Thr |
|  |  |  | 870 |  |  |  |  | 875 |  |  |  |  | 880 |  |  |
| GGG | AGC | AGC | AGA | CCA | TCT | CAG | CCT | CTC | CTG | AGC | AAC | TCC | CCT | CCA | GAT | 2983 |
| Gly | Ser | Ser | Arg | Pro | Ser | Gln | Pro | Leu | Leu | Ser | Asn | Ser | Pro | Pro | Asp |
|  |  | 885 |  |  |  | 890 |  |  |  |  | 895 |  |  |  |  |
| TTT | CCT | TCA | CTC | AGC | AAT | GCC | CAC | GAG | TGG | TTG | GAT | GCC | ATC | AAG | ATG | 3031 |
| Phe | Pro | Ser | Leu | Ser | Asn | Ala | His | Glu | Trp | Leu | Asp | Ala | Ile | Lys | Met |
|  | 900 |  |  |  |  | 905 |  |  |  |  | 910 |  |  |  |  |
| GGT | CGT | TAC | AAG | GAG | AAT | TTT | GAC | CAG | GCT | GGT | CTG | ATT | ACA | TTT | GAT | 3079 |
| Gly | Arg | Tyr | Lys | Glu | Asn | Phe | Asp | Gln | Ala | Gly | Leu | Ile | Thr | Phe | Asp |
| 915 |  |  |  |  | 920 |  |  |  |  | 925 |  |  |  |  | 930 |
| GTC | ATA | TCA | CGC | ATG | ACT | CTG | GAA | GAT | CTC | CAG | CGT | ATT | GGA | ATC | ACC | 3127 |
| Val | Ile | Ser | Arg | Met | Thr | Leu | Glu | Asp | Leu | Gln | Arg | Ile | Gly | Ile | Thr |
|  |  |  |  | 935 |  |  |  |  | 940 |  |  |  |  | 945 |  |
| CTG | GTT | GGT | CAC | CAG | AAA | AAG | ATT | CTA | AAC | AGC | ATC | CAG | CTC | ATG | AAA | 3175 |
| Leu | Val | Gly | His | Gln | Lys | Lys | Ile | Leu | Asn | Ser | Ile | Gln | Leu | Met | Lys |
|  |  |  | 950 |  |  |  |  | 955 |  |  |  |  | 960 |  |  |
| GTT | CAT | TTG | AAC | CAG | CTT | GAA | CCA | GTT | GAA | GTG | TGATGCTTTA | AGTCTCTATT | 3228 |
| Val | His | Leu | Asn | Gln | Leu | Glu | Pro | Val | Glu | Val |
|  | 965 |  |  |  |  | 970 |  |  |  |  |

| | | | | |
|--|--|--|--|--|
| TCACCAGACT | CAAATTCTGA | AAGAGTCCTG | AGGGGATTCA | GAGGGATTGT | CACTGTATGA | 3288 |
| AAAGGAAATG | GCAAGATGCT | CCTTGAAGAC | TTACTGCACC | TAGAGAGTAG | ACATTACACA | 3348 |
| TTCCATTCCA | CCAGCAAAAA | GAGAATCTTG | CCATCATTTA | AAAGCAGAGT | TAAATAGCTG | 3408 |
| GTGGTTAAAT | ATGACTGGCA | TCATACACTA | GGAGTAGGTC | AGGGAGGGAA | AGTTATAGTA | 3468 |
| ATGCAGAGTG | GAGCTGGTAT | AATAGTTTGG | ACAGACCACA | AGCACCTGCT | AGCTCTTCTC | 3528 |
| CACTAAATAA | AAAATCAGAC | AATTCTCCAG | TGCCATCAGC | AGGCTTTATC | TGTGACTGGG | 3588 |
| AACAAGAAA | TCACAATTTT | TCCAAGAGAG | TATCAGCACA | TTGTGAGAGT | TATCACTCAG | 3648 |
| TTGGAAATGG | ACATCACTTG | CTATGCCAGA | TTTGTGAGAA | ACTGGAGTTC | CACTGAGTGC | 3708 |
| ACCATATGTG | GTAAACAATA | AGGTACATCA | CCTCGTAATT | TTTACAGAGG | TTGAGAGTAA | 3768 |
| AGGGCCCA | | | | | | 3776 |

( 2 ) INFORMATION FOR SEQ ID NO:8:

( i ) SEQUENCE CHARACTERISTICS:
        ( A ) LENGTH: 973 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| | | | | | | | | | | | | | | |
|--|--|--|--|--|--|--|--|--|--|--|--|--|--|--|
| Met | Thr | Glu | Ile | Leu | Leu | Asp | Thr | Thr | Gly | Glu | Thr | Ser | Glu | Ile | Gly |
| 1 | | | | 5 | | | | | 10 | | | | | 15 | |
| Trp | Thr | Ser | His | Pro | Pro | Asp | Gly | Trp | Glu | Glu | Val | Ser | Val | Arg | Asp |
| | | | 20 | | | | | 25 | | | | | 30 | | |
| Asp | Lys | Glu | Arg | Gln | Ile | Arg | Thr | Phe | Gln | Val | Cys | Asn | Met | Asp | Glu |

-continued

|  | 35 |  |  |  |  | 40 |  |  |  |  | 45 |  |  |  |
|---|---|---|---|---|---|---|---|---|---|---|---|---|---|---|

Pro Gly Gln Asn Asn Trp Leu Arg Thr His Phe Ile Glu Arg Arg Gly
 50                          55                         60

Ala His Arg Val His Val Arg Leu His Phe Ser Val Arg Asp Cys Ala
 65                          70                         75                         80

Ser Met Arg Thr Val Ala Ser Thr Cys Lys Glu Thr Phe Thr Leu Tyr
                         85                         90                         95

Tyr His Gln Ser Asp Val Asp Ile Ala Ser Gln Glu Leu Pro Glu Trp
                        100                        105                        110

His Glu Gly Pro Trp Thr Lys Val Asp Thr Ile Ala Ala Asp Glu Ser
                115                        120                        125

Phe Ser Gln Val Asp Arg Thr Gly Lys Val Val Arg Met Asn Val Lys
    130                        135                        140

Val Arg Ser Phe Gly Pro Leu Thr Lys His Gly Phe Tyr Leu Ala Phe
145                        150                        155                        160

Gln Asp Ser Gly Ala Cys Met Ser Leu Val Ala Val Gln Val Phe Phe
                        165                        170                        175

Tyr Lys Cys Pro Ala Val Val Lys Gly Phe Ala Ser Phe Pro Glu Thr
                180                        185                        190

Phe Ala Gly Gly Glu Arg Thr Ser Leu Val Glu Ser Leu Gly Thr Cys
            195                        200                        205

Val Ala Asn Ala Glu Glu Ala Ser Thr Thr Gly Ser Ser Gly Val Arg
    210                        215                        220

Leu His Cys Asn Gly Glu Gly Glu Trp Met Val Ala Thr Gly Arg Cys
225                        230                        235                        240

Ser Cys Lys Ala Gly Tyr Gln Ser Val Asp Asn Glu Gln Ala Cys Gln
                    245                        250                        255

Ala Cys Pro Ile Gly Ser Phe Lys Ala Ser Val Gly Asp Asp Pro Cys
                260                        265                        270

Leu Leu Cys Pro Ala His Ser His Ala Pro Leu Pro Leu Pro Gly Ser
        275                        280                        285

Ile Glu Cys Val Cys Gln Ser His Tyr Tyr Arg Ser Ala Ser Asp Asn
290                        295                        300

Ser Asp Ala Pro Cys Thr Gly Ile Pro Ser Ala Pro Arg Asp Leu Ser
305                        310                        315                        320

Tyr Glu Ile Val Gly Ser Asn Val Leu Leu Thr Trp Arg Leu Pro Lys
                        325                        330                        335

Asp Leu Gly Gly Arg Lys Asp Val Phe Phe Asn Val Ile Cys Lys Glu
            340                        345                        350

Cys Pro Thr Arg Ser Ala Gly Thr Cys Val Arg Cys Gly Asp Asn Val
        355                        360                        365

Gln Phe Glu Pro Arg Gln Val Gly Leu Thr Glu Ser Arg Val Gln Val
    370                        375                        380

Ser Asn Leu Leu Ala Arg Val Gln Tyr Thr Phe Glu Ile Gln Ala Val
385                        390                        395                        400

Asn Leu Val Thr Glu Leu Ser Ser Glu Ala Pro Gln Tyr Ala Thr Ile
                        405                        410                        415

Asn Val Ser Thr Ser Gln Ser Val Pro Ser Ala Ile Pro Met Met His
                420                        425                        430

Gln Val Ser Arg Ala Thr Ser Ser Ile Thr Leu Ser Trp Pro Gln Pro
        435                        440                        445

Asp Gln Pro Asn Gly Val Ile Leu Asp Tyr Gln Leu Arg Tyr Phe Asp
    450                        455                        460

```
Lys  Ala  Glu  Asp  Glu  Asp  Asn  Ser  Phe  Thr  Leu  Thr  Ser  Glu  Thr  Asn
465                 470                      475                      480

Met  Ala  Thr  Ile  Leu  Asn  Leu  Ser  Pro  Gly  Lys  Ile  Tyr  Val  Phe  Gln
                    485                      490                      495

Val  Arg  Ala  Arg  Thr  Ala  Val  Gly  Tyr  Gly  Pro  Tyr  Ser  Gly  Lys  Met
               500                      505                      510

Tyr  Phe  Gln  Thr  Leu  Met  Ala  Gly  Glu  His  Ser  Glu  Met  Ala  Gln  Asp
          515                      520                      525

Arg  Leu  Pro  Leu  Ile  Val  Gly  Ser  Ala  Leu  Gly  Gly  Leu  Ala  Phe  Leu
          530                      535                      540

Val  Ile  Ala  Ala  Ile  Ala  Ile  Leu  Ala  Ile  Ile  Phe  Lys  Ser  Lys  Arg
545                      550                      555                      560

Arg  Glu  Thr  Pro  Tyr  Thr  Asp  Arg  Leu  Gln  Gln  Tyr  Ile  Ser  Thr  Arg
                    565                      570                      575

Gly  Leu  Gly  Val  Lys  Tyr  Tyr  Ile  Asp  Pro  Ser  Thr  Tyr  Glu  Asp  Pro
               580                      585                      590

Asn  Glu  Ala  Ile  Arg  Glu  Phe  Ala  Lys  Glu  Ile  Asp  Val  Ser  Phe  Ile
               595                      600                      605

Lys  Ile  Glu  Glu  Val  Ile  Gly  Ser  Gly  Glu  Phe  Gly  Glu  Val  Cys  Phe
     610                      615                      620

Gly  Arg  Leu  Lys  His  Pro  Gly  Lys  Arg  Glu  Tyr  Thr  Val  Ala  Ile  Lys
625                      630                      635                      640

Thr  Leu  Lys  Ser  Gly  Tyr  Thr  Asp  Glu  Gln  Arg  Arg  Glu  Phe  Leu  Ser
               645                      650                      655

Glu  Ala  Ser  Ile  Met  Gly  Gln  Phe  Glu  His  Pro  Asn  Val  Ile  His  Leu
               660                      665                      670

Glu  Gly  Val  Val  Thr  Lys  Ser  Arg  Pro  Val  Met  Ile  Val  Thr  Glu  Phe
          675                      680                      685

Met  Glu  Asn  Gly  Ser  Leu  Asp  Ser  Phe  Leu  Arg  Glu  Lys  Glu  Gly  Gln
     690                      695                      700

Phe  Ser  Val  Leu  Gln  Leu  Val  Gly  Met  Leu  Arg  Gly  Ile  Ala  Ala  Gly
705                      710                      715                      720

Met  Arg  Tyr  Leu  Ser  Asp  Met  Asn  Tyr  Val  His  Arg  Asp  Leu  Ala  Ala
               725                      730                      735

Arg  Asn  Ile  Leu  Val  Asn  Ser  Asn  Leu  Val  Cys  Lys  Val  Ser  Asp  Phe
               740                      745                      750

Gly  Leu  Ser  Arg  Phe  Leu  Glu  Asp  Asp  Ala  Ser  Asn  Pro  Thr  Tyr  Thr
          755                      760                      765

Gly  Ala  Leu  Gly  Cys  Lys  Ile  Pro  Ile  Arg  Trp  Thr  Ala  Pro  Glu  Ala
          770                      775                      780

Val  Gln  Tyr  Arg  Lys  Phe  Thr  Ser  Ser  Ser  Asp  Val  Trp  Ser  Tyr  Gly
785                      790                      795                      800

Ile  Val  Met  Trp  Glu  Val  Met  Ser  Tyr  Gly  Glu  Arg  Pro  Tyr  Trp  Asp
                    805                      810                      815

Met  Ser  Asn  Gln  Asp  Val  Ile  Asn  Ala  Ile  Asp  Gln  Asp  Tyr  Arg  Leu
               820                      825                      830

Pro  Pro  Pro  Pro  Asp  Cys  Pro  Thr  Val  Leu  His  Leu  Leu  Met  Leu  Asp
               835                      840                      845

Cys  Trp  Gln  Lys  Asp  Arg  Val  Gln  Arg  Pro  Lys  Phe  Glu  Gln  Ile  Val
     850                      855                      860

Ser  Ala  Leu  Asp  Lys  Met  Ile  Arg  Lys  Pro  Ser  Ala  Leu  Lys  Ala  Thr
865                      870                      875                      880
```

|  |  |  |  |  |  |  |  |  |  |  |  |  |  |  |  |
|---|---|---|---|---|---|---|---|---|---|---|---|---|---|---|---|
| Gly | Thr | Gly | Ser | Ser<br>885 | Arg | Pro | Ser | Gln<br>890 | Pro | Leu | Leu | Ser | Asn<br>895 | Ser | Pro |
| Pro | Asp | Phe | Pro<br>900 | Ser | Leu | Ser | Asn | Ala<br>905 | His | Glu | Trp | Leu | Asp<br>910 | Ala | Ile |
| Lys | Met | Gly<br>915 | Arg | Tyr | Lys | Glu | Asn<br>920 | Phe | Asp | Gln | Ala | Gly<br>925 | Leu | Ile | Thr |
| Phe | Asp<br>930 | Val | Ile | Ser | Arg | Met<br>935 | Thr | Leu | Glu | Asp | Leu<br>940 | Gln | Arg | Ile | Gly |
| Ile<br>945 | Thr | Leu | Val | Gly | His<br>950 | Gln | Lys | Lys | Ile | Leu<br>955 | Asn | Ser | Ile | Gln | Leu<br>960 |
| Met | Lys | Val | His | Leu<br>965 | Asn | Gln | Leu | Glu | Pro<br>970 | Val | Glu | Val |  |  |  |

( 2 ) INFORMATION FOR SEQ ID NO:9:

( i ) SEQUENCE CHARACTERISTICS:
        ( A ) LENGTH: 3546 base pairs
        ( B ) TYPE: nucleic acid
        ( C ) STRANDEDNESS: both
        ( D ) TOPOLOGY: linear ( i x ) FEATURE:
        ( A ) NAME/KEY: CDS
        ( B ) LOCATION: 2..2920

( x i ) SEQUENCE DESCRIPTION: SEQ ID NO:9:

|  |  |  |  |  |  |  |  |  |  |  |  |  |  |  |  |  |
|---|---|---|---|---|---|---|---|---|---|---|---|---|---|---|---|---|
| C | GGG<br>Gly<br>1 | GTC<br>Val | TCC<br>Ser | TCG<br>Ser | AGG<br>Arg<br>5 | GCG<br>Ala | CGG<br>Arg | CGG<br>Arg | CCG<br>Pro | CCG<br>Pro<br>10 | GGC<br>Gly | AGC<br>Ser | AGC<br>Ser | AGG<br>Arg | AGC<br>Ser<br>15 | 46 |
| AGC<br>Ser | AGG<br>Arg | AGG<br>Arg | GGG<br>Gly | GTG<br>Val<br>20 | ACC<br>Thr | TCG<br>Ser | GAG<br>Glu | CTG<br>Leu | GCA<br>Ala<br>25 | TGG<br>Trp | ACA<br>Thr | ACC<br>Thr | CAT<br>His | CCG<br>Pro<br>30 | GAG<br>Glu | 94 |
| ACG<br>Thr | GGG<br>Gly | TGG<br>Trp | GAA<br>Glu<br>35 | GAG<br>Glu | GTC<br>Val | AGT<br>Ser | GGT<br>Gly | TAC<br>Tyr<br>40 | GAC<br>Asp | GAG<br>Glu | GCT<br>Ala | ATG<br>Met | AAC<br>Asn<br>45 | CCC<br>Pro | ATC<br>Ile | 142 |
| CGC<br>Arg | ACA<br>Thr | TAC<br>Tyr<br>50 | CAG<br>Gln | GTG<br>Val | TGC<br>Cys | AAC<br>Asn | GTG<br>Val<br>55 | CGG<br>Arg | GAG<br>Glu | GCC<br>Ala | AAC<br>Asn | CAG<br>Gln<br>60 | AAC<br>Asn | AAC<br>Asn | TGG<br>Trp | 190 |
| CTT<br>Leu | CGC<br>Arg<br>65 | ACC<br>Thr | AAG<br>Lys | TTC<br>Phe | ATT<br>Ile | CAG<br>Gln<br>70 | CGC<br>Arg | CAG<br>Gln | GAC<br>Asp | GTC<br>Val | CAG<br>Gln<br>75 | CGT<br>Arg | GTC<br>Val | TAC<br>Tyr | GTG<br>Val | 238 |
| GAG<br>Glu<br>80 | CTG<br>Leu | AAA<br>Lys | TTC<br>Phe | ACT<br>Thr | GTG<br>Val<br>85 | CGG<br>Arg | GAC<br>Asp | TGC<br>Cys | AAC<br>Asn | AGC<br>Ser<br>90 | ATC<br>Ile | CCC<br>Pro | AAC<br>Asn | ATC<br>Ile | CCT<br>Pro<br>95 | 286 |
| GGT<br>Gly | TCC<br>Ser | TGC<br>Cys | AAA<br>Lys | GAG<br>Glu<br>100 | ACC<br>Thr | TTC<br>Phe | AAC<br>Asn | CTC<br>Leu | TTT<br>Phe<br>105 | TAT<br>Tyr | TAT<br>Tyr | GAG<br>Glu | TCA<br>Ser | GAT<br>Asp<br>110 | ACG<br>Thr | 334 |
| GAT<br>Asp | TCT<br>Ser | GCC<br>Ala | TCT<br>Ser<br>115 | GCC<br>Ala | AAT<br>Asn | AGC<br>Ser | CCT<br>Pro | TTC<br>Phe<br>120 | TGG<br>Trp | ATG<br>Met | GAG<br>Glu | AAC<br>Asn | CCC<br>Pro<br>125 | TAT<br>Tyr | ATC<br>Ile | 382 |
| AAA<br>Lys | GTG<br>Val | GAT<br>Asp<br>130 | ACA<br>Thr | ATT<br>Ile | GCT<br>Ala | CCG<br>Pro | GAT<br>Asp<br>135 | GAG<br>Glu | AGC<br>Ser | TTC<br>Phe | TCC<br>Ser | AAA<br>Lys<br>140 | CTG<br>Leu | GAG<br>Glu | TCC<br>Ser | 430 |
| GGC<br>Gly | CGT<br>Arg<br>145 | GTG<br>Val | AAC<br>Asn | ACC<br>Thr | AAG<br>Lys | GTG<br>Val<br>150 | CGC<br>Arg | AGC<br>Ser | TTT<br>Phe | GGG<br>Gly | CCG<br>Pro<br>155 | CTC<br>Leu | TCC<br>Ser | AAG<br>Lys | AAT<br>Asn | 478 |
| GGC<br>Gly<br>160 | TTT<br>Phe | TAT<br>Tyr | CTG<br>Leu | GCT<br>Ala | TTC<br>Phe<br>165 | CAG<br>Gln | GAC<br>Asp | CTG<br>Leu | GGG<br>Gly | GCC<br>Ala<br>170 | TGC<br>Cys | ATG<br>Met | TCC<br>Ser | CTT<br>Leu | ATC<br>Ile<br>175 | 526 |
| TCC<br>Ser | GTC<br>Val | CGG<br>Arg | GCT<br>Ala | TTC<br>Phe | TAC<br>Tyr | AAG<br>Lys | AAA<br>Lys | TGT<br>Cys | TCC<br>Ser | AAC<br>Asn | ACC<br>Thr | ATC<br>Ile | GCT<br>Ala | GGC<br>Gly | TTT<br>Phe | 574 |

-continued

```
                                       180                              185                              190
GCT ATC TTC CCG GAG ACC CTA ACG GGG GCT GAG CCC ACG TCG CTG GTC                                                622
Ala Ile Phe Pro Glu Thr Leu Thr Gly Ala Glu Pro Thr Ser Leu Val
            195                     200                     205

ATT GCG CCG GGC ACC TGC ATC CCC AAC GCA GTG GAA GTG TCT GTG CCC                                                670
Ile Ala Pro Gly Thr Cys Ile Pro Asn Ala Val Glu Val Ser Val Pro
            210                     215                     220

CTG AAG CTG TAC TGC AAC GGT GAT GGC GAG TGG ATG GTG CCT GTG GGA                                                718
Leu Lys Leu Tyr Cys Asn Gly Asp Gly Glu Trp Met Val Pro Val Gly
        225                     230                     235

GCG TGC ACG TGT GCT GCT GGG TAC GAG CCA GCC ATG AAG GAT ACC CAG                                                766
Ala Cys Thr Cys Ala Ala Gly Tyr Glu Pro Ala Met Lys Asp Thr Gln
240                     245                     250                     255

TGC CAA GCA TGC GGC CCG GGG ACG TTC AAA TCC AAG CAG GGC GAG GGC                                                814
Cys Gln Ala Cys Gly Pro Gly Thr Phe Lys Ser Lys Gln Gly Glu Gly
                    260                     265                     270

CCC TGC TCC CCC TGC CCT CCC AAC AGC CGC ACC ACC GCG GGG GCA GCC                                                862
Pro Cys Ser Pro Cys Pro Pro Asn Ser Arg Thr Thr Ala Gly Ala Ala
                275                     280                     285

ACA GTC TGC ATA TGT CGC AGC GGC TTC TTC CGA GCA GAC GCG GAC CCC                                                910
Thr Val Cys Ile Cys Arg Ser Gly Phe Phe Arg Ala Asp Ala Asp Pro
            290                     295                     300

GCA GAC AGC GCC TGC ACC AGT GTG CCC TCA GCC CCA CGC AGC GTC ATC                                                958
Ala Asp Ser Ala Cys Thr Ser Val Pro Ser Ala Pro Arg Ser Val Ile
305                     310                     315

TCC AAC GTG AAT GAG ACG TCG TTG GTG CTG GAG TGG AGC GAG CCG CAG                                                1006
Ser Asn Val Asn Glu Thr Ser Leu Val Leu Glu Trp Ser Glu Pro Gln
320                     325                     330                     335

GAC GCG GGC GGG CGG GAT GAC CTG CTC TAC AAC GTC ATC TGC AAG AAG                                                1054
Asp Ala Gly Gly Arg Asp Asp Leu Leu Tyr Asn Val Ile Cys Lys Lys
                    340                     345                     350

TGC AGC GTG GAG CGG CGG CTG TGC AGC CGC TGC GAC GAC AAC GTG GAG                                                1102
Cys Ser Val Glu Arg Arg Leu Cys Ser Arg Cys Asp Asp Asn Val Glu
                355                     360                     365

TTC GTG CCG CGC CAG CTG GGC CTC ACT GGC CTC ACT GAG CGA CGC ATC                                                1150
Phe Val Pro Arg Gln Leu Gly Leu Thr Gly Leu Thr Glu Arg Arg Ile
            370                     375                     380

TAC ATC AGC AAG GTG ATG GCC CAC CCC CAG TAC ACC TTC GAG ATC CAG                                                1198
Tyr Ile Ser Lys Val Met Ala His Pro Gln Tyr Thr Phe Glu Ile Gln
        385                     390                     395

GCG GTG AAT GGC ATC TCC AGC AAG AGC CCC TAC CCT CCC CAT TTT GCC                                                1246
Ala Val Asn Gly Ile Ser Ser Lys Ser Pro Tyr Pro Pro His Phe Ala
400                     405                     410                     415

TCC GTC AAC ATC ACG ACC AAC CAG GCA GCC CCA TCT GCC GTG CCC ACC                                                1294
Ser Val Asn Ile Thr Thr Asn Gln Ala Ala Pro Ser Ala Val Pro Thr
                    420                     425                     430

ATG CAT CTG CAC AGC AGC ACC GGG AAC AGC ATG ACA CTG TCA TGG ACT                                                1342
Met His Leu His Ser Ser Thr Gly Asn Ser Met Thr Leu Ser Trp Thr
                435                     440                     445

CCC CCG GAA AGG CCC AAC GGC ATC ATT CTC GAC TAT GAA ATC AAG TAC                                                1390
Pro Pro Glu Arg Pro Asn Gly Ile Ile Leu Asp Tyr Glu Ile Lys Tyr
            450                     455                     460

TCC GAG AAG CAA GGC CAG GGT GAC GGC ATT GCC AAC ACT GTC ACC AGC                                                1438
Ser Glu Lys Gln Gly Gln Gly Asp Gly Ile Ala Asn Thr Val Thr Ser
        465                     470                     475

CAG AAG AAC TCG GTG CGG CTG GAC GGA CTG AAG GCC AAT GCT CGG TAC                                                1486
Gln Lys Asn Ser Val Arg Leu Asp Gly Leu Lys Ala Asn Ala Arg Tyr
480                     485                     490                     495

ATG GTG CAG GTC CGG GCG CGC ACA GTG GCT GGA TAC GGC CGC TAC AGC                                                1534
```

-continued

| | | | | | | | | | | | | | | | | |
|---|---|---|---|---|---|---|---|---|---|---|---|---|---|---|---|---|
| Met | Val | Gln | Val | Arg | Ala | Arg | Thr | Val | Ala | Gly | Tyr | Gly | Arg | Tyr | Ser | |
| | | | | 500 | | | | | 505 | | | | | 510 | | |

| CTC | CCC | ACC | GAG | TTC | CAG | ACG | ACT | GCG | GAG | GAT | GGC | TCC | ACC | AGC | AAG | 1582 |
|---|---|---|---|---|---|---|---|---|---|---|---|---|---|---|---|---|
| Leu | Pro | Thr | Glu | Phe | Gln | Thr | Thr | Ala | Glu | Asp | Gly | Ser | Thr | Ser | Lys | |
| | | | 515 | | | | | 520 | | | | | 525 | | | |

| ACT | TTC | CAG | GAG | CTT | CCT | CTC | ATC | GTG | GGT | TCA | GCC | ACC | GCG | GGA | CTG | 1630 |
|---|---|---|---|---|---|---|---|---|---|---|---|---|---|---|---|---|
| Thr | Phe | Gln | Glu | Leu | Pro | Leu | Ile | Val | Gly | Ser | Ala | Thr | Ala | Gly | Leu | |
| | | 530 | | | | | 535 | | | | | 540 | | | | |

| CTG | TTT | GTC | ATC | GTG | GTG | GTC | ATC | ATC | GCT | ATT | GTC | TGC | TTC | AGG | AAG | 1678 |
|---|---|---|---|---|---|---|---|---|---|---|---|---|---|---|---|---|
| Leu | Phe | Val | Ile | Val | Val | Val | Ile | Ile | Ala | Ile | Val | Cys | Phe | Arg | Lys | |
| | 545 | | | | | 550 | | | | | 555 | | | | | |

| CAG | CGC | AAC | AGC | ACA | GAT | CCC | GAG | TAC | ACA | GAG | AAG | CTG | CAG | CAA | TAT | 1726 |
|---|---|---|---|---|---|---|---|---|---|---|---|---|---|---|---|---|
| Gln | Arg | Asn | Ser | Thr | Asp | Pro | Glu | Tyr | Thr | Glu | Lys | Leu | Gln | Gln | Tyr | |
| 560 | | | | | 565 | | | | | 570 | | | | | 575 | |

| GTC | ACT | CCT | GGG | ATG | AAG | GTC | TAC | ATT | GAC | CCC | TTC | ACC | TAT | GAA | GAC | 1774 |
|---|---|---|---|---|---|---|---|---|---|---|---|---|---|---|---|---|
| Val | Thr | Pro | Gly | Met | Lys | Val | Tyr | Ile | Asp | Pro | Phe | Thr | Tyr | Glu | Asp | |
| | | | | 580 | | | | | 585 | | | | | 590 | | |

| CCA | AAT | GAA | GCT | GTC | CGG | GAA | TTC | GCC | AAA | GAG | ATT | GAT | ATC | TCC | TGT | 1822 |
|---|---|---|---|---|---|---|---|---|---|---|---|---|---|---|---|---|
| Pro | Asn | Glu | Ala | Val | Arg | Glu | Phe | Ala | Lys | Glu | Ile | Asp | Ile | Ser | Cys | |
| | | | | 595 | | | | | 600 | | | | | 605 | | |

| GTC | AAA | ATT | GAG | GAG | GTC | ATT | GGA | GCA | GGA | GAG | TTT | GGT | GAG | GTG | TGC | 1870 |
|---|---|---|---|---|---|---|---|---|---|---|---|---|---|---|---|---|
| Val | Lys | Ile | Glu | Glu | Val | Ile | Gly | Ala | Gly | Glu | Phe | Gly | Glu | Val | Cys | |
| | | 610 | | | | | 615 | | | | | 620 | | | | |

| CGT | GGG | CGC | CTG | AAG | CTG | CCT | GGC | CGC | CGT | GAG | ATC | TTT | GTG | GCC | ATC | 1918 |
|---|---|---|---|---|---|---|---|---|---|---|---|---|---|---|---|---|
| Arg | Gly | Arg | Leu | Lys | Leu | Pro | Gly | Arg | Arg | Glu | Ile | Phe | Val | Ala | Ile | |
| | 625 | | | | | 630 | | | | | 635 | | | | | |

| AAG | ACA | CTG | AAG | GTG | GGC | TAC | ACA | GAG | AGG | CAG | CGG | CGG | GAC | TTC | CTG | 1966 |
|---|---|---|---|---|---|---|---|---|---|---|---|---|---|---|---|---|
| Lys | Thr | Leu | Lys | Val | Gly | Tyr | Thr | Glu | Arg | Gln | Arg | Arg | Asp | Phe | Leu | |
| 640 | | | | | 645 | | | | | 650 | | | | | 655 | |

| AGT | GAG | GCC | AGC | ATC | ATG | GGC | CAG | TTC | GAC | CAC | CCC | AAC | ATC | ATC | CAC | 2014 |
|---|---|---|---|---|---|---|---|---|---|---|---|---|---|---|---|---|
| Ser | Glu | Ala | Ser | Ile | Met | Gly | Gln | Phe | Asp | His | Pro | Asn | Ile | Ile | His | |
| | | | | 660 | | | | | 665 | | | | | 670 | | |

| CTG | GAG | GGC | GTG | GTG | ACC | AAG | AGC | CGC | CCT | GTC | ATG | ATC | ATC | ACA | GAG | 2062 |
|---|---|---|---|---|---|---|---|---|---|---|---|---|---|---|---|---|
| Leu | Glu | Gly | Val | Val | Thr | Lys | Ser | Arg | Pro | Val | Met | Ile | Ile | Thr | Glu | |
| | | | | 675 | | | | | 680 | | | | | 685 | | |

| TTC | ATG | GAG | AAC | TGC | GCT | CTC | GAC | TCC | TTC | CTC | CGG | CTG | AAT | GAT | GGG | 2110 |
|---|---|---|---|---|---|---|---|---|---|---|---|---|---|---|---|---|
| Phe | Met | Glu | Asn | Cys | Ala | Leu | Asp | Ser | Phe | Leu | Arg | Leu | Asn | Asp | Gly | |
| | | 690 | | | | | 695 | | | | | 700 | | | | |

| CAG | TTC | ACG | GTC | ATC | CAG | CTG | GTG | GGG | ATG | CTG | CGA | GGC | ATC | GCT | GCT | 2158 |
|---|---|---|---|---|---|---|---|---|---|---|---|---|---|---|---|---|
| Gln | Phe | Thr | Val | Ile | Gln | Leu | Val | Gly | Met | Leu | Arg | Gly | Ile | Ala | Ala | |
| | 705 | | | | | 710 | | | | | 715 | | | | | |

| GGC | ATG | AAG | TAC | CTC | TCA | GAG | ATG | AAC | TAC | GTG | CAC | CGA | GAC | CTG | GCT | 2206 |
|---|---|---|---|---|---|---|---|---|---|---|---|---|---|---|---|---|
| Gly | Met | Lys | Tyr | Leu | Ser | Glu | Met | Asn | Tyr | Val | His | Arg | Asp | Leu | Ala | |
| 720 | | | | | 725 | | | | | 730 | | | | | 735 | |

| GCC | CGC | AAC | ATC | CTG | GTC | AAC | AGC | AAC | TTG | GTC | TGC | AAA | GTG | TCT | GAC | 2254 |
|---|---|---|---|---|---|---|---|---|---|---|---|---|---|---|---|---|
| Ala | Arg | Asn | Ile | Leu | Val | Asn | Ser | Asn | Leu | Val | Cys | Lys | Val | Ser | Asp | |
| | | | | 740 | | | | | 745 | | | | | 750 | | |

| TTC | GGG | CTC | TCC | CGC | TTT | TTG | GAG | GAT | GAT | CCA | GCC | GAC | CCC | ACC | TAC | 2302 |
|---|---|---|---|---|---|---|---|---|---|---|---|---|---|---|---|---|
| Phe | Gly | Leu | Ser | Arg | Phe | Leu | Glu | Asp | Asp | Pro | Ala | Asp | Pro | Thr | Tyr | |
| | | | 755 | | | | | 760 | | | | | 765 | | | |

| ACC | AGC | TCC | CTG | GGA | GGC | AAG | ATC | CCC | ATC | AGG | TGG | ACA | GCT | CCT | GAG | 2350 |
|---|---|---|---|---|---|---|---|---|---|---|---|---|---|---|---|---|
| Thr | Ser | Ser | Leu | Gly | Gly | Lys | Ile | Pro | Ile | Arg | Trp | Thr | Ala | Pro | Glu | |
| | | | 770 | | | | | 775 | | | | | 780 | | | |

| GCC | ATC | GCC | TAC | CGC | AAA | TTC | ACG | TCG | GCC | AGC | GAC | GTG | TGG | AGC | TAC | 2398 |
|---|---|---|---|---|---|---|---|---|---|---|---|---|---|---|---|---|
| Ala | Ile | Ala | Tyr | Arg | Lys | Phe | Thr | Ser | Ala | Ser | Asp | Val | Trp | Ser | Tyr | |
| | | 785 | | | | | 790 | | | | | 795 | | | | |

| GGC | ATC | GTC | ATG | TGG | GAA | GTG | ATG | TCC | TAC | GGG | GAG | CGA | CCC | TAC | TGG | 2446 |
|---|---|---|---|---|---|---|---|---|---|---|---|---|---|---|---|---|
| Gly | Ile | Val | Met | Trp | Glu | Val | Met | Ser | Tyr | Gly | Glu | Arg | Pro | Tyr | Trp | |
| 800 | | | | | 805 | | | | | 810 | | | | | 815 | |

|      |      |      |      |      |      |      |      |      |      |      |      |      |      |      |      |      |
|------|------|------|------|------|------|------|------|------|------|------|------|------|------|------|------|------|
| GAC  | ATG  | TCC  | AAC  | CAG  | GAT  | GTG  | ATC  | AAC  | GCG  | GTG  | GAG  | CAG  | GAT  | TAC  | CGC  | 2494 |
| Asp  | Met  | Ser  | Asn  | Gln  | Asp  | Val  | Ile  | Asn  | Ala  | Val  | Glu  | Gln  | Asp  | Tyr  | Arg  |      |
|      |      |      |      | 820  |      |      |      |      | 825  |      |      |      |      | 830  |      |      |
| CTG  | CCA  | CCC  | CCC  | ATG  | GAC  | TGC  | CCC  | ACA  | GCA  | CTG  | CAC  | CAG  | CTG  | ATG  | CTG  | 2542 |
| Leu  | Pro  | Pro  | Pro  | Met  | Asp  | Cys  | Pro  | Thr  | Ala  | Leu  | His  | Gln  | Leu  | Met  | Leu  |      |
|      |      |      | 835  |      |      |      |      | 840  |      |      |      |      | 845  |      |      |      |
| GAC  | TGC  | TGG  | GTG  | CGG  | GAC  | CGC  | AAC  | CTG  | CGG  | CCC  | AAG  | TTT  | GCA  | CAG  | ATT  | 2590 |
| Asp  | Cys  | Trp  | Val  | Arg  | Asp  | Arg  | Asn  | Leu  | Arg  | Pro  | Lys  | Phe  | Ala  | Gln  | Ile  |      |
|      |      | 850  |      |      |      |      | 855  |      |      |      |      | 860  |      |      |      |      |
| GTC  | AAC  | ACG  | CTG  | GAC  | AAG  | CTG  | ATC  | CGC  | AAT  | GCT  | GCC  | AGC  | CTG  | AAG  | GTC  | 2638 |
| Val  | Asn  | Thr  | Leu  | Asp  | Lys  | Leu  | Ile  | Arg  | Asn  | Ala  | Ala  | Ser  | Leu  | Lys  | Val  |      |
|      | 865  |      |      |      |      | 870  |      |      |      |      | 875  |      |      |      |      |      |
| ATC  | GCC  | AGC  | GTC  | CAG  | TCC  | GGT  | GTC  | TCC  | CAG  | CCG  | CTC  | CTG  | GAC  | CGC  | ACC  | 2686 |
| Ile  | Ala  | Ser  | Val  | Gln  | Ser  | Gly  | Val  | Ser  | Gln  | Pro  | Leu  | Leu  | Asp  | Arg  | Thr  |      |
| 880  |      |      |      |      | 885  |      |      |      |      | 890  |      |      |      |      | 895  |      |
| GTG  | CCC  | GAT  | TAC  | ACC  | ACC  | TTC  | ACC  | ACC  | GTG  | GGA  | GAC  | TGG  | CTG  | GAT  | GCC  | 2734 |
| Val  | Pro  | Asp  | Tyr  | Thr  | Thr  | Phe  | Thr  | Thr  | Val  | Gly  | Asp  | Trp  | Leu  | Asp  | Ala  |      |
|      |      |      |      | 900  |      |      |      |      | 905  |      |      |      |      | 910  |      |      |
| ATC  | AAA  | ATG  | GGA  | CGG  | TAC  | AAG  | GAG  | AAC  | TTC  | GTC  | AAC  | GCC  | GGC  | TTC  | GCC  | 2782 |
| Ile  | Lys  | Met  | Gly  | Arg  | Tyr  | Lys  | Glu  | Asn  | Phe  | Val  | Asn  | Ala  | Gly  | Phe  | Ala  |      |
|      |      |      | 915  |      |      |      |      | 920  |      |      |      |      | 925  |      |      |      |
| TCC  | TTT  | GAC  | CTG  | GTG  | GCA  | CAG  | ATG  | ACA  | GCA  | GAG  | GAC  | CTG  | CTA  | AGG  | ATA  | 2830 |
| Ser  | Phe  | Asp  | Leu  | Val  | Ala  | Gln  | Met  | Thr  | Ala  | Glu  | Asp  | Leu  | Leu  | Arg  | Ile  |      |
|      |      | 930  |      |      |      |      | 935  |      |      |      |      | 940  |      |      |      |      |
| GGA  | GTG  | ACG  | CTA  | GCA  | GGG  | CAC  | CAG  | AAG  | AAG  | ATC  | CTG  | AGC  | AGC  | ATT  | CAG  | 2878 |
| Gly  | Val  | Thr  | Leu  | Ala  | Gly  | His  | Gln  | Lys  | Lys  | Ile  | Leu  | Ser  | Ser  | Ile  | Gln  |      |
|      | 945  |      |      |      |      | 950  |      |      |      |      | 955  |      |      |      |      |      |
| GAC  | ATG  | AGG  | CTG  | CAG  | ATG  | AAC  | CAG  | ACG  | CTG  | CCG  | GTT  | CAG  | GTT  |      |      | 2920 |
| Asp  | Met  | Arg  | Leu  | Gln  | Met  | Asn  | Gln  | Thr  | Leu  | Pro  | Val  | Gln  | Val  |      |      |      |
| 960  |      |      |      |      | 965  |      |      |      |      | 970  |      |      |      |      |      |      |

| | | | | |
|---|---|---|---|---|
| TGACCGCAGG | GACTCTGCAT | TGGAACGGAC | TGAGGGAACC | TGCCAACCAG | GTTCTGTTTG | 2980 |
| CGGTGCAGCC | CGGCTTCCCG | ATTTCCCCTT | CCCGTGGCGC | TCCTCTGCCT | CGGACGCTCG | 3040 |
| CCGGGGACAG | GCTGGGCCGG | GCCACCCTTC | CCTGGATCAG | AGGCACTCGT | GCCGGGAGGG | 3100 |
| AGCCCGGCTT | TTCGTCCCGT | GTCCCGCAGC | GGCGAGGCAG | TGAACGCAGT | CTTCATATTG | 3160 |
| AAGATGGATT | ATGGGACGGA | GATGGCGCAT | CCGCTTCCCG | CCCTGTCTCA | GTGCTCATCA | 3220 |
| GTTTGAAGAG | ATGTTCTGCT | TCTTGGATTT | CTTTACACCC | CGGTTTTCCC | CCCTCGAGTC | 3280 |
| CTCACTTCCC | CCTATCCCTG | AGGCCACAGA | CTGTTGACCC | GTCCGCTGAG | TCCGTCAGAC | 3340 |
| GCTCCGAAGC | CTTCCCCGAG | CCCGGTCCCC | GCGTGGAGAC | GGCGCCAGGG | ACGGGGCTAC | 3400 |
| GGCCCCAGAC | AATCACTCCA | CCCCTCCGCA | CGAGGGTCCT | CACTGGGACG | TGTCTGAAGG | 3460 |
| GGAAAGGCTC | TGCTCCCTTT | TTGGCTTTGC | ACGCCAGAAC | CCGAACCCCG | TGAGATTTAC | 3520 |
| TATGCAGGGA | GTTAGGCAAA | AAAAAG |  |  |  | 3546 |

( 2 ) INFORMATION FOR SEQ ID NO:10:

( i ) SEQUENCE CHARACTERISTICS:
        ( A ) LENGTH: 973 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

| | | | | | | | | | | | | | | |
|---|---|---|---|---|---|---|---|---|---|---|---|---|---|---|
| Gly | Val | Ser | Ser | Arg | Ala | Arg | Arg | Pro | Pro | Gly | Ser | Ser | Arg | Ser | Ser |
| 1 | | | | 5 | | | | | 10 | | | | | 15 | |
| Arg | Arg | Gly | Val | Thr | Ser | Glu | Leu | Ala | Trp | Thr | Thr | His | Pro | Glu | Thr |
| | | | 20 | | | | | 25 | | | | | 30 | | |

-continued

| | | | | | | | | | | | | | |
|---|---|---|---|---|---|---|---|---|---|---|---|---|---|
|Gly|Trp|Glu|Glu|Val|Ser|Gly|Tyr|Asp|Glu|Ala|Met|Asn|Pro|Ile|Arg|
| | |35| | | |40| | | |45| | | |
|Thr|Tyr|Gln|Val|Cys|Asn|Val|Arg|Glu|Ala|Asn|Gln|Asn|Asn|Trp|Leu|
| |50| | | |55| | | | |60| | | | |
|Arg|Thr|Lys|Phe|Ile|Gln|Arg|Gln|Asp|Val|Gln|Arg|Val|Tyr|Val|Glu|
|65| | | |70| | | |75| | | | | |80|
|Leu|Lys|Phe|Thr|Val|Arg|Asp|Cys|Asn|Ser|Ile|Pro|Asn|Ile|Pro|Gly|
| | | |85| | | |90| | | | |95| | |
|Ser|Cys|Lys|Glu|Thr|Phe|Asn|Leu|Phe|Tyr|Glu|Ser|Asp|Thr|Asp|
| | | |100| | | |105| | | |110| | |
|Ser|Ala|Ser|Ala|Asn|Ser|Pro|Phe|Trp|Met|Glu|Asn|Pro|Tyr|Ile|Lys|
| | |115| | | |120| | | |125| | | | |
|Val|Asp|Thr|Ile|Ala|Pro|Asp|Glu|Ser|Phe|Ser|Lys|Leu|Glu|Ser|Gly|
| |130| | | |135| | | |140| | | | | |
|Arg|Val|Asn|Thr|Lys|Val|Arg|Ser|Phe|Gly|Pro|Leu|Ser|Lys|Asn|Gly|
|145| | | |150| | | |155| | | | | |160|
|Phe|Tyr|Leu|Ala|Phe|Gln|Asp|Leu|Gly|Ala|Cys|Met|Ser|Leu|Ile|Ser|
| | | |165| | | |170| | | | |175| | |
|Val|Arg|Ala|Phe|Tyr|Lys|Lys|Cys|Ser|Asn|Thr|Ile|Ala|Gly|Phe|Ala|
| | |180| | | |185| | | | |190| | | |
|Ile|Phe|Pro|Glu|Thr|Leu|Thr|Gly|Ala|Glu|Pro|Thr|Ser|Leu|Val|Ile|
| |195| | | |200| | | |205| | | | | |
|Ala|Pro|Gly|Thr|Cys|Ile|Pro|Asn|Ala|Val|Glu|Val|Ser|Val|Pro|Leu|
|210| | | |215| | | |220| | | | | | |
|Lys|Leu|Tyr|Cys|Asn|Gly|Asp|Gly|Glu|Trp|Met|Val|Pro|Val|Gly|Ala|
|225| | | |230| | | |235| | | | | |240|
|Cys|Thr|Cys|Ala|Ala|Gly|Tyr|Glu|Pro|Ala|Met|Lys|Asp|Thr|Gln|Cys|
| | | |245| | | |250| | | | |255| | |
|Gln|Ala|Cys|Gly|Pro|Gly|Thr|Phe|Lys|Ser|Lys|Gln|Gly|Glu|Gly|Pro|
| | |260| | | |265| | | | |270| | | |
|Cys|Ser|Pro|Cys|Pro|Pro|Asn|Ser|Arg|Thr|Thr|Ala|Gly|Ala|Ala|Thr|
| | |275| | | |280| | | | |285| | | |
|Val|Cys|Ile|Cys|Arg|Ser|Gly|Phe|Phe|Arg|Ala|Asp|Ala|Asp|Pro|Ala|
| |290| | | |295| | | |300| | | | | |
|Asp|Ser|Ala|Cys|Thr|Ser|Val|Pro|Ser|Ala|Pro|Arg|Ser|Val|Ile|Ser|
|305| | | |310| | | |315| | | | | |320|
|Asn|Val|Asn|Glu|Thr|Ser|Leu|Val|Leu|Glu|Trp|Ser|Glu|Pro|Gln|Asp|
| | | |325| | | |330| | | | |335| | |
|Ala|Gly|Gly|Arg|Asp|Asp|Leu|Leu|Tyr|Asn|Val|Ile|Cys|Lys|Lys|Cys|
| | |340| | | |345| | | | |350| | | |
|Ser|Val|Glu|Arg|Arg|Leu|Cys|Ser|Arg|Cys|Asp|Asp|Asn|Val|Glu|Phe|
| |355| | | |360| | | |365| | | | | |
|Val|Pro|Arg|Gln|Leu|Gly|Leu|Thr|Gly|Leu|Thr|Glu|Arg|Arg|Ile|Tyr|
| |370| | | |375| | | |380| | | | | |
|Ile|Ser|Lys|Val|Met|Ala|His|Pro|Gln|Tyr|Thr|Phe|Glu|Ile|Gln|Ala|
|385| | | |390| | | |395| | | | | |400|
|Val|Asn|Gly|Ile|Ser|Ser|Lys|Ser|Pro|Tyr|Pro|Pro|His|Phe|Ala|Ser|
| | | |405| | | |410| | | | |415| | |
|Val|Asn|Ile|Thr|Thr|Asn|Gln|Ala|Ala|Pro|Ser|Ala|Val|Pro|Thr|Met|
| | |420| | | |425| | | | |430| | | |
|His|Leu|His|Ser|Ser|Thr|Gly|Asn|Ser|Met|Thr|Leu|Ser|Trp|Thr|Pro|
| | |435| | | |440| | | | |445| | | |

-continued

| | | | | | | | | | | | | | | |
|---|---|---|---|---|---|---|---|---|---|---|---|---|---|---|
| Pro | Glu | Arg | Pro | Asn | Gly | Ile | Ile | Leu | Asp | Tyr | Glu | Ile | Lys | Tyr | Ser |
| | 450 | | | | 455 | | | | 460 | | | | | |
| Glu | Lys | Gln | Gly | Gln | Gly | Asp | Gly | Ile | Ala | Asn | Thr | Val | Thr | Ser | Gln |
| 465 | | | | | 470 | | | | 475 | | | | | 480 |
| Lys | Asn | Ser | Val | Arg | Leu | Asp | Gly | Leu | Lys | Ala | Asn | Ala | Arg | Tyr | Met |
| | | | | 485 | | | | | 490 | | | | | 495 |
| Val | Gln | Val | Arg | Ala | Arg | Thr | Val | Ala | Gly | Tyr | Gly | Arg | Tyr | Ser | Leu |
| | | | 500 | | | | | 505 | | | | | 510 | |
| Pro | Thr | Glu | Phe | Gln | Thr | Thr | Ala | Glu | Asp | Gly | Ser | Thr | Ser | Lys | Thr |
| | | 515 | | | | | 520 | | | | | 525 | | |
| Phe | Gln | Glu | Leu | Pro | Leu | Ile | Val | Gly | Ser | Ala | Thr | Ala | Gly | Leu | Leu |
| | 530 | | | | | 535 | | | | | 540 | | | |
| Phe | Val | Ile | Val | Val | Ile | Ile | Ala | Ile | Val | Cys | Phe | Arg | Lys | Gln |
| 545 | | | | | 550 | | | | 555 | | | | | 560 |
| Arg | Asn | Ser | Thr | Asp | Pro | Glu | Tyr | Thr | Glu | Lys | Leu | Gln | Gln | Tyr | Val |
| | | | | 565 | | | | 570 | | | | | 575 | |
| Thr | Pro | Gly | Met | Lys | Val | Tyr | Ile | Asp | Pro | Phe | Thr | Tyr | Glu | Asp | Pro |
| | | | 580 | | | | | 585 | | | | | 590 | |
| Asn | Glu | Ala | Val | Arg | Glu | Phe | Ala | Lys | Glu | Ile | Asp | Ile | Ser | Cys | Val |
| | | 595 | | | | | 600 | | | | | 605 | | |
| Lys | Ile | Glu | Glu | Val | Ile | Gly | Ala | Gly | Glu | Phe | Gly | Glu | Val | Cys | Arg |
| 610 | | | | | 615 | | | | | 620 | | | | |
| Gly | Arg | Leu | Lys | Leu | Pro | Gly | Arg | Arg | Glu | Ile | Phe | Val | Ala | Ile | Lys |
| 625 | | | | | 630 | | | | 635 | | | | | 640 |
| Thr | Leu | Lys | Val | Gly | Tyr | Thr | Glu | Arg | Gln | Arg | Arg | Asp | Phe | Leu | Ser |
| | | | | 645 | | | | | 650 | | | | | 655 |
| Glu | Ala | Ser | Ile | Met | Gly | Gln | Phe | Asp | His | Pro | Asn | Ile | Ile | His | Leu |
| | | | | 660 | | | | 665 | | | | | 670 | |
| Glu | Gly | Val | Val | Thr | Lys | Ser | Arg | Pro | Val | Met | Ile | Ile | Thr | Glu | Phe |
| | | | 675 | | | | | 680 | | | | | 685 | |
| Met | Glu | Asn | Cys | Ala | Leu | Asp | Ser | Phe | Leu | Arg | Leu | Asn | Asp | Gly | Gln |
| | 690 | | | | | 695 | | | | | 700 | | | |
| Phe | Thr | Val | Ile | Gln | Leu | Val | Gly | Met | Leu | Arg | Gly | Ile | Ala | Ala | Gly |
| 705 | | | | | 710 | | | | | 715 | | | | | 720 |
| Met | Lys | Tyr | Leu | Ser | Glu | Met | Asn | Tyr | Val | His | Arg | Asp | Leu | Ala | Ala |
| | | | | 725 | | | | | 730 | | | | | 735 |
| Arg | Asn | Ile | Leu | Val | Asn | Ser | Asn | Leu | Val | Cys | Lys | Val | Ser | Asp | Phe |
| | | | 740 | | | | | 745 | | | | | 750 | |
| Gly | Leu | Ser | Arg | Phe | Leu | Glu | Asp | Asp | Pro | Ala | Asp | Pro | Thr | Tyr | Thr |
| | | 755 | | | | | 760 | | | | | 765 | | |
| Ser | Ser | Leu | Gly | Gly | Lys | Ile | Pro | Ile | Arg | Trp | Thr | Ala | Pro | Glu | Ala |
| | 770 | | | | | 775 | | | | | 780 | | | |
| Ile | Ala | Tyr | Arg | Lys | Phe | Thr | Ser | Ala | Ser | Asp | Val | Trp | Ser | Tyr | Gly |
| 785 | | | | | 790 | | | | | 795 | | | | | 800 |
| Ile | Val | Met | Trp | Glu | Val | Met | Ser | Tyr | Gly | Glu | Arg | Pro | Tyr | Trp | Asp |
| | | | | 805 | | | | | 810 | | | | | 815 |
| Met | Ser | Asn | Gln | Asp | Val | Ile | Asn | Ala | Val | Glu | Gln | Asp | Tyr | Arg | Leu |
| | | | 820 | | | | | 825 | | | | | 830 | |
| Pro | Pro | Pro | Met | Asp | Cys | Pro | Thr | Ala | Leu | His | Gln | Leu | Met | Leu | Asp |
| | | 835 | | | | | 840 | | | | | 845 | | |
| Cys | Trp | Val | Arg | Asp | Arg | Asn | Leu | Arg | Pro | Lys | Phe | Ala | Gln | Ile | Val |
| | 850 | | | | | 855 | | | | | 860 | | | |
| Asn | Thr | Leu | Asp | Lys | Leu | Ile | Arg | Asn | Ala | Ala | Ser | Leu | Lys | Val | Ile |

5,457,048

-continued

| 865 | | | | | 870 | | | | | 875 | | | | | 880 |
|---|---|---|---|---|---|---|---|---|---|---|---|---|---|---|---|
| Ala | Ser | Val | Gln | Ser | Gly | Val | Ser | Gln | Pro | Leu | Leu | Asp | Arg | Thr | Val |
| | | | | 885 | | | | | 890 | | | | | 895 | |
| Pro | Asp | Tyr | Thr | Thr | Phe | Thr | Thr | Val | Gly | Asp | Trp | Leu | Asp | Ala | Ile |
| | | | 900 | | | | | 905 | | | | | 910 | | |
| Lys | Met | Gly | Arg | Tyr | Lys | Glu | Asn | Phe | Val | Asn | Ala | Gly | Phe | Ala | Ser |
| | | 915 | | | | | 920 | | | | | 925 | | | |
| Phe | Asp | Leu | Val | Ala | Gln | Met | Thr | Ala | Glu | Asp | Leu | Leu | Arg | Ile | Gly |
| | 930 | | | | | 935 | | | | | 940 | | | | |
| Val | Thr | Leu | Ala | Gly | His | Gln | Lys | Lys | Ile | Leu | Ser | Ser | Ile | Gln | Asp |
| 945 | | | | | 950 | | | | | 955 | | | | | 960 |
| Met | Arg | Leu | Gln | Met | Asn | Gln | Thr | Leu | Pro | Val | Gln | Val | | | |
| | | | | 965 | | | | | 970 | | | | | | |

( 2 ) INFORMATION FOR SEQ ID NO:11:

( i ) SEQUENCE CHARACTERISTICS:
        ( A ) LENGTH: 4097 base pairs
        ( B ) TYPE: nucleic acid
        ( C ) STRANDEDNESS: both
        ( D ) TOPOLOGY: linear ( i x ) FEATURE:
        ( A ) NAME/KEY: CDS
        ( B ) LOCATION: 10..3042

( x i ) SEQUENCE DESCRIPTION: SEQ ID NO:11:

| CGGCTTCTG | ATG | CCC | GGC | CCG | GAG | CGC | ACC | ATG | GGG | CCG | TTG | TGG | TTC | 48 |
|---|---|---|---|---|---|---|---|---|---|---|---|---|---|---|
| | Met | Pro | Gly | Pro | Glu | Arg | Thr | Met | Gly | Pro | Leu | Trp | Phe | |
| | 1 | | | | 5 | | | | | 10 | | | | |

| TGC | TGT | TTG | CCC | CTC | GCC | CTC | TTG | CCT | CTG | CTC | GCC | GCC | GTG | GAA | GAG | 96 |
|---|---|---|---|---|---|---|---|---|---|---|---|---|---|---|---|---|
| Cys | Cys | Leu | Pro | Leu | Ala | Leu | Leu | Pro | Leu | Leu | Ala | Ala | Val | Glu | Glu | |
| | 15 | | | | 20 | | | | | 25 | | | | | | |

| ACG | CTG | ATG | GAC | TCC | ACA | ACG | GCC | ACA | GCA | GAG | CTG | GGC | TGG | ATG | GTG | 144 |
|---|---|---|---|---|---|---|---|---|---|---|---|---|---|---|---|---|
| Thr | Leu | Met | Asp | Ser | Thr | Thr | Ala | Thr | Ala | Glu | Leu | Gly | Trp | Met | Val | |
| 30 | | | | | 35 | | | | | 40 | | | | | 45 | |

| CAT | CCT | CCC | TCA | GGG | TGG | GAA | GAG | GTG | AGT | GGA | TAC | GAT | GAG | AAC | ATG | 192 |
|---|---|---|---|---|---|---|---|---|---|---|---|---|---|---|---|---|
| His | Pro | Pro | Ser | Gly | Trp | Glu | Glu | Val | Ser | Gly | Tyr | Asp | Glu | Asn | Met | |
| | | | | 50 | | | | | 55 | | | | | 60 | | |

| AAC | ACC | ATC | CGC | ACC | TAC | CAG | GTG | TGC | AAC | GTC | TTT | GAA | TCC | AGC | CAA | 240 |
|---|---|---|---|---|---|---|---|---|---|---|---|---|---|---|---|---|
| Asn | Thr | Ile | Arg | Thr | Tyr | Gln | Val | Cys | Asn | Val | Phe | Glu | Ser | Ser | Gln | |
| | | | 65 | | | | | 70 | | | | | 75 | | | |

| AAC | AAC | TGG | CTG | CGG | ACC | AAG | TAC | ATC | CGG | AGG | CGA | GGA | GCG | CAC | CGC | 288 |
|---|---|---|---|---|---|---|---|---|---|---|---|---|---|---|---|---|
| Asn | Asn | Trp | Leu | Arg | Thr | Lys | Tyr | Ile | Arg | Arg | Arg | Gly | Ala | His | Arg | |
| | | 80 | | | | | 85 | | | | | 90 | | | | |

| ATC | CAC | GTG | GAG | ATG | AAA | TTC | TCC | GTT | CGG | GAC | TGC | AGC | AGC | ATC | CCC | 336 |
|---|---|---|---|---|---|---|---|---|---|---|---|---|---|---|---|---|
| Ile | His | Val | Glu | Met | Lys | Phe | Ser | Val | Arg | Asp | Cys | Ser | Ser | Ile | Pro | |
| | 95 | | | | | 100 | | | | | 105 | | | | | |

| AAC | GTC | CCG | GGC | TCC | TGT | AAG | GAG | ACT | TTT | AAC | CTC | TAT | TAC | TAC | GAA | 384 |
|---|---|---|---|---|---|---|---|---|---|---|---|---|---|---|---|---|
| Asn | Val | Pro | Gly | Ser | Cys | Lys | Glu | Thr | Phe | Asn | Leu | Tyr | Tyr | Tyr | Glu | |
| 110 | | | | | 115 | | | | | 120 | | | | | 125 | |

| TCA | GAC | TTT | GAC | TCT | GCC | ACC | AAG | ACT | TTT | CCT | AAC | TGG | ATG | GAA | AAC | 432 |
|---|---|---|---|---|---|---|---|---|---|---|---|---|---|---|---|---|
| Ser | Asp | Phe | Asp | Ser | Ala | Thr | Lys | Thr | Phe | Pro | Asn | Trp | Met | Glu | Asn | |
| | | | | 130 | | | | | 135 | | | | | 140 | | |

| CCT | TGG | ATG | AAG | GTA | GAT | ACA | ATT | GCT | GCC | GAC | GAG | AGC | TTC | TCG | CAG | 480 |
|---|---|---|---|---|---|---|---|---|---|---|---|---|---|---|---|---|
| Pro | Trp | Met | Lys | Val | Asp | Thr | Ile | Ala | Ala | Asp | Glu | Ser | Phe | Ser | Gln | |
| | | | 145 | | | | | 150 | | | | | 155 | | | |

| GTG | GAC | CTT | GGT | GGG | CGG | GTG | ATG | AAG | ATT | AAC | ACC | GAG | GTG | CGC | AGT | 528 |
|---|---|---|---|---|---|---|---|---|---|---|---|---|---|---|---|---|
| Val | Asp | Leu | Gly | Gly | Arg | Val | Met | Lys | Ile | Asn | Thr | Glu | Val | Arg | Ser | |
| | | 160 | | | | | 165 | | | | | 170 | | | | |

-continued

| | | | | | | | | | | | | | | | | |
|---|---|---|---|---|---|---|---|---|---|---|---|---|---|---|---|---|
| TTT | GGG | CCT | GTC | TCC | AAA | AAC | GGT | TTC | TAC | CTG | GCC | TTC | CAG | GAC | TAC | 576 |
| Phe | Gly | Pro | Val | Ser | Lys | Asn | Gly | Phe | Tyr | Leu | Ala | Phe | Gln | Asp | Tyr | |
| | 175 | | | | 180 | | | | | 185 | | | | | | |
| GGG | GGC | TGC | ATG | TCC | TTG | ATT | GCA | GTC | CGT | GTC | TTT | TAC | CGC | AAG | TGT | 624 |
| Gly | Gly | Cys | Met | Ser | Leu | Ile | Ala | Val | Arg | Val | Phe | Tyr | Arg | Lys | Cys | |
| 190 | | | | | 195 | | | | | 200 | | | | | 205 | |
| CCC | CGT | GTG | ATC | CAG | AAC | GGG | GCG | GTC | TTC | CAG | GAA | ACC | CTC | TCG | GGA | 672 |
| Pro | Arg | Val | Ile | Gln | Asn | Gly | Ala | Val | Phe | Gln | Glu | Thr | Leu | Ser | Gly | |
| | | | | 210 | | | | | 215 | | | | | 220 | | |
| GCG | GAG | AGC | ACA | TCT | CTG | GTG | GCA | GCC | CGG | GGG | ACG | TGC | ATC | AGC | AAT | 720 |
| Ala | Glu | Ser | Thr | Ser | Leu | Val | Ala | Ala | Arg | Gly | Thr | Cys | Ile | Ser | Asn | |
| | | | 225 | | | | | 230 | | | | | 235 | | | |
| GCG | GAG | GAG | GTG | GAT | GTG | CCC | ATC | AAG | CTG | TAC | TGC | AAT | GGG | GAT | GGC | 768 |
| Ala | Glu | Glu | Val | Asp | Val | Pro | Ile | Lys | Leu | Tyr | Cys | Asn | Gly | Asp | Gly | |
| | | 240 | | | | | 245 | | | | | 250 | | | | |
| GAG | TGG | CTG | GTG | CCC | ATC | GGC | CGC | TGC | ATG | TGC | AGG | CCG | GGC | TAT | GAG | 816 |
| Glu | Trp | Leu | Val | Pro | Ile | Gly | Arg | Cys | Met | Cys | Arg | Pro | Gly | Tyr | Glu | |
| | 255 | | | | | 260 | | | | | 265 | | | | | |
| TCG | GTG | GAG | AAT | GGG | ACC | GTC | TGC | AGA | GGC | TGC | CCA | TCA | GGG | ACC | TTC | 864 |
| Ser | Val | Glu | Asn | Gly | Thr | Val | Cys | Arg | Gly | Cys | Pro | Ser | Gly | Thr | Phe | |
| 270 | | | | | 275 | | | | | 280 | | | | | 285 | |
| AAG | GCC | AGC | CAA | GGA | GAT | GAA | GGA | TGT | GTC | CAT | TGT | CCA | ATT | AAC | AGC | 912 |
| Lys | Ala | Ser | Gln | Gly | Asp | Glu | Gly | Cys | Val | His | Cys | Pro | Ile | Asn | Ser | |
| | | | | 290 | | | | | 295 | | | | | 300 | | |
| CGG | ACG | ACT | TCG | GAA | GGG | GCC | ACG | AAC | TGC | GTG | TGC | CGA | AAC | GGA | TAT | 960 |
| Arg | Thr | Thr | Ser | Glu | Gly | Ala | Thr | Asn | Cys | Val | Cys | Arg | Asn | Gly | Tyr | |
| | | | 305 | | | | | 310 | | | | | 315 | | | |
| TAC | CGG | GCA | GAT | GCT | GAC | CCC | GTC | GAC | ATG | CCA | TGC | ACC | ACC | ATC | CCA | 1008 |
| Tyr | Arg | Ala | Asp | Ala | Asp | Pro | Val | Asp | Met | Pro | Cys | Thr | Thr | Ile | Pro | |
| | | 320 | | | | | 325 | | | | | 330 | | | | |
| TCT | GCC | CCC | CAG | GCC | GTG | ATC | TCC | AGC | GTG | AAT | GAA | ACC | TCC | CTG | ATG | 1056 |
| Ser | Ala | Pro | Gln | Ala | Val | Ile | Ser | Ser | Val | Asn | Glu | Thr | Ser | Leu | Met | |
| | 335 | | | | | 340 | | | | | 345 | | | | | |
| CTG | GAG | TGG | ACC | CCA | CCA | CGA | GAC | TCA | GGG | GGC | CGG | GAG | GAT | CTG | GTA | 1104 |
| Leu | Glu | Trp | Thr | Pro | Pro | Arg | Asp | Ser | Gly | Gly | Arg | Glu | Asp | Leu | Val | |
| 350 | | | | | 355 | | | | | 360 | | | | | 365 | |
| TAC | AAC | ATC | ATC | TGC | AAG | AGC | TGT | GGG | TCA | GGC | CGT | GGG | GCG | TGC | ACG | 1152 |
| Tyr | Asn | Ile | Ile | Cys | Lys | Ser | Cys | Gly | Ser | Gly | Arg | Gly | Ala | Cys | Thr | |
| | | | | 370 | | | | | 375 | | | | | 380 | | |
| CGC | TGT | GGG | GAC | AAC | GTG | CAG | TTT | GCC | CCA | CGC | CAG | CTG | GGC | CTG | ACG | 1200 |
| Arg | Cys | Gly | Asp | Asn | Val | Gln | Phe | Ala | Pro | Arg | Gln | Leu | Gly | Leu | Thr | |
| | | | 385 | | | | | 390 | | | | | 395 | | | |
| GAG | CCT | CGC | ATC | TAC | ATC | AGC | GAC | CTG | CTG | GCC | CAC | ACG | CAG | TAC | ACC | 1248 |
| Glu | Pro | Arg | Ile | Tyr | Ile | Ser | Asp | Leu | Leu | Ala | His | Thr | Gln | Tyr | Thr | |
| | | 400 | | | | | 405 | | | | | 410 | | | | |
| TTT | GAG | ATC | CAG | GCT | GTG | AAT | GGG | GTC | ACC | GAC | CAG | AGC | CCC | TTC | TCC | 1296 |
| Phe | Glu | Ile | Gln | Ala | Val | Asn | Gly | Val | Thr | Asp | Gln | Ser | Pro | Phe | Ser | |
| | 415 | | | | | 420 | | | | | 425 | | | | | |
| CCA | CAG | TTT | GCA | TCA | GTG | AAT | ATC | ACC | ACC | AAC | CAG | GCT | GCT | CCT | TCA | 1344 |
| Pro | Gln | Phe | Ala | Ser | Val | Asn | Ile | Thr | Thr | Asn | Gln | Ala | Ala | Pro | Ser | |
| 430 | | | | | 435 | | | | | 440 | | | | | 445 | |
| GCC | GTG | TCC | ATA | ATG | CAC | CAG | GTC | AGC | CGC | ACT | GTG | GAC | AGC | ATT | ACC | 1392 |
| Ala | Val | Ser | Ile | Met | His | Gln | Val | Ser | Arg | Thr | Val | Asp | Ser | Ile | Thr | |
| | | | | 450 | | | | | 455 | | | | | 460 | | |
| CTC | TCG | TGG | TCT | CAA | CCT | GAC | CAG | CCC | AAT | GGA | GTC | ATC | CTG | GAT | TAT | 1440 |
| Leu | Ser | Trp | Ser | Gln | Pro | Asp | Gln | Pro | Asn | Gly | Val | Ile | Leu | Asp | Tyr | |
| | | | 465 | | | | | 470 | | | | | 475 | | | |
| GAG | CTG | CAA | TAC | TAT | GAG | AAG | AAC | CTG | AGT | GAG | TTA | AAT | TCA | ACA | GCA | 1488 |
| Glu | Leu | Gln | Tyr | Tyr | Glu | Lys | Asn | Leu | Ser | Glu | Leu | Asn | Ser | Thr | Ala | |
| | | 480 | | | | | 485 | | | | | 490 | | | | |

| | | | | | | | | | | | | | | | | |
|---|---|---|---|---|---|---|---|---|---|---|---|---|---|---|---|---|
| GTG | AAG | AGC | CCC | ACC | AAC | ACT | GTG | ACA | GTG | CAA | AAC | CTC | AAA | GCT | GGC | 1536 |
| Val | Lys | Ser | Pro | Thr | Asn | Thr | Val | Thr | Val | Gln | Asn | Leu | Lys | Ala | Gly | |
| | 495 | | | | 500 | | | | | 505 | | | | | | |
| ACC | ATC | TAT | GTC | TTC | CAA | GTG | CGA | GCA | CGT | ACC | GTG | GCT | GGG | TAT | GGC | 1584 |
| Thr | Ile | Tyr | Val | Phe | Gln | Val | Arg | Ala | Arg | Thr | Val | Ala | Gly | Tyr | Gly | |
| 510 | | | | | 515 | | | | | 520 | | | | | 525 | |
| CGG | TAT | AGT | GGC | AAG | ATG | TAC | TTC | CAG | ACC | ATG | ACT | GAA | GCC | GAG | TAC | 1632 |
| Arg | Tyr | Ser | Gly | Lys | Met | Tyr | Phe | Gln | Thr | Met | Thr | Glu | Ala | Glu | Tyr | |
| | | | | 530 | | | | | 535 | | | | | 540 | | |
| CAG | ACC | AGT | GTC | CAG | GAG | AAG | CTG | CCA | CTC | ATC | ATT | GGC | TCC | TCT | GCA | 1680 |
| Gln | Thr | Ser | Val | Gln | Glu | Lys | Leu | Pro | Leu | Ile | Ile | Gly | Ser | Ser | Ala | |
| | | | 545 | | | | | 550 | | | | | 555 | | | |
| GCA | GGA | CTG | GTG | TTT | CTC | ATT | GCT | GTT | GTC | GTC | ATC | ATT | ATT | GTC | TGC | 1728 |
| Ala | Gly | Leu | Val | Phe | Leu | Ile | Ala | Val | Val | Val | Ile | Ile | Ile | Val | Cys | |
| | | 560 | | | | | 565 | | | | | 570 | | | | |
| AAC | AGA | AGA | CGG | GGC | TTT | GAA | CGT | GCT | GAC | TCT | GAG | TAC | ACT | GAC | AAG | 1776 |
| Asn | Arg | Arg | Arg | Gly | Phe | Glu | Arg | Ala | Asp | Ser | Glu | Tyr | Thr | Asp | Lys | |
| | 575 | | | | | 580 | | | | | 585 | | | | | |
| CTG | CAG | CAC | TAT | ACC | AGT | GGC | CAC | AGT | ACG | TAC | CGT | GGT | CCC | CCG | CCA | 1824 |
| Leu | Gln | His | Tyr | Thr | Ser | Gly | His | Ser | Thr | Tyr | Arg | Gly | Pro | Pro | Pro | |
| 590 | | | | | 595 | | | | | 600 | | | | | 605 | |
| GGC | CTG | GGG | GTC | CGC | TCT | CTC | TTC | GTG | ACT | CCA | GGG | ATG | AAG | ATT | TAT | 1872 |
| Gly | Leu | Gly | Val | Arg | Ser | Leu | Phe | Val | Thr | Pro | Gly | Met | Lys | Ile | Tyr | |
| | | | | 610 | | | | | 615 | | | | | 620 | | |
| ATC | GAT | CCA | TTT | ACC | TAC | GAA | GAT | CCC | AAT | GAG | GCT | GTC | AGG | GAA | TTT | 1920 |
| Ile | Asp | Pro | Phe | Thr | Tyr | Glu | Asp | Pro | Asn | Glu | Ala | Val | Arg | Glu | Phe | |
| | | | 625 | | | | | 630 | | | | | 635 | | | |
| GCA | AAA | GAA | ATT | GAT | ATC | TCC | TGT | GTG | AAA | ATC | GAG | CAG | GTG | ATT | GGG | 1968 |
| Ala | Lys | Glu | Ile | Asp | Ile | Ser | Cys | Val | Lys | Ile | Glu | Gln | Val | Ile | Gly | |
| | | | 640 | | | | | 645 | | | | | 650 | | | |
| GCA | GGG | GAG | TTT | GGT | GAG | GTG | TGC | AGT | GGG | CAT | CTC | AAG | CTT | CCT | GGC | 2016 |
| Ala | Gly | Glu | Phe | Gly | Glu | Val | Cys | Ser | Gly | His | Leu | Lys | Leu | Pro | Gly | |
| | 655 | | | | | 660 | | | | | 665 | | | | | |
| AAA | AGA | GAG | ATC | TTT | GTG | GCC | ATC | AAG | ACC | CTG | AAG | TCT | GGT | TAC | ACA | 2064 |
| Lys | Arg | Glu | Ile | Phe | Val | Ala | Ile | Lys | Thr | Leu | Lys | Ser | Gly | Tyr | Thr | |
| 670 | | | | | 675 | | | | | 680 | | | | | 685 | |
| GAG | AAG | CAG | AGA | CGG | GAC | TTC | CTG | AGT | GAA | GCC | AGC | ATC | ATG | GGG | CAG | 2112 |
| Glu | Lys | Gln | Arg | Arg | Asp | Phe | Leu | Ser | Glu | Ala | Ser | Ile | Met | Gly | Gln | |
| | | | | 690 | | | | | 695 | | | | | 700 | | |
| TTT | GAC | CAC | CCC | AAT | GTC | ATC | CAC | CTG | GAA | GGG | GTG | GTG | ACC | AAG | AGT | 2160 |
| Phe | Asp | His | Pro | Asn | Val | Ile | His | Leu | Glu | Gly | Val | Val | Thr | Lys | Ser | |
| | | | 705 | | | | | 710 | | | | | 715 | | | |
| TCC | CCA | GTC | ATG | ATC | ATT | ACA | GAG | TTC | ATG | GAG | AAT | GGC | TCG | TTG | GAC | 2208 |
| Ser | Pro | Val | Met | Ile | Ile | Thr | Glu | Phe | Met | Glu | Asn | Gly | Ser | Leu | Asp | |
| | | 720 | | | | | 725 | | | | | 730 | | | | |
| TCC | TTC | TTG | AGG | CAA | AAT | GAT | GGG | CAG | TTC | ACA | GTG | ATC | CAG | CTG | GTG | 2256 |
| Ser | Phe | Leu | Arg | Gln | Asn | Asp | Gly | Gln | Phe | Thr | Val | Ile | Gln | Leu | Val | |
| | 735 | | | | | 740 | | | | | 745 | | | | | |
| GGC | ATG | TTG | CGT | GGC | ATT | GCA | GCA | GGC | ATG | AAG | TAC | CTG | GCT | GAT | ATG | 2304 |
| Gly | Met | Leu | Arg | Gly | Ile | Ala | Ala | Gly | Met | Lys | Tyr | Leu | Ala | Asp | Met | |
| 750 | | | | | 755 | | | | | 760 | | | | | 765 | |
| AAC | TAC | GTG | CAC | CGG | GAC | CTG | GCT | GCC | CGC | AAC | ATC | CTG | GTC | AAC | AGC | 2352 |
| Asn | Tyr | Val | His | Arg | Asp | Leu | Ala | Ala | Arg | Asn | Ile | Leu | Val | Asn | Ser | |
| | | | | 770 | | | | | 775 | | | | | 780 | | |
| AAC | CTG | GTC | TGC | AAG | GTG | TCC | GAC | TTC | GGC | CTC | TCC | CGT | TTC | CTG | GAG | 2400 |
| Asn | Leu | Val | Cys | Lys | Val | Ser | Asp | Phe | Gly | Leu | Ser | Arg | Phe | Leu | Glu | |
| | | | 785 | | | | | 790 | | | | | 795 | | | |
| GAT | GAC | ACC | TCT | GAT | CCC | ACT | TAC | ACC | AGC | GCA | CTG | GGT | GGA | AAG | ATC | 2448 |
| Asp | Asp | Thr | Ser | Asp | Pro | Thr | Tyr | Thr | Ser | Ala | Leu | Gly | Gly | Lys | Ile | |

```
          800                         805                          810
CCA ATA CGG TGG ACA GCG CCT GAG GCA ATT CAG TAC CGA AAA TTC ACA      2496
Pro Ile Arg Trp Thr Ala Pro Glu Ala Ile Gln Tyr Arg Lys Phe Thr
    815                 820                 825

TCA GCC AGC GAT GTG TGG AGC TAT GGA ATA GTC ATG TGG GAG GTG ATG      2544
Ser Ala Ser Asp Val Trp Ser Tyr Gly Ile Val Met Trp Glu Val Met
830                 835                 840                 845

TCG TAC GGC GAG CGG CCT TAC TGG GAC ATG ACC AAT CAA GAT GTG ATA      2592
Ser Tyr Gly Glu Arg Pro Tyr Trp Asp Met Thr Asn Gln Asp Val Ile
                850                 855                 860

AAT GCT ATT GAG CAG GAC TAT CGG CTA CCA CCC CCT ATG GAT TGT CCA      2640
Asn Ala Ile Glu Gln Asp Tyr Arg Leu Pro Pro Pro Met Asp Cys Pro
            865                 870                 875

AAT GCC CTG CAC CAG CTA ATG CTT GAC TGC TGG CAG AAG GAT CGA AAC      2688
Asn Ala Leu His Gln Leu Met Leu Asp Cys Trp Gln Lys Asp Arg Asn
        880                 885                 890

CAC AGA CCC AAA TTT GGA CAG ATT GTC AAC ACT TTA GAC AAA ATG ATC      2736
His Arg Pro Lys Phe Gly Gln Ile Val Asn Thr Leu Asp Lys Met Ile
    895                 900                 905

CGA AAT CCT AAT AGT CTG AAA GCC ATG GCA CCT CTC TCC TCT GGG GTT      2784
Arg Asn Pro Asn Ser Leu Lys Ala Met Ala Pro Leu Ser Ser Gly Val
910                 915                 920                 925

AAC CTC CCT CTA CTT GAC CGC ACA ATC CCA GAT TAT ACC AGC TTC AAC      2832
Asn Leu Pro Leu Leu Asp Arg Thr Ile Pro Asp Tyr Thr Ser Phe Asn
                930                 935                 940

ACT GTG GAT GAA TGG CTG GAT GCC ATC AAG ATG AGC CAG TAC AAG GAG      2880
Thr Val Asp Glu Trp Leu Asp Ala Ile Lys Met Ser Gln Tyr Lys Glu
            945                 950                 955

AGC TTT GCC AGT GCT GGC TTC ACC ACC TTT GAT ATA GTA TCT CAG ATG      2928
Ser Phe Ala Ser Ala Gly Phe Thr Thr Phe Asp Ile Val Ser Gln Met
        960                 965                 970

ACT GTA GAG GAC ATT CTA CGA GTT GGG GTC ACT TTA GCA GGA CAC CAG      2976
Thr Val Glu Asp Ile Leu Arg Val Gly Val Thr Leu Ala Gly His Gln
    975                 980                 985

AAG AAA ATT CTG AAC AGT ATC CAG GTG ATG AGA GCA CAG ATG AAC CAA      3024
Lys Lys Ile Leu Asn Ser Ile Gln Val Met Arg Ala Gln Met Asn Gln
990                 995                 1000                1005

ATT CAG TCT GTG GAG GTT TGATAGCAAC ACGTCCTCGT GCTCCACTTC             3072
Ile Gln Ser Val Glu Val
                1010
```

| | | | | |
|---|---|---|---|---|
| CTTGAGGCCC | TGCTCCCCTC | TGCCCCTGTG | TGTCTGAGCT | CCAGTTCTTG AGTGTTCTGC | 3132 |
| GTGGATCAGA | GACAGGCAGC | TGCTCTGAGG | ATCATGGCAA | CAGGAAGAAA TGCCCTATCA | 3192 |
| TTGACAACGA | GAAGTCATCA | AGAGGTGAAA | CAATGGAAAA | CAATGGAAAA AGGGAACAAG | 3252 |
| TAAAGACAGC | TATTTTGAAA | ACCGAAAACA | AACAGTGAAT | TATTTTTAAA TAATAATAAA | 3312 |
| GCAATTGCAG | TCTTGAAAAG | GGCTCCAAGA | CCAATGGGAG | TCTCCAAAGG AAGAGAATAG | 3372 |
| AGCAGCTTCA | TCTATTTCCT | CTTACACAAG | GGTTGCTGCA | GCTGGGCCCA GACACTTCTG | 3432 |
| GAGTAACGAG | ACTTTTCAAG | AAGATGAATG | CAAAGAATGG | TCACAAGAAG CACTTCTCTT | 3492 |
| TCTCACATGG | GATGGCAGCT | CTGGGAATGC | CGGCAGTCC | TTCCTGAAAG CCCTGTTGGC | 3552 |
| AAATCGAAGA | GGAGAGCCGA | AGCTCTTTGG | TGCTGTGGAA | CCAAGTGCAT CTCAGAAATT | 3612 |
| GTTGGACTTC | TACAAAAGCT | GAAGACATTC | TTTTTTTTA | AACAAGTAAA CTGATACTAG | 3672 |
| AAGAGGCTGT | TTCCGTCAAA | TGAGAAGGAA | TCTGTAACAC | TGGCCCGGGG GGGGTGGGGA | 3732 |
| ATGGGGGAAA | TCAGTCCTTT | TTACATCTCT | TTATTTTCTC | TTGTCATGGA ACAGTTTTGT | 3792 |
| GAGTGACAGT | TTCCTAAGGG | TCCGTCCATC | CACCCTCCAA | TGGCATCATT GTTTCATACA | 3852 |

```
TATCATATGC ACAAGACTTA TAGTGATGTC CTCACTCGAT GCCAATGATC TTTCCCCAGA      3912

AGACTTCCCA AGTACAGTAT GTAGTAGATT TTGATTACAA ATGCTGACGT GTACCTTTAT      3972

TTTTCGGTTG TCGTTGTTGG GAGATTCGTC CTTTTACCTT GCTTTGTTAA CACCAATTTG      4032

TGAGTTTGGG GTTGGAATTT TTTTGGTCGA TTGGGGTTGT TTTTTTTTTT TTTTTTTTT       4092

AACCG                                                                   4097
```

( 2 ) INFORMATION FOR SEQ ID NO:12:

( i ) SEQUENCE CHARACTERISTICS:
        ( A ) LENGTH: 1011 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Met Pro Gly Pro Glu Arg Thr Met Gly Pro Leu Trp Phe Cys Cys Leu
 1               5                  10                  15

Pro Leu Ala Leu Leu Pro Leu Leu Ala Ala Val Glu Glu Thr Leu Met
            20                  25                  30

Asp Ser Thr Thr Ala Thr Ala Glu Leu Gly Trp Met Val His Pro Pro
        35                  40                  45

Ser Gly Trp Glu Glu Val Ser Gly Tyr Asp Glu Asn Met Asn Thr Ile
    50                  55                  60

Arg Thr Tyr Gln Val Cys Asn Val Phe Glu Ser Ser Gln Asn Asn Trp
65                  70                  75                  80

Leu Arg Thr Lys Tyr Ile Arg Arg Arg Gly Ala His Arg Ile His Val
                85                  90                  95

Glu Met Lys Phe Ser Val Arg Asp Cys Ser Ser Ile Pro Asn Val Pro
           100                 105                 110

Gly Ser Cys Lys Glu Thr Phe Asn Leu Tyr Tyr Tyr Glu Ser Asp Phe
       115                 120                 125

Asp Ser Ala Thr Lys Thr Phe Pro Asn Trp Met Glu Asn Pro Trp Met
   130                 135                 140

Lys Val Asp Thr Ile Ala Ala Asp Glu Ser Phe Ser Gln Val Asp Leu
145                 150                 155                 160

Gly Gly Arg Val Met Lys Ile Asn Thr Glu Val Arg Ser Phe Gly Pro
                165                 170                 175

Val Ser Lys Asn Gly Phe Tyr Leu Ala Phe Gln Asp Tyr Gly Gly Cys
           180                 185                 190

Met Ser Leu Ile Ala Val Arg Val Phe Tyr Arg Lys Cys Pro Arg Val
       195                 200                 205

Ile Gln Asn Gly Ala Val Phe Gln Glu Thr Leu Ser Gly Ala Glu Ser
   210                 215                 220

Thr Ser Leu Val Ala Ala Arg Gly Thr Cys Ile Ser Asn Ala Glu Glu
225                 230                 235                 240

Val Asp Val Pro Ile Lys Leu Tyr Cys Asn Gly Asp Gly Glu Trp Leu
                245                 250                 255

Val Pro Ile Gly Arg Cys Met Cys Arg Pro Gly Tyr Glu Ser Val Glu
           260                 265                 270

Asn Gly Thr Val Cys Arg Gly Cys Pro Ser Gly Thr Phe Lys Ala Ser
       275                 280                 285

Gln Gly Asp Glu Gly Cys Val His Cys Pro Ile Asn Ser Arg Thr Thr
   290                 295                 300
```

-continued

| | | | | | | | | | | | | | | |
|---|---|---|---|---|---|---|---|---|---|---|---|---|---|---|
| Ser 305 | Glu | Gly | Ala | Thr | Asn 310 | Cys | Val | Cys | Arg 315 | Asn | Gly | Tyr | Tyr | Arg Ala 320 |
| Asp | Ala | Asp | Pro | Val 325 | Asp | Met | Pro | Cys | Thr 330 | Thr | Ile | Pro | Ser | Ala Pro 335 |
| Gln | Ala | Val | Ile 340 | Ser | Ser | Val | Asn | Glu 345 | Thr | Ser | Leu | Met | Leu 350 | Glu Trp |
| Thr | Pro | Pro 355 | Arg | Asp | Ser | Gly | Gly 360 | Arg | Glu | Asp | Leu | Val 365 | Tyr | Asn Ile |
| Ile | Cys 370 | Lys | Ser | Cys | Gly | Ser 375 | Gly | Arg | Gly | Ala | Cys 380 | Thr | Arg | Cys Gly |
| Asp 385 | Asn | Val | Gln | Phe | Ala 390 | Pro | Arg | Gln | Leu | Gly 395 | Leu | Thr | Glu | Pro Arg 400 |
| Ile | Tyr | Ile | Ser | Asp 405 | Leu | Leu | Ala | His | Thr 410 | Gln | Tyr | Thr | Phe | Glu Ile 415 |
| Gln | Ala | Val | Asn 420 | Gly | Val | Thr | Asp | Gln 425 | Ser | Pro | Phe | Ser | Pro 430 | Gln Phe |
| Ala | Ser | Val 435 | Asn | Ile | Thr | Thr | Asn 440 | Gln | Ala | Ala | Pro | Ser 445 | Ala | Val Ser |
| Ile | Met 450 | His | Gln | Val | Ser | Arg 455 | Thr | Val | Asp | Ser | Ile 460 | Thr | Leu | Ser Trp |
| Ser 465 | Gln | Pro | Asp | Gln | Pro 470 | Asn | Gly | Val | Ile | Leu 475 | Asp | Tyr | Glu | Leu Gln 480 |
| Tyr | Tyr | Glu | Lys | Asn 485 | Leu | Ser | Glu | Leu | Asn 490 | Ser | Thr | Ala | Val | Lys Ser 495 |
| Pro | Thr | Asn | Thr 500 | Val | Thr | Val | Gln | Asn 505 | Leu | Lys | Ala | Gly | Thr 510 | Ile Tyr |
| Val | Phe | Gln 515 | Val | Arg | Ala | Arg | Thr 520 | Val | Ala | Gly | Tyr | Gly 525 | Arg | Tyr Ser |
| Gly | Lys 530 | Met | Tyr | Phe | Gln | Thr 535 | Met | Thr | Glu | Ala | Glu 540 | Tyr | Gln | Thr Ser |
| Val 545 | Gln | Glu | Lys | Leu | Pro 550 | Leu | Ile | Ile | Gly | Ser 555 | Ser | Ala | Ala | Gly Leu 560 |
| Val | Phe | Leu | Ile | Ala 565 | Val | Val | Val | Ile | Ile 570 | Ile | Val | Cys | Asn | Arg Arg 575 |
| Arg | Gly | Phe | Glu 580 | Arg | Ala | Asp | Ser | Glu 585 | Tyr | Thr | Asp | Lys | Leu 590 | Gln His |
| Tyr | Thr | Ser 595 | Gly | His | Ser | Thr | Tyr 600 | Arg | Gly | Pro | Pro | Pro 605 | Gly | Leu Gly |
| Val | Arg 610 | Ser | Leu | Phe | Val | Thr 615 | Pro | Gly | Met | Lys | Ile 620 | Tyr | Ile | Asp Pro |
| Phe 625 | Thr | Tyr | Glu | Asp | Pro 630 | Asn | Glu | Ala | Val | Arg 635 | Glu | Phe | Ala | Lys Glu 640 |
| Ile | Asp | Ile | Ser | Cys 645 | Val | Lys | Ile | Glu | Gln 650 | Val | Ile | Gly | Ala | Gly Glu 655 |
| Phe | Gly | Glu | Val 660 | Cys | Ser | Gly | His | Leu 665 | Lys | Leu | Pro | Gly | Lys 670 | Arg Glu |
| Ile | Phe | Val 675 | Ala | Ile | Lys | Thr | Leu 680 | Lys | Ser | Gly | Tyr | Thr 685 | Glu | Lys Gln |
| Arg | Arg 690 | Asp | Phe | Leu | Ser | Glu 695 | Ala | Ser | Ile | Met | Gly 700 | Gln | Phe | Asp His |
| Pro 705 | Asn | Val | Ile | His | Leu 710 | Glu | Gly | Val | Val | Thr 715 | Lys | Ser | Ser | Pro Val 720 |

|     |     |     |     |     |     |     |     |     |     |     |     |     |     |     |
|-----|-----|-----|-----|-----|-----|-----|-----|-----|-----|-----|-----|-----|-----|-----|
| Met | Ile | Ile | Thr | Glu<br>725 | Phe | Met | Glu | Asn | Gly<br>730 | Ser | Leu | Asp | Ser | Phe<br>735 | Leu |
| Arg | Gln | Asn | Asp<br>740 | Gly | Gln | Phe | Thr | Val<br>745 | Ile | Gln | Leu | Val | Gly<br>750 | Met | Leu |
| Arg | Gly | Ile<br>755 | Ala | Ala | Gly | Met | Lys<br>760 | Tyr | Leu | Ala | Asp | Met<br>765 | Asn | Tyr | Val |
| His | Arg<br>770 | Asp | Leu | Ala | Ala | Arg<br>775 | Asn | Ile | Leu | Val | Asn<br>780 | Ser | Asn | Leu | Val |
| Cys<br>785 | Lys | Val | Ser | Asp | Phe<br>790 | Gly | Leu | Ser | Arg | Phe<br>795 | Leu | Glu | Asp | Asp | Thr<br>800 |
| Ser | Asp | Pro | Thr | Tyr<br>805 | Thr | Ser | Ala | Leu | Gly<br>810 | Gly | Lys | Ile | Pro | Ile<br>815 | Arg |
| Trp | Thr | Ala | Pro<br>820 | Glu | Ala | Ile | Gln | Tyr<br>825 | Arg | Lys | Phe | Thr | Ser<br>830 | Ala | Ser |
| Asp | Val | Trp<br>835 | Ser | Tyr | Gly | Ile | Val<br>840 | Met | Trp | Glu | Val | Met<br>845 | Ser | Tyr | Gly |
| Glu | Arg<br>850 | Pro | Tyr | Trp | Asp | Met<br>855 | Thr | Asn | Gln | Asp | Val<br>860 | Ile | Asn | Ala | Ile |
| Glu<br>865 | Gln | Asp | Tyr | Arg | Leu<br>870 | Pro | Pro | Pro | Met | Asp<br>875 | Cys | Pro | Asn | Ala | Leu<br>880 |
| His | Gln | Leu | Met | Leu<br>885 | Asp | Cys | Trp | Gln | Lys<br>890 | Asp | Arg | Asn | His | Arg<br>895 | Pro |
| Lys | Phe | Gly | Gln<br>900 | Ile | Val | Asn | Thr | Leu<br>905 | Asp | Lys | Met | Ile | Arg<br>910 | Asn | Pro |
| Asn | Ser | Leu<br>915 | Lys | Ala | Met | Ala | Pro<br>920 | Leu | Ser | Ser | Gly | Val<br>925 | Asn | Leu | Pro |
| Leu | Leu<br>930 | Asp | Arg | Thr | Ile | Pro<br>935 | Asp | Tyr | Thr | Ser | Phe<br>940 | Asn | Thr | Val | Asp |
| Glu<br>945 | Trp | Leu | Asp | Ala | Ile<br>950 | Lys | Met | Ser | Gln | Tyr<br>955 | Lys | Glu | Ser | Phe | Ala<br>960 |
| Ser | Ala | Gly | Phe | Thr<br>965 | Thr | Phe | Asp | Ile | Val<br>970 | Ser | Gln | Met | Thr | Val<br>975 | Glu |
| Asp | Ile | Leu | Arg<br>980 | Val | Gly | Val | Thr | Leu<br>985 | Ala | Gly | His | Gln | Lys<br>990 | Lys | Ile |
| Leu | Asn | Ser<br>995 | Ile | Gln | Val | Met | Arg<br>1000 | Ala | Gln | Met | Asn | Gln<br>1005 | Ile | Gln | Ser |
| Val | Glu | Val<br>1010 |     |     |     |     |     |     |     |     |     |     |     |     |     |

( 2 ) INFORMATION FOR SEQ ID NO:13:

( i ) SEQUENCE CHARACTERISTICS:
        ( A ) LENGTH: 3591 base pairs
        ( B ) TYPE: nucleic acid
        ( C ) STRANDEDNESS: both
        ( D ) TOPOLOGY: linear ( i x ) FEATURE:
        ( A ) NAME/KEY: CDS
        ( B ) LOCATION: 2..2965

( x i ) SEQUENCE DESCRIPTION: SEQ ID NO:13:

| C | GGG | GTC | TCC | TCG | AGG | GCG | CGG | CGG | CCG | CCG | GGC | AGC | AGC | AGG | AGC | 46 |
|---|-----|-----|-----|-----|-----|-----|-----|-----|-----|-----|-----|-----|-----|-----|-----|-----|
|   | Gly | Val | Ser | Ser | Arg | Ala | Arg | Arg | Pro | Pro | Gly | Ser | Ser | Arg | Ser |    |
|   | 1   |     |     | 5   |     |     |     |     | 10  |     |     |     |     | 15  |     |    |

| AGC | AGG | AGG | GGG | GTG | ACC | TCG | GAG | CTG | GCA | TGG | ACA | ACC | CAT | CCG | GAG | 94 |
|-----|-----|-----|-----|-----|-----|-----|-----|-----|-----|-----|-----|-----|-----|-----|-----|-----|
| Ser | Arg | Arg | Gly | Val | Thr | Ser | Glu | Leu | Ala | Trp | Thr | Thr | His | Pro | Glu |    |
|     |     |     | 20  |     |     |     | 25  |     |     |     |     | 30  |     |     |     |    |

| | | | | | | | | | | | | | | | | |
|---|---|---|---|---|---|---|---|---|---|---|---|---|---|---|---|---|
| ACG | GGG | TGG | GAA | GAG | GTC | AGT | GGT | TAC | GAC | GAG | GCT | ATG | AAC | CCC | ATC | 142 |
| Thr | Gly | Trp | Glu | Glu | Val | Ser | Gly | Tyr | Asp | Glu | Ala | Met | Asn | Pro | Ile | |
| | | | 35 | | | | 40 | | | | | 45 | | | | |
| CGC | ACA | TAC | CAG | GTG | TGC | AAC | GTG | CGG | GAG | GCC | AAC | CAG | AAC | AAC | TGG | 190 |
| Arg | Thr | Tyr | Gln | Val | Cys | Asn | Val | Arg | Glu | Ala | Asn | Gln | Asn | Asn | Trp | |
| | 50 | | | | 55 | | | | | 60 | | | | | | |
| CTT | CGC | ACC | AAG | TTC | ATT | CAG | CGC | CAG | GAC | GTC | CAG | CGT | GTC | TAC | GTG | 238 |
| Leu | Arg | Thr | Lys | Phe | Ile | Gln | Arg | Gln | Asp | Val | Gln | Arg | Val | Tyr | Val | |
| | 65 | | | | 70 | | | | | 75 | | | | | | |
| GAG | CTG | AAA | TTC | ACT | GTG | CGG | GAC | TGC | AAC | AGC | ATC | CCC | AAC | ATC | CCT | 286 |
| Glu | Leu | Lys | Phe | Thr | Val | Arg | Asp | Cys | Asn | Ser | Ile | Pro | Asn | Ile | Pro | |
| 80 | | | | | 85 | | | | | 90 | | | | | 95 | |
| GGT | TCC | TGC | AAA | GAG | ACC | TTC | AAC | CTC | TTC | TAT | TAT | GAG | TCA | GAT | ACG | 334 |
| Gly | Ser | Cys | Lys | Glu | Thr | Phe | Asn | Leu | Phe | Tyr | Tyr | Glu | Ser | Asp | Thr | |
| | | | | 100 | | | | | 105 | | | | | 110 | | |
| GAT | TCT | GCC | TCT | GCC | AAT | AGC | CCT | TTC | TGG | ATG | GAG | AAC | CCC | TAT | ATC | 382 |
| Asp | Ser | Ala | Ser | Ala | Asn | Ser | Pro | Phe | Trp | Met | Glu | Asn | Pro | Tyr | Ile | |
| | | | 115 | | | | 120 | | | | | 125 | | | | |
| AAA | GTG | GAT | ACA | ATT | GCT | CCG | GAT | GAG | AGC | TTC | TCC | AAA | CTG | GAG | TCC | 430 |
| Lys | Val | Asp | Thr | Ile | Ala | Pro | Asp | Glu | Ser | Phe | Ser | Lys | Leu | Glu | Ser | |
| | | 130 | | | | | 135 | | | | | 140 | | | | |
| GGC | CGT | GTG | AAC | ACC | AAG | GTG | CGC | AGC | TTT | GGG | CCG | CTC | TCC | AAG | AAT | 478 |
| Gly | Arg | Val | Asn | Thr | Lys | Val | Arg | Ser | Phe | Gly | Pro | Leu | Ser | Lys | Asn | |
| | 145 | | | | | 150 | | | | | 155 | | | | | |
| GGC | TTT | TAT | CTG | GCT | TTC | CAG | GAC | CTG | GGG | GCC | TGC | ATG | TCC | CTT | ATC | 526 |
| Gly | Phe | Tyr | Leu | Ala | Phe | Gln | Asp | Leu | Gly | Ala | Cys | Met | Ser | Leu | Ile | |
| 160 | | | | | 165 | | | | | 170 | | | | | 175 | |
| TCC | GTC | CGG | GCT | TTC | TAC | AAG | AAA | TGT | TCC | AAC | ACC | ATC | GCT | GGC | TTT | 574 |
| Ser | Val | Arg | Ala | Phe | Tyr | Lys | Lys | Cys | Ser | Asn | Thr | Ile | Ala | Gly | Phe | |
| | | | | 180 | | | | | 185 | | | | | 190 | | |
| GCT | ATC | TTC | CCG | GAG | ACC | CTA | ACG | GGG | GCT | GAG | CCC | ACG | TCG | CTG | GTC | 622 |
| Ala | Ile | Phe | Pro | Glu | Thr | Leu | Thr | Gly | Ala | Glu | Pro | Thr | Ser | Leu | Val | |
| | | | 195 | | | | | 200 | | | | | 205 | | | |
| ATT | GCG | CCG | GGC | ACC | TGC | ATC | CCC | AAC | GCA | GTG | GAA | GTG | TCT | GTG | CCC | 670 |
| Ile | Ala | Pro | Gly | Thr | Cys | Ile | Pro | Asn | Ala | Val | Glu | Val | Ser | Val | Pro | |
| | | 210 | | | | | 215 | | | | | 220 | | | | |
| CTG | AAG | CTG | TAC | TGC | AAC | GGT | GAT | GGC | GAG | TGG | ATG | GTG | CCT | GTG | GGA | 718 |
| Leu | Lys | Leu | Tyr | Cys | Asn | Gly | Asp | Gly | Glu | Trp | Met | Val | Pro | Val | Gly | |
| | 225 | | | | | 230 | | | | | 235 | | | | | |
| GCG | TGC | ACG | TGT | GCT | GCT | GGG | TAC | GAG | CCA | GCC | ATG | AAG | GAT | ACC | CAG | 766 |
| Ala | Cys | Thr | Cys | Ala | Ala | Gly | Tyr | Glu | Pro | Ala | Met | Lys | Asp | Thr | Gln | |
| 240 | | | | | 245 | | | | | 250 | | | | | 255 | |
| TGC | CAA | GCA | TGC | GGC | CCG | GGG | ACG | TTC | AAA | TCC | AAG | CAG | GGC | GAG | GGC | 814 |
| Cys | Gln | Ala | Cys | Gly | Pro | Gly | Thr | Phe | Lys | Ser | Lys | Gln | Gly | Glu | Gly | |
| | | | | 260 | | | | | 265 | | | | | 270 | | |
| CCC | TGC | TCC | CCC | TGC | CCT | CCC | AAC | AGC | CGC | ACC | ACC | GCG | GGG | GCA | GCC | 862 |
| Pro | Cys | Ser | Pro | Cys | Pro | Pro | Asn | Ser | Arg | Thr | Thr | Ala | Gly | Ala | Ala | |
| | | | 275 | | | | | 280 | | | | | 285 | | | |
| ACA | GTC | TGC | ATA | TGT | CGC | AGC | GGC | TTC | TTC | CGA | GCA | GAC | GCG | GAC | CCC | 910 |
| Thr | Val | Cys | Ile | Cys | Arg | Ser | Gly | Phe | Phe | Arg | Ala | Asp | Ala | Asp | Pro | |
| | | 290 | | | | | 295 | | | | | 300 | | | | |
| GCA | GAC | AGC | GCC | TGC | ACC | AGT | GTG | CCC | TCA | GCC | CCA | CGC | AGC | GTC | ATC | 958 |
| Ala | Asp | Ser | Ala | Cys | Thr | Ser | Val | Pro | Ser | Ala | Pro | Arg | Ser | Val | Ile | |
| | | 305 | | | | | 310 | | | | | 315 | | | | |
| TCC | AAC | GTG | AAT | GAG | ACG | TCG | TTG | GTG | CTG | GAG | TGG | AGC | GAG | CCG | CAG | 1006 |
| Ser | Asn | Val | Asn | Glu | Thr | Ser | Leu | Val | Leu | Glu | Trp | Ser | Glu | Pro | Gln | |
| 320 | | | | | 325 | | | | | 330 | | | | | 335 | |
| GAC | GCG | GGC | GGG | CGG | GAT | GAC | CTG | CTC | TAC | AAC | GTC | ATC | TGC | AAG | AAG | 1054 |
| Asp | Ala | Gly | Gly | Arg | Asp | Asp | Leu | Leu | Tyr | Asn | Val | Ile | Cys | Lys | Lys | |

|     |     |     |     |     |     |     |     |     |     |     |     |     |     |     |     |
| --- | --- | --- | --- | --- | --- | --- | --- | --- | --- | --- | --- | --- | --- | --- | --- |
|     |     |     |     | 340 |     |     |     |     | 345 |     |     |     |     | 350 |     |

| TGC | AGC | GTG | GAG | CGG | CGG | CTG | TGC | AGC | CGC | TGC | GAC | GAC | AAC | GTG | GAG | 1102 |
| --- | --- | --- | --- | --- | --- | --- | --- | --- | --- | --- | --- | --- | --- | --- | --- | --- |
| Cys | Ser | Val | Glu | Arg | Arg | Leu | Cys | Ser | Arg | Cys | Asp | Asp | Asn | Val | Glu |      |
|     |     |     | 355 |     |     |     |     |     | 360 |     |     |     |     | 365 |     |      |
| TTC | GTG | CCG | CGC | CAG | CTG | GGC | CTC | ACT | GGC | CTC | ACT | GAG | CGA | CGC | ATC | 1150 |
| Phe | Val | Pro | Arg | Gln | Leu | Gly | Leu | Thr | Gly | Leu | Thr | Glu | Arg | Arg | Ile |      |
|     |     | 370 |     |     |     |     | 375 |     |     |     |     | 380 |     |     |     |      |
| TAC | ATC | AGC | AAG | GTG | ATG | GCC | CAC | CCC | CAG | TAC | ACC | TTC | GAG | ATC | CAG | 1198 |
| Tyr | Ile | Ser | Lys | Val | Met | Ala | His | Pro | Gln | Tyr | Thr | Phe | Glu | Ile | Gln |      |
|     | 385 |     |     |     |     | 390 |     |     |     |     | 395 |     |     |     |     |      |
| GCG | GTG | AAT | GGC | ATC | TCC | AGC | AAG | AGC | CCC | TAC | CCT | CCC | CAT | TTT | GCC | 1246 |
| Ala | Val | Asn | Gly | Ile | Ser | Ser | Lys | Ser | Pro | Tyr | Pro | Pro | His | Phe | Ala |      |
| 400 |     |     |     | 405 |     |     |     |     | 410 |     |     |     |     | 415 |     |      |
| TCC | GTC | AAC | ATC | ACG | ACC | AAC | CAG | GCA | GCC | CCA | TCT | GCC | GTG | CCC | ACC | 1294 |
| Ser | Val | Asn | Ile | Thr | Thr | Asn | Gln | Ala | Ala | Pro | Ser | Ala | Val | Pro | Thr |      |
|     |     |     | 420 |     |     |     |     | 425 |     |     |     |     | 430 |     |     |      |
| ATG | CAT | CTG | CAC | AGC | AGC | ACC | GGG | AAC | AGC | ATG | ACA | CTG | TCA | TGG | ACT | 1342 |
| Met | His | Leu | His | Ser | Ser | Thr | Gly | Asn | Ser | Met | Thr | Leu | Ser | Trp | Thr |      |
|     |     |     | 435 |     |     |     |     | 440 |     |     |     |     | 445 |     |     |      |
| CCC | CCG | GAA | AGG | CCC | AAC | GGC | ATC | ATT | CTC | GAC | TAT | GAA | ATC | AAG | TAC | 1390 |
| Pro | Pro | Glu | Arg | Pro | Asn | Gly | Ile | Ile | Leu | Asp | Tyr | Glu | Ile | Lys | Tyr |      |
|     |     | 450 |     |     |     |     | 455 |     |     |     |     | 460 |     |     |     |      |
| TCC | GAG | AAG | CAA | GGC | CAG | GGT | GAC | GGC | ATT | GCC | AAC | ACT | GTC | ACC | AGC | 1438 |
| Ser | Glu | Lys | Gln | Gly | Gln | Gly | Asp | Gly | Ile | Ala | Asn | Thr | Val | Thr | Ser |      |
|     | 465 |     |     |     |     | 470 |     |     |     |     | 475 |     |     |     |     |      |
| CAG | AAG | AAC | TCG | GTG | CGG | CTG | GAC | GGA | CTG | AAG | GCC | AAT | GCT | CGG | TAC | 1486 |
| Gln | Lys | Asn | Ser | Val | Arg | Leu | Asp | Gly | Leu | Lys | Ala | Asn | Ala | Arg | Tyr |      |
| 480 |     |     |     |     | 485 |     |     |     |     | 490 |     |     |     |     | 495 |      |
| ATG | GTG | CAG | GTC | CGG | GCG | CGC | ACA | GTG | GCT | GGA | TAC | GGC | CGC | TAC | AGC | 1534 |
| Met | Val | Gln | Val | Arg | Ala | Arg | Thr | Val | Ala | Gly | Tyr | Gly | Arg | Tyr | Ser |      |
|     |     |     |     | 500 |     |     |     |     | 505 |     |     |     |     | 510 |     |      |
| CTC | CCC | ACC | GAG | TTC | CAG | ACG | ACT | GCG | GAG | GAT | GGC | TCC | ACC | AGC | AAG | 1582 |
| Leu | Pro | Thr | Glu | Phe | Gln | Thr | Thr | Ala | Glu | Asp | Gly | Ser | Thr | Ser | Lys |      |
|     |     |     | 515 |     |     |     |     | 520 |     |     |     |     | 525 |     |     |      |
| ACT | TTC | CAG | GAG | CTT | CCT | CTC | ATC | GTG | GGT | TCA | GCC | ACC | GCG | GGA | CTG | 1630 |
| Thr | Phe | Gln | Glu | Leu | Pro | Leu | Ile | Val | Gly | Ser | Ala | Thr | Ala | Gly | Leu |      |
|     |     | 530 |     |     |     |     | 535 |     |     |     |     | 540 |     |     |     |      |
| CTG | TTT | GTC | ATC | GTG | GTG | GTC | ATC | ATC | GCT | ATT | GTC | TGC | TTC | AGG | AAA | 1678 |
| Leu | Phe | Val | Ile | Val | Val | Val | Ile | Ile | Ala | Ile | Val | Cys | Phe | Arg | Lys |      |
|     |     | 545 |     |     |     |     | 550 |     |     |     |     | 555 |     |     |     |      |
| GGG | ATG | GTT | ACT | GAA | CAA | CTC | CTC | TCG | TCT | CCT | TTG | GGC | AGG | AAG | CAG | 1726 |
| Gly | Met | Val | Thr | Glu | Gln | Leu | Leu | Ser | Ser | Pro | Leu | Gly | Arg | Lys | Gln |      |
| 560 |     |     |     |     | 565 |     |     |     |     | 570 |     |     |     |     | 575 |      |
| CGC | AAC | AGC | ACA | GAT | CCC | GAG | TAC | ACA | GAG | AAG | CTG | CAG | CAA | TAT | GTC | 1774 |
| Arg | Asn | Ser | Thr | Asp | Pro | Glu | Tyr | Thr | Glu | Lys | Leu | Gln | Gln | Tyr | Val |      |
|     |     |     |     | 580 |     |     |     |     | 585 |     |     |     |     | 590 |     |      |
| ACT | CCT | GGG | ATG | AAG | GTC | TAC | ATT | GAC | CCC | TTC | ACC | TAT | GAA | GAC | CCA | 1822 |
| Thr | Pro | Gly | Met | Lys | Val | Tyr | Ile | Asp | Pro | Phe | Thr | Tyr | Glu | Asp | Pro |      |
|     |     |     | 595 |     |     |     |     | 600 |     |     |     |     | 605 |     |     |      |
| AAT | GAA | GCT | GTC | CGG | GAA | TTC | GCC | AAA | GAG | ATT | GAT | ATC | TCC | TGT | GTC | 1870 |
| Asn | Glu | Ala | Val | Arg | Glu | Phe | Ala | Lys | Glu | Ile | Asp | Ile | Ser | Cys | Val |      |
|     |     | 610 |     |     |     |     | 615 |     |     |     |     | 620 |     |     |     |      |
| AAA | ATT | GAG | GAG | GTC | ATT | GGA | GCA | GGA | GAG | TTT | GGT | GAG | GTG | TGC | CGT | 1918 |
| Lys | Ile | Glu | Glu | Val | Ile | Gly | Ala | Gly | Glu | Phe | Gly | Glu | Val | Cys | Arg |      |
|     | 625 |     |     |     |     | 630 |     |     |     |     | 635 |     |     |     |     |      |
| GGG | CGC | CTG | AAG | CTG | CCT | GGC | CGC | CGT | GAG | ATC | TTT | GTG | GCC | ATC | AAG | 1966 |
| Gly | Arg | Leu | Lys | Leu | Pro | Gly | Arg | Arg | Glu | Ile | Phe | Val | Ala | Ile | Lys |      |
| 640 |     |     |     |     | 645 |     |     |     |     | 650 |     |     |     |     | 655 |      |
| ACA | CTG | AAG | GTG | GGC | TAC | ACA | GAG | AGG | CAG | CGG | CGG | GAC | TTC | CTG | AGT | 2014 |

| | | | | | | | | | | | | | | | | |
|---|---|---|---|---|---|---|---|---|---|---|---|---|---|---|---|---|
| Thr | Leu | Lys | Val | Gly | Tyr | Thr | Glu | Arg | Gln | Arg | Arg | Asp | Phe | Leu | Ser | |
| | | | | 660 | | | | 665 | | | | | | 670 | | |
| GAG | GCC | AGC | ATC | ATG | GGC | CAG | TTC | GAC | CAC | CCC | AAC | ATC | ATC | CAC | CTG | 2062 |
| Glu | Ala | Ser | Ile | Met | Gly | Gln | Phe | Asp | His | Pro | Asn | Ile | Ile | His | Leu | |
| | | | 675 | | | | 680 | | | | | | 685 | | | |
| GAG | GGC | GTG | GTG | ACC | AAG | AGC | CGC | CCT | GTC | ATG | ATC | ATC | ACA | GAG | TTC | 2110 |
| Glu | Gly | Val | Val | Thr | Lys | Ser | Arg | Pro | Val | Met | Ile | Ile | Thr | Glu | Phe | |
| | | | 690 | | | | 695 | | | | | 700 | | | | |
| ATG | GAG | AAC | TGC | GCT | CTC | GAC | TCC | TTC | CTC | CGG | CTG | AAT | GAT | GGG | CAG | 2158 |
| Met | Glu | Asn | Cys | Ala | Leu | Asp | Ser | Phe | Leu | Arg | Leu | Asn | Asp | Gly | Gln | |
| | 705 | | | | 710 | | | | | 715 | | | | | | |
| TTC | ACG | GTC | ATC | CAG | CTG | GTG | GGG | ATG | CTG | CGA | GGC | ATC | GCT | GCT | GGC | 2206 |
| Phe | Thr | Val | Ile | Gln | Leu | Val | Gly | Met | Leu | Arg | Gly | Ile | Ala | Ala | Gly | |
| 720 | | | | | 725 | | | | | 730 | | | | | 735 | |
| ATG | AAG | TAC | CTC | TCA | GAG | ATG | AAC | TAC | GTG | CAC | CGA | GAC | CTG | GCT | GCC | 2254 |
| Met | Lys | Tyr | Leu | Ser | Glu | Met | Asn | Tyr | Val | His | Arg | Asp | Leu | Ala | Ala | |
| | | | | 740 | | | | | 745 | | | | | 750 | | |
| CGC | AAC | ATC | CTG | GTC | AAC | AGC | AAC | TTG | GTC | TGC | AAA | GTG | TCT | GAC | TTC | 2302 |
| Arg | Asn | Ile | Leu | Val | Asn | Ser | Asn | Leu | Val | Cys | Lys | Val | Ser | Asp | Phe | |
| | | | 755 | | | | | 760 | | | | | 765 | | | |
| GGG | CTC | TCC | CGC | TTT | TTG | GAG | GAT | GAT | CCA | GCC | GAC | CCC | ACC | TAC | ACC | 2350 |
| Gly | Leu | Ser | Arg | Phe | Leu | Glu | Asp | Asp | Pro | Ala | Asp | Pro | Thr | Tyr | Thr | |
| | | 770 | | | | | 775 | | | | | 780 | | | | |
| AGC | TCC | CTG | GGA | GGC | AAG | ATC | CCC | ATC | AGG | TGG | ACA | GCT | CCT | GAG | GCC | 2398 |
| Ser | Ser | Leu | Gly | Gly | Lys | Ile | Pro | Ile | Arg | Trp | Thr | Ala | Pro | Glu | Ala | |
| 785 | | | | | 790 | | | | | 795 | | | | | | |
| ATC | GCC | TAC | CGC | AAA | TTC | ACG | TCG | GCC | AGC | GAC | GTG | TGG | AGC | TAC | GGC | 2446 |
| Ile | Ala | Tyr | Arg | Lys | Phe | Thr | Ser | Ala | Ser | Asp | Val | Trp | Ser | Tyr | Gly | |
| 800 | | | | | 805 | | | | | 810 | | | | | 815 | |
| ATC | GTC | ATG | TGG | GAA | GTG | ATG | TCC | TAC | GGG | GAG | CGA | CCC | TAC | TGG | GAC | 2494 |
| Ile | Val | Met | Trp | Glu | Val | Met | Ser | Tyr | Gly | Glu | Arg | Pro | Tyr | Trp | Asp | |
| | | | | 820 | | | | | 825 | | | | | 830 | | |
| ATG | TCC | AAC | CAG | GAT | GTG | ATC | AAC | GCG | GTG | GAG | CAG | GAT | TAC | CGC | CTG | 2542 |
| Met | Ser | Asn | Gln | Asp | Val | Ile | Asn | Ala | Val | Glu | Gln | Asp | Tyr | Arg | Leu | |
| | | | 835 | | | | | 840 | | | | | 845 | | | |
| CCA | CCC | CCC | ATG | GAC | TGC | CCC | ACA | GCA | CTG | CAC | CAG | CTG | ATG | CTG | GAC | 2590 |
| Pro | Pro | Pro | Met | Asp | Cys | Pro | Thr | Ala | Leu | His | Gln | Leu | Met | Leu | Asp | |
| | | 850 | | | | | 855 | | | | | 860 | | | | |
| TGC | TGG | GTG | CGG | GAC | CGC | AAC | CTG | CGG | CCC | AAG | TTT | GCA | CAG | ATT | GTC | 2638 |
| Cys | Trp | Val | Arg | Asp | Arg | Asn | Leu | Arg | Pro | Lys | Phe | Ala | Gln | Ile | Val | |
| | 865 | | | | | 870 | | | | | 875 | | | | | |
| AAC | ACG | CTG | GAC | AAG | CTG | ATC | CGC | AAT | GCT | GCC | AGC | CTG | AAG | GTC | ATC | 2686 |
| Asn | Thr | Leu | Asp | Lys | Leu | Ile | Arg | Asn | Ala | Ala | Ser | Leu | Lys | Val | Ile | |
| 880 | | | | | 885 | | | | | 890 | | | | | 895 | |
| GCC | AGC | GTC | CAG | TCC | GGT | GTC | TCC | CAG | CCG | CTC | CTG | GAC | CGC | ACC | GTG | 2734 |
| Ala | Ser | Val | Gln | Ser | Gly | Val | Ser | Gln | Pro | Leu | Leu | Asp | Arg | Thr | Val | |
| | | | | 900 | | | | | 905 | | | | | 910 | | |
| CCC | GAT | TAC | ACC | ACC | TTC | ACC | ACC | GTG | GGA | GAC | TGG | CTG | GAT | GCC | ATC | 2782 |
| Pro | Asp | Tyr | Thr | Thr | Phe | Thr | Thr | Val | Gly | Asp | Trp | Leu | Asp | Ala | Ile | |
| | | | 915 | | | | | 920 | | | | | 925 | | | |
| AAA | ATG | GGA | CGG | TAC | AAG | GAG | AAC | TTC | GTC | AAC | GCC | GGC | TTC | GCC | TCC | 2830 |
| Lys | Met | Gly | Arg | Tyr | Lys | Glu | Asn | Phe | Val | Asn | Ala | Gly | Phe | Ala | Ser | |
| | | 930 | | | | | 935 | | | | | 940 | | | | |
| TTT | GAC | CTG | GTG | GCA | CAG | ATG | ACA | GCA | GAG | GAC | CTG | CTA | AGG | ATA | GGA | 2878 |
| Phe | Asp | Leu | Val | Ala | Gln | Met | Thr | Ala | Glu | Asp | Leu | Leu | Arg | Ile | Gly | |
| | 945 | | | | | 950 | | | | | 955 | | | | | |
| GTG | ACG | CTA | GCA | GGG | CAC | CAG | AAG | AAG | ATC | CTG | AGC | AGC | ATT | CAG | GAC | 2926 |
| Val | Thr | Leu | Ala | Gly | His | Gln | Lys | Lys | Ile | Leu | Ser | Ser | Ile | Gln | Asp | |
| 960 | | | | | 965 | | | | | 970 | | | | | 975 | |

```
ATG AGG CTG CAG ATG AAC CAG ACG CTG CCG GTT CAG GTT TGACCGCAGG          2975
Met Arg Leu Gln Met Asn Gln Thr Leu Pro Val Gln Val
                    980                 985
GACTCTGCAT TGGAACGGAC TGAGGGAACC TGCCAACCAG GTTCTGTTTG CGGTGCAGCC       3035
CGGCTTCCCG ATTTCCCCTT CCCGTGGCGC TCCTCTGCCT CGGACGCTCG CCGGGGACAG       3095
GCTGGGCCGG GCCACCCTTC CCTGGATCAG AGGCACTCGT GCCGGGAGGG AGCCCGGCTT       3155
TTCGTCCCGT GTCCCGCAGC GGCGAGGCAG TGAACGCAGT CTTCATATTG AAGATGGATT       3215
ATGGGACGGA GATGGCGCAT CCGCTTCCCG CCCTGTCTCA GTGCTCATCA GTTTGAAGAG       3275
ATGTTCTGCT TCTTGGATTT CTTTACACCC CGGTTTTCCC CCCTCGAGTC CTCACTTCCC       3335
CCTATCCCTG AGGCCACAGA CTGTTGACCC GTCCGCTGAG TCCGTCAGAC GCTCCGAAGC       3395
CTTCCCCGAG CCCGGTCCCC GCGTGGAGAC GGCGCCAGGG ACGGGCTAC GGCCCCAGAC        3455
AATCACTCCA CCCCTCCGCA CGAGGGTCCT CACTGGGACG TGTCTGAAGG GGAAAGGCTC       3515
TGCTCCCTTT TTGGCTTTGC ACGCCAGAAC CCGAACCCCG TGAGATTTAC TATGCAGGGA       3575
GTTAGGCAAA AAAAAG                                                      3591
```

( 2 ) INFORMATION FOR SEQ ID NO:14:

( i ) SEQUENCE CHARACTERISTICS:
        ( A ) LENGTH: 988 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Gly Val Ser Ser Arg Ala Arg Arg Pro Pro Gly Ser Ser Arg Ser Ser
 1               5                  10                  15

Arg Arg Gly Val Thr Ser Glu Leu Ala Trp Thr Thr His Pro Glu Thr
             20                  25                  30

Gly Trp Glu Glu Val Ser Gly Tyr Asp Glu Ala Met Asn Pro Ile Arg
         35                  40                  45

Thr Tyr Gln Val Cys Asn Val Arg Glu Ala Asn Gln Asn Asn Trp Leu
     50                  55                  60

Arg Thr Lys Phe Ile Gln Arg Gln Asp Val Gln Arg Val Tyr Val Glu
 65                  70                  75                  80

Leu Lys Phe Thr Val Arg Asp Cys Asn Ser Ile Pro Asn Ile Pro Gly
                 85                  90                  95

Ser Cys Lys Glu Thr Phe Asn Leu Phe Tyr Tyr Glu Ser Asp Thr Asp
             100                 105                 110

Ser Ala Ser Ala Asn Ser Pro Phe Trp Met Glu Asn Pro Tyr Ile Lys
         115                 120                 125

Val Asp Thr Ile Ala Pro Asp Glu Ser Phe Ser Lys Leu Glu Ser Gly
     130                 135                 140

Arg Val Asn Thr Lys Val Arg Ser Phe Gly Pro Leu Ser Lys Asn Gly
 145                 150                 155                 160

Phe Tyr Leu Ala Phe Gln Asp Leu Gly Ala Cys Met Ser Leu Ile Ser
                 165                 170                 175

Val Arg Ala Phe Tyr Lys Lys Cys Ser Asn Thr Ile Ala Gly Phe Ala
             180                 185                 190

Ile Phe Pro Glu Thr Leu Thr Gly Ala Glu Pro Thr Ser Leu Val Ile
         195                 200                 205

Ala Pro Gly Thr Cys Ile Pro Asn Ala Val Glu Val Ser Val Pro Leu
     210                 215                 220
```

```
Lys Leu Tyr Cys Asn Gly Asp Gly Glu Trp Met Val Pro Val Gly Ala
225                 230                 235                 240

Cys Thr Cys Ala Ala Gly Tyr Glu Pro Ala Met Lys Asp Thr Gln Cys
                245                 250                 255

Gln Ala Cys Gly Pro Gly Thr Phe Lys Ser Lys Gln Gly Glu Gly Pro
            260                 265                 270

Cys Ser Pro Cys Pro Pro Asn Ser Arg Thr Thr Ala Gly Ala Ala Thr
        275                 280                 285

Val Cys Ile Cys Arg Ser Gly Phe Phe Arg Ala Asp Ala Asp Pro Ala
    290                 295                 300

Asp Ser Ala Cys Thr Ser Val Pro Ser Ala Pro Arg Ser Val Ile Ser
305                 310                 315                 320

Asn Val Asn Glu Thr Ser Leu Val Leu Glu Trp Ser Glu Pro Gln Asp
                325                 330                 335

Ala Gly Gly Arg Asp Asp Leu Leu Tyr Asn Val Ile Cys Lys Lys Cys
            340                 345                 350

Ser Val Glu Arg Arg Leu Cys Ser Arg Cys Asp Asp Asn Val Glu Phe
        355                 360                 365

Val Pro Arg Gln Leu Gly Leu Thr Gly Leu Thr Glu Arg Arg Ile Tyr
    370                 375                 380

Ile Ser Lys Val Met Ala His Pro Gln Tyr Thr Phe Glu Ile Gln Ala
385                 390                 395                 400

Val Asn Gly Ile Ser Ser Lys Ser Pro Tyr Pro Pro His Phe Ala Ser
                405                 410                 415

Val Asn Ile Thr Thr Asn Gln Ala Ala Pro Ser Ala Val Pro Thr Met
            420                 425                 430

His Leu His Ser Ser Thr Gly Asn Ser Met Thr Leu Ser Trp Thr Pro
        435                 440                 445

Pro Glu Arg Pro Asn Gly Ile Ile Leu Asp Tyr Glu Ile Lys Tyr Ser
    450                 455                 460

Glu Lys Gln Gly Gln Gly Asp Gly Ile Ala Asn Thr Val Thr Ser Gln
465                 470                 475                 480

Lys Asn Ser Val Arg Leu Asp Gly Leu Lys Ala Asn Ala Arg Tyr Met
                485                 490                 495

Val Gln Val Arg Ala Arg Thr Val Ala Gly Tyr Gly Arg Tyr Ser Leu
            500                 505                 510

Pro Thr Glu Phe Gln Thr Thr Ala Glu Asp Gly Ser Thr Ser Lys Thr
        515                 520                 525

Phe Gln Glu Leu Pro Leu Ile Val Gly Ser Ala Thr Ala Gly Leu Leu
    530                 535                 540

Phe Val Ile Val Val Ile Ile Ala Ile Val Cys Phe Arg Lys Gly
545                 550                 555                 560

Met Val Thr Glu Gln Leu Leu Ser Ser Pro Leu Gly Arg Lys Gln Arg
                565                 570                 575

Asn Ser Thr Asp Pro Glu Tyr Thr Glu Lys Leu Gln Gln Tyr Val Thr
            580                 585                 590

Pro Gly Met Lys Val Tyr Ile Asp Pro Phe Thr Tyr Glu Asp Pro Asn
        595                 600                 605

Glu Ala Val Arg Glu Phe Ala Lys Glu Ile Asp Ile Ser Cys Val Lys
    610                 615                 620

Ile Glu Glu Val Ile Gly Ala Gly Glu Phe Gly Glu Val Cys Arg Gly
625                 630                 635                 640
```

-continued

| | | | | | | | | | | | | | | |
|---|---|---|---|---|---|---|---|---|---|---|---|---|---|---|
| Arg | Leu | Lys | Leu | Pro 645 | Gly | Arg | Arg | Glu 650 | Ile | Phe | Val | Ala | Ile 655 | Thr |
| Leu | Lys | Val | Gly 660 | Tyr | Thr | Glu | Arg | Gln 665 | Arg | Arg | Asp | Phe | Leu 670 | Ser | Glu |
| Ala | Ser | Ile 675 | Met | Gly | Gln | Phe | Asp 680 | His | Pro | Asn | Ile | Ile 685 | His | Leu | Glu |
| Gly | Val 690 | Val | Thr | Lys | Ser | Arg 695 | Pro | Val | Met | Ile | Ile 700 | Thr | Glu | Phe | Met |
| Glu 705 | Asn | Cys | Ala | Leu | Asp 710 | Ser | Phe | Leu | Arg | Leu 715 | Asn | Asp | Gly | Gln | Phe 720 |
| Thr | Val | Ile | Gln | Leu 725 | Val | Gly | Met | Leu | Arg 730 | Gly | Ile | Ala | Ala | Gly 735 | Met |
| Lys | Tyr | Leu | Ser 740 | Glu | Met | Asn | Tyr | Val 745 | His | Arg | Asp | Leu | Ala 750 | Ala | Arg |
| Asn | Ile | Leu 755 | Val | Asn | Ser | Asn | Leu 760 | Val | Cys | Lys | Val | Ser 765 | Asp | Phe | Gly |
| Leu | Ser 770 | Arg | Phe | Leu | Glu | Asp 775 | Asp | Pro | Ala | Asp | Pro 780 | Thr | Tyr | Thr | Ser |
| Ser 785 | Leu | Gly | Gly | Lys | Ile 790 | Pro | Ile | Arg | Trp | Thr 795 | Ala | Pro | Glu | Ala | Ile 800 |
| Ala | Tyr | Arg | Lys | Phe 805 | Thr | Ser | Ala | Ser | Asp 810 | Val | Trp | Ser | Tyr | Gly 815 | Ile |
| Val | Met | Trp | Glu 820 | Val | Met | Ser | Tyr | Gly 825 | Glu | Arg | Pro | Tyr | Trp 830 | Asp | Met |
| Ser | Asn | Gln 835 | Asp | Val | Ile | Asn | Ala 840 | Val | Glu | Gln | Asp | Tyr 845 | Arg | Leu | Pro |
| Pro | Pro 850 | Met | Asp | Cys | Pro | Thr 855 | Ala | Leu | His | Gln | Leu 860 | Met | Leu | Asp | Cys |
| Trp 865 | Val | Arg | Asp | Arg | Asn 870 | Leu | Arg | Pro | Lys | Phe 875 | Ala | Gln | Ile | Val | Asn 880 |
| Thr | Leu | Asp | Lys | Leu 885 | Ile | Arg | Asn | Ala | Ala 890 | Ser | Leu | Lys | Val | Ile 895 | Ala |
| Ser | Val | Gln | Ser 900 | Gly | Val | Ser | Gln | Pro 905 | Leu | Leu | Asp | Arg | Thr 910 | Val | Pro |
| Asp | Tyr | Thr 915 | Thr | Phe | Thr | Thr | Val 920 | Gly | Asp | Trp | Leu | Asp 925 | Ala | Ile | Lys |
| Met | Gly 930 | Arg | Tyr | Lys | Glu | Asn 935 | Phe | Val | Asn | Ala | Gly 940 | Phe | Ala | Ser | Phe |
| Asp 945 | Leu | Val | Ala | Gln | Met 950 | Thr | Ala | Glu | Asp | Leu 955 | Leu | Arg | Ile | Gly | Val 960 |
| Thr | Leu | Ala | Gly | His 965 | Gln | Lys | Lys | Ile | Leu 970 | Ser | Ser | Ile | Gln | Asp 975 | Met |
| Arg | Leu | Gln | Met 980 | Asn | Gln | Thr | Leu | Pro 985 | Val | Gln | Val | | | | |

( 2 ) INFORMATION FOR SEQ ID NO:15:

( i ) SEQUENCE CHARACTERISTICS:
    ( A ) LENGTH: 3254 base pairs
    ( B ) TYPE: nucleic acid
    ( C ) STRANDEDNESS: both
    ( D ) TOPOLOGY: linear ( i x ) FEATURE:
    ( A ) NAME/KEY: CDS
    ( B ) LOCATION: 32..2980

( x i ) SEQUENCE DESCRIPTION: SEQ ID NO:15:

| | | | | | | | | | | | | | | | | |
|---|---|---|---|---|---|---|---|---|---|---|---|---|---|---|---|---|
| CGCTCTGCTC | GCGCGCTGCT | GCCCCGCCGA | C ATG GAC CGC CGC CGC CTG CCG | | | | | | | | | | | | | 52 |
| | | | | Met Asp Arg Arg Arg Leu Pro | | | | | | | | | | | | |
| | | | | 1 | | | | 5 | | | | | | | | |
| CTG | CTG | CTG | CTC | TGC | GCT | GCC | CTC | GGC | TCC | GCC | GGG | CGT | CTG | AGC | GCC | 100 |
| Leu | Leu | Leu | Leu | Cys | Ala | Ala | Leu | Gly | Ser | Ala | Gly | Arg | Leu | Ser | Ala | |
| | | 10 | | | | | 15 | | | | | 20 | | | | |
| CGC | CCC | GGC | AAC | GAA | GTT | AAT | CTG | CTG | GAT | TCA | AAA | ACA | ATT | CAA | GGG | 148 |
| Arg | Pro | Gly | Asn | Glu | Val | Asn | Leu | Leu | Asp | Ser | Lys | Thr | Ile | Gln | Gly | |
| | 25 | | | | | 30 | | | | | 35 | | | | | |
| GAG | CTG | GGC | TGG | ATC | TCC | TAC | CCA | TCA | CAT | GGG | TGG | GAA | GAG | ATT | AGT | 196 |
| Glu | Leu | Gly | Trp | Ile | Ser | Tyr | Pro | Ser | His | Gly | Trp | Glu | Glu | Ile | Ser | |
| 40 | | | | | 45 | | | | | 50 | | | | | 55 | |
| GGT | GTT | GAT | GAG | CAT | TAT | ACT | CCA | ATC | AGA | ACT | TAC | CAA | GAG | AGC | AAT | 244 |
| Gly | Val | Asp | Glu | His | Tyr | Thr | Pro | Ile | Arg | Thr | Tyr | Gln | Glu | Ser | Asn | |
| | | | | 60 | | | | | 65 | | | | | 70 | | |
| GTT | ATG | GAT | CAC | AGT | CAA | AAC | AAT | TGG | CTG | CGA | ACA | AAC | TGG | ATT | CCA | 292 |
| Val | Met | Asp | His | Ser | Gln | Asn | Asn | Trp | Leu | Arg | Thr | Asn | Trp | Ile | Pro | |
| | | | 75 | | | | | 80 | | | | | 85 | | | |
| CGC | AAT | TCA | GCG | CAG | AAG | ATA | TAT | GTG | GAG | CTC | AAG | TTT | ACC | TTG | AGG | 340 |
| Arg | Asn | Ser | Ala | Gln | Lys | Ile | Tyr | Val | Glu | Leu | Lys | Phe | Thr | Leu | Arg | |
| | | 90 | | | | | 95 | | | | | 100 | | | | |
| GAC | TGC | AAT | AGT | ATC | CCT | CTA | GTT | CTG | GGC | ACT | TGC | AAA | GAG | ACT | TTC | 388 |
| Asp | Cys | Asn | Ser | Ile | Pro | Leu | Val | Leu | Gly | Thr | Cys | Lys | Glu | Thr | Phe | |
| | 105 | | | | | 110 | | | | | 115 | | | | | |
| AAT | CTG | TAT | TAC | ATG | GAA | TCC | GAT | GAT | GAC | CAT | TTG | GCA | AAG | TTC | AGA | 436 |
| Asn | Leu | Tyr | Tyr | Met | Glu | Ser | Asp | Asp | Asp | His | Leu | Ala | Lys | Phe | Arg | |
| 120 | | | | | 125 | | | | | 130 | | | | | 135 | |
| GAG | CAC | CAA | TTT | ACG | AAG | ATT | GAC | ACC | ATG | GCG | GCT | GAT | GAG | AGC | TTC | 484 |
| Glu | His | Gln | Phe | Thr | Lys | Ile | Asp | Thr | Met | Ala | Ala | Asp | Glu | Ser | Phe | |
| | | | 140 | | | | | 145 | | | | | 150 | | | |
| ACC | CAG | ATG | GAT | CTT | GGG | GAC | CGG | ATT | CTC | AAG | CTG | AAT | ACC | GAA | GTC | 532 |
| Thr | Gln | Met | Asp | Leu | Gly | Asp | Arg | Ile | Leu | Lys | Leu | Asn | Thr | Glu | Val | |
| | | | 155 | | | | | 160 | | | | | 165 | | | |
| CGC | GAG | GTG | GGA | CCT | GTT | AGT | AAG | AAG | GGC | TTT | TAC | TTG | GCT | TTC | CAA | 580 |
| Arg | Glu | Val | Gly | Pro | Val | Ser | Lys | Lys | Gly | Phe | Tyr | Leu | Ala | Phe | Gln | |
| | | 170 | | | | | 175 | | | | | 180 | | | | |
| GAT | GTA | GGT | GCA | TGT | GTT | GCC | TTA | GTC | TCG | GTG | CGA | GTG | TAC | TTC | AAG | 628 |
| Asp | Val | Gly | Ala | Cys | Val | Ala | Leu | Val | Ser | Val | Arg | Val | Tyr | Phe | Lys | |
| | 185 | | | | | 190 | | | | | 195 | | | | | |
| AAG | TGC | CCT | TTC | ACT | GTC | AAG | AAC | CTC | GCC | ATG | TTT | CCA | GAT | ACA | GTT | 676 |
| Lys | Cys | Pro | Phe | Thr | Val | Lys | Asn | Leu | Ala | Met | Phe | Pro | Asp | Thr | Val | |
| 200 | | | | | 205 | | | | | 210 | | | | | 215 | |
| CCT | ATG | GAC | TCC | CAG | TCC | CTG | GTG | GAG | GTG | CGG | GGT | TCT | TGT | GTC | AAT | 724 |
| Pro | Met | Asp | Ser | Gln | Ser | Leu | Val | Glu | Val | Arg | Gly | Ser | Cys | Val | Asn | |
| | | | | 220 | | | | | 225 | | | | | 230 | | |
| CAT | TCC | AAG | GAG | GAA | GAG | CCA | CCC | AAG | ATG | TAC | TGC | AGC | ACG | GAA | GGA | 772 |
| His | Ser | Lys | Glu | Glu | Glu | Pro | Pro | Lys | Met | Tyr | Cys | Ser | Thr | Glu | Gly | |
| | | | 235 | | | | | 240 | | | | | 245 | | | |
| GAA | TGG | CTA | GTG | CCC | ATA | GGG | AAG | TGC | TTG | TGT | AAT | GCT | GGC | TAT | GAA | 820 |
| Glu | Trp | Leu | Val | Pro | Ile | Gly | Lys | Cys | Leu | Cys | Asn | Ala | Gly | Tyr | Glu | |
| | | 250 | | | | | 255 | | | | | 260 | | | | |
| GAG | AGA | GGC | TTT | GCG | TGC | CAA | GCT | TGT | CGA | CCT | GGG | TTC | TAT | AAA | GCT | 868 |
| Glu | Arg | Gly | Phe | Ala | Cys | Gln | Ala | Cys | Arg | Pro | Gly | Phe | Tyr | Lys | Ala | |
| | 265 | | | | | 270 | | | | | 275 | | | | | |
| TCT | GCT | GGC | AAT | GTG | AAG | TGT | GCC | AAA | TGC | CCA | CCT | CAC | AGC | TCT | ACC | 916 |
| Ser | Ala | Gly | Asn | Val | Lys | Cys | Ala | Lys | Cys | Pro | Pro | His | Ser | Ser | Thr | |
| 280 | | | | | 285 | | | | | 290 | | | | | 295 | |
| TAT | GAA | GAT | GCA | TCT | CTG | AAC | TGC | AGG | TGT | GAA | AAG | AAT | TAC | TTT | CGC | 964 |

|  |  |  |  |  |  |  |  |  |  |  |  |  |  |  |  |
|---|---|---|---|---|---|---|---|---|---|---|---|---|---|---|---|
| Tyr | Glu | Asp | Ala | Ser | Leu | Asn | Cys | Arg | Cys | Glu | Lys | Asn | Tyr | Phe | Arg |
|  |  |  |  | 300 |  |  |  | 305 |  |  |  |  | 310 |  |  |
| TCT | GAG | AAA | GAC | CCT | CCA | TCC | ATG | GCT | TGC | ACC | AGA | CCA | CCA | TCT | GCT |
| Ser | Glu | Lys | Asp | Pro | Pro | Ser | Met | Ala | Cys | Thr | Arg | Pro | Pro | Ser | Ala |
|  |  |  | 315 |  |  |  |  | 320 |  |  |  |  | 325 |  |  |
| CCA | AGA | AAC | GTT | ATT | TCT | AAC | ATC | AAT | GAG | ACA | TCT | GTT | ATT | CTG | GAC |
| Pro | Arg | Asn | Val | Ile | Ser | Asn | Ile | Asn | Glu | Thr | Ser | Val | Ile | Leu | Asp |
|  |  | 330 |  |  |  |  | 335 |  |  |  |  | 340 |  |  |  |
| TGG | AGC | TGG | CCT | CTT | GAT | ACA | GGA | GGT | CGA | AAA | GAT | GTC | ACT | TTC | AAC |
| Trp | Ser | Trp | Pro | Leu | Asp | Thr | Gly | Gly | Arg | Lys | Asp | Val | Thr | Phe | Asn |
|  | 345 |  |  |  |  | 350 |  |  |  |  | 355 |  |  |  |  |
| ATC | ATT | TGC | AAA | AAA | TGT | GGA | GGA | AGC | AGC | AAG | ATA | TGT | GAG | CCT | TGC |
| Ile | Ile | Cys | Lys | Lys | Cys | Gly | Gly | Ser | Ser | Lys | Ile | Cys | Glu | Pro | Cys |
| 360 |  |  |  |  | 365 |  |  |  |  | 370 |  |  |  |  | 375 |
| AGT | GAC | AAC | GTA | CGG | TTC | TTA | CCC | CGT | CAG | ACT | GGC | CTC | ACC | AAC | ACC |
| Ser | Asp | Asn | Val | Arg | Phe | Leu | Pro | Arg | Gln | Thr | Gly | Leu | Thr | Asn | Thr |
|  |  |  |  | 380 |  |  |  |  | 385 |  |  |  |  | 390 |  |
| ACG | GTG | ACA | GTA | GTG | GAC | CTT | TTG | GCA | CAT | ACC | AAT | TAC | ACT | TTT | GAG |
| Thr | Val | Thr | Val | Val | Asp | Leu | Leu | Ala | His | Thr | Asn | Tyr | Thr | Phe | Glu |
|  |  |  | 395 |  |  |  |  | 400 |  |  |  |  | 405 |  |  |
| ATT | GAT | GCA | GTC | AAC | GGG | GTA | TCT | GAC | TTG | AGT | ACA | CTT | TCG | AGA | CAA |
| Ile | Asp | Ala | Val | Asn | Gly | Val | Ser | Asp | Leu | Ser | Thr | Leu | Ser | Arg | Gln |
|  |  | 410 |  |  |  |  | 415 |  |  |  |  | 420 |  |  |  |
| TTT | GCT | GCT | GTC | AGC | ATC | ACG | ACT | AAT | CAG | GCT | GCG | CCA | TCC | CCC | ATC |
| Phe | Ala | Ala | Val | Ser | Ile | Thr | Thr | Asn | Gln | Ala | Ala | Pro | Ser | Pro | Ile |
| 425 |  |  |  |  | 430 |  |  |  |  | 435 |  |  |  |  |  |
| ACA | GTG | ATA | AGG | AAC | GAC | CGG | ACA | TCC | AGG | AAC | AGC | GTG | TCT | CTG | TCT |
| Thr | Val | Ile | Arg | Asn | Asp | Arg | Thr | Ser | Arg | Asn | Ser | Val | Ser | Leu | Ser |
| 440 |  |  |  |  | 445 |  |  |  |  | 450 |  |  |  |  | 455 |
| TGG | CAG | GAG | CCT | GAG | CAC | CCA | AAT | GGA | ATC | ATC | TTG | GAC | TAC | GAG | GTC |
| Trp | Gln | Glu | Pro | Glu | His | Pro | Asn | Gly | Ile | Ile | Leu | Asp | Tyr | Glu | Val |
|  |  |  |  | 460 |  |  |  |  | 465 |  |  |  |  | 470 |  |
| AAA | TAC | TAC | GAA | AAG | CAG | GAA | CAA | GAG | ACA | AGC | TAT | ACT | ATT | CTG | AGA |
| Lys | Tyr | Tyr | Glu | Lys | Gln | Glu | Gln | Glu | Thr | Ser | Tyr | Thr | Ile | Leu | Arg |
|  |  |  | 475 |  |  |  |  | 480 |  |  |  |  | 485 |  |  |
| GCC | AAA | AGC | ACT | AAC | GTT | ACT | ATC | AGC | GGC | CTC | AAA | CCT | GAT | ACC | ACC |
| Ala | Lys | Ser | Thr | Asn | Val | Thr | Ile | Ser | Gly | Leu | Lys | Pro | Asp | Thr | Thr |
|  |  | 490 |  |  |  |  | 495 |  |  |  |  | 500 |  |  |  |
| TAC | GTC | TTC | CAA | ATT | CGA | GCC | CGA | ACT | GCA | GCT | AGA | TAT | GGG | ACA | AGC |
| Tyr | Val | Phe | Gln | Ile | Arg | Ala | Arg | Thr | Ala | Ala | Arg | Tyr | Gly | Thr | Ser |
|  | 505 |  |  |  |  | 510 |  |  |  |  | 515 |  |  |  |  |
| AGC | CGC | AAG | TTT | GAA | TTT | GAA | ACC | AGT | CCA | GAT | TCA | TTC | TCC | ATT | TCC |
| Ser | Arg | Lys | Phe | Glu | Phe | Glu | Thr | Ser | Pro | Asp | Ser | Phe | Ser | Ile | Ser |
| 520 |  |  |  |  | 525 |  |  |  |  | 530 |  |  |  |  | 535 |
| AGT | GAA | AAT | AGC | CAG | GTC | GTT | ATG | ATT | GCC | ATT | TCA | GCT | GCA | GTT | GCC |
| Ser | Glu | Asn | Ser | Gln | Val | Val | Met | Ile | Ala | Ile | Ser | Ala | Ala | Val | Ala |
|  |  |  |  | 540 |  |  |  |  | 545 |  |  |  |  | 550 |  |
| ATC | ATT | CTC | CTC | ACG | GTT | GTT | GTG | TAC | GTC | TTG | ATT | GGG | AGA | TTC | TGC |
| Ile | Ile | Leu | Leu | Thr | Val | Val | Val | Tyr | Val | Leu | Ile | Gly | Arg | Phe | Cys |
|  |  |  | 555 |  |  |  |  | 560 |  |  |  |  | 565 |  |  |
| GGA | TAC | AAG | AAG | TCT | AAA | CAT | GGT | ACC | GAT | GAG | AAA | AGA | CTA | CAT | TTT |
| Gly | Tyr | Lys | Lys | Ser | Lys | His | Gly | Thr | Asp | Glu | Lys | Arg | Leu | His | Phe |
|  |  | 570 |  |  |  |  | 575 |  |  |  |  | 580 |  |  |  |
| GGG | AAT | GGC | CAC | TTA | AAA | CTC | CCA | GGC | CTG | AGA | ACT | TAT | GTA | GAT | CCA |
| Gly | Asn | Gly | His | Leu | Lys | Leu | Pro | Gly | Leu | Arg | Thr | Tyr | Val | Asp | Pro |
|  | 585 |  |  |  |  | 590 |  |  |  |  | 595 |  |  |  |  |
| CAT | ACG | TAC | GAA | GAT | CCC | AAT | CAA | GCT | GTA | CAT | GAA | TTT | GCC | AAG | GAA |
| His | Thr | Tyr | Glu | Asp | Pro | Asn | Gln | Ala | Val | His | Glu | Phe | Ala | Lys | Glu |
| 600 |  |  |  |  | 605 |  |  |  |  | 610 |  |  |  |  | 615 |

| | |
|---|---|
| | 1012 |
| | 1060 |
| | 1108 |
| | 1156 |
| | 1204 |
| | 1252 |
| | 1300 |
| | 1348 |
| | 1396 |
| | 1444 |
| | 1492 |
| | 1540 |
| | 1588 |
| | 1636 |
| | 1684 |
| | 1732 |
| | 1780 |
| | 1828 |
| | 1876 |

| | |
|---|---|
| CTA GAT GCT TCT AAT ATA TCA ATT GAT AAA GTT GTT GGA GCA GGG GAA<br>Leu Asp Ala Ser Asn Ile Ser Ile Asp Lys Val Val Gly Ala Gly Glu<br>620 625 630 | 1924 |
| TTT GGA GAA GTG TGC AGT GGG CGC CTG AAG CTG CCT TCT AAA AAG GAA<br>Phe Gly Glu Val Cys Ser Gly Arg Leu Lys Leu Pro Ser Lys Lys Glu<br>635 640 645 | 1972 |
| ATT TCA GTG GCC ATC AAA ACT CTG AAA GCT GGC TAC ACA GAA AAA CAG<br>Ile Ser Val Ala Ile Lys Thr Leu Lys Ala Gly Tyr Thr Glu Lys Gln<br>650 655 660 | 2020 |
| AGA AGG GAT TTC CTG GGA GAA GCA AGC ATC ATG GGG CAG TTT GAC CAC<br>Arg Arg Asp Phe Leu Gly Glu Ala Ser Ile Met Gly Gln Phe Asp His<br>665 670 675 | 2068 |
| CCC AAC ATC ATC CGA CTG GAG GGC GTT GTG ACT AAA AGT AAA CCA GTT<br>Pro Asn Ile Ile Arg Leu Glu Gly Val Val Thr Lys Ser Lys Pro Val<br>680 685 690 695 | 2116 |
| ATG ATT GTT ACT GAA TAC ATG GAA AAC GGT TCC TTG GAC AGC TTC CTA<br>Met Ile Val Thr Glu Tyr Met Glu Asn Gly Ser Leu Asp Ser Phe Leu<br>700 705 710 | 2164 |
| CGG AAA CAT GAT GCC CAG TTC ACA GTC ATT CAG CTA GTA GGC ATG CTT<br>Arg Lys His Asp Ala Gln Phe Thr Val Ile Gln Leu Val Gly Met Leu<br>715 720 725 | 2212 |
| CGT GGG ATC GCA TCT GGC ATG AAA TAT TTG TCA GAT ATG GGT TAT GTC<br>Arg Gly Ile Ala Ser Gly Met Lys Tyr Leu Ser Asp Met Gly Tyr Val<br>730 735 740 | 2260 |
| CAC CGA GAT CTA GCT GCT CGT AAT ATA CTC ATC AAT AGT AAC TTG GTG<br>His Arg Asp Leu Ala Ala Arg Asn Ile Leu Ile Asn Ser Asn Leu Val<br>745 750 755 | 2308 |
| TGC AAA GTC TCA GAT TTT GGT CTT TCT CGT GTA TTG GAA GAT GAC CCA<br>Cys Lys Val Ser Asp Phe Gly Leu Ser Arg Val Leu Glu Asp Asp Pro<br>760 765 770 775 | 2356 |
| GAA GCT GCT TAC ACA ACA AGG GGG GGC AAG ATT CCC ATC CGA TGG ACG<br>Glu Ala Ala Tyr Thr Thr Arg Gly Gly Lys Ile Pro Ile Arg Trp Thr<br>780 785 790 | 2404 |
| TCA CCA GAA GCC ATT GCA TAC CGG AAG TTC ACA TCA GCC AGT GAT GCG<br>Ser Pro Glu Ala Ile Ala Tyr Arg Lys Phe Thr Ser Ala Ser Asp Ala<br>795 800 805 | 2452 |
| TGG AGC TAT GGG ATT GTC CTC TGG GAG GTG ATG TCT TAT GGA GAA AGG<br>Trp Ser Tyr Gly Ile Val Leu Trp Glu Val Met Ser Tyr Gly Glu Arg<br>810 815 820 | 2500 |
| CCG TAC TGG GAG ATG TCC TTC CAG GAC GTA ATT AAA GCC GTT GAT GAA<br>Pro Tyr Trp Glu Met Ser Phe Gln Asp Val Ile Lys Ala Val Asp Glu<br>825 830 835 | 2548 |
| GGG TAT CGC TTG CCA CCT CCT ATG GAC TGC CCA GCT GCC TTG TAT CAG<br>Gly Tyr Arg Leu Pro Pro Pro Met Asp Cys Pro Ala Ala Leu Tyr Gln<br>840 845 850 855 | 2596 |
| CTG ATG CTG GAC TGC TGG CAG AAA GAC AGA AAC AAC AGA CCC AAG TTT<br>Leu Met Leu Asp Cys Trp Gln Lys Asp Arg Asn Asn Arg Pro Lys Phe<br>860 865 870 | 2644 |
| GAG CAG ATT GTC AGC ATC CTG GAT AAG CTG ATC CGT AAT CCC AGC AGT<br>Glu Gln Ile Val Ser Ile Leu Asp Lys Leu Ile Arg Asn Pro Ser Ser<br>875 880 885 | 2692 |
| CTG AAA ATA ATC ACC AAT GCG GCA GCA AGG CCA TCA AAT CTT CTC CTG<br>Leu Lys Ile Ile Thr Asn Ala Ala Ala Arg Pro Ser Asn Leu Leu Leu<br>890 895 900 | 2740 |
| GAC CAA AGT AAC ATT GAC ATT TCA GCG TTC CGC ACG GCA GGT GAT TGG<br>Asp Gln Ser Asn Ile Asp Ile Ser Ala Phe Arg Thr Ala Gly Asp Trp<br>905 910 915 | 2788 |
| CTC AAT GGT TTT CGA ACA GGA CAG TGC AAA GGC ATT TTC ACG GGT GTG<br>Leu Asn Gly Phe Arg Thr Gly Gln Cys Lys Gly Ile Phe Thr Gly Val<br>920 925 930 935 | 2836 |

-continued

```
GAG  TAC  AGC  TCC  TGT  GAT  ACA  ATA  GCC  AAG  ATT  TCC  ACT  GAT  GAC  ATG    2884
Glu  Tyr  Ser  Ser  Cys  Asp  Thr  Ile  Ala  Lys  Ile  Ser  Thr  Asp  Asp  Met
               940                     945                     950

AAG  AAA  GTT  GGT  GTT  ACA  GTT  GTG  GGG  CCT  CAA  AAG  AAG  ATT  GTT  AGC    2932
Lys  Lys  Val  Gly  Val  Thr  Val  Val  Gly  Pro  Gln  Lys  Lys  Ile  Val  Ser
               955                     960                     965

AGT  ATC  AAA  ACT  CTA  GAA  ACT  CAT  ACG  AAG  AAC  AGC  CCT  GTT  CCT  GTG    2980
Ser  Ile  Lys  Thr  Leu  Glu  Thr  His  Thr  Lys  Asn  Ser  Pro  Val  Pro  Val
               970                     975                     980

TAAGGTACCA  AAATGATGTT  GCTGAGGACA  GAAAAAAAAG  AAAAGTCGCA  TCAAAGTGCA           3040

AAAGCGATGG  CTGATAAACG  GCACGGTTTA  AAGGAGTTCT  TTGCAGCAGT  TTTGGAAACA           3100

TAATGGTTGA  AATTTCAAAC  CCACTGAGAC  ACTCAAATAC  TGAGTATAAA  TGCCTTAAAA          3160

ATAGGAGCGA  ACTTGTTTTC  TATCTGTTAA  TCCTGAAGGG  TGGGTGCTCT  TAACTGACTG          3220

TTAATGCAGA  TAGTAAATTT  CAAAAAAAAA  AACG                                        3254
```

( 2 ) INFORMATION FOR SEQ ID NO:16:

( i ) SEQUENCE CHARACTERISTICS:
        ( A ) LENGTH: 983 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
Met  Asp  Arg  Arg  Arg  Leu  Pro  Leu  Leu  Leu  Leu  Cys  Ala  Ala  Leu  Gly
 1                  5                    10                       15

Ser  Ala  Gly  Arg  Leu  Ser  Ala  Arg  Pro  Gly  Asn  Glu  Val  Asn  Leu  Leu
               20                    25                       30

Asp  Ser  Lys  Thr  Ile  Gln  Gly  Glu  Leu  Gly  Trp  Ile  Ser  Tyr  Pro  Ser
          35                    40                    45

His  Gly  Trp  Glu  Glu  Ile  Ser  Gly  Val  Asp  Glu  His  Tyr  Thr  Pro  Ile
     50                    55                    60

Arg  Thr  Tyr  Gln  Glu  Ser  Asn  Val  Met  Asp  His  Ser  Gln  Asn  Asn  Trp
65                   70                    75                         80

Leu  Arg  Thr  Asn  Trp  Ile  Pro  Arg  Asn  Ser  Ala  Gln  Lys  Ile  Tyr  Val
               85                    90                       95

Glu  Leu  Lys  Phe  Thr  Leu  Arg  Asp  Cys  Asn  Ser  Ile  Pro  Leu  Val  Leu
               100                   105                      110

Gly  Thr  Cys  Lys  Glu  Thr  Phe  Asn  Leu  Tyr  Tyr  Met  Glu  Ser  Asp  Asp
               115                   120                      125

Asp  His  Leu  Ala  Lys  Phe  Arg  Glu  His  Gln  Phe  Thr  Lys  Ile  Asp  Thr
     130                   135                   140

Met  Ala  Ala  Asp  Glu  Ser  Phe  Thr  Gln  Met  Asp  Leu  Gly  Asp  Arg  Ile
145                  150                   155                        160

Leu  Lys  Leu  Asn  Thr  Glu  Val  Arg  Glu  Val  Gly  Pro  Val  Ser  Lys  Lys
               165                   170                      175

Gly  Phe  Tyr  Leu  Ala  Phe  Gln  Asp  Val  Gly  Ala  Cys  Val  Ala  Leu  Val
               180                   185                      190

Ser  Val  Arg  Val  Tyr  Phe  Lys  Lys  Cys  Pro  Phe  Thr  Val  Lys  Asn  Leu
          195                   200                   205

Ala  Met  Phe  Pro  Asp  Thr  Val  Pro  Met  Asp  Ser  Gln  Ser  Leu  Val  Glu
     210                   215                   220

Val  Arg  Gly  Ser  Cys  Val  Asn  His  Ser  Lys  Glu  Glu  Pro  Pro  Lys
225                  230                   235                        240
```

```
Met Tyr Cys Ser Thr Glu Gly Glu Trp Leu Val Pro Ile Gly Lys Cys
                245                 250                 255

Leu Cys Asn Ala Gly Tyr Glu Glu Arg Gly Phe Ala Cys Gln Ala Cys
                260                 265                 270

Arg Pro Gly Phe Tyr Lys Ala Ser Ala Gly Asn Val Lys Cys Ala Lys
            275                 280                 285

Cys Pro Pro His Ser Ser Thr Tyr Glu Asp Ala Ser Leu Asn Cys Arg
        290                 295                 300

Cys Glu Lys Asn Tyr Phe Arg Ser Glu Lys Asp Pro Pro Ser Met Ala
305                 310                 315                 320

Cys Thr Arg Pro Pro Ser Ala Pro Arg Asn Val Ile Ser Asn Ile Asn
                325                 330                 335

Glu Thr Ser Val Ile Leu Asp Trp Ser Trp Pro Leu Asp Thr Gly Gly
            340                 345                 350

Arg Lys Asp Val Thr Phe Asn Ile Ile Cys Lys Lys Cys Gly Gly Ser
            355                 360                 365

Ser Lys Ile Cys Glu Pro Cys Ser Asp Asn Val Arg Phe Leu Pro Arg
    370                 375                 380

Gln Thr Gly Leu Thr Asn Thr Thr Val Thr Val Asp Leu Leu Ala
385                 390                 395                 400

His Thr Asn Tyr Thr Phe Glu Ile Asp Ala Val Asn Gly Val Ser Asp
                405                 410                 415

Leu Ser Thr Leu Ser Arg Gln Phe Ala Ala Val Ser Ile Thr Thr Asn
            420                 425                 430

Gln Ala Ala Pro Ser Pro Ile Thr Val Ile Arg Asn Asp Arg Thr Ser
        435                 440                 445

Arg Asn Ser Val Ser Leu Ser Trp Gln Glu Pro Glu His Pro Asn Gly
    450                 455                 460

Ile Ile Leu Asp Tyr Glu Val Lys Tyr Tyr Glu Lys Gln Glu Gln Glu
465                 470                 475                 480

Thr Ser Tyr Thr Ile Leu Arg Ala Lys Ser Thr Asn Val Thr Ile Ser
            485                 490                 495

Gly Leu Lys Pro Asp Thr Thr Tyr Val Phe Gln Ile Arg Ala Arg Thr
            500                 505                 510

Ala Ala Arg Tyr Gly Thr Ser Ser Arg Lys Phe Glu Phe Glu Thr Ser
        515                 520                 525

Pro Asp Ser Phe Ser Ile Ser Ser Glu Asn Ser Gln Val Val Met Ile
    530                 535                 540

Ala Ile Ser Ala Ala Val Ala Ile Ile Leu Leu Thr Val Val Val Tyr
545                 550                 555                 560

Val Leu Ile Gly Arg Phe Cys Gly Tyr Lys Lys Ser Lys His Gly Thr
            565                 570                 575

Asp Glu Lys Arg Leu His Phe Gly Asn Gly His Leu Lys Leu Pro Gly
            580                 585                 590

Leu Arg Thr Tyr Val Asp Pro His Thr Tyr Glu Asp Pro Asn Gln Ala
        595                 600                 605

Val His Glu Phe Ala Lys Glu Leu Asp Ala Ser Asn Ile Ser Ile Asp
    610                 615                 620

Lys Val Val Gly Ala Gly Glu Phe Gly Glu Val Cys Ser Gly Arg Leu
625                 630                 635                 640

Lys Leu Pro Ser Lys Lys Glu Ile Ser Val Ala Ile Lys Thr Leu Lys
                645                 650                 655
```

-continued

| | | | | | | | | | | | | | | |
|---|---|---|---|---|---|---|---|---|---|---|---|---|---|---|
| Ala | Gly | Tyr | Thr 660 | Glu | Lys | Gln | Arg | Arg 665 | Asp | Phe | Leu | Gly 670 | Ala | Ser |
| Ile | Met | Gly 675 | Gln | Phe | Asp | His | Pro 680 | Asn | Ile | Ile | Arg | Leu 685 | Glu | Gly | Val |
| Val | Thr 690 | Lys | Ser | Lys | Pro | Val 695 | Met | Ile | Val | Thr | Glu 700 | Tyr | Met | Glu | Asn |
| Gly 705 | Ser | Leu | Asp | Ser | Phe 710 | Leu | Arg | Lys | His | Asp 715 | Ala | Gln | Phe | Thr | Val 720 |
| Ile | Gln | Leu | Val | Gly 725 | Met | Leu | Arg | Gly | Ile 730 | Ala | Ser | Gly | Met | Lys 735 | Tyr |
| Leu | Ser | Asp | Met 740 | Gly | Tyr | Val | His | Arg 745 | Asp | Leu | Ala | Ala | Arg 750 | Asn | Ile |
| Leu | Ile | Asn 755 | Ser | Asn | Leu | Val | Cys 760 | Lys | Val | Ser | Asp | Phe 765 | Gly | Leu | Ser |
| Arg | Val 770 | Leu | Glu | Asp | Asp | Pro 775 | Glu | Ala | Ala | Tyr | Thr 780 | Thr | Arg | Gly | Gly |
| Lys 785 | Ile | Pro | Ile | Arg | Trp 790 | Thr | Ser | Pro | Glu | Ala 795 | Ile | Ala | Tyr | Arg | Lys 800 |
| Phe | Thr | Ser | Ala | Ser 805 | Asp | Ala | Trp | Ser | Tyr 810 | Gly | Ile | Val | Leu | Trp 815 | Glu |
| Val | Met | Ser | Tyr 820 | Gly | Glu | Arg | Pro | Tyr 825 | Trp | Glu | Met | Ser | Phe 830 | Gln | Asp |
| Val | Ile | Lys 835 | Ala | Val | Asp | Glu | Gly 840 | Tyr | Arg | Leu | Pro | Pro 845 | Pro | Met | Asp |
| Cys | Pro 850 | Ala | Ala | Leu | Tyr | Gln 855 | Leu | Met | Leu | Asp | Cys 860 | Trp | Gln | Lys | Asp |
| Arg 865 | Asn | Asn | Arg | Pro | Lys 870 | Phe | Glu | Gln | Ile | Val 875 | Ser | Ile | Leu | Asp | Lys 880 |
| Leu | Ile | Arg | Asn | Pro 885 | Ser | Ser | Leu | Lys | Ile 890 | Thr | Asn | Ala | Ala | Ala 895 |
| Arg | Pro | Ser | Asn 900 | Leu | Leu | Leu | Asp | Gln 905 | Ser | Asn | Ile | Asp | Ile 910 | Ser | Ala |
| Phe | Arg | Thr 915 | Ala | Gly | Asp | Trp | Leu 920 | Asn | Gly | Phe | Arg | Thr 925 | Gly | Gln | Cys |
| Lys | Gly 930 | Ile | Phe | Thr | Gly | Val 935 | Glu | Tyr | Ser | Ser | Cys 940 | Asp | Thr | Ile | Ala |
| Lys 945 | Ile | Ser | Thr | Asp | Asp 950 | Met | Lys | Lys | Val | Gly 955 | Val | Thr | Val | Val | Gly 960 |
| Pro | Gln | Lys | Lys | Ile 965 | Val | Ser | Ser | Ile | Lys 970 | Thr | Leu | Glu | Thr | His 975 | Thr |
| Lys | Asn | Ser | Pro 980 | Val | Pro | Val | | | | | | | | | |

(2) INFORMATION FOR SEQ ID NO:17:

(i) SEQUENCE CHARACTERISTICS:
        (A) LENGTH: 4049 base pairs
        (B) TYPE: nucleic acid
        (C) STRANDEDNESS: both
        (D) TOPOLOGY: linear (ix) FEATURE:
        (A) NAME/KEY: CDS
        (B) LOCATION: 10..2994

(xi) SEQUENCE DESCRIPTION: SEQ ID NO:17:

CGGCTTCTG ATG CCC GGC CCG GAG CGC ACC ATG GGG CCG TTG TGG TTC    48

|     |     |     | Met<br>1 | Pro | Gly | Pro | Glu<br>5 | Arg | Thr | Met | Gly | Pro<br>10 | Leu | Trp | Phe |     |
|---|---|---|---|---|---|---|---|---|---|---|---|---|---|---|---|---|
| TGC | TGT | TTG | CCC | CTC | GCC | CTC | TTG | CCT | CTG | CTC | GCC | GCC | GTG | GAA | GAG | 96 |
| Cys | Cys<br>15 | Leu | Pro | Leu | Ala<br>20 | Leu | Leu | Pro | Leu | Leu<br>25 | Ala | Ala | Val | Glu | Glu |  |
| ACG | CTG | ATG | GAC | TCC | ACA | ACG | GCC | ACA | GCA | GAG | CTG | GGC | TGG | ATG | GTG | 144 |
| Thr<br>30 | Leu | Met | Asp | Ser | Thr<br>35 | Thr | Ala | Thr | Ala | Glu<br>40 | Leu | Gly | Trp | Met | Val<br>45 |  |
| CAT | CCT | CCC | TCA | GGG | TGG | GAA | GAG | GTG | AGT | GGA | TAC | GAT | GAG | AAC | ATG | 192 |
| His | Pro | Pro | Ser<br>50 | Gly | Trp | Glu | Glu | Val | Ser<br>55 | Gly | Tyr | Asp | Glu | Asn<br>60 | Met |  |
| AAC | ACC | ATC | CGC | ACC | TAC | CAG | GTG | TGC | AAC | GTC | TTT | GAA | TCC | AGC | CAA | 240 |
| Asn | Thr | Ile | Arg<br>65 | Thr | Tyr | Gln | Val | Cys<br>70 | Asn | Val | Phe | Glu | Ser<br>75 | Ser | Gln |  |
| AAC | AAC | TGG | CTG | CGG | ACC | AAG | TAC | ATC | CGG | AGG | CGA | GGA | GCG | CAC | CGC | 288 |
| Asn | Asn | Trp<br>80 | Leu | Arg | Thr | Lys | Tyr<br>85 | Ile | Arg | Arg | Arg | Gly<br>90 | Ala | His | Arg |  |
| ATC | CAC | GTG | GAG | ATG | AAA | TTC | TCC | GTT | CGG | GAC | TGC | AGC | AGC | ATC | CCC | 336 |
| Ile | His<br>95 | Val | Glu | Met | Lys<br>100 | Phe | Ser | Val | Arg | Asp<br>105 | Cys | Ser | Ser | Ile | Pro |  |
| AAC | GTC | CCG | GGC | TCC | TGT | AAG | GAG | ACT | TTT | AAC | CTC | TAT | TAC | TAC | GAA | 384 |
| Asn<br>110 | Val | Pro | Gly | Ser | Cys<br>115 | Lys | Glu | Thr | Phe | Asn<br>120 | Leu | Tyr | Tyr | Tyr | Glu<br>125 |  |
| TCA | GAC | TTT | GAC | TCT | GCC | ACC | AAG | ACT | TTT | CCT | AAC | TGG | ATG | GAA | AAC | 432 |
| Ser | Asp | Phe | Asp | Ser<br>130 | Ala | Thr | Lys | Thr | Phe<br>135 | Pro | Asn | Trp | Met | Glu<br>140 | Asn |  |
| CCT | TGG | ATG | AAG | GTA | GAT | ACA | ATT | GCT | GCC | GAC | GAG | AGC | TTC | TCG | CAG | 480 |
| Pro | Trp | Met | Lys<br>145 | Val | Asp | Thr | Ile | Ala<br>150 | Ala | Asp | Glu | Ser | Phe<br>155 | Ser | Gln |  |
| GTG | GAC | CTT | GGT | GGG | CGG | GTG | ATG | AAG | ATT | AAC | ACC | GAG | GTG | CGC | AGT | 528 |
| Val | Asp | Leu<br>160 | Gly | Gly | Arg | Val | Met<br>165 | Lys | Ile | Asn | Thr | Glu<br>170 | Val | Arg | Ser |  |
| TTT | GGG | CCT | GTC | TCC | AAA | AAC | GGT | TTC | TAC | CTG | GCC | TTC | CAG | GAC | TAC | 576 |
| Phe | Gly<br>175 | Pro | Val | Ser | Lys | Asn<br>180 | Gly | Phe | Tyr | Leu | Ala<br>185 | Phe | Gln | Asp | Tyr |  |
| GGG | GGC | TGC | ATG | TCC | TTG | ATT | GCA | GTC | CGT | GTC | TTT | TAC | CGC | AAG | TGT | 624 |
| Gly | Gly | Cys | Met | Ser | Leu<br>195 | Ile | Ala | Val | Arg | Val<br>200 | Phe | Tyr | Arg | Lys | Cys<br>205 |  |
| CCC | CGT | GTG | ATC | CAG | AAC | GGG | GCG | GTC | TTC | CAG | GAA | ACC | CTC | TCG | GGA | 672 |
| Pro | Arg | Val | Ile | Gln<br>210 | Asn | Gly | Ala | Val | Phe<br>215 | Gln | Glu | Thr | Leu | Ser<br>220 | Gly |  |
| GCG | GAG | AGC | ACA | TCT | CTG | GTG | GCA | GCC | CGG | GGG | ACG | TGC | ATC | AGC | AAT | 720 |
| Ala | Glu | Ser | Thr<br>225 | Ser | Leu | Val | Ala | Ala<br>230 | Arg | Gly | Thr | Cys | Ile<br>235 | Ser | Asn |  |
| GCG | GAG | GAG | GTG | GAT | GTG | CCC | ATC | AAG | CTG | TAC | TGC | AAT | GGG | GAT | GGC | 768 |
| Ala | Glu | Glu | Val<br>240 | Asp | Val | Pro | Ile | Lys<br>245 | Leu | Tyr | Cys | Asn | Gly<br>250 | Asp | Gly |  |
| GAG | TGG | CTG | GTG | CCC | ATC | GGC | CGC | TGC | ATG | TGC | AGG | CCG | GGC | TAT | GAG | 816 |
| Glu | Trp<br>255 | Leu | Val | Pro | Ile | Gly<br>260 | Arg | Cys | Met | Cys | Arg<br>265 | Pro | Gly | Tyr | Glu |  |
| TCG | GTG | GAG | AAT | GGG | ACC | GTC | TGC | AGA | GGC | TGC | CCA | TCA | GGG | ACC | TTC | 864 |
| Ser<br>270 | Val | Glu | Asn | Gly | Thr<br>275 | Val | Cys | Arg | Gly | Cys<br>280 | Pro | Ser | Gly | Thr | Phe<br>285 |  |
| AAG | GCC | AGC | CAA | GGA | GAT | GAA | GGA | TGT | GTC | CAT | TGT | CCA | ATT | AAC | AGC | 912 |
| Lys | Ala | Ser | Gln | Gly<br>290 | Asp | Glu | Gly | Cys | Val<br>295 | His | Cys | Pro | Ile | Asn<br>300 | Ser |  |
| CGG | ACG | ACT | TCG | GAA | GGG | GCC | ACG | AAC | TGC | GTG | TGC | CGA | AAC | GGA | TAT | 960 |
| Arg | Thr | Thr | Ser<br>305 | Glu | Gly | Ala | Thr | Asn<br>310 | Cys | Val | Cys | Arg | Asn<br>315 | Gly | Tyr |  |

| | | | | | | | | | | | | | | | |
|---|---|---|---|---|---|---|---|---|---|---|---|---|---|---|---|
| TAC | CGG | GCA | GAT | GCT | GAC | CCC | GTC | GAC | ATG | CCA | TGC | ACC | ACC | ATC | CCA | 1008 |
| Tyr | Arg | Ala | Asp | Ala | Asp | Pro | Val | Asp | Met | Pro | Cys | Thr | Thr | Ile | Pro | |
| | | 320 | | | | 325 | | | | | 330 | | | | | |
| TCT | GCC | CCC | CAG | GCC | GTG | ATC | TCC | AGC | GTG | AAT | GAA | ACC | TCC | CTG | ATG | 1056 |
| Ser | Ala | Pro | Gln | Ala | Val | Ile | Ser | Ser | Val | Asn | Glu | Thr | Ser | Leu | Met | |
| | 335 | | | | 340 | | | | | 345 | | | | | | |
| CTG | GAG | TGG | ACC | CCA | CCA | CGA | GAC | TCA | GGG | GGC | CGG | GAG | GAT | CTG | GTA | 1104 |
| Leu | Glu | Trp | Thr | Pro | Pro | Arg | Asp | Ser | Gly | Gly | Arg | Glu | Asp | Leu | Val | |
| 350 | | | | | 355 | | | | | 360 | | | | | 365 | |
| TAC | AAC | ATC | ATC | TGC | AAG | AGC | TGT | GGG | TCA | GGC | CGT | GGG | GCG | TGC | ACG | 1152 |
| Tyr | Asn | Ile | Ile | Cys | Lys | Ser | Cys | Gly | Ser | Gly | Arg | Gly | Ala | Cys | Thr | |
| | | | | 370 | | | | | 375 | | | | | 380 | | |
| CGC | TGT | GGG | GAC | AAC | GTG | CAG | TTT | GCC | CCA | CGC | CAG | CTG | GGC | CTG | ACG | 1200 |
| Arg | Cys | Gly | Asp | Asn | Val | Gln | Phe | Ala | Pro | Arg | Gln | Leu | Gly | Leu | Thr | |
| | | | 385 | | | | | 390 | | | | | 395 | | | |
| GAG | CCT | CGC | ATC | TAC | ATC | AGC | GAC | CTG | CTG | GCC | CAC | ACG | CAG | TAC | ACC | 1248 |
| Glu | Pro | Arg | Ile | Tyr | Ile | Ser | Asp | Leu | Leu | Ala | His | Thr | Gln | Tyr | Thr | |
| | | 400 | | | | | 405 | | | | | 410 | | | | |
| TTT | GAG | ATC | CAG | GCT | GTG | AAT | GGG | GTC | ACC | GAC | CAG | AGC | CCC | TTC | TCC | 1296 |
| Phe | Glu | Ile | Gln | Ala | Val | Asn | Gly | Val | Thr | Asp | Gln | Ser | Pro | Phe | Ser | |
| 415 | | | | | 420 | | | | | 425 | | | | | | |
| CCA | CAG | TTT | GCA | TCA | GTG | AAT | ATC | ACC | ACC | AAC | CAG | GCT | GCT | CCT | TCA | 1344 |
| Pro | Gln | Phe | Ala | Ser | Val | Asn | Ile | Thr | Thr | Asn | Gln | Ala | Ala | Pro | Ser | |
| 430 | | | | | 435 | | | | | 440 | | | | | 445 | |
| GCC | GTG | TCC | ATA | ATG | CAC | CAG | GTC | AGC | CGC | ACT | GTG | GAC | AGC | ATT | ACC | 1392 |
| Ala | Val | Ser | Ile | Met | His | Gln | Val | Ser | Arg | Thr | Val | Asp | Ser | Ile | Thr | |
| | | | | 450 | | | | | 455 | | | | | 460 | | |
| CTC | TCG | TGG | TCT | CAA | CCT | GAC | CAG | CCC | AAT | GGA | GTC | ATC | CTG | GAT | TAT | 1440 |
| Leu | Ser | Trp | Ser | Gln | Pro | Asp | Gln | Pro | Asn | Gly | Val | Ile | Leu | Asp | Tyr | |
| | | | 465 | | | | | 470 | | | | | 475 | | | |
| GAG | CTG | CAA | TAC | TAT | GAG | AAG | AAC | CTG | AGT | GAG | TTA | AAT | TCA | ACA | GCA | 1488 |
| Glu | Leu | Gln | Tyr | Tyr | Glu | Lys | Asn | Leu | Ser | Glu | Leu | Asn | Ser | Thr | Ala | |
| | | 480 | | | | | 485 | | | | | 490 | | | | |
| GTG | AAG | AGC | CCC | ACC | AAC | ACT | GTG | ACA | GTG | CAA | AAC | CTC | AAA | GCT | GGC | 1536 |
| Val | Lys | Ser | Pro | Thr | Asn | Thr | Val | Thr | Val | Gln | Asn | Leu | Lys | Ala | Gly | |
| | 495 | | | | 500 | | | | | 505 | | | | | | |
| ACC | ATC | TAT | GTC | TTC | CAA | GTG | CGA | GCA | CGT | ACC | GTG | GCT | GGG | TAT | GGC | 1584 |
| Thr | Ile | Tyr | Val | Phe | Gln | Val | Arg | Ala | Arg | Thr | Val | Ala | Gly | Tyr | Gly | |
| 510 | | | | | 515 | | | | | 520 | | | | | 525 | |
| CGG | TAT | AGT | GGC | AAG | ATG | TAC | TTC | CAG | ACC | ATG | ACT | GAA | GCC | GAG | TAC | 1632 |
| Arg | Tyr | Ser | Gly | Lys | Met | Tyr | Phe | Gln | Thr | Met | Thr | Glu | Ala | Glu | Tyr | |
| | | | | 530 | | | | | 535 | | | | | 540 | | |
| CAG | ACC | AGT | GTC | CAG | GAG | AAG | CTG | CCA | CTC | ATC | ATT | GGC | TCC | TCT | GCA | 1680 |
| Gln | Thr | Ser | Val | Gln | Glu | Lys | Leu | Pro | Leu | Ile | Ile | Gly | Ser | Ser | Ala | |
| | | | 545 | | | | | 550 | | | | | 555 | | | |
| GCA | GGA | CTG | GTG | TTT | CTC | ATT | GCT | GTT | GTC | GTC | ATC | ATT | ATT | GTC | TGC | 1728 |
| Ala | Gly | Leu | Val | Phe | Leu | Ile | Ala | Val | Val | Val | Ile | Ile | Ile | Val | Cys | |
| | | 560 | | | | | 565 | | | | | 570 | | | | |
| AAC | AGA | AGA | CGG | GGC | TTT | GAA | CGT | GCT | GAC | TCT | GAG | TAC | ACT | GAC | AAG | 1776 |
| Asn | Arg | Arg | Arg | Gly | Phe | Glu | Arg | Ala | Asp | Ser | Glu | Tyr | Thr | Asp | Lys | |
| | 575 | | | | 580 | | | | | 585 | | | | | | |
| CTG | CAG | CAC | TAT | ACC | AGT | GGC | CAC | ATG | ACT | CCA | GGG | ATG | AAG | ATT | TAT | 1824 |
| Leu | Gln | His | Tyr | Thr | Ser | Gly | His | Met | Thr | Pro | Gly | Met | Lys | Ile | Tyr | |
| 590 | | | | | 595 | | | | | 600 | | | | | 605 | |
| ATC | GAT | CCA | TTT | ACC | TAC | GAA | GAT | CCC | AAT | GAG | GCT | GTC | AGG | GAA | TTT | 1872 |
| Ile | Asp | Pro | Phe | Thr | Tyr | Glu | Asp | Pro | Asn | Glu | Ala | Val | Arg | Glu | Phe | |
| | | | | 610 | | | | | 615 | | | | | 620 | | |
| GCA | AAA | GAA | ATT | GAT | ATC | TCC | TGT | GTG | AAA | ATC | GAG | CAG | GTG | ATT | GGG | 1920 |
| Ala | Lys | Glu | Ile | Asp | Ile | Ser | Cys | Val | Lys | Ile | Glu | Gln | Val | Ile | Gly | |
| | | | 625 | | | | | 630 | | | | | 635 | | | |

| | | | | | | | | | | | | | | | | |
|---|---|---|---|---|---|---|---|---|---|---|---|---|---|---|---|---|
| GCA | GGG | GAG | TTT | GGT | GAG | GTG | TGC | AGT | GGG | CAT | CTC | AAG | CTT | CCT | GGC | 1968 |
| Ala | Gly | Glu 640 | Phe | Gly | Glu | Val | Cys | Ser 645 | Gly | His | Leu | Lys 650 | Leu | Pro | Gly | |
| AAA | AGA | GAG | ATC | TTT | GTG | GCC | ATC | AAG | ACC | CTG | AAG | TCT | GGT | TAC | ACA | 2016 |
| Lys | Arg 655 | Glu | Ile | Phe | Val | Ala | Ile 660 | Lys | Thr | Leu | Lys 665 | Ser | Gly | Tyr | Thr | |
| GAG | AAG | CAG | AGA | CGG | GAC | TTC | CTG | AGT | GAA | GCC | AGC | ATC | ATG | GGG | CAG | 2064 |
| Glu | Lys | Gln | Arg | Arg 675 | Asp | Phe | Leu | Ser | Glu | Ala 680 | Ser | Ile | Met | Gly | Gln 685 | |
| | | | | | | | | | | | | | | | | |
| | | | | | | | | | | | | | | | | |
| TTT | GAC | CAC | CCC | AAT | GTC | ATC | CAC | CTG | GAA | GGG | GTG | GTG | ACC | AAG | AGT | 2112 |
| Phe 670 | Asp | His | Pro | Asn 690 | Val | Ile | His | Leu | Glu 695 | Gly | Val | Val | Thr | Lys 700 | Ser | |
| TCC | CCA | GTC | ATG | ATC | ATT | ACA | GAG | TTC | ATG | GAG | AAT | GGC | TCG | TTG | GAC | 2160 |
| Ser | Pro | Val | Met 705 | Ile | Ile | Thr | Glu | Phe 710 | Met | Glu | Asn | Gly | Ser 715 | Leu | Asp | |
| TCC | TTC | TTG | AGG | CAA | AAT | GAT | GGG | CAG | TTC | ACA | GTG | ATC | CAG | CTG | GTG | 2208 |
| Ser | Phe | Leu 720 | Arg | Gln | Asn | Asp | Gly 725 | Gln | Phe | Thr | Val | Ile 730 | Gln | Leu | Val | |
| GGC | ATG | TTG | CGT | GGC | ATT | GCA | GCA | GGC | ATG | AAG | TAC | CTG | GCT | GAT | ATG | 2256 |
| Gly | Met 735 | Leu | Arg | Gly | Ile | Ala 740 | Ala | Gly | Met | Lys | Tyr 745 | Leu | Ala | Asp | Met | |
| AAC | TAC | GTG | CAC | CGG | GAC | CTG | GCT | GCC | CGC | AAC | ATC | CTG | GTC | AAC | AGC | 2304 |
| Asn | Tyr | Val | His | Arg 755 | Asp | Leu | Ala | Ala | Arg 760 | Asn | Ile | Leu | Val | Asn 765 | Ser | |
| Asn 750 | | | | | | | | | | | | | | | | |
| AAC | CTG | GTC | TGC | AAG | GTG | TCC | GAC | TTC | GGC | CTC | TCC | CGT | TTC | CTG | GAG | 2352 |
| Asn | Leu | Val | Cys | Lys 770 | Val | Ser | Asp | Phe | Gly 775 | Leu | Ser | Arg | Phe | Leu 780 | Glu | |
| GAT | GAC | ACC | TCT | GAT | CCC | ACT | TAC | ACC | AGC | GCA | CTG | GGT | GGA | AAG | ATC | 2400 |
| Asp | Asp | Thr | Ser 785 | Asp | Pro | Thr | Tyr | Thr 790 | Ser | Ala | Leu | Gly | Gly 795 | Lys | Ile | |
| CCA | ATA | CGG | TGG | ACA | GCG | CCT | GAG | GCA | ATT | CAG | TAC | CGA | AAA | TTC | ACA | 2448 |
| Pro | Ile | Arg 800 | Trp | Thr | Ala | Pro | Glu 805 | Ala | Ile | Gln | Tyr | Arg 810 | Lys | Phe | Thr | |
| TCA | GCC | AGC | GAT | GTG | TGG | AGC | TAT | GGA | ATA | GTC | ATG | TGG | GAG | GTG | ATG | 2496 |
| Ser | Ala 815 | Ser | Asp | Val | Trp | Ser 820 | Tyr | Gly | Ile | Val | Met 825 | Trp | Glu | Val | Met | |
| TCG | TAC | GGC | GAG | CGG | CCT | TAC | TGG | GAC | ATG | ACC | AAT | CAA | GAT | GTG | ATA | 2544 |
| Ser 830 | Tyr | Gly | Glu | Arg | Pro 835 | Tyr | Trp | Asp | Met | Thr 840 | Asn | Gln | Asp | Val | Ile 845 | |
| AAT | GCT | ATT | GAG | CAG | GAC | TAT | CGG | CTA | CCA | CCC | CCT | ATG | GAT | TGT | CCA | 2592 |
| Asn | Ala | Ile | Glu | Gln 850 | Asp | Tyr | Arg | Leu | Pro 855 | Pro | Pro | Met | Asp | Cys 860 | Pro | |
| AAT | GCC | CTG | CAC | CAG | CTA | ATG | CTT | GAC | TGC | TGG | CAG | AAG | GAT | CGA | AAC | 2640 |
| Asn | Ala | Leu | His 865 | Gln | Leu | Met | Leu | Asp 870 | Cys | Trp | Gln | Lys | Asp 875 | Arg | Asn | |
| CAC | AGA | CCC | AAA | TTT | GGA | CAG | ATT | GTC | AAC | ACT | TTA | GAC | AAA | ATG | ATC | 2688 |
| His | Arg | Pro 880 | Lys | Phe | Gly | Gln | Ile 885 | Val | Asn | Thr | Leu | Asp 890 | Lys | Met | Ile | |
| CGA | AAT | CCT | AAT | AGT | CTG | AAA | GCC | ATG | GCA | CCT | CTC | TCC | TCT | GGG | GTT | 2736 |
| Arg | Asn 895 | Pro | Asn | Ser | Leu | Lys 900 | Ala | Met | Ala | Pro | Leu 905 | Ser | Ser | Gly | Val | |
| AAC | CTC | CCT | CTA | CTT | GAC | CGC | ACA | ATC | CCA | GAT | TAT | ACC | AGC | TTC | AAC | 2784 |
| Asn | Leu | Pro | Leu 910 | Leu | Asp | Arg | Thr | Ile 915 | Pro | Asp | Tyr | Thr | Ser 920 | Phe | Asn 925 | |
| ACT | GTG | GAT | GAA | TGG | CTG | GAT | GCC | ATC | AAG | ATG | AGC | CAG | TAC | AAG | GAG | 2832 |
| Thr | Val | Asp | Glu | Trp 930 | Leu | Asp | Ala | Ile | Lys 935 | Met | Ser | Gln | Tyr | Lys 940 | Glu | |
| AGC | TTT | GCC | AGT | GCT | GGC | TTC | ACC | ACC | TTT | GAT | ATA | GTA | TCT | CAG | ATG | 2880 |
| Ser | Phe | Ala | Ser | Ala | Gly | Phe | Thr | Thr | Phe | Asp | Ile | Val | Ser | Gln | Met | |

|  |  |  |  |  |  |  |  |  |  |  |  |  |  |  |  |
|---|---|---|---|---|---|---|---|---|---|---|---|---|---|---|---|
|  |  |  |  | 945 |  |  |  |  | 950 |  |  |  |  | 955 |  |
| ACT | GTA | GAG | GAC | ATT | CTA | CGA | GTT | GGG | GTC | ACT | TTA | GCA | GGA | CAC | CAG |
| Thr | Val | Glu | Asp | Ile | Leu | Arg | Val | Gly | Val | Thr | Leu | Ala | Gly | His | Gln |
|  |  | 960 |  |  |  |  | 965 |  |  |  |  | 970 |  |  |  |

2928

AAG AAA ATT CTG AAC AGT ATC CAG GTG ATG AGA GCA CAG ATG AAC CAA    2976
Lys Lys Ile Leu Asn Ser Ile Gln Val Met Arg Ala Gln Met Asn Gln
        975             980             985

ATT CAG TCT GTG GAG GTT TGATAGCAAC ACGTCCTCGT GCTCCACTTC          3024
Ile Gln Ser Val Glu Val
990             995

CTTGAGGCCC TGCTCCCCTC TGCCCCTGTG TGTCTGAGCT CCAGTTCTTG AGTGTTCTGC    3084
GTGGATCAGA GACAGGCAGC TGCTCTGAGG ATCATGGCAA CAGGAAGAAA TGCCCTATCA    3144
TTGACAACGA GAAGTCATCA AGAGGTGAAA CAATGGAAAA CAATGGAAAA AGGGAACAAG    3204
TAAAGACAGC TATTTTGAAA ACCGAAAACA AACAGTGAAT TATTTTAAA TAATAATAAA     3264
GCAATTGCAG TCTTGAAAAG GGCTCCAAGA CCAATGGGAG TCTCCAAAGG AAGAGAATAG    3324
AGCAGCTTCA TCTATTTCCT CTTACACAAG GGTTGCTGCA GCTGGGCCCA GACACTTCTG    3384
GAGTAACGAG ACTTTTCAAG AAGATGAATG CAAAGAATGG TCACAAGAAG CACTTCTCTT    3444
TCTCACATGG GATGGCAGCT CTGGGAATGC CCGGCAGTCC TTCCTGAAAG CCCTGTTGGC    3504
AAATCGAAGA GGAGAGCCGA AGCTCTTTGG TGCTGTGGAA CCAAGTGCAT CTCAGAAATT    3564
GTTGGACTTC TACAAAAGCT GAAGACATTC TTTTTTTTA AACAAGTAAA CTGATACTAG     3624
AAGAGGCTGT TTCCGTCAAA TGAGAAGGAA TCTGTAACAC TGGCCCGGGG GGGGTGGGGA    3684
ATGGGGGAAA TCAGTCCTTT TTACATCTCT TTATTTTCTC TTGTCATGGA ACAGTTTTGT    3744
GAGTGACAGT TTCCTAAGGG TCCGTCCATC CACCCTCCAA TGGCATCATT GTTTCATACA    3804
TATCATATGC ACAAGACTTA TAGTGATGTC CTCACTCGAT GCCAATGATC TTTCCCCAGA    3864
AGACTTCCCA AGTACAGTAT GTAGTAGATT TTGATTACAA ATGCTGACGT GTACCTTTAT    3924
TTTTCGGTTG TCGTTGTTGG GAGATTCGTC CTTTTACCTT GCTTTGTTAA CACCAATTTG    3984
TGAGTTTGGG GTTGGAATTT TTTTGGTCGA TTGGGGTTGT TTTTTTTTT TTTTTTTTT     4044
AACCG                                                               4049

( 2 ) INFORMATION FOR SEQ ID NO:18:

( i ) SEQUENCE CHARACTERISTICS:
        ( A ) LENGTH: 995 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

Met Pro Gly Pro Glu Arg Thr Met Gly Pro Leu Trp Phe Cys Cys Leu
 1               5                  10                  15

Pro Leu Ala Leu Leu Pro Leu Leu Ala Ala Val Glu Glu Thr Leu Met
            20                  25                  30

Asp Ser Thr Thr Ala Thr Ala Glu Leu Gly Trp Met Val His Pro Pro
        35                  40                  45

Ser Gly Trp Glu Glu Val Ser Gly Tyr Asp Glu Asn Met Asn Thr Ile
    50                  55                  60

Arg Thr Tyr Gln Val Cys Asn Val Phe Glu Ser Ser Gln Asn Asn Trp
65                  70                  75                  80

Leu Arg Thr Lys Tyr Ile Arg Arg Arg Gly Ala His Arg Ile His Val
                85                  90                  95

-continued

```
Glu Met Lys Phe Ser Val Arg Asp Cys Ser Ser Ile Pro Asn Val Pro
            100                 105                 110
Gly Ser Cys Lys Glu Thr Phe Asn Leu Tyr Tyr Tyr Glu Ser Asp Phe
        115                 120                 125
Asp Ser Ala Thr Lys Thr Phe Pro Asn Trp Met Glu Asn Pro Trp Met
    130                 135                 140
Lys Val Asp Thr Ile Ala Ala Asp Glu Ser Phe Ser Gln Val Asp Leu
145                 150                 155                 160
Gly Gly Arg Val Met Lys Ile Asn Thr Glu Val Arg Ser Phe Gly Pro
                165                 170                 175
Val Ser Lys Asn Gly Phe Tyr Leu Ala Phe Gln Asp Tyr Gly Gly Cys
            180                 185                 190
Met Ser Leu Ile Ala Val Arg Val Phe Tyr Arg Lys Cys Pro Arg Val
        195                 200                 205
Ile Gln Asn Gly Ala Val Phe Gln Glu Thr Leu Ser Gly Ala Glu Ser
    210                 215                 220
Thr Ser Leu Val Ala Ala Arg Gly Thr Cys Ile Ser Asn Ala Glu Glu
225                 230                 235                 240
Val Asp Val Pro Ile Lys Leu Tyr Cys Asn Gly Asp Gly Glu Trp Leu
                245                 250                 255
Val Pro Ile Gly Arg Cys Met Cys Arg Pro Gly Tyr Glu Ser Val Glu
            260                 265                 270
Asn Gly Thr Val Cys Arg Gly Cys Pro Ser Gly Thr Phe Lys Ala Ser
        275                 280                 285
Gln Gly Asp Glu Gly Cys Val His Cys Pro Ile Asn Ser Arg Thr Thr
    290                 295                 300
Ser Glu Gly Ala Thr Asn Cys Val Cys Arg Asn Gly Tyr Tyr Arg Ala
305                 310                 315                 320
Asp Ala Asp Pro Val Asp Met Pro Cys Thr Thr Ile Pro Ser Ala Pro
                325                 330                 335
Gln Ala Val Ile Ser Ser Val Asn Glu Thr Ser Leu Met Leu Glu Trp
            340                 345                 350
Thr Pro Pro Arg Asp Ser Gly Gly Arg Glu Asp Leu Val Tyr Asn Ile
        355                 360                 365
Ile Cys Lys Ser Cys Gly Ser Gly Arg Gly Ala Cys Thr Arg Cys Gly
    370                 375                 380
Asp Asn Val Gln Phe Ala Pro Arg Gln Leu Gly Leu Thr Glu Pro Arg
385                 390                 395                 400
Ile Tyr Ile Ser Asp Leu Leu Ala His Thr Gln Tyr Thr Phe Glu Ile
                405                 410                 415
Gln Ala Val Asn Gly Val Thr Asp Gln Ser Pro Phe Ser Pro Gln Phe
            420                 425                 430
Ala Ser Val Asn Ile Thr Thr Asn Gln Ala Ala Pro Ser Ala Val Ser
        435                 440                 445
Ile Met His Gln Val Ser Arg Thr Val Asp Ser Ile Thr Leu Ser Trp
    450                 455                 460
Ser Gln Pro Asp Gln Pro Asn Gly Val Ile Leu Asp Tyr Glu Leu Gln
465                 470                 475                 480
Tyr Tyr Glu Lys Asn Leu Ser Glu Leu Asn Ser Thr Ala Val Lys Ser
                485                 490                 495
Pro Thr Asn Thr Val Thr Val Gln Asn Leu Lys Ala Gly Thr Ile Tyr
            500                 505                 510
```

-continued

| | | | | | | | | | | | | | | |
|---|---|---|---|---|---|---|---|---|---|---|---|---|---|---|
| Val | Phe | Gln | Val | Arg | Ala | Arg | Thr | Val | Ala | Gly | Tyr | Gly | Arg | Tyr | Ser |
| | | 515 | | | | | 520 | | | | 525 | | | |
| Gly | Lys | Met | Tyr | Phe | Gln | Thr | Met | Thr | Glu | Ala | Glu | Tyr | Gln | Thr | Ser |
| | 530 | | | | | 535 | | | | | 540 | | | | |
| Val | Gln | Glu | Lys | Leu | Pro | Leu | Ile | Ile | Gly | Ser | Ser | Ala | Ala | Gly | Leu |
| 545 | | | | | 550 | | | | | 555 | | | | | 560 |
| Val | Phe | Leu | Ile | Ala | Val | Val | Val | Ile | Ile | Ile | Val | Cys | Asn | Arg | Arg |
| | | | | 565 | | | | | 570 | | | | | 575 | |
| Arg | Gly | Phe | Glu | Arg | Ala | Asp | Ser | Glu | Tyr | Thr | Asp | Lys | Leu | Gln | His |
| | | | 580 | | | | | 585 | | | | | 590 | | |
| Tyr | Thr | Ser | Gly | His | Met | Thr | Pro | Gly | Met | Lys | Ile | Tyr | Ile | Asp | Pro |
| | | 595 | | | | | 600 | | | | | 605 | | | |
| Phe | Thr | Tyr | Glu | Asp | Pro | Asn | Glu | Ala | Val | Arg | Glu | Phe | Ala | Lys | Glu |
| | 610 | | | | | 615 | | | | | 620 | | | | |
| Ile | Asp | Ile | Ser | Cys | Val | Lys | Ile | Glu | Gln | Val | Ile | Gly | Ala | Gly | Glu |
| 625 | | | | | 630 | | | | | 635 | | | | | 640 |
| Phe | Gly | Glu | Val | Cys | Ser | Gly | His | Leu | Lys | Leu | Pro | Gly | Lys | Arg | Glu |
| | | | | 645 | | | | | 650 | | | | | 655 | |
| Ile | Phe | Val | Ala | Ile | Lys | Thr | Leu | Lys | Ser | Gly | Tyr | Thr | Glu | Lys | Gln |
| | | | | 660 | | | | 665 | | | | | 670 | | |
| Arg | Arg | Asp | Phe | Leu | Ser | Glu | Ala | Ser | Ile | Met | Gly | Gln | Phe | Asp | His |
| | | 675 | | | | | 680 | | | | | 685 | | | |
| Pro | Asn | Val | Ile | His | Leu | Glu | Gly | Val | Val | Thr | Lys | Ser | Ser | Pro | Val |
| | | 690 | | | | | 695 | | | | 700 | | | | |
| Met | Ile | Ile | Thr | Glu | Phe | Met | Glu | Asn | Gly | Ser | Leu | Asp | Ser | Phe | Leu |
| 705 | | | | | 710 | | | | | 715 | | | | | 720 |
| Arg | Gln | Asn | Asp | Gly | Gln | Phe | Thr | Val | Ile | Gln | Leu | Val | Gly | Met | Leu |
| | | | | 725 | | | | | 730 | | | | | 735 | |
| Arg | Gly | Ile | Ala | Ala | Gly | Met | Lys | Tyr | Leu | Ala | Asp | Met | Asn | Tyr | Val |
| | | | 740 | | | | | 745 | | | | | 750 | | |
| His | Arg | Asp | Leu | Ala | Ala | Arg | Asn | Ile | Leu | Val | Asn | Ser | Asn | Leu | Val |
| | | 755 | | | | | 760 | | | | | 765 | | | |
| Cys | Lys | Val | Ser | Asp | Phe | Gly | Leu | Ser | Arg | Phe | Leu | Glu | Asp | Asp | Thr |
| | 770 | | | | | 775 | | | | | 780 | | | | |
| Ser | Asp | Pro | Thr | Tyr | Thr | Ser | Ala | Leu | Gly | Gly | Lys | Ile | Pro | Ile | Arg |
| 785 | | | | | 790 | | | | | 795 | | | | | 800 |
| Trp | Thr | Ala | Pro | Glu | Ala | Ile | Gln | Tyr | Arg | Lys | Phe | Thr | Ser | Ala | Ser |
| | | | | 805 | | | | | 810 | | | | | 815 | |
| Asp | Val | Trp | Ser | Tyr | Gly | Ile | Val | Met | Trp | Glu | Val | Met | Ser | Tyr | Gly |
| | | | 820 | | | | | 825 | | | | | 830 | | |
| Glu | Arg | Pro | Tyr | Trp | Asp | Met | Thr | Asn | Gln | Asp | Val | Ile | Asn | Ala | Ile |
| | | 835 | | | | | 840 | | | | | 845 | | | |
| Glu | Gln | Asp | Tyr | Arg | Leu | Pro | Pro | Met | Asp | Cys | Pro | Asn | Ala | Leu |
| | 850 | | | | | 855 | | | | | 860 | | | | |
| His | Gln | Leu | Met | Leu | Asp | Cys | Trp | Gln | Lys | Asp | Arg | Asn | His | Arg | Pro |
| 865 | | | | | 870 | | | | | 875 | | | | | 880 |
| Lys | Phe | Gly | Gln | Ile | Val | Asn | Thr | Leu | Asp | Lys | Met | Ile | Arg | Asn | Pro |
| | | | | 885 | | | | | 890 | | | | | 895 | |
| Asn | Ser | Leu | Lys | Ala | Met | Ala | Pro | Leu | Ser | Ser | Gly | Val | Asn | Leu | Pro |
| | | | 900 | | | | | 905 | | | | | 910 | | |
| Leu | Leu | Asp | Arg | Thr | Ile | Pro | Asp | Tyr | Thr | Ser | Phe | Asn | Thr | Val | Asp |
| | | 915 | | | | | 920 | | | | | 925 | | | |
| Glu | Trp | Leu | Asp | Ala | Ile | Lys | Met | Ser | Gln | Tyr | Lys | Glu | Ser | Phe | Ala |

```
                  930                      935                       940
Ser  Ala  Gly  Phe  Thr  Thr  Phe  Asp  Ile  Val  Ser  Gln  Met  Thr  Val  Glu
945                      950                      955                       960

Asp  Ile  Leu  Arg  Val  Gly  Val  Thr  Leu  Ala  Gly  His  Gln  Lys  Lys  Ile
                    965                      970                      975

Leu  Asn  Ser  Ile  Gln  Val  Met  Arg  Ala  Gln  Met  Asn  Gln  Ile  Gln  Ser
                980                      985                      990

Val  Glu  Val
          995
```

( 2 ) INFORMATION FOR SEQ ID NO:19:

( i ) SEQUENCE CHARACTERISTICS:
        ( A ) LENGTH: 3125 base pairs
        ( B ) TYPE: nucleic acid
        ( C ) STRANDEDNESS: both
        ( D ) TOPOLOGY: linear ( i x ) FEATURE:
        ( A ) NAME/KEY: CDS
        ( B ) LOCATION: 2..2233

( x i ) SEQUENCE DESCRIPTION: SEQ ID NO:19:

```
C  CTC  AAA  TTC  ACC  CTG  AGG  GAC  TGT  AAC  AGC  CTT  CCA  GGA  GGA  CTT            46
   Leu  Lys  Phe  Thr  Leu  Arg  Asp  Cys  Asn  Ser  Leu  Pro  Gly  Gly  Leu
   1              5                       10                      15

GGG  ACT  TGC  AAG  GAG  ACT  TTT  AAC  ATG  TAC  TAC  TTT  GAG  TCA  GAT  GAT        94
Gly  Thr  Cys  Lys  Glu  Thr  Phe  Asn  Met  Tyr  Tyr  Phe  Glu  Ser  Asp  Asp
                    20                       25                      30

GAA  GAT  GGG  AGG  AAC  ATC  AGA  GAG  AAT  CAG  TAC  ATC  AAG  ATA  GAT  ACC       142
Glu  Asp  Gly  Arg  Asn  Ile  Arg  Glu  Asn  Gln  Tyr  Ile  Lys  Ile  Asp  Thr
               35                       40                      45

ATT  GCT  GCT  GAT  GAG  AGC  TTC  ACG  GAG  TTG  GAC  CTC  GGC  GAC  AGA  GTT       190
Ile  Ala  Ala  Asp  Glu  Ser  Phe  Thr  Glu  Leu  Asp  Leu  Gly  Asp  Arg  Val
          50                       55                      60

ATG  AAG  TTA  AAC  ACA  GAA  GTG  AGA  GAT  GTT  GGG  CCT  CTA  ACA  AAA  AAA       238
Met  Lys  Leu  Asn  Thr  Glu  Val  Arg  Asp  Val  Gly  Pro  Leu  Thr  Lys  Lys
     65                       70                      75

GGA  TTT  TAC  CTT  GCT  TTC  CAG  GAT  GTG  GGC  GCC  TGC  ATT  GCC  CTG  GTC       286
Gly  Phe  Tyr  Leu  Ala  Phe  Gln  Asp  Val  Gly  Ala  Cys  Ile  Ala  Leu  Val
80                       85                      90                       95

TCT  GTG  CGT  GTG  TAC  TAC  AAG  AAA  TGC  CCA  TCA  GTG  ATC  CGC  AAC  CTG       334
Ser  Val  Arg  Val  Tyr  Tyr  Lys  Lys  Cys  Pro  Ser  Val  Ile  Arg  Asn  Leu
                    100                      105                     110

GCA  CGC  TTT  CCA  GAT  ACC  ATC  ACA  GGA  GCA  GAT  TCC  TCG  CAG  CTG  CTA       382
Ala  Arg  Phe  Pro  Asp  Thr  Ile  Thr  Gly  Ala  Asp  Ser  Ser  Gln  Leu  Leu
               115                      120                     125

GAA  GTG  TCA  GGC  GTC  TGT  GTC  AAC  CAC  TCA  GTG  ACT  GAT  GAG  GCA  CCA       430
Glu  Val  Ser  Gly  Val  Cys  Val  Asn  His  Ser  Val  Thr  Asp  Glu  Ala  Pro
          130                      135                     140

AAG  ATG  CAC  TGC  AGT  TCA  GAG  GGA  GAA  TGG  CTG  GTG  CCC  ATT  GGG  AAG       478
Lys  Met  His  Cys  Ser  Ser  Glu  Gly  Glu  Trp  Leu  Val  Pro  Ile  Gly  Lys
     145                     150                      155

TGT  TTG  TGC  AAG  GCA  GGG  TAC  GAG  GAG  AAG  AAC  AAC  ACC  TGC  CAA  GCA       526
Cys  Leu  Cys  Lys  Ala  Gly  Tyr  Glu  Glu  Lys  Asn  Asn  Thr  Cys  Gln  Ala
160                      165                     170                      175

CCT  TCT  CCA  GTC  AGT  AGT  GTG  AAA  AAA  GGG  AAG  ATA  ACT  AAA  AAT  AGC       574
Pro  Ser  Pro  Val  Ser  Ser  Val  Lys  Lys  Gly  Lys  Ile  Thr  Lys  Asn  Ser
                    180                      185                     190

ATC  TCC  CTT  TCC  TGG  CAG  GAG  CCA  GAT  CGA  CCC  AAC  GGC  ATC  ATC  CTG       622
Ile  Ser  Leu  Ser  Trp  Gln  Glu  Pro  Asp  Arg  Pro  Asn  Gly  Ile  Ile  Leu
```

-continued

| | | 195 | | | | | 200 | | | | | 205 | | | | |
|---|---|---|---|---|---|---|---|---|---|---|---|---|---|---|---|---|
| GAA | TAC | GAA | ATC | AAA | TAT | TTT | GAA | AAG | GAC | CAG | GAG | ACA | AGC | TAC | ACC | 670 |
| Glu | Tyr | Glu 210 | Ile | Lys | Tyr | Phe | Glu 215 | Lys | Asp | Gln | Glu | Thr 220 | Ser | Tyr | Thr | |
| ATC | ATC | AAA | TCC | AAA | GAG | ACC | GCA | ATT | ACG | GCA | GAT | GGC | TTG | AAA | CCA | 718 |
| Ile | Ile | Lys 225 | Ser | Lys | Glu | Thr 230 | Ala | Ile | Thr | Ala | Asp 235 | Gly | Leu | Lys | Pro | |
| GGC | TCA | GCG | TAC | GTC | TTC | CAG | ATC | CGA | GCC | CGG | ACA | GCT | GCT | GGC | TAC | 766 |
| Gly | Ser | Ala | Tyr 240 | Val | Phe | Gln | Ile 245 | Arg | Ala | Arg | Thr 250 | Ala | Ala | Gly | Tyr 255 | |
| GGT | GGC | TTC | AGT | CGA | AGA | TTT | GAG | TTT | GAA | ACC | AGC | CCA | GTG | TTA | GCT | 814 |
| Gly | Gly | Phe | Ser | Arg 260 | Arg | Phe | Glu | Phe 265 | Glu | Thr | Ser | Pro | Val 270 | Leu | Ala | |
| GCA | TCC | AGT | GAC | CAG | AGC | CAG | ATT | CCT | ATA | ATT | GTT | GTG | TCT | GTA | ACA | 862 |
| Ala | Ser | Ser | Asp 275 | Gln | Ser | Gln | Ile | Pro 280 | Ile | Ile | Val | Val | Ser 285 | Val | Thr | |
| GTG | GGA | GTT | ATT | CTG | CTG | GCT | GTT | GTT | ATC | GGT | TTC | CTT | CTC | AGT | GGA | 910 |
| Val | Gly | Val | Ile | Leu 290 | Leu | Ala | Val | Val | Ile 295 | Gly | Phe | Leu | Leu | Ser 300 | Gly | |
| AGT | TGC | TGC | GAT | CAT | GGC | TGT | GGG | TGG | GCT | TCT | TCT | CTG | CGT | GCT | GTT | 958 |
| Ser | Cys | Cys | Asp | His 305 | Gly | Cys | Gly | Trp | Ala 310 | Ser | Ser | Leu | Arg | Ala 315 | Val | |
| GCC | TAT | CCG | AGC | CTA | ATA | TGG | CGC | TGT | GGC | TAC | AGC | AAG | GCT | AAA | CAA | 1006 |
| Ala | Tyr 320 | Pro | Ser | Leu | Ile 325 | Trp | Arg | Cys | Gly | Tyr 330 | Ser | Lys | Ala | Lys 335 | Gln | |
| GAC | CCA | GAA | GAA | GAA | AAG | ATG | CAT | TTT | CAT | AAT | GGC | CAC | ATT | AAA | CTG | 1054 |
| Asp | Pro | Glu | Glu | Glu 340 | Lys | Met | His | Phe | His 345 | Asn | Gly | His | Ile | Lys 350 | Leu | |
| CCT | GGT | GTA | AGA | ACC | TAC | ATT | GAT | CCC | CAC | ACC | TAT | GAG | GAC | CCT | AAT | 1102 |
| Pro | Gly | Val | Arg 355 | Thr | Tyr | Ile | Asp | Pro 360 | His | Thr | Tyr | Glu | Asp 365 | Pro | Asn | |
| CAA | GCT | GTC | CAC | GAG | TTT | GCC | AAG | GAA | ATA | GAA | GCT | TCG | TGC | ATA | ACC | 1150 |
| Gln | Ala | Val | His 370 | Glu | Phe | Ala | Lys | Glu 375 | Ile | Glu | Ala | Ser | Cys 380 | Ile | Thr | |
| ATC | GAG | AGA | GTT | ATC | GGA | GCT | GGT | GAA | TTT | GGA | GAA | GTC | TGC | AGT | GGA | 1198 |
| Ile | Glu | Arg 385 | Val | Ile | Gly | Ala | Gly 390 | Glu | Phe | Gly | Glu | Val 395 | Cys | Ser | Gly | |
| CGG | CTG | AAA | CTG | CAG | GGA | AAA | CGC | GAG | TTT | CCA | GTG | GCT | ATC | AAA | ACC | 1246 |
| Arg 400 | Leu | Lys | Leu | Gln | Gly 405 | Lys | Arg | Glu | Phe | Pro 410 | Val | Ala | Ile | Lys 415 | Thr | |
| CTG | AAG | GTG | GGC | TAC | ACA | GAG | AAG | CAA | AGG | CGA | GAT | TTC | CTG | GGA | GAA | 1294 |
| Leu | Lys | Val | Gly | Tyr 420 | Thr | Glu | Lys | Gln | Arg 425 | Arg | Asp | Phe | Leu | Gly 430 | Glu | |
| GCG | AGC | ATC | ATG | GGG | CAG | TTC | GAC | CAC | CCC | AAC | ATC | ATC | CAC | CTG | GAA | 1342 |
| Ala | Ser | Ile | Met 435 | Gly | Gln | Phe | Asp | His 440 | Pro | Asn | Ile | Ile | His 445 | Leu | Glu | |
| GGT | GTC | GTC | ACA | AAA | AGC | AAA | CCT | GTA | ATG | ATA | GTA | ACG | GAA | TAC | ATG | 1390 |
| Gly | Val | Val | Thr 450 | Lys | Ser | Lys | Pro | Val 455 | Met | Ile | Val | Thr | Glu 460 | Tyr | Met | |
| GAA | AAT | GGT | TCT | CTG | GAT | ACA | TTT | TTA | AAG | AAG | AAC | GAT | GGG | CAG | TTC | 1438 |
| Glu | Asn 465 | Gly | Ser | Leu | Asp | Thr 470 | Phe | Leu | Lys | Lys | Asn 475 | Asp | Gly | Gln | Phe | |
| ACG | GTC | ATT | CAG | CTG | GTC | GGG | ATG | CTG | CGA | GGC | ATC | GCA | TCA | GGG | ATG | 1486 |
| Thr 480 | Val | Ile | Gln | Leu | Val 485 | Gly | Met | Leu | Arg | Gly 490 | Ile | Ala | Ser | Gly 495 | Met | |
| AAG | TAC | CTG | TCT | GAC | ATG | GGT | TAC | GTA | CAC | AGA | GAC | CTC | GCT | GCC | AGG | 1534 |
| Lys | Tyr | Leu | Ser | Asp 500 | Met | Gly | Tyr | Val | His 505 | Arg | Asp | Leu | Ala | Ala 510 | Arg | |
| AAT | ATC | CTC | ATC | AAC | AGC | AAC | TTA | GTC | TGC | AAG | GTG | TCT | GAC | TTT | GGC | 1582 |

|  |  |  |  |  |  |  |  |  |  |  |  |  |  |  |  |
|---|---|---|---|---|---|---|---|---|---|---|---|---|---|---|---|
| Asn | Ile | Leu | Ile<br>515 | Asn | Ser | Asn | Leu<br>520 | Val | Cys | Lys | Val | Ser<br>525 | Asp | Phe | Gly |

| CTC | TCC | AGA | GTC | CTA | GAA | GAT | GAT | CCT | GAA | GCA | GCG | TAC | ACA | ACC | AGG | 1630 |
|---|---|---|---|---|---|---|---|---|---|---|---|---|---|---|---|---|
| Leu | Ser | Arg<br>530 | Val | Leu | Glu | Asp | Asp<br>535 | Pro | Glu | Ala | Ala | Tyr<br>540 | Thr | Thr | Arg | |

| GGA | GGG | AAG | ATC | CCC | ATC | CGA | TGG | ACG | GCA | CCT | GAA | GCA | ATC | GCC | TTC | 1678 |
|---|---|---|---|---|---|---|---|---|---|---|---|---|---|---|---|---|
| Gly | Gly<br>545 | Lys | Ile | Pro | Ile | Arg<br>550 | Trp | Thr | Ala | Pro | Glu<br>555 | Ala | Ile | Ala | Phe | |

| CGC | AAA | TTC | ACG | TCG | GCC | AGC | GAT | GTG | TGG | AGC | TAC | GGC | ATT | GTG | ATG | 1726 |
|---|---|---|---|---|---|---|---|---|---|---|---|---|---|---|---|---|
| Arg<br>560 | Lys | Phe | Thr | Ser | Ala<br>565 | Ser | Asp | Val | Trp | Ser<br>570 | Tyr | Gly | Ile | Val | Met<br>575 | |

| TGG | GAA | GTG | ATG | TCC | TAT | GGC | GAG | AGA | CCT | TAC | TGG | GAA | ATG | ACA | AAC | 1774 |
|---|---|---|---|---|---|---|---|---|---|---|---|---|---|---|---|---|
| Trp | Glu | Val | Met | Ser<br>580 | Tyr | Gly | Glu | Arg | Pro<br>585 | Tyr | Trp | Glu | Met | Thr<br>590 | Asn | |

| CAA | GAT | GTG | ATT | AAA | GCC | GTG | GAG | GAA | GGC | TAT | CGC | CTG | CCA | AGT | CCC | 1822 |
|---|---|---|---|---|---|---|---|---|---|---|---|---|---|---|---|---|
| Gln | Asp | Val | Ile<br>595 | Lys | Ala | Val | Glu | Glu<br>600 | Gly | Tyr | Arg | Leu | Pro<br>605 | Ser | Pro | |

| ATG | GAC | TGC | CCT | GCT | GCT | CTC | TAC | CAG | TTG | ATG | CTT | GAC | TGC | TGG | CAG | 1870 |
|---|---|---|---|---|---|---|---|---|---|---|---|---|---|---|---|---|
| Met | Asp | Cys<br>610 | Pro | Ala | Ala | Leu | Tyr<br>615 | Gln | Leu | Met | Leu | Asp<br>620 | Cys | Trp | Gln | |

| AAA | GAC | CGC | AAC | AGC | AGG | CCC | AAG | TTT | GAT | GAA | ATT | GTC | AGC | ATG | TTG | 1918 |
|---|---|---|---|---|---|---|---|---|---|---|---|---|---|---|---|---|
| Lys | Asp<br>625 | Arg | Asn | Ser | Arg | Pro<br>630 | Lys | Phe | Asp | Glu | Ile<br>635 | Val | Ser | Met | Leu | |

| GAC | AAG | CTC | ATC | CGT | AAC | CCA | AGC | AGC | TTG | AAG | ACG | TTG | GTT | AAT | GCA | 1966 |
|---|---|---|---|---|---|---|---|---|---|---|---|---|---|---|---|---|
| Asp<br>640 | Lys | Leu | Ile | Arg | Asn<br>645 | Pro | Ser | Ser | Leu | Lys<br>650 | Thr | Leu | Val | Asn | Ala<br>655 | |

| TCG | AGC | AGA | GTA | TCA | AAT | TTG | TTG | GTA | GAA | CAC | AGT | CCA | GTG | GGG | AGC | 2014 |
|---|---|---|---|---|---|---|---|---|---|---|---|---|---|---|---|---|
| Ser | Ser | Arg | Val | Ser<br>660 | Asn | Leu | Leu | Val | Glu<br>665 | His | Ser | Pro | Val | Gly<br>670 | Ser | |

| GGT | GCC | TAC | AGG | TCA | GTG | GGT | GAG | TGG | CTG | GAA | GCC | ATC | AAA | ATG | GGT | 2062 |
|---|---|---|---|---|---|---|---|---|---|---|---|---|---|---|---|---|
| Gly | Ala | Tyr | Arg<br>675 | Ser | Val | Gly | Glu | Trp<br>680 | Leu | Glu | Ala | Ile | Lys<br>685 | Met | Gly | |

| CGA | TAC | ACC | GAG | ATT | TTC | ATG | GAG | AAT | GGA | TAC | AGT | TCG | ATG | GAT | TCT | 2110 |
|---|---|---|---|---|---|---|---|---|---|---|---|---|---|---|---|---|
| Arg | Tyr | Thr<br>690 | Glu | Ile | Phe | Met | Glu<br>695 | Asn | Gly | Tyr | Ser | Ser<br>700 | Met | Asp | Ser | |

| GTG | GCT | CAG | GTG | ACC | CTA | GAG | GAT | TTG | AGG | CGG | CTG | GGA | GTG | ACA | CTT | 2158 |
|---|---|---|---|---|---|---|---|---|---|---|---|---|---|---|---|---|
| Val | Ala | Gln | Val | Thr<br>705 | Leu | Glu | Asp | Leu | Arg<br>710 | Arg | Leu | Gly | Val | Thr<br>715 | Leu | |

| GTT | GGT | CAC | CAG | AAG | AAG | ATA | ATG | AAC | AGC | CTT | CAA | GAG | ATG | AAG | GTC | 2206 |
|---|---|---|---|---|---|---|---|---|---|---|---|---|---|---|---|---|
| Val<br>720 | Gly | His | Gln | Lys | Lys<br>725 | Ile | Met | Asn | Ser | Leu<br>730 | Gln | Glu | Met | Lys | Val<br>735 | |

| CAG | TTG | GTG | AAT | GGG | ATG | GTG | CCA | TTG | TAACTCGGTT | TTTAAGTCAC | 2253 |
|---|---|---|---|---|---|---|---|---|---|---|---|
| Gln | Leu | Val | Asn | Gly<br>740 | Met | Val | Pro | Leu | | | |

| TTCCTCGAGT | GGTCGGTCCT | GCACTTTGTA | TACTAGCTCT | GAGATTTATT | TTGACTAAAG | 2313 |
|---|---|---|---|---|---|---|
| AAGAAAAAG | GGAAATTCAG | TGGTTTCTGT | AACTGAAGGA | CGCTGGCTTC | TGCCACAGCA | 2373 |
| TTTATAAAGC | AGTGTTTGAC | TGAAGTTTTC | ATTTCTTCC | TATTTGTGTC | CTCATTCTCA | 2433 |
| TGAAGTAAAT | GTAACATGCA | TGGAACATGG | AAATGGATCT | ACTGTACATG | AGGTTACCCA | 2493 |
| ATTTCTTGCG | CTTCAGCATG | ACAACAGCAA | GCCTTCCCAC | CACATGTTGT | CTATACATGG | 2553 |
| GAGATATATA | TATATGCATA | TATATATATA | GCACCTTTAT | ATACTGAATT | ACAGCAGCAG | 2613 |
| CACATGTTAA | TACTTCCAAG | GACTTACTTG | ACTAGAGAAG | TTTTGCAGCC | ATTGTGGGCT | 2673 |
| CACACAAGCT | GCGGTTTACT | GAAGTTTACT | TCAAGTCTTA | CTTGTCTACA | GAAGTGTATT | 2733 |
| GAAGAGCAAT | ATGATTAGAT | TATTTCTGGA | TAGATATTTT | GTTTTGTAAA | TTTAAAAAAT | 2793 |
| CGTGTTACAC | AGCGTTAAGT | TATAGAGACT | AGTGTATAAA | CATGTTGCTT | GCTCAATGGC | 2853 |

```
AAATACAATA CAGGGTGTAT ATTTTTTTCT CTCTGTGTTG CAAAGTTCTT TTAGTTTGCT    2913

CTTCTGTGAG GATAATACGT TATGATGTAT ATACTGTACA GTTTGCTACA CATCAGGTAC    2973

AAGATTGGGG CTTTCTCAAT GTTTTGTTCT TTTTCCCTCT TTTGTTTCAT TTTGTCTTCC    3033

TTTTGTGTTA ACCACTATGC TTTGTATTTT TGCTGCTGTT TGGTTTGAGG CAACATATAA    3093

AGCTTTCAGG TGTTTTGATT ATAAAAAAAA AG                                  3125
```

( 2 ) INFORMATION FOR SEQ ID NO:20:

( i ) SEQUENCE CHARACTERISTICS:
        ( A ) LENGTH: 744 amino acids
        ( B ) TYPE: amino acid
        ( D ) TOPOLOGY: linear ( i i ) MOLECULE TYPE: protein ( x i ) SEQUENCE DESCRIPTION: SEQ ID NO:20:

```
Leu Lys Phe Thr Leu Arg Asp Cys Asn Ser Leu Pro Gly Gly Leu Gly
 1               5                  10                  15

Thr Cys Lys Glu Thr Phe Asn Met Tyr Tyr Phe Glu Ser Asp Asp Glu
                20                  25                  30

Asp Gly Arg Asn Ile Arg Glu Asn Gln Tyr Ile Lys Ile Asp Thr Ile
                35                  40                  45

Ala Ala Asp Glu Ser Phe Thr Glu Leu Asp Leu Gly Asp Arg Val Met
        50                  55                  60

Lys Leu Asn Thr Glu Val Arg Asp Val Gly Pro Leu Thr Lys Lys Gly
 65                  70                  75                  80

Phe Tyr Leu Ala Phe Gln Asp Val Gly Ala Cys Ile Ala Leu Val Ser
                85                  90                  95

Val Arg Val Tyr Tyr Lys Lys Cys Pro Ser Val Ile Arg Asn Leu Ala
               100                 105                 110

Arg Phe Pro Asp Thr Ile Thr Gly Ala Asp Ser Ser Gln Leu Leu Glu
           115                 120                 125

Val Ser Gly Val Cys Val Asn His Ser Val Thr Asp Glu Ala Pro Lys
    130                 135                 140

Met His Cys Ser Ser Glu Gly Glu Trp Leu Val Pro Ile Gly Lys Cys
145                 150                 155                 160

Leu Cys Lys Ala Gly Tyr Glu Glu Lys Asn Asn Thr Cys Gln Ala Pro
               165                 170                 175

Ser Pro Val Ser Ser Val Lys Lys Gly Lys Ile Thr Lys Asn Ser Ile
           180                 185                 190

Ser Leu Ser Trp Gln Glu Pro Asp Arg Pro Asn Gly Ile Ile Leu Glu
    195                 200                 205

Tyr Glu Ile Lys Tyr Phe Glu Lys Asp Gln Glu Thr Ser Tyr Thr Ile
210                 215                 220

Ile Lys Ser Lys Glu Thr Ala Ile Thr Ala Asp Gly Leu Lys Pro Gly
225                 230                 235                 240

Ser Ala Tyr Val Phe Gln Ile Arg Ala Arg Thr Ala Ala Gly Tyr Gly
               245                 250                 255

Gly Phe Ser Arg Arg Phe Glu Phe Glu Thr Ser Pro Val Leu Ala Ala
           260                 265                 270

Ser Ser Asp Gln Ser Gln Ile Pro Ile Ile Val Val Ser Val Thr Val
    275                 280                 285

Gly Val Ile Leu Leu Ala Val Val Ile Gly Phe Leu Leu Ser Gly Ser
    290                 295                 300
```

```
Cys  Cys  Asp  His  Gly  Cys  Gly  Trp  Ala  Ser  Ser  Leu  Arg  Ala  Val  Ala
305            310                      315                           320

Tyr  Pro  Ser  Leu  Ile  Trp  Arg  Cys  Gly  Tyr  Ser  Lys  Ala  Lys  Gln  Asp
                    325                      330                      335

Pro  Glu  Glu  Glu  Lys  Met  His  Phe  His  Asn  Gly  His  Ile  Lys  Leu  Pro
               340                      345                      350

Gly  Val  Arg  Thr  Tyr  Ile  Asp  Pro  His  Thr  Tyr  Glu  Asp  Pro  Asn  Gln
          355                      360                      365

Ala  Val  His  Glu  Phe  Ala  Lys  Glu  Ile  Glu  Ala  Ser  Cys  Ile  Thr  Ile
          370                 375                 380

Glu  Arg  Val  Ile  Gly  Ala  Gly  Glu  Phe  Gly  Glu  Val  Cys  Ser  Gly  Arg
385                      390                 395                           400

Leu  Lys  Leu  Gln  Gly  Lys  Arg  Glu  Phe  Pro  Val  Ala  Ile  Lys  Thr  Leu
               405                      410                      415

Lys  Val  Gly  Tyr  Thr  Glu  Lys  Gln  Arg  Arg  Asp  Phe  Leu  Gly  Glu  Ala
               420                      425                      430

Ser  Ile  Met  Gly  Gln  Phe  Asp  His  Pro  Asn  Ile  Ile  His  Leu  Glu  Gly
          435                      440                      445

Val  Val  Thr  Lys  Ser  Lys  Pro  Val  Met  Ile  Val  Thr  Glu  Tyr  Met  Glu
     450                      455                      460

Asn  Gly  Ser  Leu  Asp  Thr  Phe  Leu  Lys  Lys  Asn  Asp  Gly  Gln  Phe  Thr
465                           470                      475                 480

Val  Ile  Gln  Leu  Val  Gly  Met  Leu  Arg  Gly  Ile  Ala  Ser  Gly  Met  Lys
               485                      490                      495

Tyr  Leu  Ser  Asp  Met  Gly  Tyr  Val  His  Arg  Asp  Leu  Ala  Ala  Arg  Asn
               500                      505                      510

Ile  Leu  Ile  Asn  Ser  Asn  Leu  Val  Cys  Lys  Val  Ser  Asp  Phe  Gly  Leu
          515                      520                 525

Ser  Arg  Val  Leu  Glu  Asp  Asp  Pro  Glu  Ala  Ala  Tyr  Thr  Thr  Arg  Gly
     530                      535                      540

Gly  Lys  Ile  Pro  Ile  Arg  Trp  Thr  Ala  Pro  Glu  Ala  Ile  Ala  Phe  Arg
545                      550                      555                      560

Lys  Phe  Thr  Ser  Ala  Ser  Asp  Val  Trp  Ser  Tyr  Gly  Ile  Val  Met  Trp
                    565                      570                      575

Glu  Val  Met  Ser  Tyr  Gly  Glu  Arg  Pro  Tyr  Trp  Glu  Met  Thr  Asn  Gln
               580                      585                      590

Asp  Val  Ile  Lys  Ala  Val  Glu  Glu  Gly  Tyr  Arg  Leu  Pro  Ser  Pro  Met
          595                      600                      605

Asp  Cys  Pro  Ala  Ala  Leu  Tyr  Gln  Leu  Met  Leu  Asp  Cys  Trp  Gln  Lys
     610                      615                 620

Asp  Arg  Asn  Ser  Arg  Pro  Lys  Phe  Asp  Glu  Ile  Val  Ser  Met  Leu  Asp
625                      630                      635                      640

Lys  Leu  Ile  Arg  Asn  Pro  Ser  Ser  Leu  Lys  Thr  Leu  Val  Asn  Ala  Ser
               645                      650                      655

Ser  Arg  Val  Ser  Asn  Leu  Leu  Val  Glu  His  Ser  Pro  Val  Gly  Ser  Gly
               660                      665                      670

Ala  Tyr  Arg  Ser  Val  Gly  Glu  Trp  Leu  Glu  Ala  Ile  Lys  Met  Gly  Arg
          675                      680                      685

Tyr  Thr  Glu  Ile  Phe  Met  Glu  Asn  Gly  Tyr  Ser  Ser  Met  Asp  Ser  Val
          690                      695                      700

Ala  Gln  Val  Thr  Leu  Glu  Asp  Leu  Arg  Arg  Leu  Gly  Val  Thr  Leu  Val
705                      710                      715                      720

Gly  His  Gln  Lys  Lys  Ile  Met  Asn  Ser  Leu  Gln  Glu  Met  Lys  Val  Gln
```

|  |  |  |  | 725 |  |  |  |  | 730 |  |  |  |  | 735 |  |
|---|---|---|---|---|---|---|---|---|---|---|---|---|---|---|---|
| Leu | Val | Asn | Gly | Met | Val | Pro | Leu |  |  |  |  |  |  |  |  |
|  |  |  |  | 740 |  |  |  |  |  |  |  |  |  |  |  |

( 2 ) INFORMATION FOR SEQ ID NO:21:

( i ) SEQUENCE CHARACTERISTICS:
        ( A ) LENGTH: 3056 base pairs
        ( B ) TYPE: nucleic acid
        ( C ) STRANDEDNESS: both
        ( D ) TOPOLOGY: linear ( i x ) FEATURE:
        ( A ) NAME/KEY: CDS
        ( B ) LOCATION: 2..2131

( x i ) SEQUENCE DESCRIPTION: SEQ ID NO:21:

| C | CTC | AAA | TTC | ACC | CTG | AGG | GAC | TGT | AAC | AGC | CTT | CCA | GGA | GGA | CTT | 46 |
|---|---|---|---|---|---|---|---|---|---|---|---|---|---|---|---|---|
|  | Leu | Lys | Phe | Thr | Leu | Arg | Asp | Cys | Asn | Ser | Leu | Pro | Gly | Gly | Leu |  |
|  | 1 |  |  |  | 5 |  |  |  |  | 10 |  |  |  |  | 15 |  |

| GGG | ACT | TGC | AAG | GAG | ACT | TTT | AAC | ATG | TAC | TAC | TTT | GAG | TCA | GAT | GAT | 94 |
|---|---|---|---|---|---|---|---|---|---|---|---|---|---|---|---|---|
| Gly | Thr | Cys | Lys | Glu | Thr | Phe | Asn | Met | Tyr | Tyr | Phe | Glu | Ser | Asp | Asp |  |
|  |  |  |  | 20 |  |  |  |  | 25 |  |  |  |  | 30 |  |  |

| GAA | GAT | GGG | AGG | AAC | ATC | AGA | GAG | AAT | CAG | TAC | ATC | AAG | ATA | GAT | ACC | 142 |
|---|---|---|---|---|---|---|---|---|---|---|---|---|---|---|---|---|
| Glu | Asp | Gly | Arg | Asn | Ile | Arg | Glu | Asn | Gln | Tyr | Ile | Lys | Ile | Asp | Thr |  |
|  |  |  | 35 |  |  |  |  | 40 |  |  |  |  | 45 |  |  |  |

| ATT | GCT | GCT | GAT | GAG | AGC | TTC | ACG | GAG | TTG | GAC | CTC | GGC | GAC | AGA | GTT | 190 |
|---|---|---|---|---|---|---|---|---|---|---|---|---|---|---|---|---|
| Ile | Ala | Ala | Asp | Glu | Ser | Phe | Thr | Glu | Leu | Asp | Leu | Gly | Asp | Arg | Val |  |
|  |  | 50 |  |  |  |  | 55 |  |  |  |  | 60 |  |  |  |  |

| ATG | AAG | TTA | AAC | ACA | GAA | GTG | AGA | GAT | GTT | GGG | CCT | CTA | ACA | AAA | AAA | 238 |
|---|---|---|---|---|---|---|---|---|---|---|---|---|---|---|---|---|
| Met | Lys | Leu | Asn | Thr | Glu | Val | Arg | Asp | Val | Gly | Pro | Leu | Thr | Lys | Lys |  |
| 65 |  |  |  |  | 70 |  |  |  |  | 75 |  |  |  |  |  |  |

| GGA | TTT | TAC | CTT | GCT | TTC | CAG | GAT | GTG | GGC | GCC | TGC | ATT | GCC | CTG | GTC | 286 |
|---|---|---|---|---|---|---|---|---|---|---|---|---|---|---|---|---|
| Gly | Phe | Tyr | Leu | Ala | Phe | Gln | Asp | Val | Gly | Ala | Cys | Ile | Ala | Leu | Val |  |
| 80 |  |  |  |  | 85 |  |  |  |  | 90 |  |  |  |  | 95 |  |

| TCT | GTG | CGT | GTG | TAC | TAC | AAG | AAA | TGC | CCA | TCA | GTG | ATC | CGC | AAC | CTG | 334 |
|---|---|---|---|---|---|---|---|---|---|---|---|---|---|---|---|---|
| Ser | Val | Arg | Val | Tyr | Tyr | Lys | Lys | Cys | Pro | Ser | Val | Ile | Arg | Asn | Leu |  |
|  |  |  |  | 100 |  |  |  |  | 105 |  |  |  |  | 110 |  |  |

| GCA | CGC | TTT | CCA | GAT | ACC | ATC | ACA | GGA | GCA | GAT | TCC | TCG | CAG | CTG | CTA | 382 |
|---|---|---|---|---|---|---|---|---|---|---|---|---|---|---|---|---|
| Ala | Arg | Phe | Pro | Asp | Thr | Ile | Thr | Gly | Ala | Asp | Ser | Ser | Gln | Leu | Leu |  |
|  |  |  | 115 |  |  |  |  | 120 |  |  |  |  | 125 |  |  |  |

| GAA | GTG | TCA | GGC | GTC | TGT | GTC | AAC | CAC | TCA | GTG | ACT | GAT | GAG | GCA | CCA | 430 |
|---|---|---|---|---|---|---|---|---|---|---|---|---|---|---|---|---|
| Glu | Val | Ser | Gly | Val | Cys | Val | Asn | His | Ser | Val | Thr | Asp | Glu | Ala | Pro |  |
|  |  | 130 |  |  |  |  | 135 |  |  |  |  | 140 |  |  |  |  |

| AAG | ATG | CAC | TGC | AGT | TCA | GAG | GGA | GAA | TGG | CTG | GTG | CCC | ATT | GGG | AAG | 478 |
|---|---|---|---|---|---|---|---|---|---|---|---|---|---|---|---|---|
| Lys | Met | His | Cys | Ser | Ser | Glu | Gly | Glu | Trp | Leu | Val | Pro | Ile | Gly | Lys |  |
| 145 |  |  |  |  | 150 |  |  |  |  | 155 |  |  |  |  |  |  |

| TGT | TTG | TGC | AAG | GCA | GGG | TAC | GAG | GAG | AAG | AAC | AAC | ACC | TGC | CAA | GCA | 526 |
|---|---|---|---|---|---|---|---|---|---|---|---|---|---|---|---|---|
| Cys | Leu | Cys | Lys | Ala | Gly | Tyr | Glu | Glu | Lys | Asn | Asn | Thr | Cys | Gln | Ala |  |
| 160 |  |  |  |  | 165 |  |  |  |  | 170 |  |  |  |  | 175 |  |

| CCT | TCT | CCA | GTC | AGT | AGT | GTG | AAA | AAA | GGG | AAG | ATA | ACT | AAA | AAT | AGC | 574 |
|---|---|---|---|---|---|---|---|---|---|---|---|---|---|---|---|---|
| Pro | Ser | Pro | Val | Ser | Ser | Val | Lys | Lys | Gly | Lys | Ile | Thr | Lys | Asn | Ser |  |
|  |  |  |  | 180 |  |  |  |  | 185 |  |  |  |  | 190 |  |  |

| ATC | TCC | CTT | TCC | TGG | CAG | GAG | CCA | GAT | CGA | CCC | AAC | GGC | ATC | ATC | CTG | 622 |
|---|---|---|---|---|---|---|---|---|---|---|---|---|---|---|---|---|
| Ile | Ser | Leu | Ser | Trp | Gln | Glu | Pro | Asp | Arg | Pro | Asn | Gly | Ile | Ile | Leu |  |
|  |  |  | 195 |  |  |  |  | 200 |  |  |  |  | 205 |  |  |  |

| GAA | TAC | GAA | ATC | AAA | TAT | TTT | GAA | AAG | GAC | CAG | GAG | ACA | AGC | TAC | ACC | 670 |
|---|---|---|---|---|---|---|---|---|---|---|---|---|---|---|---|---|
| Glu | Tyr | Glu | Ile | Lys | Tyr | Phe | Glu | Lys | Asp | Gln | Glu | Thr | Ser | Tyr | Thr |  |
|  |  | 210 |  |  |  |  | 215 |  |  |  |  | 220 |  |  |  |  |

| ATC | ATC | AAA | TCC | AAA | GAG | ACC | GCA | ATT | ACG | GCA | GAT | GGC | TTG | AAA | CCA | 718 |
|---|---|---|---|---|---|---|---|---|---|---|---|---|---|---|---|---|
| Ile | Ile | Lys | Ser | Lys | Glu | Thr | Ala | Ile | Thr | Ala | Asp | Gly | Leu | Lys | Pro |  |
| 225 |  |  |  |  | 230 |  |  |  |  | 235 |  |  |  |  |  |  |

| | | | | | | | | | | | | | | | | |
|---|---|---|---|---|---|---|---|---|---|---|---|---|---|---|---|---|
| GGC | TCA | GCG | TAC | GTC | TTC | CAG | ATC | CGA | GCC | CGG | ACA | GCT | GCT | GGC | TAC | 766 |
| Gly | Ser | Ala | Tyr | Val | Phe | Gln | Ile | Arg | Ala | Arg | Thr | Ala | Ala | Gly | Tyr | |
| 240 | | | | | 245 | | | | | 250 | | | | | 255 | |
| GGT | GGC | TTC | AGT | CGA | AGA | TTT | GAG | TTT | GAA | ACC | AGC | CCA | GTG | TTA | GCT | 814 |
| Gly | Gly | Phe | Ser | Arg | Arg | Phe | Glu | Phe | Glu | Thr | Ser | Pro | Val | Leu | Ala | |
| | | | | 260 | | | | | 265 | | | | | 270 | | |
| GCA | TCC | AGT | GAC | CAG | AGC | CAG | ATT | CCT | ATA | ATT | GTT | GTG | TCT | GTA | ACA | 862 |
| Ala | Ser | Ser | Asp | Gln | Ser | Gln | Ile | Pro | Ile | Ile | Val | Val | Ser | Val | Thr | |
| | | | 275 | | | | | 280 | | | | | 285 | | | |
| GTG | GGA | GTT | ATT | CTG | CTG | GCT | GTT | GTT | ATC | GGT | TTC | CTT | CTC | AGT | GGA | 910 |
| Val | Gly | Val | Ile | Leu | Leu | Ala | Val | Val | Ile | Gly | Phe | Leu | Leu | Ser | Gly | |
| | | | 290 | | | | | 295 | | | | | 300 | | | |
| AGG | CGC | TGT | GGC | TAC | AGC | AAG | GCT | AAA | CAA | GAC | CCA | GAA | GAA | GAA | AAG | 958 |
| Arg | Arg | Cys | Gly | Tyr | Ser | Lys | Ala | Lys | Gln | Asp | Pro | Glu | Glu | Glu | Lys | |
| | | 305 | | | | | 310 | | | | | 315 | | | | |
| ATG | CAT | TTT | CAT | AAT | GGC | CAC | ATT | AAA | CTG | CCT | GGT | GTA | AGA | ACC | TAC | 1006 |
| Met | His | Phe | His | Asn | Gly | His | Ile | Lys | Leu | Pro | Gly | Val | Arg | Thr | Tyr | |
| 320 | | | | | 325 | | | | | 330 | | | | | 335 | |
| ATT | GAT | CCC | CAC | ACC | TAT | GAG | GAC | CCT | AAT | CAA | GCT | GTC | CAC | GAG | TTT | 1054 |
| Ile | Asp | Pro | His | Thr | Tyr | Glu | Asp | Pro | Asn | Gln | Ala | Val | His | Glu | Phe | |
| | | | | 340 | | | | | 345 | | | | | 350 | | |
| GCC | AAG | GAA | ATA | GAA | GCT | TCG | TGC | ATA | ACC | ATC | GAG | AGA | GTT | ATC | GGA | 1102 |
| Ala | Lys | Glu | Ile | Glu | Ala | Ser | Cys | Ile | Thr | Ile | Glu | Arg | Val | Ile | Gly | |
| | | | 355 | | | | | 360 | | | | | 365 | | | |
| GCT | GGT | GAA | TTT | GGA | GAA | GTC | TGC | AGT | GGA | CGG | CTG | AAA | CTG | CAG | GGA | 1150 |
| Ala | Gly | Glu | Phe | Gly | Glu | Val | Cys | Ser | Gly | Arg | Leu | Lys | Leu | Gln | Gly | |
| | | | 370 | | | | | 375 | | | | | 380 | | | |
| AAA | CGC | GAG | TTT | CCA | GTG | GCT | ATC | AAA | ACC | CTG | AAG | GTG | GGC | TAC | ACA | 1198 |
| Lys | Arg | Glu | Phe | Pro | Val | Ala | Ile | Lys | Thr | Leu | Lys | Val | Gly | Tyr | Thr | |
| | 385 | | | | | 390 | | | | | 395 | | | | | |
| GAG | AAG | CAA | AGG | CGA | GAT | TTC | CTG | GGA | GAA | GCG | AGC | ATC | ATG | GGG | CAG | 1246 |
| Glu | Lys | Gln | Arg | Arg | Asp | Phe | Leu | Gly | Glu | Ala | Ser | Ile | Met | Gly | Gln | |
| 400 | | | | 405 | | | | | 410 | | | | | 415 | | |
| TTC | GAC | CAC | CCC | AAC | ATC | ATC | CAC | CTG | GAA | GGT | GTC | GTC | ACA | AAA | AGC | 1294 |
| Phe | Asp | His | Pro | Asn | Ile | Ile | His | Leu | Glu | Gly | Val | Val | Thr | Lys | Ser | |
| | | | | 420 | | | | | 425 | | | | | 430 | | |
| AAA | CCT | GTA | ATG | ATA | GTA | ACG | GAA | TAC | ATG | GAA | AAT | GGT | TCT | CTG | GAT | 1342 |
| Lys | Pro | Val | Met | Ile | Val | Thr | Glu | Tyr | Met | Glu | Asn | Gly | Ser | Leu | Asp | |
| | | | 435 | | | | | 440 | | | | | 445 | | | |
| ACA | TTT | TTA | AAG | AAG | AAC | GAT | GGG | CAG | TTC | ACG | GTC | ATT | CAG | CTG | GTC | 1390 |
| Thr | Phe | Leu | Lys | Lys | Asn | Asp | Gly | Gln | Phe | Thr | Val | Ile | Gln | Leu | Val | |
| | | 450 | | | | | 455 | | | | | 460 | | | | |
| GGG | ATG | CTG | CGA | GGC | ATC | GCA | TCA | GGG | ATG | AAG | TAC | CTG | TCT | GAC | ATG | 1438 |
| Gly | Met | Leu | Arg | Gly | Ile | Ala | Ser | Gly | Met | Lys | Tyr | Leu | Ser | Asp | Met | |
| 465 | | | | | 470 | | | | | 475 | | | | | | |
| GGT | TAC | GTA | CAC | AGA | GAC | CTC | GCT | GCC | AGG | AAT | ATC | CTC | ATC | AAC | AGC | 1486 |
| Gly | Tyr | Val | His | Arg | Asp | Leu | Ala | Ala | Arg | Asn | Ile | Leu | Ile | Asn | Ser | |
| 480 | | | | | 485 | | | | | 490 | | | | | 495 | |
| AAC | TTA | GTC | TGC | AAG | GTG | TCT | GAC | TTT | GGC | CTC | TCC | AGA | GTC | CTA | GAA | 1534 |
| Asn | Leu | Val | Cys | Lys | Val | Ser | Asp | Phe | Gly | Leu | Ser | Arg | Val | Leu | Glu | |
| | | | | 500 | | | | | 505 | | | | | 510 | | |
| GAT | GAT | CCT | GAA | GCA | GCG | TAC | ACA | ACC | AGG | GGA | GGG | AAG | ATC | CCC | ATC | 1582 |
| Asp | Asp | Pro | Glu | Ala | Ala | Tyr | Thr | Thr | Arg | Gly | Gly | Lys | Ile | Pro | Ile | |
| | | | 515 | | | | | 520 | | | | | 525 | | | |
| CGA | TGG | ACG | GCA | CCT | GAA | GCA | ATC | GCC | TTC | CGC | AAA | TTC | ACG | TCG | GCC | 1630 |
| Arg | Trp | Thr | Ala | Pro | Glu | Ala | Ile | Ala | Phe | Arg | Lys | Phe | Thr | Ser | Ala | |
| | | 530 | | | | | 535 | | | | | 540 | | | | |
| AGC | GAT | GTG | TGG | AGC | TAC | GGC | ATT | GTG | ATG | TGG | GAA | GTG | ATG | TCC | TAT | 1678 |
| Ser | Asp | Val | Trp | Ser | Tyr | Gly | Ile | Val | Met | Trp | Glu | Val | Met | Ser | Tyr | |

```
                    545                         550                         555
GGC  GAG  AGA  CCT  TAC  TGG  GAA  ATG  ACA  AAC  CAA  GAT  GTG  ATT  AAA  GCC      1726
Gly  Glu  Arg  Pro  Tyr  Trp  Glu  Met  Thr  Asn  Gln  Asp  Val  Ile  Lys  Ala
560                      565                      570                      575

GTG  GAG  GAA  GGC  TAT  CGC  CTG  CCA  AGT  CCC  ATG  GAC  TGC  CCT  GCT  GCT      1774
Val  Glu  Glu  Gly  Tyr  Arg  Leu  Pro  Ser  Pro  Met  Asp  Cys  Pro  Ala  Ala
                    580                      585                      590

CTC  TAC  CAG  TTG  ATG  CTT  GAC  TGC  TGG  CAG  AAA  GAC  CGC  AAC  AGC  AGG      1822
Leu  Tyr  Gln  Leu  Met  Leu  Asp  Cys  Trp  Gln  Lys  Asp  Arg  Asn  Ser  Arg
               595                      600                      605

CCC  AAG  TTT  GAT  GAA  ATT  GTC  AGC  ATG  TTG  GAC  AAG  CTC  ATC  CGT  AAC      1870
Pro  Lys  Phe  Asp  Glu  Ile  Val  Ser  Met  Leu  Asp  Lys  Leu  Ile  Arg  Asn
          610                      615                      620

CCA  AGC  AGC  TTG  AAG  ACG  TTG  GTT  AAT  GCA  TCG  AGC  AGA  GTA  TCA  AAT      1918
Pro  Ser  Ser  Leu  Lys  Thr  Leu  Val  Asn  Ala  Ser  Ser  Arg  Val  Ser  Asn
     625                      630                      635

TTG  TTG  GTA  GAA  CAC  AGT  CCA  GTG  GGG  AGC  GGT  GCC  TAC  AGG  TCA  GTG      1966
Leu  Leu  Val  Glu  His  Ser  Pro  Val  Gly  Ser  Gly  Ala  Tyr  Arg  Ser  Val
640                      645                      650                      655

GGT  GAG  TGG  CTG  GAA  GCC  ATC  AAA  ATG  GGT  CGA  TAC  ACC  GAG  ATT  TTC      2014
Gly  Glu  Trp  Leu  Glu  Ala  Ile  Lys  Met  Gly  Arg  Tyr  Thr  Glu  Ile  Phe
                    660                      665                      670

ATG  GAG  AAT  GGA  TAC  AGT  TCG  ATG  GAT  TCT  GTG  GCT  CAG  GTG  ACC  CTA      2062
Met  Glu  Asn  Gly  Tyr  Ser  Ser  Met  Asp  Ser  Val  Ala  Gln  Val  Thr  Leu
               675                      680                      685

GAG  GAC  GAA  TCA  CCT  TGT  GAA  AAG  TGG  AGC  CTC  ACC  CTC  CAC  CCC  CTC      2110
Glu  Asp  Glu  Ser  Pro  Cys  Glu  Lys  Trp  Ser  Leu  Thr  Leu  His  Pro  Leu
          690                      695                      700

TTT  CCA  ACT  GGA  TAT  CAG  ACT  TGAAGGAAAC  CTTTCCAGTG  GACCAGACCT              2161
Phe  Pro  Thr  Gly  Tyr  Gln  Thr
705                      710

GCTCTTTAAA  CTTGTGGACC  ACCTAGTGAC  TTTGAGTGTG  TCTGGAGCTC  TTTCAATCCA              2221

CTGCAAGAAT  AACTTTACCA  GGACAGTACT  CAAGAATAGA  TAGATCCATG  ACATGAGTTT              2281

CAGTCTGATA  TTTGACTGGA  CCAATTACTA  ACAAAATGTG  GACTGCATAC  TTACACCTTT              2341

TGAAAGATCT  GTACTCACCG  AATCTCAGGA  CACCCTGTTG  TTTGTTATTA  GATGAAGAAC              2401

TCTGAATATT  TGTAATAATA  TGTGATGTGT  TGCTTTGCAT  TGTATTTTTT  TCTTATAAAA              2461

TAAAATAAAT  TATTTATTAA  AAGTTATACT  GGGATGAAGA  CCATTTAAGA  GTTCACCTGC              2521

TCTAGATGCT  TATTCTTAAC  CTGAAACCTC  AGTTCCGGAT  AGTGATACTG  CACACGCTTG              2581

TGAACAAACC  CATTCTCGTG  TCATAACCAA  ACAGGATGGG  AGTAATGAAT  AAGAGCAGAT              2641

GAACTCTTAA  AAGAAAGATC  CTAATCTCAT  GCAAGGTCC   CTTGCAAGTG  GATTCCTCTC              2701

TCCCTAGCGT  CTTCTAAAGG  TCTTTGAGGT  TATTCTTTCC  CCTCTTTCAA  ACTGACAGCT              2761

AACTCTGTGA  GTAGTGTCAG  TCTGCATGGG  CCAGTGTAGA  ACTGCACCAT  GTTGAAGAAG              2821

AGTGCTGCAA  TATGGCTGGG  GTGGGAGATG  AAATGCAAAG  TAATCTCTGG  TAGGCTGATG              2881

GCTTCCAGCC  ATGGAGGTAT  TTCAGGAACC  TGGCCCTTTT  GCTTGCATGA  GTAATGAATG              2941

GAGTGGTGAG  GAGTGTTGTA  TTTTATGTGG  CAATCCAGTC  CTAGTCTACA  CTGTGTTTGA              3001

CAAATTGGTC  CATGGTGTAT  AAGTAGTTCT  ATTTGTAAAT  AAAATGTTTT  AAATG                   3056
```

( 2 ) INFORMATION FOR SEQ ID NO:22:

( i ) SEQUENCE CHARACTERISTICS:
        ( A ) LENGTH: 710 amino acids
        ( B ) TYPE: amino acid
        ( D ) TOPOLOGY: linear ( i i ) MOLECULE TYPE: protein ( x i ) SEQUENCE DESCRIPTION: SEQ ID NO:22:

| Leu | Lys | Phe | Thr | Leu | Arg | Asp | Cys | Asn | Ser | Leu | Pro | Gly | Gly | Leu | Gly |
|---|---|---|---|---|---|---|---|---|---|---|---|---|---|---|---|
| 1 | | | | 5 | | | | | 10 | | | | | 15 | |
| Thr | Cys | Lys | Glu | Thr | Phe | Asn | Met | Tyr | Tyr | Phe | Glu | Ser | Asp | Asp | Glu |
| | | | 20 | | | | 25 | | | | | 30 | | | |
| Asp | Gly | Arg | Asn | Ile | Arg | Glu | Asn | Gln | Tyr | Ile | Lys | Ile | Asp | Thr | Ile |
| | | 35 | | | | 40 | | | | | | 45 | | | |
| Ala | Ala | Asp | Glu | Ser | Phe | Thr | Glu | Leu | Asp | Leu | Gly | Asp | Arg | Val | Met |
| | 50 | | | | | 55 | | | | | 60 | | | | |
| Lys | Leu | Asn | Thr | Glu | Val | Arg | Asp | Val | Gly | Pro | Leu | Thr | Lys | Lys | Gly |
| 65 | | | | | 70 | | | | | 75 | | | | | 80 |
| Phe | Tyr | Leu | Ala | Phe | Gln | Asp | Val | Gly | Ala | Cys | Ile | Ala | Leu | Val | Ser |
| | | | | 85 | | | | | 90 | | | | | 95 | |
| Val | Arg | Val | Tyr | Tyr | Lys | Lys | Cys | Pro | Ser | Val | Ile | Arg | Asn | Leu | Ala |
| | | | 100 | | | | | 105 | | | | | 110 | | |
| Arg | Phe | Pro | Asp | Thr | Ile | Thr | Gly | Ala | Asp | Ser | Ser | Gln | Leu | Leu | Glu |
| | | | 115 | | | | 120 | | | | | 125 | | | |
| Val | Ser | Gly | Val | Cys | Val | Asn | His | Ser | Val | Thr | Asp | Glu | Ala | Pro | Lys |
| | | 130 | | | | 135 | | | | | 140 | | | | |
| Met | His | Cys | Ser | Ser | Glu | Gly | Glu | Trp | Leu | Val | Pro | Ile | Gly | Lys | Cys |
| 145 | | | | | 150 | | | | | 155 | | | | | 160 |
| Leu | Cys | Lys | Ala | Gly | Tyr | Glu | Glu | Lys | Asn | Asn | Thr | Cys | Gln | Ala | Pro |
| | | | | 165 | | | | | 170 | | | | | 175 | |
| Ser | Pro | Val | Ser | Ser | Val | Lys | Lys | Gly | Lys | Ile | Thr | Lys | Asn | Ser | Ile |
| | | | 180 | | | | | 185 | | | | | 190 | | |
| Ser | Leu | Ser | Trp | Gln | Glu | Pro | Asp | Arg | Pro | Asn | Gly | Ile | Ile | Leu | Glu |
| | | 195 | | | | | 200 | | | | | 205 | | | |
| Tyr | Glu | Ile | Lys | Tyr | Phe | Glu | Lys | Asp | Gln | Glu | Thr | Ser | Tyr | Thr | Ile |
| | 210 | | | | | 215 | | | | | 220 | | | | |
| Ile | Lys | Ser | Lys | Glu | Thr | Ala | Ile | Thr | Ala | Asp | Gly | Leu | Lys | Pro | Gly |
| 225 | | | | | 230 | | | | | 235 | | | | | 240 |
| Ser | Ala | Tyr | Val | Phe | Gln | Ile | Arg | Ala | Arg | Thr | Ala | Ala | Gly | Tyr | Gly |
| | | | | 245 | | | | | 250 | | | | | 255 | |
| Gly | Phe | Ser | Arg | Arg | Phe | Glu | Phe | Glu | Thr | Ser | Pro | Val | Leu | Ala | Ala |
| | | | 260 | | | | | 265 | | | | | 270 | | |
| Ser | Ser | Asp | Gln | Ser | Gln | Ile | Pro | Ile | Ile | Val | Val | Ser | Val | Thr | Val |
| | | 275 | | | | | 280 | | | | | 285 | | | |
| Gly | Val | Ile | Leu | Leu | Ala | Val | Val | Ile | Gly | Phe | Leu | Leu | Ser | Gly | Arg |
| | 290 | | | | | 295 | | | | | 300 | | | | |
| Arg | Cys | Gly | Tyr | Ser | Lys | Ala | Lys | Gln | Asp | Pro | Glu | Glu | Glu | Lys | Met |
| 305 | | | | | 310 | | | | | 315 | | | | | 320 |
| His | Phe | His | Asn | Gly | His | Ile | Lys | Leu | Pro | Gly | Val | Arg | Thr | Tyr | Ile |
| | | | | 325 | | | | | 330 | | | | | 335 | |
| Asp | Pro | His | Thr | Tyr | Glu | Asp | Pro | Asn | Gln | Ala | Val | His | Glu | Phe | Ala |
| | | | 340 | | | | | 345 | | | | | 350 | | |
| Lys | Glu | Ile | Glu | Ala | Ser | Cys | Ile | Thr | Ile | Glu | Arg | Val | Ile | Gly | Ala |
| | | 355 | | | | | 360 | | | | | 365 | | | |
| Gly | Glu | Phe | Gly | Glu | Val | Cys | Ser | Gly | Arg | Leu | Lys | Leu | Gln | Gly | Lys |
| | 370 | | | | | 375 | | | | | 380 | | | | |
| Arg | Glu | Phe | Pro | Val | Ala | Ile | Lys | Thr | Leu | Lys | Val | Gly | Tyr | Thr | Glu |
| 385 | | | | | 390 | | | | | 395 | | | | | 400 |

```
Lys Gln Arg Arg Asp Phe Leu Gly Glu Ala Ser Ile Met Gly Gln Phe
            405             410                 415

Asp His Pro Asn Ile Ile His Leu Glu Gly Val Val Thr Lys Ser Lys
            420             425                 430

Pro Val Met Ile Val Thr Glu Tyr Met Glu Asn Gly Ser Leu Asp Thr
            435             440                 445

Phe Leu Lys Lys Asn Asp Gly Gln Phe Thr Val Ile Gln Leu Val Gly
    450             455                 460

Met Leu Arg Gly Ile Ala Ser Gly Met Lys Tyr Leu Ser Asp Met Gly
465             470                 475                     480

Tyr Val His Arg Asp Leu Ala Ala Arg Asn Ile Leu Ile Asn Ser Asn
            485             490                 495

Leu Val Cys Lys Val Ser Asp Phe Gly Leu Ser Arg Val Leu Glu Asp
            500             505                 510

Asp Pro Glu Ala Ala Tyr Thr Thr Arg Gly Gly Lys Ile Pro Ile Arg
            515             520                 525

Trp Thr Ala Pro Glu Ala Ile Ala Phe Arg Lys Phe Thr Ser Ala Ser
    530             535                 540

Asp Val Trp Ser Tyr Gly Ile Val Met Trp Glu Val Met Ser Tyr Gly
545             550                 555                     560

Glu Arg Pro Tyr Trp Glu Met Thr Asn Gln Asp Val Ile Lys Ala Val
            565             570                 575

Glu Glu Gly Tyr Arg Leu Pro Ser Pro Met Asp Cys Pro Ala Ala Leu
            580             585                 590

Tyr Gln Leu Met Leu Asp Cys Trp Gln Lys Asp Arg Asn Ser Arg Pro
            595             600                 605

Lys Phe Asp Glu Ile Val Ser Met Leu Asp Lys Leu Ile Arg Asn Pro
    610             615                 620

Ser Ser Leu Lys Thr Leu Val Asn Ala Ser Ser Arg Val Ser Asn Leu
625             630                 635                     640

Leu Val Glu His Ser Pro Val Gly Ser Gly Ala Tyr Arg Ser Val Gly
            645             650                 655

Glu Trp Leu Glu Ala Ile Lys Met Gly Arg Tyr Thr Glu Ile Phe Met
            660             665                 670

Glu Asn Gly Tyr Ser Ser Met Asp Ser Val Ala Gln Val Thr Leu Glu
            675             680                 685

Asp Glu Ser Pro Cys Glu Lys Trp Ser Leu Thr Leu His Pro Leu Phe
    690             695                 700

Pro Thr Gly Tyr Gln Thr
705             710
```

( 2 ) INFORMATION FOR SEQ ID NO:23:

( i ) SEQUENCE CHARACTERISTICS:
        ( A ) LENGTH: 19 amino acids
        ( B ) TYPE: amino acid
        ( D ) TOPOLOGY: linear ( x i ) SEQUENCE DESCRIPTION: SEQ ID NO:23:

```
Arg Ile Cys Thr Pro Asp Val Ser Gly Thr Val Gly Ser Arg Pro Ala
 1               5                   10                      15

Ala Asp His
```

( 2 ) INFORMATION FOR SEQ ID NO:24:

```
     ( i ) SEQUENCE CHARACTERISTICS:
             ( A ) LENGTH: 13 amino acids
             ( B ) TYPE: amino acid
             ( D ) TOPOLOGY: linear ( x i ) SEQUENCE DESCRIPTION: SEQ ID NO:24:

Cys  Leu  Glu  Thr  His  Thr  Lys  Asn  Ser  Pro  Val  Pro  Val
     1                   5                        10

( 2 ) INFORMATION FOR SEQ ID NO:25:

( i ) SEQUENCE CHARACTERISTICS:
             ( A ) LENGTH: 12 amino acids
             ( B ) TYPE: amino acid
             ( D ) TOPOLOGY: linear ( x i ) SEQUENCE DESCRIPTION: SEQ ID NO:25:

Lys  Met  Gln  Gln  Met  His  Gly  Arg  Met  Val  Pro  Val
     1                   5                        10

( 2 ) INFORMATION FOR SEQ ID NO:26:

( i ) SEQUENCE CHARACTERISTICS:
             ( A ) LENGTH: 12 amino acids
             ( B ) TYPE: amino acid
             ( D ) TOPOLOGY: linear ( x i ) SEQUENCE DESCRIPTION: SEQ ID NO:26:

Lys  Val  His  Leu  Asn  Gln  Leu  Glu  Pro  Val  Glu  Val
     1                   5                        10
```